(12) United States Patent
Zhang et al.

(10) Patent No.: US 12,281,119 B2
(45) Date of Patent: Apr. 22, 2025

(54) IMIDAZO[2,1-F][1,2,4]TRIAZIN-4-AMINE DERIVATIVES AS TLR7 AGONIST

(71) Applicant: BEIGENE, LTD., Grand Cayman (KY)

(72) Inventors: Guoliang Zhang, Beijing (CN); Jianzhuang Miao, Beijing (CN); Changyou Zhou, Beijing (CN); Gang Chen, Beijing (CN); Jing Li, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 772 days.

(21) Appl. No.: 17/428,856

(22) PCT Filed: Feb. 6, 2020

(86) PCT No.: PCT/CN2020/074437
§ 371 (c)(1),
(2) Date: Aug. 5, 2021

(87) PCT Pub. No.: WO2020/160711
PCT Pub. Date: Aug. 13, 2020

(65) Prior Publication Data
US 2022/0119394 A1    Apr. 21, 2022

(30) Foreign Application Priority Data

Feb. 7, 2019   (WO) ................ PCT/CN2019/074732
Jul. 31, 2019  (WO) ................ PCT/CN2019/098757
Jan. 22, 2020  (WO) ................ PCT/CN2020/073673

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01); *C07B 2200/05* (2013.01)

(58) Field of Classification Search
CPC ..... C07D 487/04; C07D 519/00; A61P 35/00; C07B 2200/05; A61K 31/53
See application file for complete search history.

(56) References Cited

U.S. PATENT DOCUMENTS

| | | | | |
|---|---|---|---|---|
| 9,962,388 | B2* | 5/2018 | Ding | C07D 487/04 |
| 10,138,248 | B2* | 11/2018 | Buesking | C07D 487/04 |
| 11,111,249 | B2* | 9/2021 | Zhang | A61K 31/519 |
| 11,117,898 | B2* | 9/2021 | Zhang | C07D 487/04 |
| 2010/0210598 | A1 | 8/2010 | Carson et al. | |
| 2013/0324547 | A1 | 12/2013 | Boivin et al. | |
| 2017/0273983 | A1 | 9/2017 | Ding et al. | |
| 2020/0062758 | A1 | 2/2020 | Liu et al. | |
| 2020/0131187 | A1 | 4/2020 | Zhang | |
| 2021/0380593 | A1 | 12/2021 | Zhang | |
| 2022/0119394 | A1 | 4/2022 | Zhang | |
| 2022/0289752 | A1 | 9/2022 | Zhang et al. | |

FOREIGN PATENT DOCUMENTS

| | | |
|---|---|---|
| CN | 102365280 A | 2/2012 |
| CN | 102439011 A | 5/2012 |
| CN | 102596958 A | 7/2012 |
| CN | 105367576 A | 3/2016 |
| CN | 107344941 A | 11/2017 |
| CN | 108069969 A | 5/2018 |
| JP | 2014-035140 A | 2/2014 |
| JP | 2017-524037 A | 8/2017 |
| JP | 2017-538734 A | 12/2017 |
| WO | 2010084425 | 7/2010 |
| WO | 2011035231 | 3/2011 |
| WO | WO-2014035140 A2 | 3/2014 |
| WO | 2014056953 A1 | 4/2014 |
| WO | WO-2014056953 | 4/2014 |
| WO | WO-2016023511 A1 | 2/2016 |
| WO | WO-2016183094 A1 | 11/2016 |
| WO | 2017106607 | 6/2017 |
| WO | WO-2017223414 A1 | 12/2017 |
| WO | 2018095426 | 5/2018 |
| WO | 2018210298 | 11/2018 |
| WO | WO-2020160710 A1 | 8/2020 |
| WO | WO-2020160711 A1 | 8/2020 |
| WO | WO-2021023105 A1 | 2/2021 |

OTHER PUBLICATIONS

Adams, S., "Toll-like receptor agonists in cancer therapy," Immunotherapy 1(6):949-964 (2009).
Aranda, F. et al., "Trial Watch: Toll-like receptor agonists in oncological indications," Oncoimmunology 3: e29179 (Aug. 2014).
Barton, G. M. et al., "Toll-like receptors and their ligands," Curr. Top. Microbiol. Immunol. 270:81-92 (2002).
International Search Report and Written Opinion for PCT/CN2020/074436, mailed Apr. 26, 2020, 10 pages.
International Search Report and Written Opinion for PCT/CN2020/074437, mailed Apr. 26, 2020, 15 pages.
Iwasaki, A. et al., "Toll-like receptor control of the adaptive immune responses," Nat. Immunol. 5(10):987-995 (2004).
Karroum, N. B. et al., "Novel and selective TLR7 antagonists among the Imidazo[1,2-a]pyrazines, Imidazo[1,5-a]quinoxalines, and Pyrazolo[1,5-a]quinoxalines Series," J. Med. Chem., vol. 62, Jul. 2019, pp. 7015-7031.

(Continued)

*Primary Examiner* — Robert H Havlin
*Assistant Examiner* — Chihyi Lee
(74) *Attorney, Agent, or Firm* — Foley & Lardner LLP

(57) ABSTRACT

Disclosed herein is an imidazo [2, 1-f] [1, 2, 4] triazin-4-amine derivative or a stereoisomer thereof, or a pharmaceutically acceptable salt thereof useful as a TLR7 agonist, and a pharmaceutical composition comprising the same. Also disclosed herein is a method of treating cancer using the imidazo [2, 1-f] [1, 2, 4] triazin-4-amine derivative or a stereoisomer thereof, or a pharmaceutically acceptable salt thereof as TLR7 agonist.

9 Claims, No Drawings

(56) References Cited

OTHER PUBLICATIONS

Monk, B. J. et al., "A phase 2, randomized, double-bind, placebo-controlled study of chemo-immunotherapy combination using motolimod with pegylated liposomal doxorubicin in recurrent or persistent ovarian cancer: a Gynecologic Oncology Group partners study," Ann Oncol. May 1, 2017;28(5):996-1004.
Salunke, D. B. et al., "Structure-activity relationships in human toll-like receptor 8-active 2, 3-diamino-furo [2,3-c] pyridines," J. Med. Chem., vol. 55, Aug. 2012, pp. 8137-8151.
Shayan, G. et al., "Phase Ib Study of Immune Biomarker Modulation with Neoadjuvant Cetuximab and TLR8 Stimulation in Head and Neck Cancer to Overcome Suppressive Myeloid Signals," Clin. Cancer Res. Jan. 24, 2018(1):62-72.
Stary, G. et al., "Tumoricidal activity of TLR7/8-activated inflammatory dendritic cells," J. Exp. Med. 204(6):1441-1451 (2007).
Van Duin, D. et al., "Triggering TLR signaling in vaccination," Trends Immunol. 27(1):49-55 (2006).
Lochmüller, et al., "Chromatographic Resolution of Enantiomers," Journ. of Chromatography, vol. 113, pp. 283-302 (1975).
Office Action for Japan Application No. 2021-546230 dated Mar. 5, 2024.
European Search Report in EP Application No. 20752173.3, mailed Oct. 7, 2022, 7 pages.
International Search Report and Written Opinion for PCT/CN2020/106190, mailed Nov. 3, 2020, 24 pages.
Lochmuller, C. H. et al., "Chromatographic resolution of enantiomers selective review," J. Chromatogr., vol. 113, No. 3, Oct. 1975, pp. 283-302.
Search Report and Written Opinion in SG Application No. 11202108284T, mailed Dec. 5, 2022, 9 pages.

\* cited by examiner

IMIDAZO[2,1-F][1,2,4]TRIAZIN-4-AMINE DERIVATIVES AS TLR7 AGONIST

CROSS-REFERENCE TO RELATED APPLICATIONS

This application is a U.S. National Stage Application under 35 U.S.C. § 371 of International Application No. PCT/CN2020/074437, filed Feb. 6, 2020, which claims priority to Patent Application Nos. PCT/CN2019/074732 (CN), filed on Feb. 7, 2019, PCT/CN2019/098757 (CN), filed on Jul. 31, 2019, and PCT/CN2020/073673 (CN), filed on Jan. 22, 2020, the disclosures of each of which is hereby incorporated by reference in its entirety for all purposes.

FIELD OF THE INVENTION

Disclosed herein is an imidazo[2,1-f][1,2,4]triazin-4-amine derivative or a stereoisomer thereof, or a pharmaceutically acceptable salt thereof useful as a TLR7 agonist, and a pharmaceutical composition comprising the same. Also disclosed herein is a method of treating cancer using the imidazo[2,1-f][1,2,4]triazin-4-amine derivative or a stereoisomer thereof, or a pharmaceutically acceptable salt thereof as TLR7 agonist.

BACKGROUND OF THE INVENTION

Toll-like receptors (TLRs) belong to a family of pattern recognition receptors (PRRs) which play a critical role in early innate immune response by sensing highly conserved molecular patterns of diverse pathogens (PAMPs) as well as endogenous danger-associated molecular patterns (DAMPs) (Barton, G. M. and R. Medzhitov (2002). "Toll-like receptors and their ligands." Curr Top Microbiol Immunol 270: 81-92).

Ten different TLRs have been identified in human. Among them, TLR7, TLR8, and TLR9 belong to the same subfamily of TLRs based on their genomic structures, sequence similarities, and endosomal localizations. They have a restricted pattern of expression, limited to certain types of immune cells. TLR7 is expressed in B cells and plasmacytoid dendritic cells (pDC); TLR8 is expressed in monocytes and myeloid dendritic cells (mDC) (Iwasaki, A. and R. Medzhitov (2004). "Toll-like receptor control of the adaptive immune responses." Nat Immunol 5(10): 987-995).

In addition to the natural ligand single-stranded RNA, the imidazoquinolones (or 'imiquimod-like' ligands) and guanosine analogs are shown to activate TLR7 and/or 8 with varying specificity. Activation of TLR7 and/or TLR8 triggers the maturation of dendritic cells (DCs) and the secretion of proinflammatory cytokines (van Duin, D., et al. (2006). "Triggering TLR signaling in vaccination." Trends Immunol 27(1): 49-55). CTLs and NK cells are further activated and proliferated by stimulated DC through cytokines and antigen presentation. The properties of TLR agonists thus constitute an efficient strategy for boosting anticancer immunity (Adams, S. (2009). "Toll-like receptor agonists in cancer therapy." Immunotherapy 1(6): 949-964).

Imiquimod (TLR7 agonist) is being successfully used for the treatment of many primary skin tumors and cutaneous metastasis as the single antitumor agent with immunostimulatory capacity (Stary, G., et al. (2007). "Tumoricidal activity of TLR7/8-activated inflammatory dendritic cells." J Exp Med 204(6): 1441-1451, Aranda, F., et al. (2014). "Trial Watch: Toll-like receptor agonists in oncological indications." Oncoimmunology 3: e29179).

WO2016023511 disclosed pyrrolopyrimidine compounds as a TLR7 agonist for treating antiviral drugs.

Currently, intensive effort has been put into preclinical and clinical development of TLR agonists for cancer therapy. Therefore, there is a need to develop more potent TLR agonists for treating cancer.

SUMMARY OF THE INVENTION

Unexpectedly and surprisingly, the inventors found that the imidazo[2,1-f][1,2,4]triazin-4-amine derivatives disclosed herein demonstrate more potent TLR7 agonist activity, especially when ring A in Formula (I) is further directly substituted with a heterocyclyl ring. The inventors also found that the branching of the alkyl moiety in position 2 of the imidazo[2,1-f][1,2,4]triazin-4-amine derivatives unexpectedly improved the TLR7 agonist activity.

In the first aspect, disclosed herein is a compound of Formula (I),

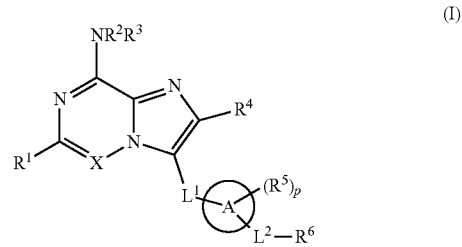

or a pharmaceutically acceptable salt thereof, or a stereoisomer thereof, wherein X is N or $CR^7$;
  wherein $R^7$ is hydrogen, alkyl, alkenyl, alkynyl, cycloalkyl, cycloalkenyl, cycloalkynyl, heterocyclyl, aryl, or heteroaryl;

$L^1$ is —$(CR^aR^b)_m$—, —O—, —S—, —S(O)—, —$SO_2$—, —C(O)—, —C(O)O—, —OC(O)—, —$NR^a$—, —C(O)$NR^a$—, —$NR^aC(O)$—, —$NR^aC(O)O$—, —$NR^aC(O)NR^b$—, —$SO_2NR^a$—, —$NR^aSO_2$—, —$NR^aS(O)_2NR^b$—, —$NR^aS(O)NR^b$—, —C(O)$NR^aSO_2$—, —C(O)$NR^aSO$—, or —C(=$NR^a$)$NR^b$—,
  wherein m is a number of 1 to 8, and one or two $CR^aR^b$ moieties in —$(CR^aR^b)_m$— are un-replaced or replaced with one or more moieties selected from O, S, SO, $SO_2$, C(O) and $NR^a$;
  $R^a$ and $R^b$, at each occurrence, are independently hydrogen, alkyl, alkenyl, alkynyl, cycloalkyl, cycloalkenyl, cycloalkynyl, heterocyclyl, aryl, heteroaryl, or —$OR^c$;
  wherein $R^c$ is hydrogen, alkyl, alkoxy-alkyl-, alkenyl, alkynyl, cycloalkyl, aryl, heterocyclyl, or heteroaryl;

$R^1$ is —$OR^{1a}$, —$SR^{1a}$, —$NR^{1a}R^{1b}$, —$COR^{1a}$, —$SO_2R^{1a}$, —C(=O)$OR^{1a}$, —C(=O)$NR^{1a}R^{1b}$, —C(=$NR^{1a}$)$NR^{1b}R^{1c}$, —$N(R^{1a})C(=O)R^{1b}$, —$N(R^{1a})C(=O)OR^{1b}$, —$N(R^{1a})C(O)NR^{1b}R^{1c}$, —$N(R^{1a})S(O)NR^{1b}R^{1c}$, —$N(R^{1a})S(O)_2NR^{1b}R^{1c}$, —$NR^{1a}SO_2R^{1b}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{1d}$;
  $R^{1a}$, $R^{1b}$, and $R^{1c}$ are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3$—$(OCH_2CH_2)_n$— (wherein n is a number of 3 to 10) or —$OR^{1f}$;
wherein $R^{1e}$ is halogen, nitro, cyano, hydroxy, amino (—$NH_2$), alkylamino, dialkylamino, or —$C_{1-6}$alkyl optionally substituted with halogen;
wherein $R^{1f}$ is alkyl, cycloalkyl, heterocyclyl, aryl, or heteroaryl, each of which is optionally substituted with —$C_{1-4}$alkyl or halogen;
$R^{1d}$, at each occurrence, is independently hydrogen, oxo, —CN, —$NO_2$, amino (—$NH_2$), alkylamino, dialkylamino, halogen, haloalkyl, alkyl, haloalkoxy, alkoxy, alkenyl, alkynyl, cycloalkyl, cycloalkenyl, cycloalkynyl, heterocyclyl, aryl, or heteroaryl;
$R^2$ and $R^3$, at each occurrence, are independently hydrogen, alkyl, alkenyl, alkynyl, cycloalkyl, cycloalkenyl, cycloalkynyl, heterocyclyl, aryl, or heteroaryl, wherein said alkyl, alkenyl, alkynyl, cycloalkyl, cycloalkenyl, cycloalkynyl, heterocyclyl, aryl, or heteroaryl is optionally substituted with 1-3 substituents selected from oxo, —CN, —$NO_2$, amino (—$NH_2$), alkylamino, dialkylamino, halogen, hydroxy, haloalkyl, alkyl, haloalkoxy, alkoxy, alkenyl, alkynyl, cycloalkyl, cycloalkenyl, cycloalkynyl, heterocyclyl, aryl, or heteroaryl;
$R^4$ is hydrogen, halogen, cyano, —$NO_2$, —$OR^{4a}$, —$SR^{4a}$, —$NR^{4a}R^{4b}$, —$COR^{4a}$, —$SO_2R^{4a}$, —$C(=O)OR^{4a}$, —$C(=O)NR^{4a}R^{4b}$, —$C(=NR^{4a})NR^{4b}R^{4c}$, —$N(R^{4a})C(=O)R^{4b}$, —$N(R^{4a})C(=O)OR^{4b}$, —$N(R^{4a})C(O)NR^{4b}R^{4c}$, —$N(R^{4a})S(O)NR^{4b}R^{4c}$, —$N(R^{4a})S(O)_2NR^{4b}R^{4c}$, —$NR^{4a}SO_2R^{4b}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{4d}$;
$R^{4a}$, $R^{4b}$, and $R^{4c}$ are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with halogen, hydroxy, $NH_2$—, alkylamino, dialkylamino or alkoxy;
$R^{4d}$, at each occurrence, is independently hydrogen, oxo, —CN, —$NO_2$, halogen, $NH_2$—, alkylamino, dialkylamino, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with halogen, hydroxy, $NH_2$—, alkylamino, dialkylamino or alkoxy;
Ring A is aryl or heteroaryl;
$R^5$ is halogen, hydroxy, alkyl, haloalkyl, alkoxy, haloalkoxy, -oxo-, or —$C(=O)OR^{5a}$, wherein $R^{5a}$ is hydrogen, alkyl, or haloalkyl;
p is a number of 0, 1, 2 or 3;
$L^2$ is a direct bond, —$(CR^fR^g)_t$—, —O—, —S—, —S(O)—, —$SO_2$—, —C(O)—, —C(O)O—, —OC(O)—, or —$NR^d$—, wherein $R^d$ is —$C_{1-6}$alkyl, wherein t is a number of 1 to 8, and one or two $CR^fR^g$ moieties in —$(CR^fR^g)_t$— are un-replaced or replaced with one or more moieties selected from O, S, SO, $SO_2$, C(O) and $NR^f$;
$R^f$ and $R^g$, at each occurrence, are independently hydrogen, alkyl, alkenyl, alkynyl, cycloalkyl, cycloalkenyl, cycloalkynyl, heterocyclyl, aryl, or heteroaryl;
$R^6$ is —$NR^{6a}R^{6b}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{6c}$;
$R^{6a}$ and $R^{6b}$, are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with halogen, hydroxy, $NH_2$—, alkylamino, dialkylamino or alkoxy;
$R^{6c}$ is independently hydrogen, halogen, cyano, —$NO_2$, —$OR^{6d}$, —$SR^{6d}$, —$NR^{6d}R^{6e}$, —$COR^{6d}$, —$SO_2R^{6d}$, —$C(=O)OR^{6d}$, —$C(=O)NR^{6d}R^{6e}$, —$C(=NR^{6d})NR^{6e}R^{6f}$, —$N(R^{6d})C(=O)R^{6e}$, —$N(R^{6d})C(=O)OR^{6e}$, —$N(R^{6d})C(O)NR^{6e}R^{6f}$, —$N(R^{6d})S(O)NR^{6e}R^{6f}$, —$N(R^{6d})S(O)_2NR^{6e}R^{6f}$, —$NR^{6d}SO_2R^{6e}$, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is independently and optionally substituted with one or two or three substituents $R^{6g}$;
$R^{6d}$, $R^{6e}$ and $R^{6f}$, are independently hydrogen, alkyl, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl, or heteroaryl is optionally substituted with one or two or three substituents $R^{6g}$;
$R^{6g}$, at each occurrence, is independently hydrogen, halogen, cyano, —$NO_2$, —$OR^{6h}$, —$SR^{6h}$, —$NR^{6h}R^{6i}$, —$COR^{6h}$, —$SO_2R^{6h}$, —$C(=O)OR^{6h}$, —$C(=O)NR^{6h}R^{6i}$, —$C(=NR^{6h})NR^{6i}R^{6j}$, —$N(R^{6h})C(=O)R^{6i}$, —$N(R^{6h})C(=O)OR^{6i}$, —$N(R^{6h})C(O)NR^{6i}R^{6j}$, —$N(R^{6h})S(O)NR^{6i}R^{6j}$, —$N(R^{6h})S(O)_2NR^{6i}R^{6h}$, —$NR^{6h}SO_2R^{6i}$, alkyl, alkenyl, alkynyl, cycloalkyl, cycloalkenyl, cycloalkynyl, heterocyclyl, aryl, or heteroaryl,
$R^{6h}$, $R^{6i}$ and $R^{6j}$, are independently hydrogen, alkyl, alkoxy, alkenyl, alkynyl, cycloalkyl, cycloalkenyl, cycloalkynyl, heterocyclyl, aryl, or heteroaryl, each of said alkyl, alkenyl, alkynyl, cycloalkyl, cycloalkenyl, cycloalkynyl, heterocyclyl, aryl or heteroaryl is independently and optionally substituted with one or two or three substituents selected from halogen, —$C_{1-4}$alkyl, —$C_{1-4}$alkoxy, hydroxy, nitro, —$NH_2$, alkylamino, dialkylamino, or cyano.

Definition of X

In some embodiments, X is N. In some embodiments, X is $CR^7$, wherein $R^7$ is defined as for Formula (I). In some embodiments, X is CH.

Definition of $L^1$

In some embodiments, m is a number of 1 to 5, or a number of 1 to 3, or a number of 1.

In some embodiments, $L^1$ is —$CR^aR^b$—, —O—, —S—, —S(O)—, —$SO_2$—, or —C(O)—, wherein $R^a$ and $R^b$, at each occurrence, are independently hydrogen, —$C_{1-8}$alkyl, or —$OR^c$, wherein $R^c$ is hydrogen or —$C_{1-4}$alkyl. In other embodiments, $L^1$ is —$CR^aR^b$—, wherein $R^a$ and $R^b$, at each occurrence, are independently hydrogen, —$C_{1-8}$alkyl (preferably —$C_{1-4}$alkyl, more preferably methyl) or —OH. In some embodiments, $L^1$ is —$CH_2$—, —CH(OH)— or —CH($CH_3$)—. In other embodiments, $L^1$ is —$CH_2$—.

Definition of $R^1$

In some embodiments, $R^1$ is —$OR^{1a}$ or —$NR^{1a}R^{1b}$, wherein $R^{1a}$ and $R^{1b}$ are defined as for Formula (I).

In some embodiments, $R^1$ is —$OR^{1a}$, or —$NR^{1a}R^{1b}$; wherein $R^{1a}$, $R^{1b}$, are independently hydrogen, —$C_{1-8}$alkyl, or —$C_{2-8}$alkenyl, each of said —$C_{1-8}$alkyl is optionally substituted with one or two or three substituents selected from heterocyclyl optionally substituted with $R^{1e}$, aryl optionally substituted with $R^{1e}$, $CH_3$—$(OCH_2CH_2)_n$— (wherein n is a number of 3 to 10, preferably 4-8, more preferably 5-7) or —$OR^{1f}$;
  wherein $R^{1e}$ is halogen, or —$C_{1-6}$alkyl optionally substituted with halogen;
  wherein $R^{1f}$ is —$C_{1-8}$alkyl, aryl, or heteroaryl, each of which is optionally substituted with —$C_{1-4}$alkyl or halogen.

In some embodiments, $R^1$ is —$OR^{1a}$, wherein $R^{1a}$ is hydrogen.

In some embodiments, $R^1$ is —$OR^{1a}$, wherein $R^{1a}$ is —$C_{1-8}$alkyl optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3$—$(OCH_2CH_2)_n$— (wherein n is a number of 3 to 10) or —$OR^{1f}$, wherein $R^{1e}$ and $R^{1f}$ are defined as for Formula (I).

In some embodiments, $R^1$ is —$OR^{1a}$, wherein $R^{1a}$ is unsubstituted $C_{1-8}$alkyl. In some embodiments, $R^1$ is —$OR^{1a}$, wherein $R^{1a}$ is straight. In some embodiments, $R^1$ is —$OR^{1a}$, wherein $R^{1a}$ is a branched alkyl. In some embodiments, $R^1$ is —$OR^{1a}$, wherein $R^{1a}$ is a branched alkyl, preferably —$C_{4-8}$alkyl, wherein the branched substituent is at the alpha position with respect to the oxygen atom, including, but not limited to butan-2-yl, pentan-2-yl, pentan-3-yl, heptan-2-yl, heptan-3-yl, heptan-4-yl, octan-2-yl, octan-3-yl, octan-4-yl, or octan-5-yl. In some embodiments, $R^1$ is methoxy, ethoxy, propoxy, butoxy, pentoxy, hexoxy, heptoxy or octoxy. In some embodiments, $R^1$ is preferably propoxy, isopropoxy, n-butoxy, isobutoxy, butan-2-yloxy (sec-butoxy), pentan-2-yloxy, pentan-3-yloxy, 2-methylbutoxy, heptan-2-yloxy, heptan-3-yloxy, heptan-4-yloxy, octan-2-yloxy, octan-3-yloxy, octan-4-yloxy, or octan-5-yloxy. In some embodiments, $R^1$ is n-butoxy, butan-2-yloxy (sec-butoxy), pentan-2-yloxy, pentan-3-yloxy, heptan-2-yloxy, heptan-3-yloxy, heptan-4-yloxy, octan-2-yloxy, octan-3-yloxy, octan-4-yloxy, or octan-5-yloxy.

In some embodiments, $R^1$ is —$OR^{1a}$, wherein $R^{1a}$ is —$C_{1-8}$alkyl, preferably —$C_{4-5}$alkyl, said alkyl is substituted with 1 to 3 halogens, e.g., fluoro.

In some embodiments, $R^1$ is —$OR^{1a}$, wherein $R^{1a}$ is —$C_{1-8}$alkyl, preferably —$C_{1-3}$alkyl, said alkyl is substituted with cycloalkyl optionally substituted with $R^{1e}$, heterocyclyl optionally substituted with $R^{1e}$, aryl optionally substituted with $R^{1e}$, or heteroaryl optionally substituted with $R^{1e}$, wherein $R^{1e}$ is defined as for Formula (I).

In some embodiments, $R^1$ is —$OR^{1a}$, wherein $R^{1a}$ is —$C_{1-8}$alkyl, preferably —$C_{1-3}$alkyl, said alkyl is substituted with heteroaryl, e.g., 5- to 6-membered heteroaryl comprising one or two or three heteroatoms selected from oxygen, nitrogen or optionally oxidized sulfur as ring members, said heteroaryl is optionally substituted with —$C_{1-6}$alkyl, preferably —$C_{1-4}$alkyl, more preferably methyl. In some embodiments, heteroaryl is pyridinyl, or imidazolyl or isoxazolyl. In some embodiments, $R^1$ is pyridin-3-ylmethoxy, 2-(1H-imidazol-1-yl)ethoxy, or (5-methylisoxazol-3-yl)methoxy.

In some embodiments, $R^1$ is —$OR^{1a}$, wherein $R^{1a}$ is —$C_{1-8}$alkyl, preferably —$C_{1-3}$alkyl, said alkyl is substituted with aryl, e.g., phenyl. In some embodiments, $R^1$ is 2-phenethoxy or 3-phenylpropoxy.

In some embodiments, $R^1$ is —$OR^{1a}$, wherein $R^{1a}$ is —$C_{1-8}$alkyl, preferably —$C_{1-3}$alkyl, said alkyl is substituted with —$OR^{1f}$, wherein $R^{1f}$ is —$C_{1-8}$alkyl or aryl (e.g., phenyl). In some embodiments, $R^1$ is 2-methoxyethoxy or 2-phenoxyethoxy.

In some embodiments, $R^1$ is —$OR^{1a}$, wherein $R^{1a}$ is —$C_{1-8}$alkyl, preferably —$C_{1-3}$alkyl, said alkyl is substituted with $CH_3$—$(OCH_2CH_2)_n$—, wherein n is a number of 3 to 10, preferably 3 or 4 or 5. In some embodiments, $R^1$ is 2,5,8,11-tetraoxatridecan-13-yloxy.

In some embodiments, $R^1$ is —$OR^{1a}$, wherein $R^{1a}$ is —$C_{2-8}$alkenyl; preferably —$C_{2-6}$alkenyl; most preferably —$C_{4-6}$alkenyl. In an example, $R^1$ is but-3-enyloxy.

In some embodiments, $R^1$ is —$NR^{1a}R^{1b}$, wherein $R^{1a}$ and $R^{1b}$ are each hydrogen, or —$C_{1-8}$alkyl, preferably —$C_{1-6}$alkyl, said alkyl is optionally substituted with one or two or three substituents selected from halogen, —$C_{1-8}$alkyl optionally substituted with $R^{1e}$, cycloalkyl optionally substituted with $R^{1e}$, heterocyclyl optionally substituted with $R^{1e}$, aryl optionally substituted with $R^{1e}$, or heteroaryl optionally substituted with $R^{1e}$, wherein $R^{1e}$ is —$C_{1-6}$alkyl, e.g., methyl.

In some embodiments, $R^1$ is —$NR^{1a}R^{1b}$, wherein $R^{1a}$ is hydrogen, and $R^{1b}$ is straight or branched —$C_{1-8}$alkyl. In some embodiments, $R^1$ is —$NR^{1a}R^{1b}$, wherein $R^{1a}$ is hydrogen, $R^{1b}$ is a branched alkyl, preferably —$C_{4-8}$alkyl, wherein the branched substituent is at the alpha position with respect to the oxygen atom, including, but not limited to butan-2-yl, pentan-2-yl, pentan-3-yl, heptan-2-yl, heptan-3-yl, heptan-4-yl, octan-2-yl, octan-3-yl, octan-4-yl, or octan-5-yl.

In some embodiments, $R^1$ is butylamino, N-butyl-N-methylamino, or isopentylamino.

In some embodiments, $R^1$ is optionally partially or fully deuterated, i.e., one or more carbon-bound hydrogen(s) in the definition of $R^1$ are replaced by one or more deuterium(s).

Definition of $R^2$ and $R^3$

In some embodiments, $R^2$ and $R^3$, at each occurrence, are independently hydrogen or $C_{1-8}$alkyl, preferably $C_{1-6}$alkyl. In some embodiments, $R^2$ and $R^3$ are both hydrogen.

Definition of $R^4$

In some embodiments, $R^4$ is hydrogen.

Definition of $R^5$

In some embodiments, $R^5$ is halogen, hydroxy, $C_{1-8}$alkyl, halo$C_{1-8}$alkyl, $C_{1-8}$alkoxy, halo$C_{1-8}$alkoxy, or —C(=O)

OR$^{5a}$, wherein R$^{5a}$ is hydrogen, C$_{1-8}$alkyl, or haloC$_{1-8}$alkyl; and p is a number of 0, 1, or 2.

In some embodiments, R$^5$ is halogen, C$_{1-3}$alkyl, haloC$_{1-3}$alkyl, C$_{1-3}$alkoxy, or haloC$_{1-8}$alkoxy. In some embodiments, R$^5$ is methyl, ethyl, propyl, methoxy, ethoxy, propoxy, isopropoxy, trifluoromethoxy, or trifluoromethyl. In some embodiments, R$^5$ is methyl.

In some embodiments, p is a number of 1.

In some embodiments, R$^5$ and L$^2$-R$^6$ are at ortho positions on ring A.

Definition of Ring A

In some embodiments, Ring A is phenyl.

In some embodiments, ring A is 5- to 8-, preferably 5- to 6-membered heteroaryl comprising one or two or three heteroatoms selected from oxygen, nitrogen or optionally oxidized sulfur as ring members, preferably 5- to 6-membered heteroaryl comprising one or two nitrogen atoms as ring members. In some embodiments, ring A is pyridyl, e.g., pyridin-2-yl, pyridin-3-yl, pyridin-4-yl, pyridin-5-yl or pyridin-6-yl, preferably pyridin-2-yl or pyridin-3-yl. In some embodiments, ring A is pyrazolyl, i.e., 1H-pyrazol-4-yl.

In some embodiments, ring A is 1,2,3,4-tetrahydroisoquinolinyl, e.g., 1,2,3,4-tetrahydroisoquinolin-6-yl or 1,2,3,4-tetrahydroisoquinolin-7-yl.

Definition of L$^2$-R$^6$

In some embodiments, L$^2$ is a direct bond, —(CH$_2$)$_t$—, —O—, —S—, —S(O)—, —SO$_2$—, —C(O)—, —C(O)O—, —OC(O)—, or —NR$^d$—, wherein R$^d$ is —C$_{1-6}$alkyl, wherein t is a number of 1 to 8, preferably 1 to 5, more preferably 1 or 2 or 3; and R$^d$ is —C$_{1-6}$alkyl.

In some embodiments, L$^2$ is a direct bond, —CH$_2$—, —CH$_2$CH$_2$—, —CH$_2$CH$_2$CH$_2$—, —O—, or —NR$^d$—, wherein R$^d$ is —C$_{1-6}$alkyl, preferably —C$_{1-4}$alkyl, more methyl.

In some embodiments, R$^6$ is —NR$^{6a}$R$^{6b}$, —C$_{1-8}$alkyl, —C$_{2-8}$alkenyl, —C$_{2-8}$alkynyl, -cycloalkyl, heterocyclyl, aryl, or heteroaryl, each of said —C$_{1-8}$alkyl, —C$_{2-8}$alkenyl, —C$_{2-8}$alkynyl, -cycloalkyl, heterocyclyl, aryl, or heteroaryl is independently and optionally substituted with one or two or three substituents R$^{6c}$;

R$^{6a}$ and R$^{6b}$, are independently hydrogen or —C$_{1-8}$alkyl;

R$^{6c}$ is independently hydrogen, halogen, —OR$^{6d}$, —SR$^{6d}$, —NR$^{6d}$R$^{6e}$, —COR$^{6d}$, —SO$_2$R$^{6d}$, —C(=O)NR$^{6d}$R$^{6e}$, or —C$_{1-8}$alkyl, said —C$_{1-8}$alkyl is independently and optionally substituted with one or two or three substituents R$^{6g}$;

R$^{6d}$ and R$^{6e}$ are independently hydrogen, —C$_{1-8}$alkyl, —C$_{2-8}$alkenyl, heterocyclyl, or aryl, each of said —C$_{1-8}$alkyl, —C$_{2-8}$alkenyl, heterocyclyl, or aryl is optionally substituted with one or two or three substituents R$^{6g}$;

R$^{6g}$, at each occurrence, is independently hydrogen, halogen, —OR$^{6h}$, —SR$^{6h}$, —NR$^{6h}$R$^{6i}$, —N(R$^{6h}$)C(=O)OR$^{6i}$, —C$_{1-8}$alkyl, heterocyclyl, aryl, or heteroaryl, wherein R$^{6h}$ and R$^{6i}$, are independently hydrogen or —C$_{1-8}$alkyl.

Definition of L$^2$-R$^6$, wherein L$^2$ is —(CR$^f$R$^g$)$_t$— and R$^6$ is heterocyclyl In some embodiments, L$^2$ is —(CR$^f$R$^g$)$_t$— (wherein t, R$^f$ and R$^g$ are defined as for Formula (I)), preferably —CH$_2$— or —CH$_2$CH$_2$—, and R$^6$ is heterocyclyl optionally substituted with one or two substituents R$^{6c}$, wherein R$^{6c}$ is defined as for Formula (I).

In some embodiments, the heterocyclyl as R$^6$ is monocyclic. In some embodiments, heterocyclyl is bicyclic. In some embodiments, heterocyclyl is saturated. In some embodiments, heterocyclyl is a 5- to 8-membered saturated monocyclic ring comprising one, two or three heteroatoms selected from oxygen, nitrogen or optionally oxidized sulfur as ring members. In some embodiments, heterocyclyl is a 5-, 6-, 7- or 8-membered saturated monocyclic ring comprising one or two or three nitrogen heteroatoms as ring members.

In some embodiments, the heterocyclyl as R$^6$ is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), piperazinyl (e.g., piperazin-1-yl, piperazin-2-yl, piperazin-3-yl) or morpholino. In some embodiments, heterocyclyl is a bicyclic ring comprising one, two or three heteroatoms selected from oxygen, nitrogen or optionally oxidized sulfur as ring members. In some example, heterocyclyl is (1S,4S)-2,5-diazabicyclo[2.2.1]heptan-2-yl. In the above embodiments, the heterocyclyl as R$^6$ is further optionally substituted with one or two substituents R$^{6c}$. In some embodiments, R$^{6c}$ is —NR$^{6d}$R$^{6e}$, —COR$^{6d}$, —OR$^{6d}$, or —C$_{1-8}$alkyl optionally substituted with hydroxy, wherein R$^{6d}$ and R$^{6e}$ are independently hydrogen or —C$_{1-8}$alkyl (preferably —C$_{1-3}$alkyl) or phenyl, wherein said alkyl is optionally substituted with NH$_2$—, alkylamino, or dialkylamino. In some embodiments, R$^{6c}$ is amino, dimethylamino, 2-(dimethylamino)acetyl, methyl, 3-hydroxypropyl or phenoxy. In some embodiments, L$^2$ is —CH$_2$— or —CH$_2$CH$_2$—. In some embodiments, R$^6$ is pyrrolidin-1-yl, morpholino, piperidin-1-yl, 4-methylpiperazin-1-yl, piperazin-1-yl, piperidin-4-yl, 4-(2-(dimethylamino)acetyl)piperazin-1-yl, (1S,4S)-2,5-diazabicyclo[2.2.1]heptan-2-yl, 4-aminopiperidin-1-yl, 3-(dimethylamino)pyrrolidin-1-yl, 4-phenoxypiperidin-1-yl, 1H-1,2,4-triazol-1-yl, 4-(3-hydroxypropyl)piperazin-1-yl, or piperidin-3-yl.

In some embodiments, L$^2$-R$^6$ is pyrrolidin-1-ylmethyl, morpholinomethyl, piperidin-1-ylmethyl, (4-methylpiperazin-1-yl)methyl, piperazin-1-ylmethyl, piperidin-4-ylmethyl, (4-(2-(dimethylamino)acetyl)piperazin-1-yl)methyl, (1S,4S)-2,5-diazabicyclo[2.2.1]heptan-2-ylmethyl, 2-(pyrrolidin-1-yl)ethyl, (4-aminopiperidin-1-yl)methyl, (3-(dimethylamino)pyrrolidin-1-yl)methyl, (4-phenoxypiperidin-1-yl)methyl, (1H-1,2,4-triazol-1-yl)methyl, (4-(3-hydroxypropyl)piperazin-1-yl)methyl, or piperidin-3-ylmethyl.

Definition of L$^2$-R$^6$, Wherein L$^2$ is —(CR$^f$R$^g$)$_t$— and R$^6$ is —NR$^{6a}$R$^{6b}$ In some embodiments, L$^2$ is —(CR$^f$R$^g$)$_t$— (wherein t, R$^f$ and R$^g$ are defined as for Formula (I)), preferably —CH$_2$— or —CH$_2$CH$_2$— and R$^6$ is —NR$^{6a}$R$^{6b}$, wherein R$^{6a}$ and R$^{6b}$ are defined as for Formula (I). In some embodiments, L$^2$ is —(CH$_2$)$_t$— (wherein t is a number of 1 to 8, preferably 1 to 5, more preferably 1 or 2 or 3), preferably —CH$_2$— or —CH$_2$CH$_2$— and R$^6$ is —NR$^{6a}$R$^{6b}$, wherein R$^{6a}$ and R$^{6b}$ are independently hydrogen or C$_{1-8}$alkyl, preferably C$_{1-6}$alkyl. In some embodiments, L$^2$-R$^6$ is aminomethyl.

Definition of $L^2$-$R^6$, Wherein $L^2$ is a Direct Bond and $R^6$ is Alkyl, Alkenyl, or Alkynyl In some embodiments, $L^2$ is a direct bond and $R^6$ is —$C_{1-8}$alkyl, —$C_{2-8}$alkenyl, or —$C_{2-8}$alkynyl.

Definition of $L^2$-$R^6$, Wherein $L^2$ is —O— or —$NR^d$— and $R^6$ is Alkyl, Alkenyl, Alkynyl, Heterocyclyl, Aryl or Heteroaryl In some embodiments, $L^2$ is —O— and $R^6$ is —$C_{1-8}$alkyl or heterocyclyl, said —$C_{1-8}$alkyl and heterocyclyl optionally substituted with one or two $R^{6c}$. In some embodiments, $R^{6c}$ is —$C_{1-8}$alkyl, —$NR^{6d}R^{6e}$ and —$COR^{6d}$, wherein $R^{6d}$ and $R^{6e}$ are independently —$C_{1-8}$alkyl (preferably —$C_{1-3}$alkyl) optionally substituted with $NH_2$-, alkylamino, or dialkylamino. In some embodiments, $L^2$-$R^6$ is 3-(methylamino) propoxy, 3-(dimethylamino)propoxy, 3-(diethylamino) propoxy, 2-aminoethoxy, 3-(dimethylamino)-2,2-dimethylpropoxy, methoxy, 2-(methylamino)ethoxy, 2-(N-methylacetamido)ethoxy, 3-(piperidin-1-yl)propoxy, 3-morpholinopropoxy, 3-(pyrrolidin-1-yl)propoxy, 3-aminopropoxy, (1R,5S)-8-azabicyclo[3.2.1]octan-3-yloxy, piperidin-4-yloxy, (1R,5S)-8-ethyl-8-azabicyclo[3.2.1]octan-3-yloxy, 1-ethylpyrrolidin-3-yloxy, or pyrrolidin-3-yloxy.

In some embodiments, $L^2$ is —$NR^d$—, wherein $R^d$ is —$C_{1-6}$alkyl, and $R^6$ is —$C_{1-8}$alkyl, —$C_{2-8}$alkenyl, or —$C_{2-8}$alkynyl, each of which is optionally substituted with one or two $R^{6c}$. In some embodiments, $R^{6c}$ is —$C_{1-8}$alkyl or —$NR^{6d}R^{6e}$, wherein $R^{6d}$ and $R^{6e}$ are independently —$C_{1-8}$alkyl (preferably —$C_{1-3}$alkyl). In some embodiments, $L^2$-$R^6$ is (2-(dimethylamino)ethyl) (methyl)amino.

Definition of $L^2$-$R^6$, Wherein $L^2$ is a Direct Bond and $R^6$ is Cycloalkyl, Heterocyclyl, Aryl, or Heteroaryl In some embodiments, $L^2$ is a direct bond and $R^6$ is cycloalkyl, heterocyclyl, aryl, or heteroaryl, each of which is independently and optionally substituted with one or two or three substituents $R^{6c}$.

In some embodiments, $L^2$ is a direct bond and $R^6$ is heterocyclyl, which is optionally substituted with one or two or three substituents $R^{6c}$.

As $R^6$, in some embodiments, the heterocyclyl is monocyclic; in some embodiments, heterocyclyl is a fused bicyclic heterocyclyl; and in some embodiments, heterocyclyl is a spiro bicyclic heterocyclyl.

In some embodiments, heterocyclyl is saturated. In some embodiments, heterocyclyl is a 4-, 5-, 6-, 7- or 8-membered saturated monocyclic ring comprising one, two or three heteroatoms selected from oxygen, nitrogen or optionally oxidized sulfur as ring members. In some embodiments, heterocyclyl is a 5-, 6-, 7- or 8-membered saturated monocyclic ring comprising one or two or three nitrogen heteroatoms as ring members. In some embodiments, heterocyclyl is a 5- or 6-membered saturated monocyclic ring comprising one or two nitrogen heteroatoms as ring members. In some embodiments, the heterocyclyl is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), diazepanyl (e.g., 1,4-diazepan-1-yl, 1,4-diazepan-2-yl, 1,4-diazepan-3-yl, 1,4-diazepan-4-yl), piperazinyl (e.g., piperazin-1-yl, piperazin-2-yl, piperazin-3-yl) or morpholino.

In some embodiments, heterocyclyl is a bicyclic ring comprising one, two or three heteroatoms selected from oxygen, nitrogen or optionally oxidized sulfur as ring members. In some example, heterocyclyl is 2,5-diazabicyclo [2.2.1]heptan-2-yl.

In some embodiments, the heterocyclyl is a 6- to 14-membered, and more preferably 7- to 10-membered spiro bicyclic heterocyclyl. In some embodiments, the heterocyclyl is spiroheptanyl, spriodecanyl or spirononanyl comprising one or two nitrogen atoms as ring members. In some embodiments, the heterocyclyl is 8-azaspiro[4.5]decan-8-yl, 2,7-diazaspiro[3.5]nonan-7-yl, 2,8-diazaspiro[4.5]decan-2-yl, 2,7-diazaspiro[3.5]nonan-2-yl, 2,8-diazaspiro[4.5]decan-8-yl.

In the above embodiments, the heterocyclyl as $R^6$ is further optionally substituted with one or two substituents $R^{6c}$.

In some embodiments, $R^{6c}$ is —$COR^{6d}$, wherein $R^{6d}$ is —$C_{1-8}$alkyl optionally substituted with one or two substituents $R^{6g}$, wherein $R^{6g}$ is —$NR^{6h}R^{6i}$, —$N(R^{6h})C(=O)R^{6i}$, —$C_{1-8}$alkyl, aryl or heteroaryl, wherein $R^{6h}$ and $R^{6i}$ are defined as for formula (I). In some embodiments, $R^{6c}$ is —$COR^{6d}$, wherein $R^{6d}$ is —$C_{1-8}$alkyl (preferably $C_{1-6}$alkyl, more preferably $C_{1-4}$alkyl) optionally substituted with one or two substituents $R^{6g}$, wherein $R^{6g}$ is —$NR^{6h}R^{6i}$, —$N(R^{6h})C(=O)R^{6i}$, —$C_{1-8}$alkyl, aryl or heteroaryl, wherein $R^{6h}$ and $R^{6i}$ are each independently hydrogen or —$C_{1-8}$alkyl (preferably $C_{1-6}$alkyl, more preferably $C_{1-4}$alkyl).

In some embodiments, $R^{6c}$ is —$COR^{6d}$, wherein $R^{6d}$ is —$C_{2-8}$alkenyl.

In some embodiments, $R^{6c}$ is —$COR^{6d}$, wherein $R^{6d}$ is heterocyclyl.

In some embodiments, $R^{6c}$ is acetyl, 2-(dimethylamino) acetyl, 2-(dimethylamino)acetyl, aminoacetyl, 2-(methylamino)acetyl, 3-(dimethylamino)propanoyl, 4-(dimethylamino)butanoyl, 5-(dimethylamino)pentanoyl, (2S,3S)-2-amino-3-methylpentanoyl, 2-(methylamino)acetyl, 2-amino-4-methylpentanoyl, 2-amino-3-methylbutanoyl, 2-(dimethylamino)acetyl, phenylpropanoyl, 2-(piperazin-1-yl)acetyl, acryloyl, piperazine-2-carbonyl, piperidine-4-carbonyl, pyrrolidine-2-carbonyl, or 2-(N-methylacetamido) acetyl.

In some embodiments, $R^{6c}$ is —$C_{1-8}$alkoxy, preferably —$C_{1-6}$alkoxy, e.g., methoxy.

In some embodiments, $R^{6c}$ is —$C_{1-8}$alkyl, preferably —$C_{1-6}$alkyl, optionally substituted with one or two substituents $R^{6g}$, wherein $R^{6g}$ is —$OR^{6h}$, —$NR^{6h}R^{6i}$, heterocyclyl, aryl, wherein $R^{6h}$ and $R^{6i}$ are defined as for Formula (I). In some aspects, $R^{6c}$ is —$C_{1-8}$alkyl, preferably —$C_{1-6}$alkyl, optionally substituted with one substituents $R^{6g}$, wherein $R^{6g}$ is —$OR^{6h}$, —$NR^{6h}R^{6i}$, heterocyclyl (e.g., morpholino), aryl (e.g., phenyl), wherein $R^{6h}$ and $R^{6i}$ are —$C_{1-4}$alkyl, preferably methyl. In some embodiments, $R^{6c}$ is methyl, ethyl, isobutyl, methoxymethyl, 2-methoxyethyl, (methylamino)methyl, 2-(dimethylamino)ethyl, (dimethylamino)methyl, 2-aminoethyl, 2-(methylamino)ethyl, 2-(dimethylamino)ethyl, morpholinomethyl, or phenethyl.

In some embodiments, $R^{6c}$ is heterocyclyl, optionally substituted with one substituent $R^{6g}$. In some embodiments, $R^{6c}$ is heterocyclyl, optionally substituted with one substituent $R^{6g}$ which is heterocyclyl. In some embodiments, $R^{6c}$ is 4-morpholinopiperidin-1-yl.

In some embodiments, $R^{6c}$ is —$C(=O)NR^{6d}R^{6e}$, wherein $R^{6d}$ and $R^{6e}$ are independently hydrogen, —$C_{1-8}$alkyl (preferably —$C_{1-3}$alkyl), or aryl, said —$C_{1-8}$alkyl or aryl is independently and optionally substituted with halogen or —$C_{1-4}$alkyl. In some embodiments, $R^{6c}$ is —C(=O)NR$^{6d}$R$^{6e}$, wherein $R^{6d}$ and $R^{6e}$ are independently hydrogen and —$C_{1-4}$alkyl. In some embodiments, $R^{6c}$ is —C(=O)NR$^{6d}$R$^{6e}$, wherein $R^{6d}$ and $R^{6e}$ are independently hydrogen and aryl optionally substituted halogen. In some embodiments, $R^{6c}$ is dimethylcarbamoyl, isopropylcarbamoyl, or 2,4,5-trifluorophenylcarbamoyl.

In some embodiments, $R^{6c}$ is —NR$^{6d}$R$^{6e}$, wherein $R^{6d}$ and $R^{6e}$ are independently hydrogen, or —$C_{1-8}$alkyl (preferably —$C_{1-6}$alkyl, more preferably —$C_{1-3}$alkyl, most preferably methyl). In some embodiments, $R^{6c}$ is dimethylamino, or amino.

In some embodiments, $R^{6c}$ is —SO$_2$R$^{6d}$, wherein $R^{6d}$ is —$C_{1-8}$alkyl, —$C_{2-8}$alkenyl, —$C_{2-8}$alkynyl, cycloalkyl, cycloalkenyl, cycloalkynyl, heterocyclyl, aryl, or heteroaryl. In some embodiments, $R^{6c}$ is —SO$_2$R$^{6d}$, wherein $R^{6d}$ is —$C_{1-8}$alkyl (preferably —$C_{1-6}$alkyl). In some embodiments, $R^{6c}$ is propylsulfonyl.

In some embodiments, $L^2$ is a direct bond, $R^6$ is pyrrolidinyl, optionally substituted with one or two or three substituents selected from methyl, (dimethylamino)methyl, or dimethylamino. In some embodiments, $L^2$-$R^6$ is 1-methylpyrrolidin-3-yl, pyrrolidin-1-yl, 3-((dimethylamino)methyl)pyrrolidin-1-yl, or 3-(dimethylamino)pyrrolidin-1-yl.

In some embodiments, $L^2$ is a direct bond, $R^6$ is piperazinyl, optionally substituted with one or two or three substituents selected from acryloyl, 2-(dimethylamino)acetyl, aminoacetyl, 2-(methylamino)acetyl, 3-(dimethylamino)propanoyl, 2-(piperazin-1-yl)acetyl, piperazine-2-carbonyl, 4-(dimethylamino)butanoyl, 5-(dimethylamino)pentanoyl, methyl, piperidine-4-carbonyl, acetyl, 2-(N-methylacetamido)acetyl, isopropylcarbamoyl, 2,4,5-trifluorophenylcarbamoyl, (2S,3S)-2-amino-3-methylpentanoyl, 2-methoxyethyl, 2-(methylamino)acetyl, ethyl, isobutyl, pyrrolidine-2-carbonyl, 2-amino-4-methylpentanoyl, 2-amino-3-methylbutanoyl, 2-(dimethylamino)acetyl, 2-(methylamino)ethyl, 2-(dimethylamino)ethyl, amino, phenylpropanoyl, propylsulfonyl, or 2-aminoethyl. In some embodiments, $L^2$-$R^6$ is piperazin-1-yl, 4-acryloylpiperazin-1-yl, 4-(2-(dimethylamino)acetyl)piperazin-1-yl, (4-aminoacetyl)piperazin-1-yl, piperazin-1-yl, 4-(2-(methylamino)acetyl)piperazin-1-yl), 4-(3-(dimethylamino)propanoyl)piperazin-1-yl, 4-(2-(piperazin-1-yl)acetyl)piperazin-1-yl, 4-(piperazine-2-carbonyl)piperazin-1-yl, 4-acryloylpiperazin-1-yl, 4-(4-(dimethylamino)butanoyl)piperazin-1-yl, 4-(5-(dimethylamino)pentanoyl)piperazin-1-yl, 3,5-dimethylpiperazin-1-yl, 4-(piperidine-4-carbonyl)piperazin-1-yl, 4-acetylpiperazin-1-yl, 4-(2-(N-methylacetamido)acetyl)piperazin-1-yl, 4-(isopropylcarbamoyl)piperazin-1-yl, 4-(2,4,5-trifluorophenylcarbamoyl)piperazin-1-yl, 4-(3,5-dimethylpiperazin-1-yl, 4-((2S,3S)-2-amino-3-methylpentanoyl)piperazin-1-yl, 4-(2-methoxyethyl)piperazin-1-yl, 4-(2-(methylamino)acetyl)piperazin-1-yl, 4-ethylpiperazin-1-yl, 4-isobutylpiperazin-1-yl, 4-(pyrrolidine-2-carbonyl)piperazin-1-yl, 4-(2-amino-4-methylpentanoyl)piperazin-1-yl, 4-(2-amino-3-methylbutanoyl)piperazin-1-yl, 4-(2-(dimethylamino)acetyl)piperazin-1-yl, (S)-2-methylpiperazin-1-yl, (R)-2-methylpiperazin-1-yl, 4-(2-(methylamino)ethyl)piperazin-1-yl, 4-(2-(dimethylamino)ethyl)piperazin-1-yl, 4-(2-amino-3-phenylpropanoyl)piperazin-1-yl, 4-(propylsulfonyl)piperazin-1-yl, 4-(2-aminoethyl)piperazin-1-yl, or 3-methylpiperazin-1-yl.

In some embodiments, $L^2$ is a direct bond, $R^6$ is piperidinyl, optionally substituted with one or two or three substituents selected from 2-(dimethylamino)acetyl, methoxy, methoxymethyl, (methylamino)methyl, 4-morpholinopiperidin-1-yl, morpholinomethyl, 2-(dimethylamino)ethyl, phenethyl, (dimethylamino)methyl, amino, dimethylamino, or dimethylcarbamoyl. In some embodiments, $L^2$-$R^6$ is piperidin-4-yl, 4-(2-(dimethylamino)acetyl)piperidin-1-yl, piperidin-3-yl, piperidin-4-yl, piperidin-1-yl, piperidin-4-yl, 4-methoxypiperidin-1-yl, 4-(methoxymethyl)piperidin-1-yl, 4-((methylamino)methyl)piperidin-1-yl, (4-morpholinopiperidin-1-yl)pyridin-3-yl, 4-(morpholinomethyl)piperidin-1-yl, 4-(2-(dimethylamino)ethyl)piperidin-1-yl, 1-phenethylpiperidin-4-yl, 4-((dimethylamino)methyl)piperidin-1-yl, 4-aminopiperidin-1-yl, 4-(dimethylamino)piperidin-1-yl, or 4-(dimethylcarbamoyl)piperidin-1-yl.

In some embodiments, $L^2$-$R^6$ is azepan-1-yl or 1,4-diazepan-1-yl.

In some embodiments, $L^2$-$R^6$ is octahydro-2H-isoindol-2-yl.

In some embodiments, $L^2$-$R^6$ is morpholino.

In some embodiments, $L^2$-$R^6$ is 8-azaspiro[4.5]decan-8-yl, 2,7-diazaspiro[3.5]nonan-7-yl, 2,8-diazaspiro[4.5]decan-2-yl, 2,7-diazaspiro[3.5]nonan-2-yl, 2,8-diazaspiro[4.5]decan-8-yl, (1R,4R)-2,5-diazabicyclo[2.2.1]heptan-2-yl.

In some embodiments, ring A is phenyl, and $L^1$ and $L^2$-$R^6$ are in para positions of the phenyl ring, and said phenyl ring is further optionally substituted with one $R^5$, wherein $L^1$, $L^2$, $R^5$ and $R^6$ are defined as in each embodiment above. In some embodiments, ring A is pyridyl, and $L^1$ and $L^2$-$R^6$ are in para positions of the pyridyl ring, and said pyridyl ring is further optionally substituted with one $R^5$, wherein $L^1$, $L^2$, $R^5$ and $R^6$ are defined as in each embodiment above.

In some embodiments, disclosed herein are a compound, or a pharmaceutically acceptable salt thereof, or a stereoisomer thereof, selected from the specific compounds exemplified herein:

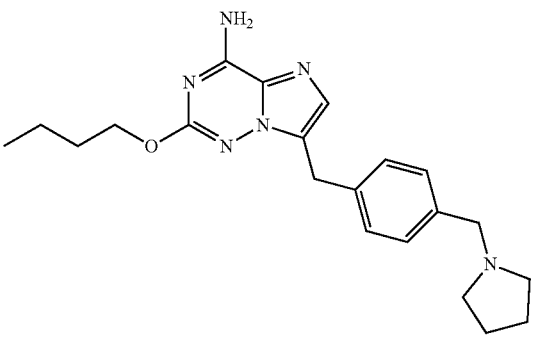

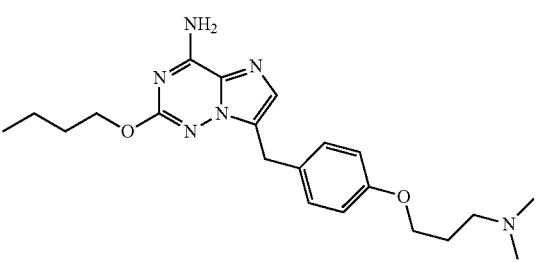

-continued
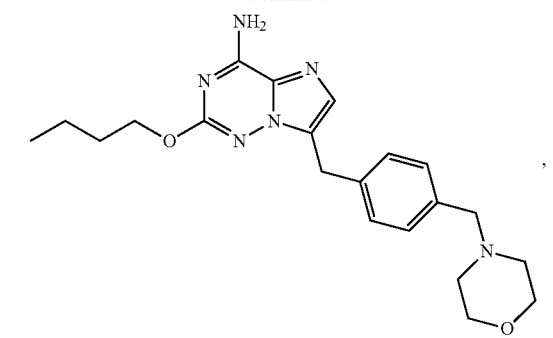
,
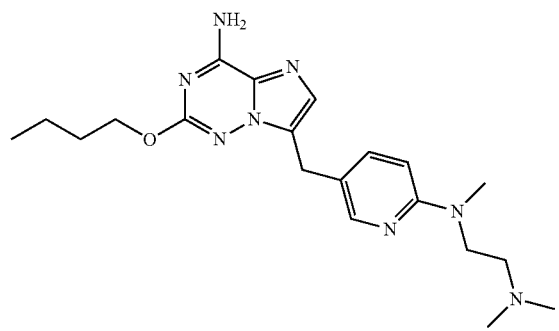
,
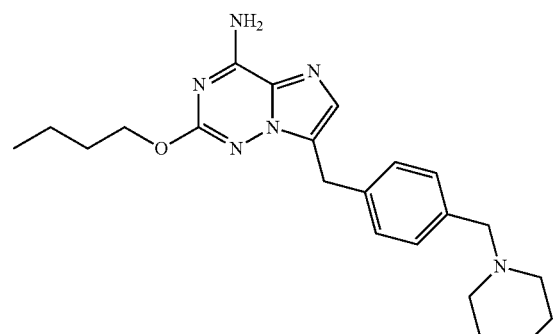
,
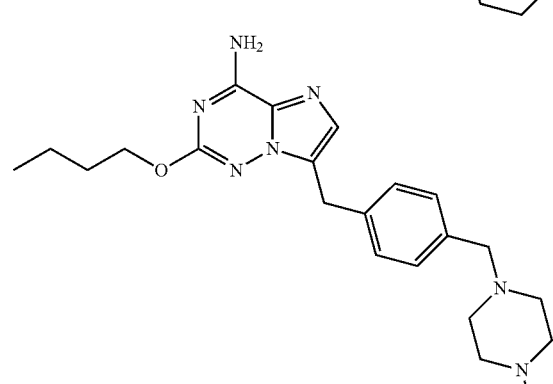
,
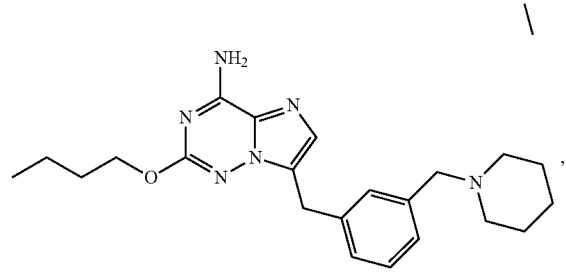
,
-continued
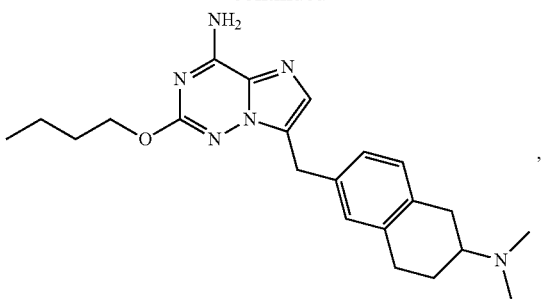
,
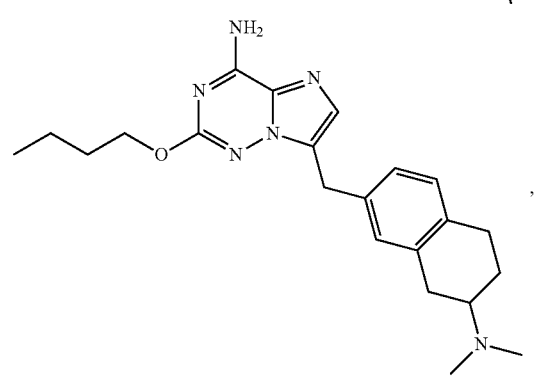
,
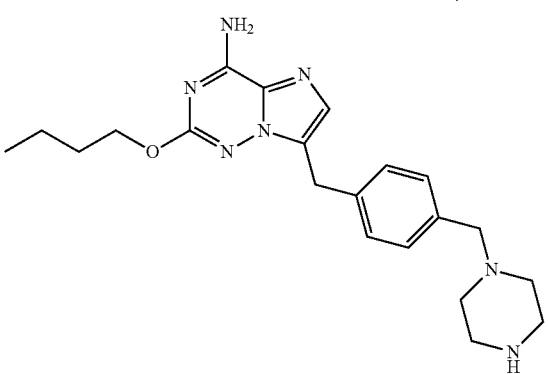
,
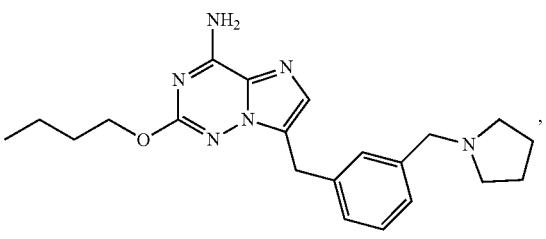
,
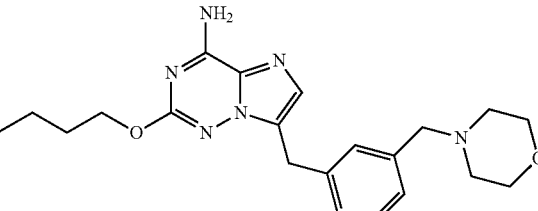
,
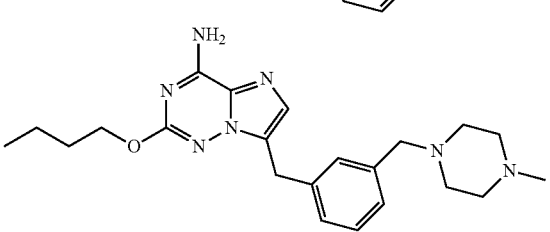
, -continued
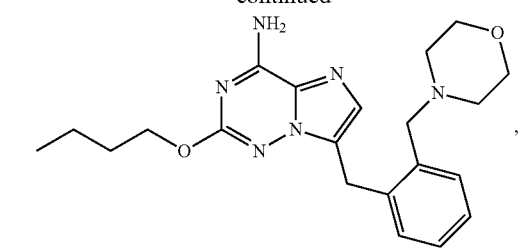
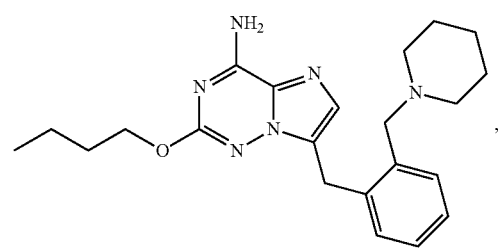
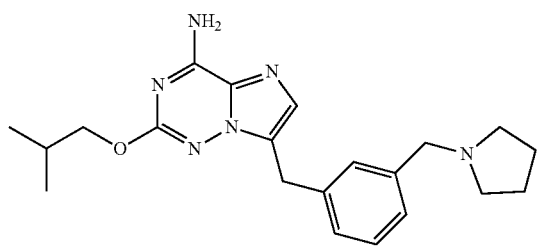
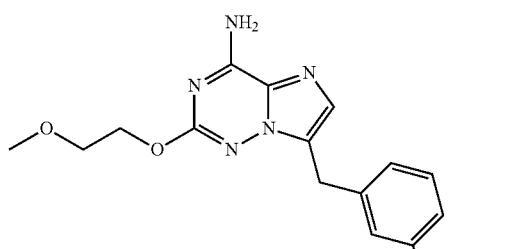
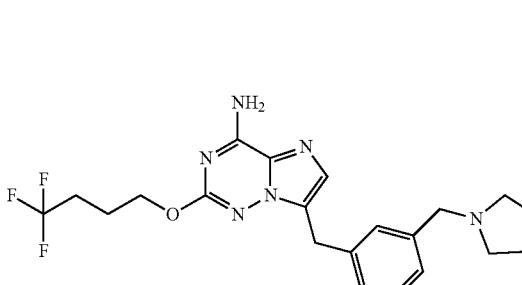
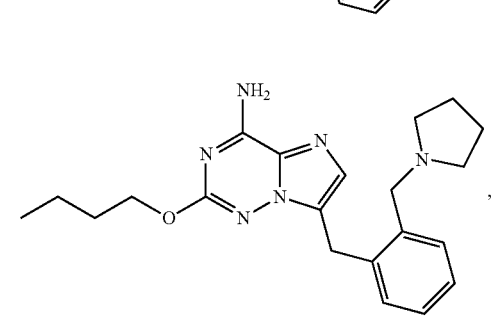
-continued
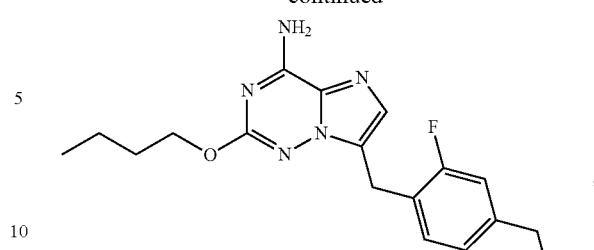
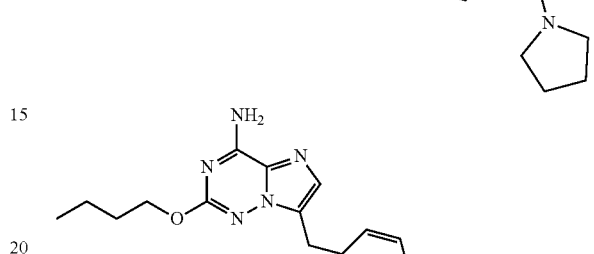
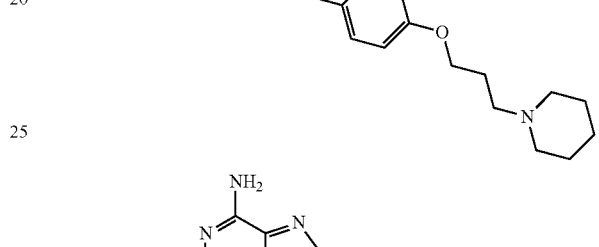
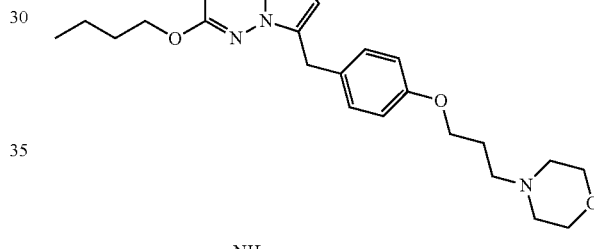
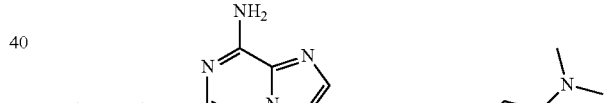
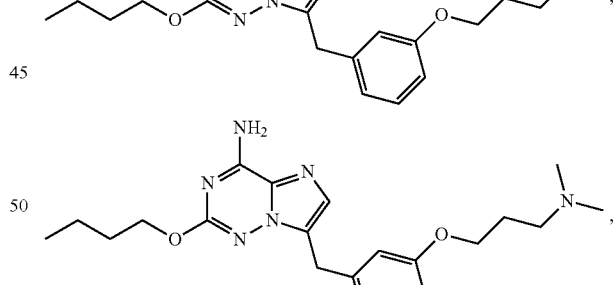
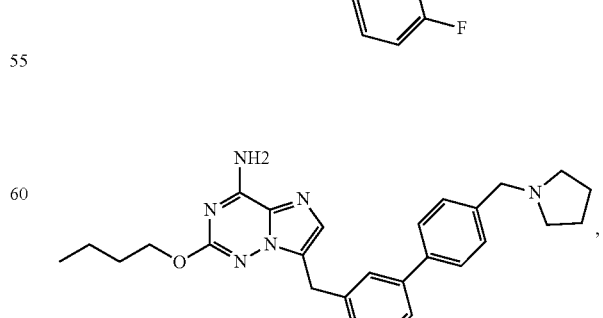

-continued
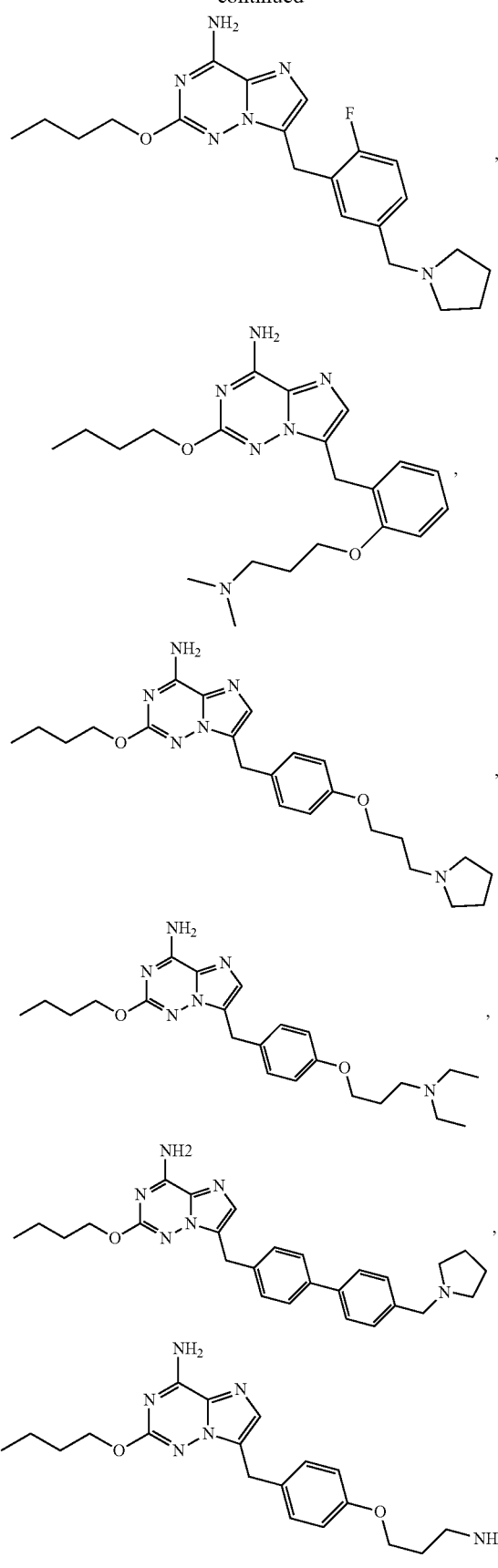
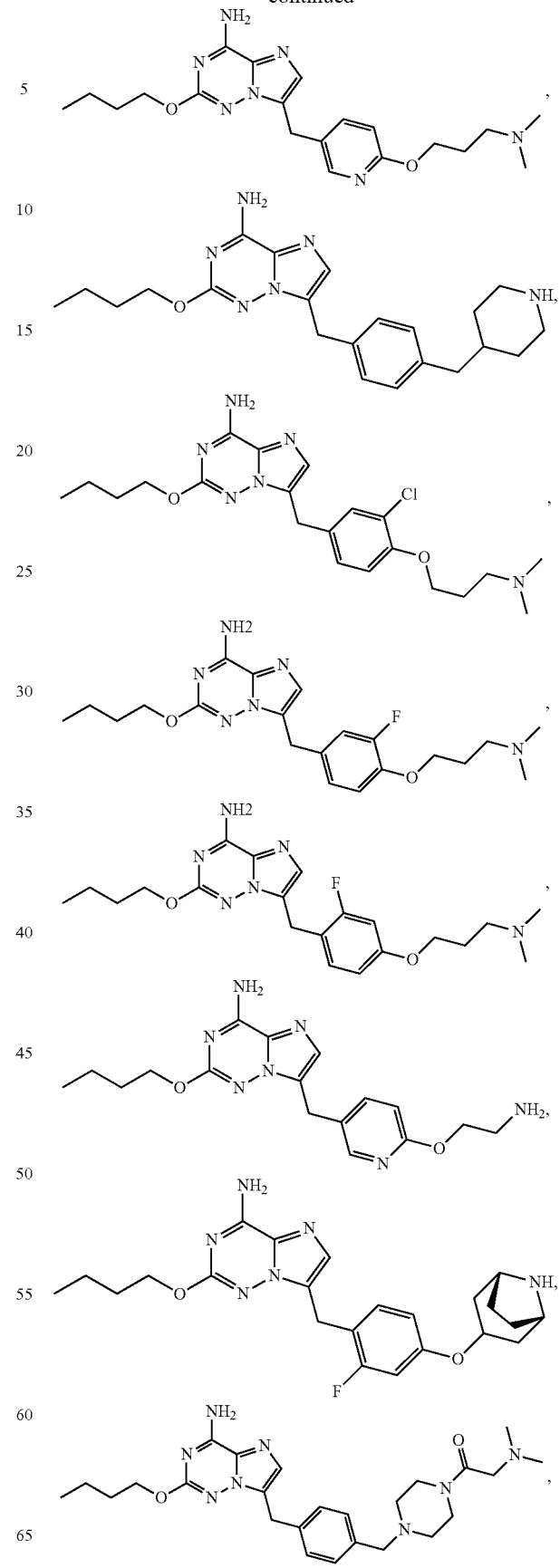

-continued
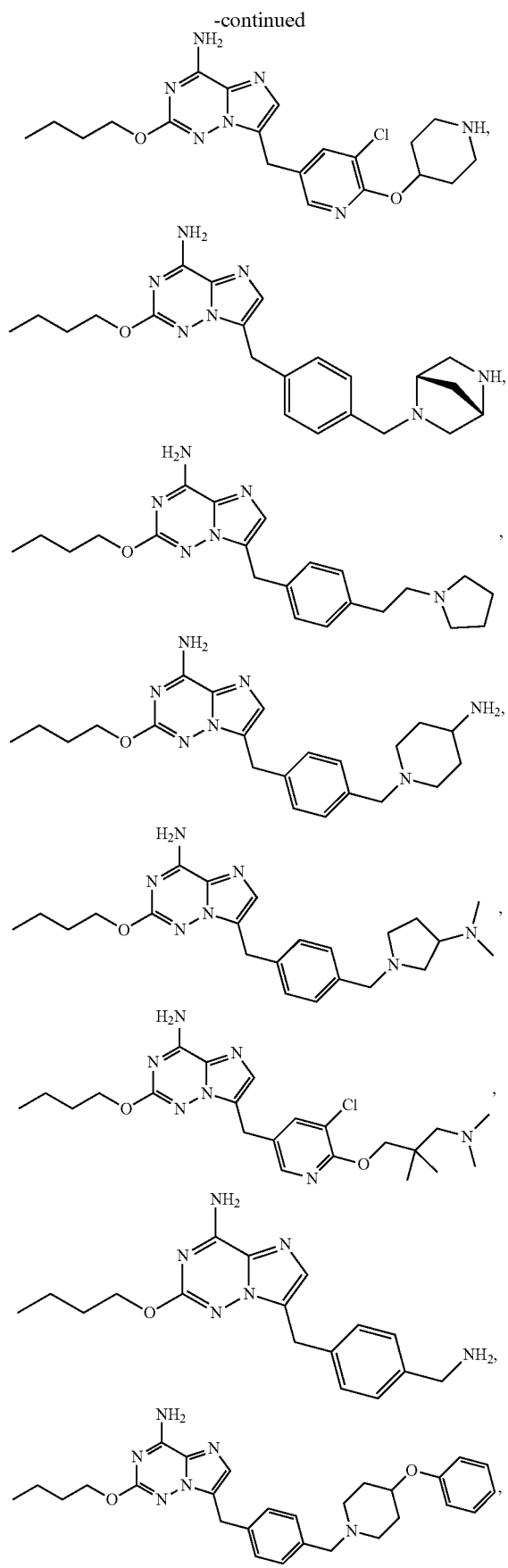
-continued
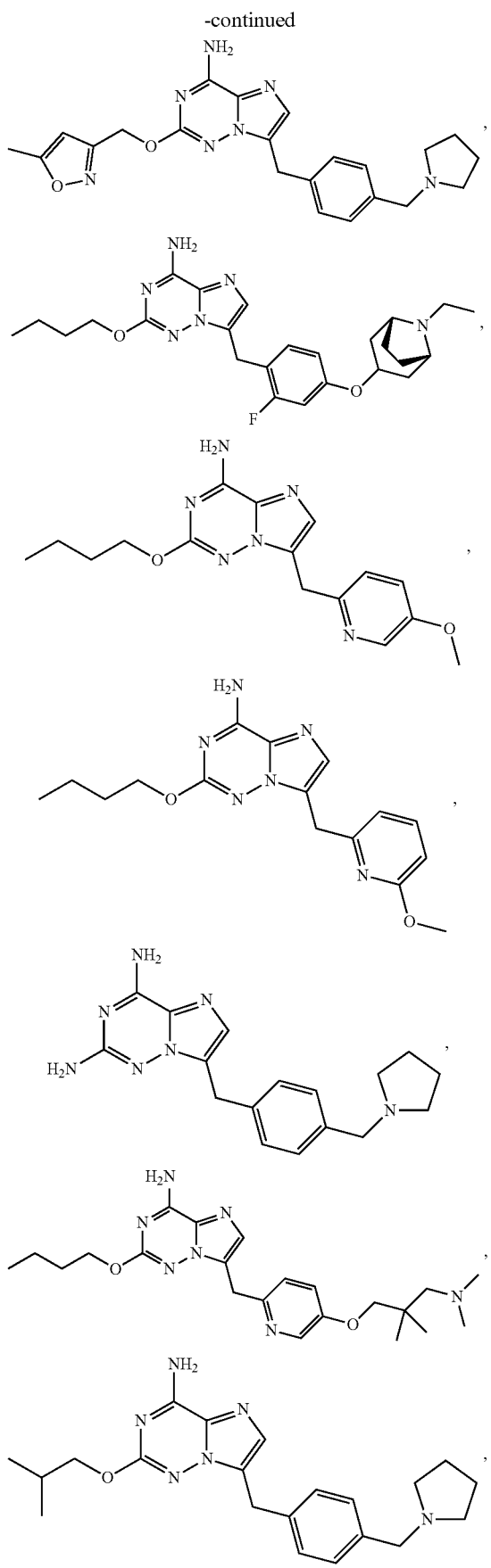

-continued
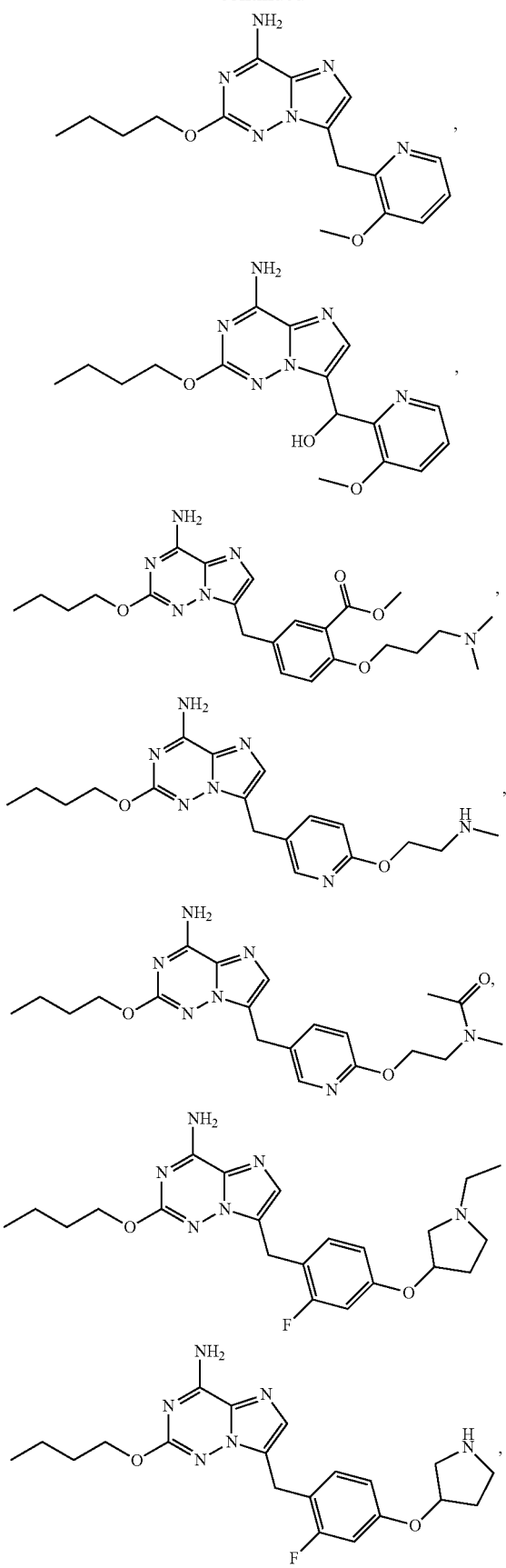
-continued
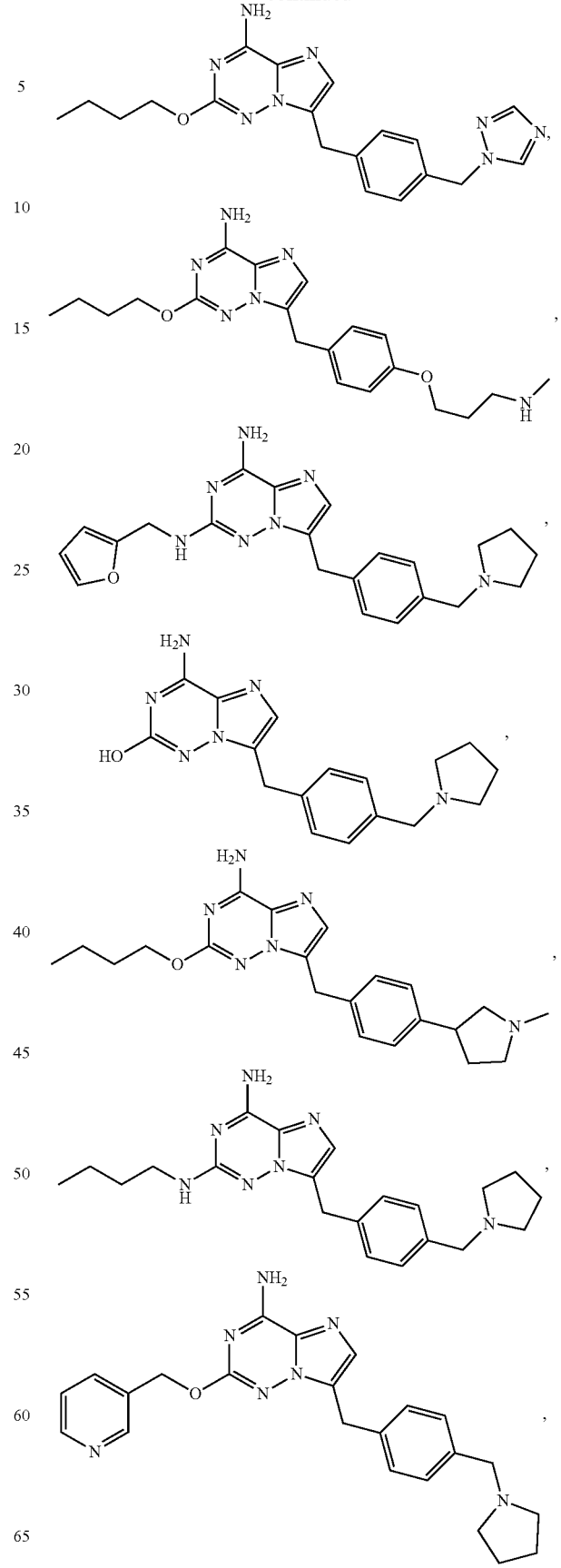

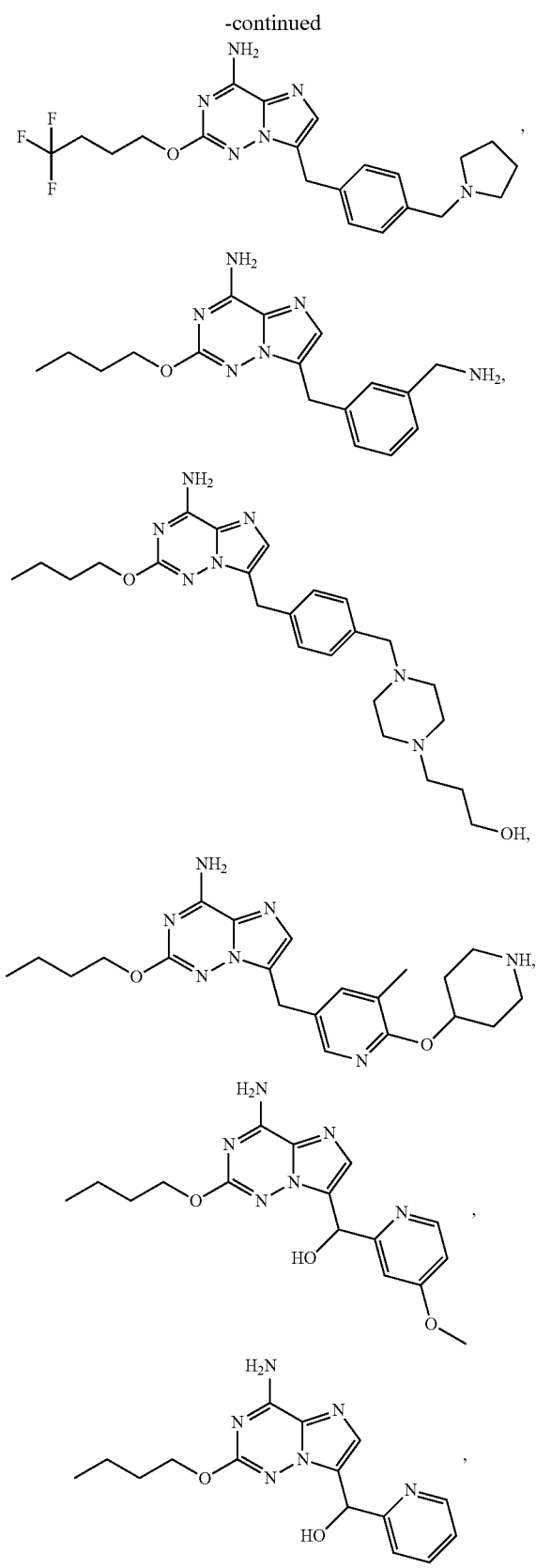
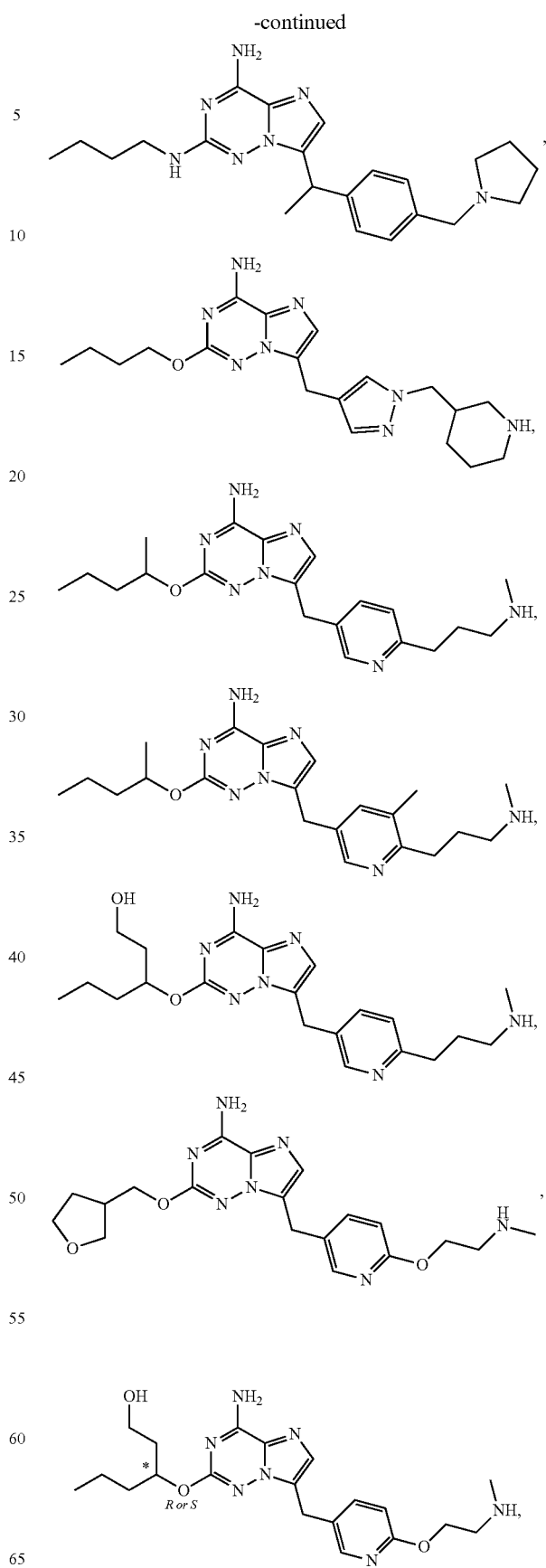

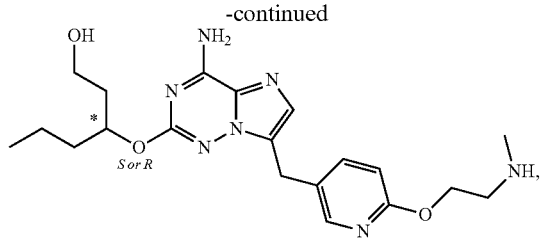
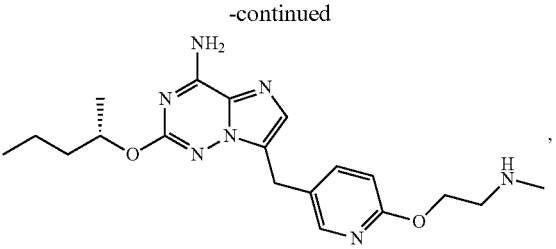
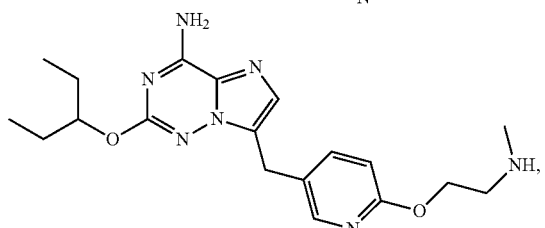
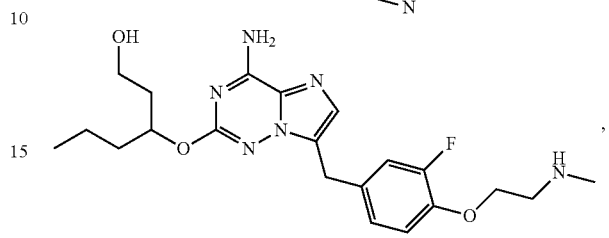
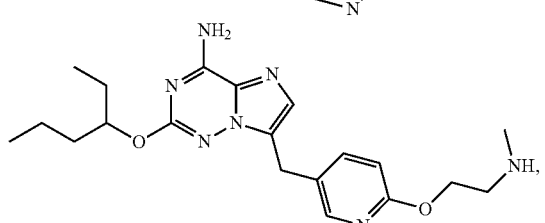
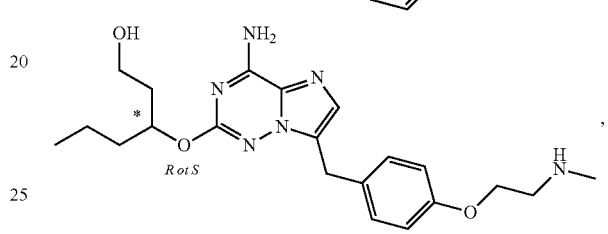
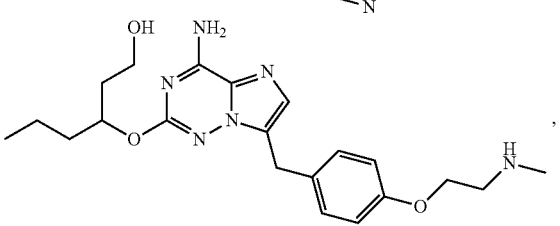
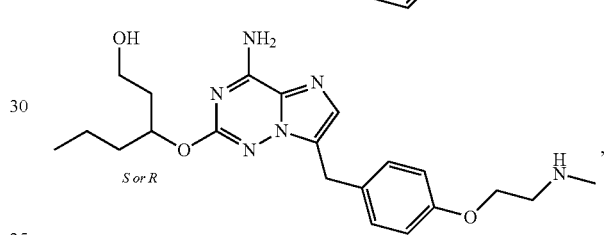
optical isomer 2
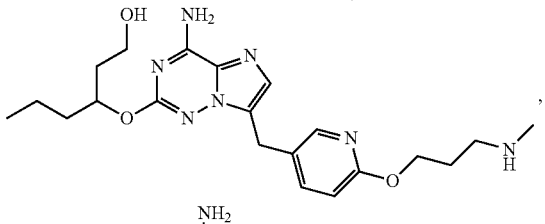
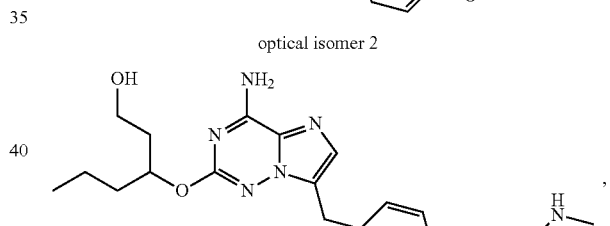
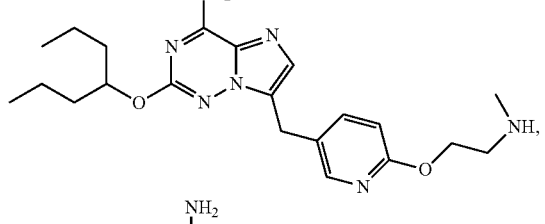
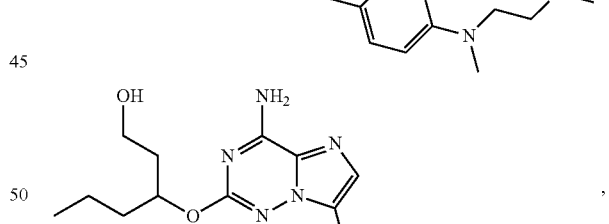
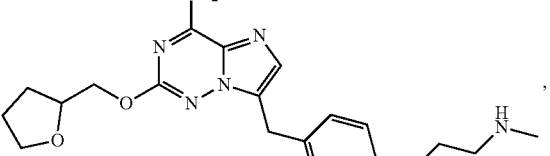
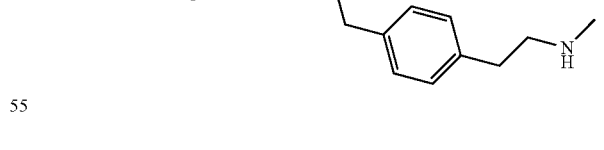
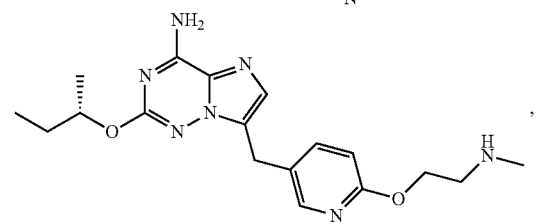
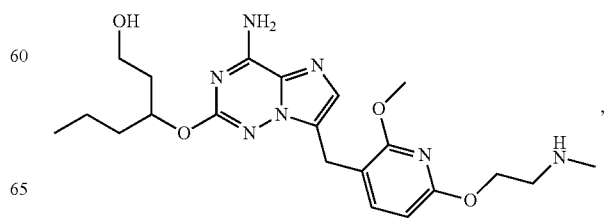

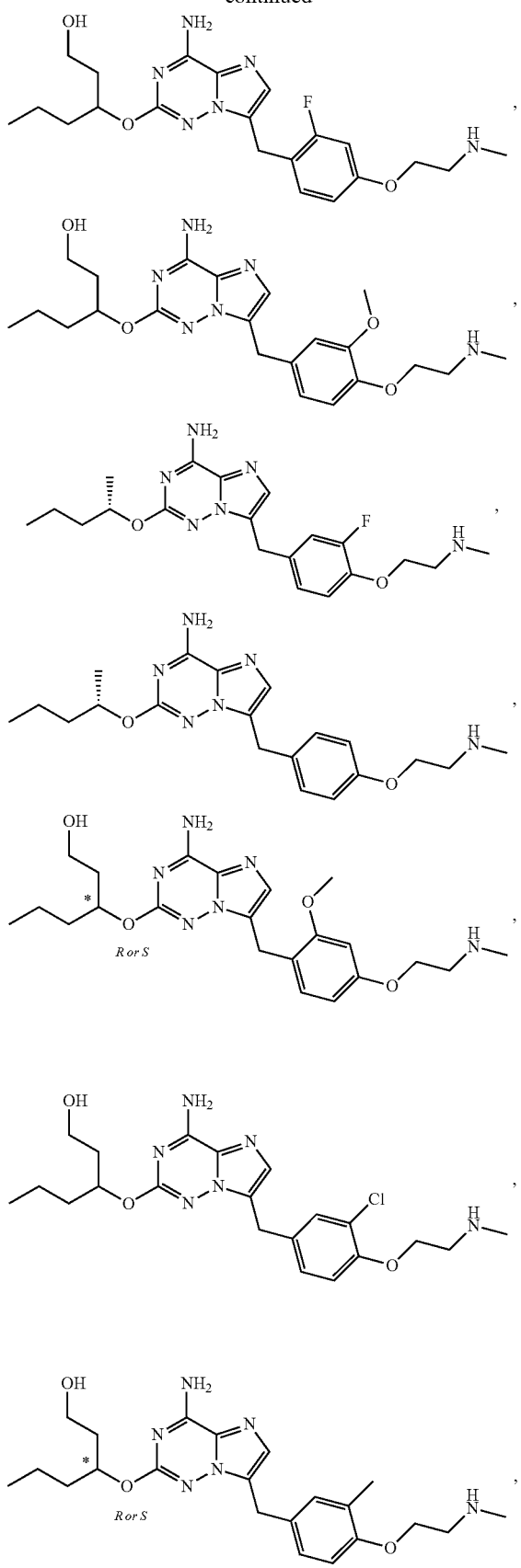
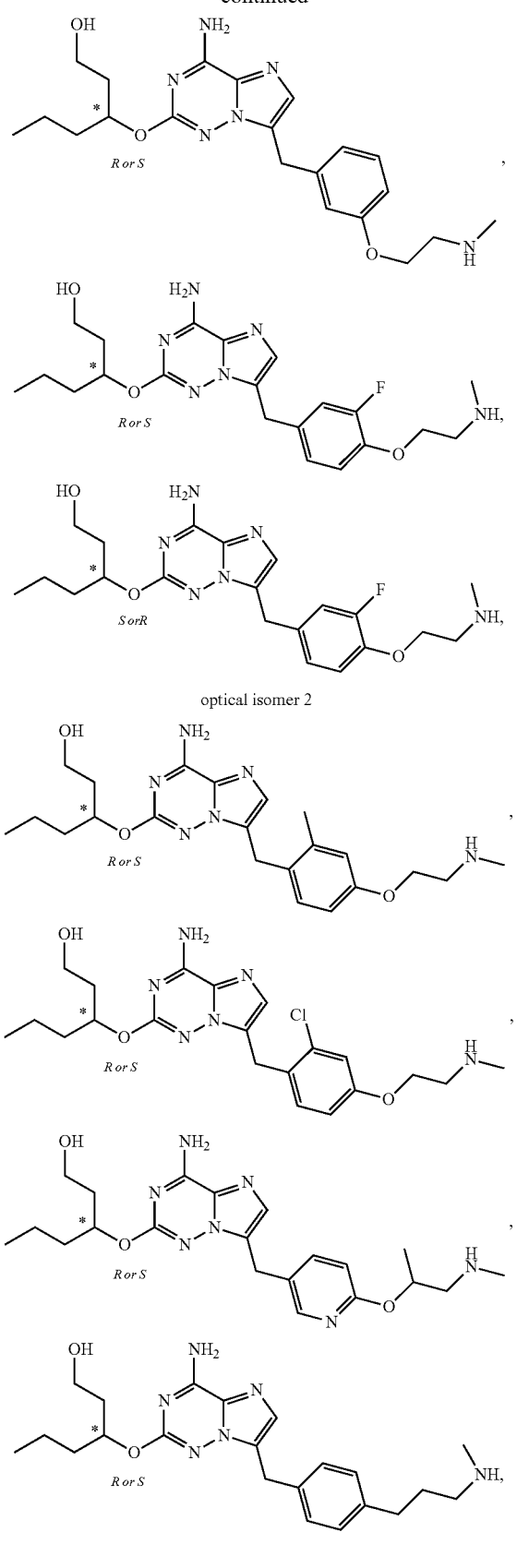

-continued
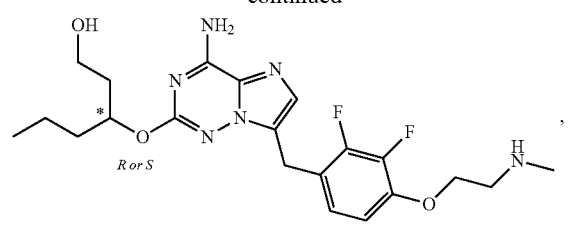
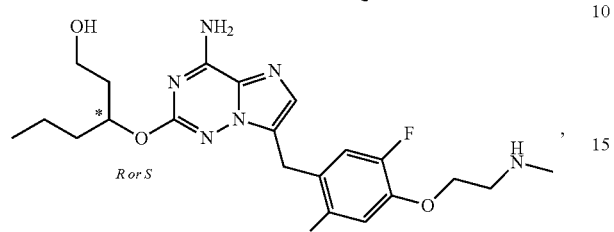
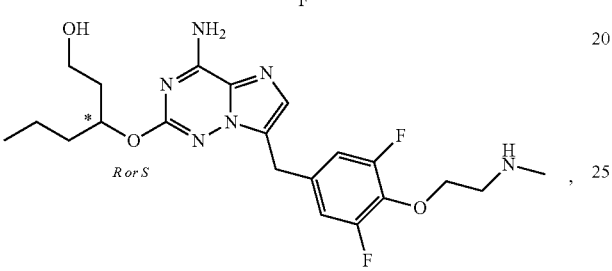
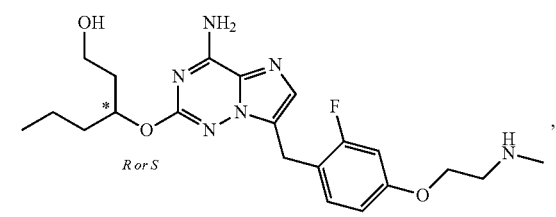
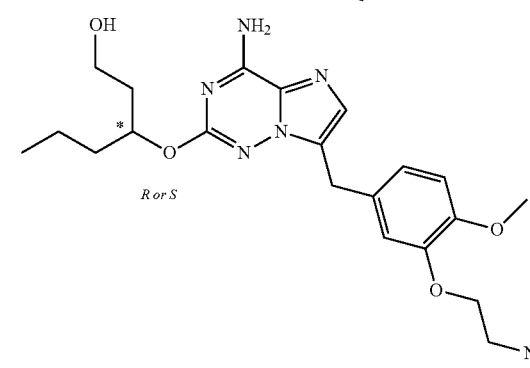
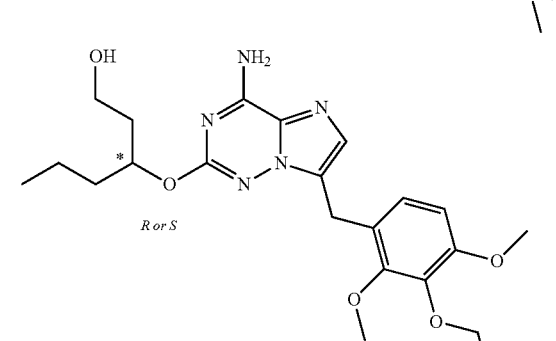
-continued
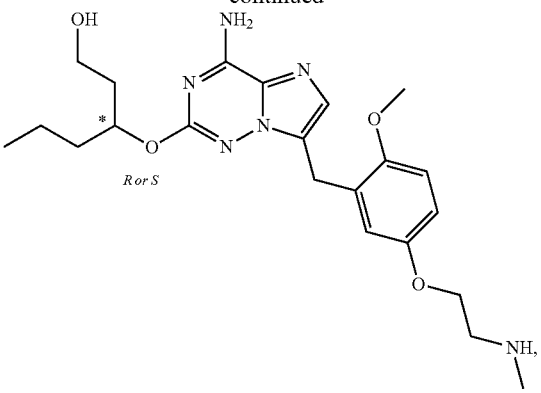
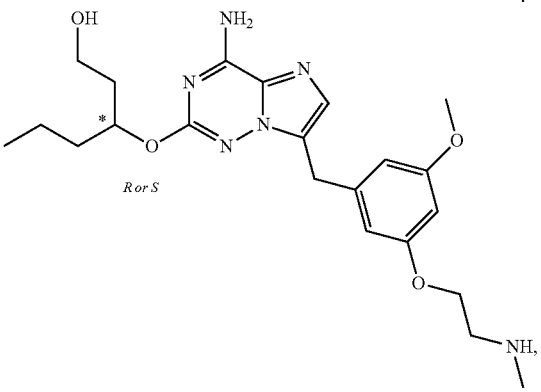
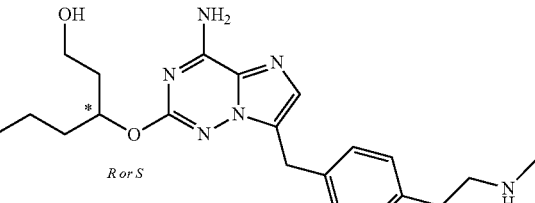
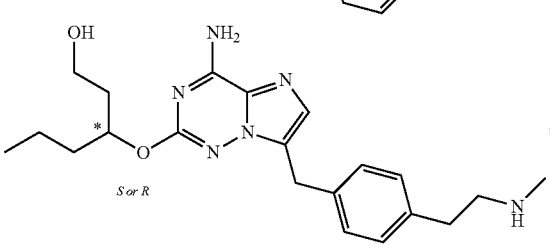
optimal isomer 2
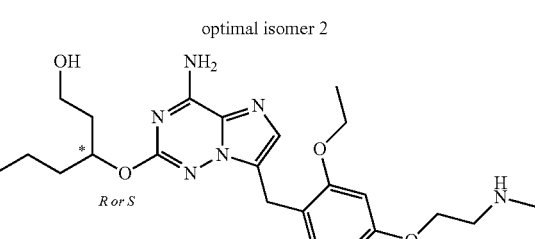
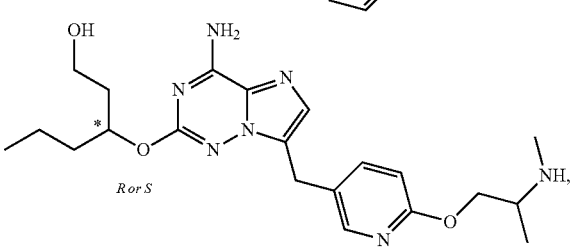

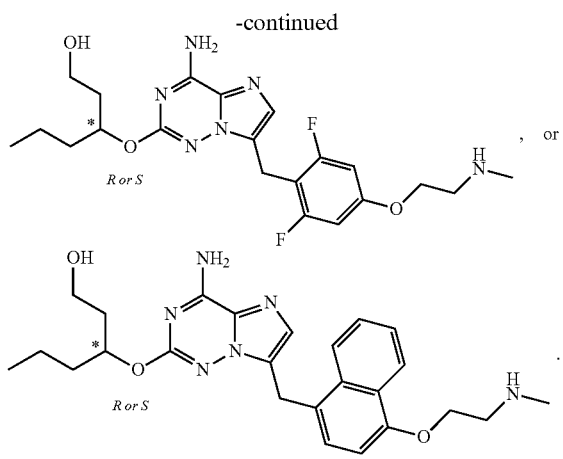

In the third aspect, disclosed herein is a pharmaceutical composition comprising the compound disclosed herein, including the compound of Formula (I) or the specific compounds exemplified herein, or a pharmaceutically acceptable salt thereof, and at least one pharmaceutically acceptable carrier or excipient.

In the fourth aspect, disclosed herein is a method of modulating TLR7, which comprise administering to an individual the compound disclosed herein, or a pharmaceutically acceptable salt thereof, including the compound of Formula (I) or the specific compounds exemplified herein.

In the fifth aspect, disclosed herein is a method of treating a disease or disorder in a patient comprising administering to the patient a therapeutically effective amount of the compound disclosed herein, or a pharmaceutically acceptable salt thereof as a TLR7 agonist, wherein the compound disclosed herein includes the compound of Formula (I) or the specific compounds exemplified herein. In some embodiments, the disease or disorder is associated with modulation of TLR, e.g., TLR-7, for example agonizing TLR-7. In some embodiments, the disease or disorder includes a viral infection caused by a virus selected from the group consisting of dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Zika virus and Hepatitis C. In some embodiments, the disease or disorder includes melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, HBV, HCV, HPV, RSV, SARS, HIV or influenza. Preferably, the disease or disorder is cancer.

DETAILED DESCRIPTION OF THE INVENTION

The following terms have the indicated meanings throughout the specification:

As used herein, including the appended claims, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" herein refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., C1-6 alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The terms "alkoxy" or "alkyloxy" refers to an alkyl group, as previously defined, attached to the parent molecular moiety through an oxygen atom.

The term "amino" refers to —NH$_2$. The term "alkylamino" refers to —NH(alkyl). The term "dialkylamino" refers to —N(alkyl)$_2$. The term "halogen" herein refers to fluoro (F), chloro (Cl), bromo (Br) and iodo (I).

The term "haloalkyl" herein refers to an alkyl group in which one or more hydrogen is/are replaced by one or more halogen atoms such as fluoro, chloro, bromo, and iodo. Examples of the haloalkyl include haloC$_{1-8}$alkyl, haloC$_{1-6}$alkyl or halo C$_{1-4}$alkyl, but not limited to —CF$_3$, —CH$_2$Cl, —CH$_2$CF$_3$, —CCl$_2$, CF$_3$, and the like.

The term "alkenyl" herein refers to a hydrocarbon group selected from linear and branched hydrocarbon groups comprising at least one C=C double bond and from 2 to 18, such as from 2 to 8, further such as from 2 to 6, carbon atoms. Examples of the alkenyl group, e.g., C2-6 alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., C2-6 alkynyl, include, but not limited to ethynyl, 1-propynyl, 2-propynyl (propargyl), 1-butynyl, 2-butynyl, and 3-butynyl groups.

The term "alkyloxy" or "alkoxy" herein refers to an alkyl group as defined above attached to the parent molecular moiety through an oxygen atom. Examples of an alkyloxy, e.g., C1-6alkyloxy or C1-4 alkyloxy includes, but not limited to, methoxy, ethoxy, isopropoxy, propoxy, n-butoxy, tert-butoxy, pentoxy and hexoxy and the like.

The term "alkoxy-alkyl-" refers to an alkyl group as defined above further substituted with an alkoxy as defined above. Examples of an alkoxy-alkyl-, e.g., C1-8alkoxy-C1-8alkyl- or C1-6alkoxy-C1-6alkyl- includes, but not limited to, methoxymethyl, ethoxymethyl, ethoxyethyl, isopropoxymethyl, or propoxymethyl and the like.

The term "cycloalkyl" refers to a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, 1-cyclopent-1-enyl, 1-cyclopent-2- enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. In particular, Examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embedment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "cycloalkenyl" refers to non-aromatic cyclic alkyl groups of from 3 to 10 carbon atoms having single or multiple rings and having at least one double bond and preferably from 1 to 2 double bonds. In one embodiment, the cycloalkenyl is cyclopentenyl or cyclohexenyl, preferably cyclohexenyl.

The term "cycloalkynyl" refers to non-aromatic cycloalkyl groups of from 5 to 10 carbon atoms having single or multiple rings and having at least one triple bond.

The term "deuterated" is used herein to modify a chemical structure or an organic group or radical, wherein one or more carbon-bound hydrogen(s) are replaced by one or more deuterium(s), e.g., "deuterated-alkyl", "deuterated-cycloalkyl", "deuterated-heterocycloalkyl", "deuterated-aryl", "deuterated-morpholinyl", and the like. For example, the term "deuterated-alkyl" defined above refers to an alkyl group as defined herein, wherein at least one hydrogen atom bound to carbon is replaced by a deuterium. In a deuterated alkyl group, at least one carbon atom is bound to a deuterium; and it is possible for a carbon atom to be bound to more than one deuterium; it is also possible that more than one carbon atom in the alkyl group is bound to a deuterium.

The term "aryl" used alone or in combination with other terms refers to a group selected from:
- 5- and 6-membered carbocyclic aromatic rings, e.g., phenyl;
- bicyclic ring systems such as 7 to 12 membered bicyclic ring systems, wherein at least one ring is carbocyclic and aromatic, e.g., naphthyl and indanyl; and,
- tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., C5-10 aryl). Examples of a monocyclic or bicyclic aromatic hydrocarbon ring includes, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "heteroaryl" herein refers to a group selected from:
- 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;
- 7- to 12-membered bicyclic rings comprising at least one heteroatom, for example, from 1 to 4, or, in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in the aromatic ring; and
- 11- to 14-membered tricyclic rings comprising at least one heteroatom, for example, from 1 to 4, or in some embodiments, from 1 to 3, or, in other embodiments, 1 or 2, heteroatoms, selected from nitrogen, oxygen or optionally oxidized sulfur as ring member(s), with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

The term "optionally oxidized sulfur" used herein refer to S, SO or $SO_2$.

The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is a 8- to 10-membered heteroaryl ring, which is bicyclic and which has 1 or 2 heteroatom ring members independently selected from nitrogen, sulfur and oxygen.

Examples of the heteroaryl group or the monocyclic or bicyclic aromatic heterocyclic ring include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (such as 1,2,3-thiadiazolyl, 1,2,4-thiadiazolyl, or 1,3,4-thiadiazolyl), tetrazolyl, thienyl (such as thien-2-yl, thien-3-yl), triazinyl, benzothienyl, furyl or furanyl, benzofuryl, benzoimidazolyl, indolyl, isoindolyl, indolinyl, oxadiazolyl (such as 1,2,3-oxadiazolyl, 1,2,4-oxadiazolyl, or 1,3,4-oxadiazolyl), phthalazinyl, pyrazinyl, pyridazinyl, pyrrolyl, triazolyl (such as 1,2,3-triazolyl, 1,2,4-triazolyl, or 1,3,4-triazolyl), quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl (such as furazan-2-yl, furazan-3-yl), benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "monocyclic heterocyclyl" refers to monocyclic groups in which at least one ring member is a heteroatom selected from nitrogen, oxygen or optionally oxidized sulfur. A heterocycle may be saturated or partially saturated.

Exemplary monocyclic 4 to 9-membered heterocyclyl groups include, but not limited to, (as numbered from the linkage position assigned priority 1) pyrrolidin-1-yl, pyrrolidin-2-yl, pyrrolidin-3-yl, imidazolidin-2-yl, imidazolidin-4-yl, pyrazolidin-2-yl, pyrazolidin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, azocan-1-yl, azocan-2-yl, azocan-3-yl, azocan-4-yl, azocan-5-yl, thiiranyl, azetidin-1-yl, azetidin-2-yl, azetidin-3-yl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepan-1-yl, azepan-2-yl, azepan-3-yl, azepan-4-yl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, or 1,1-dioxo-thiomorpholinyl.

The term "spiro heterocyclyl" refers to a 5 to 20-membered polycyclic heterocyclyl with rings connected through one common carbon atom (called a spiro atom), comprising one or more heteroatoms selected from nitrogen, oxygen or optionally oxidized sulfur as ring members, with the remaining ring members being carbon. One or more rings of a spiro heterocyclyl group may contain one or more double bonds, but none of the rings has a completely conjugated pi-electron system. Preferably a spiro heterocyclyl is 6 to 14-membered, and more preferably 7 to 12-membered. According to the number of common spiro atoms, a spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl.

The term "fused heterocyclic group" refers to a 5 to 20-membered polycyclic heterocyclyl group, wherein each ring in the system shares an adjacent pair of atoms (carbon and carbon atoms or carbon and nitrogen atoms) with another ring, comprising one or more heteroatoms selected from nitrogen, oxygen or optionally oxidized sulfur as ring members, with the remaining ring members being carbon. One or more rings of a fused heterocyclic group may contain one or more double bonds, but none of the rings has a completely conjugated pi-electron system. Preferably, a fused heterocyclyl is 6 to 14-membered, and more preferably 7 to 10-membered. According to the number of membered rings, a fused heterocyclyl is divided into bicyclic, tricyclic, tetracyclic, or polycyclic fused heterocyclyl, preferably refers to bicyclic or tricyclic fused heterocyclyl, and more preferably 5-membered/5-membered, or 5-membered/6-membered bicyclic fused heterocyclyl. Representative examples of fused heterocycles include, but not limited to, the following groups octahydrocyclopenta[c]pyrrole (e.g., octahydrocyclopenta[c]pyrrol-2-yl), octahydropyrrolo[3,4-c]pyrrolyl, octahydroisoindolyl, isoindolinyl (e.g., isoindoline-2-yl), octahydro-benzo[b][1,4]dioxin.

The term "bridged heterocyclyl" refers to a 5 to 14-membered polycyclic heterocyclic alkyl group, wherein every two rings in the system share two disconnected atoms, comprising one or more heteroatoms selected from nitrogen, oxygen or optionally oxidized sulfur as ring members, with the remaining ring members being carbon. One or more rings of a bridged heterocyclyl group may contain one or more double bonds, but none of the rings has a completely conjugated pi-electron system. Preferably, a bridged heterocyclyl is 6 to 14-membered, and more preferably 7 to 10-membered. According to the number of membered rings, a bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyls include, but not limited to, the following groups: 2-azabicyclo[2.2.1]heptyl, azabicyclo[3.1.0]hexyl, 2-azabicyclo[2.2.2]octyl and 2-azabicyclo[3.3.2]decyl.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the carbon, while trans would mean that they were on opposing sides.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. Stereochemistry of Organic Compounds. New York: John Wiley & Sons, Inc., 1994; Lochmuller, C. H., et al. "Chromatographic resolution of enantiomers: Selective review." J. Chromatogr., 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. Drug Stereochemistry: Analytical Methods and Pharmacology. New York: Marcel Dekker, Inc., 1993.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" include salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "effective amount" or "therapeutically effective amount" refers to an amount of the active ingredient, such as compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject.

In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid Formulation such as tablets, powder, granule, capsules and the like, a liquid Formulation such as water or oil suspension or other liquid Formulation such as syrup, solution, suspension or the like; for parenteral administration, the pharmaceutical composition may be solution, water solution, oil suspension concentrate, lyophilized powder or the like. Preferably, the Formulation of the pharmaceutical composition is selected from tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All Formulations of the pharmaceutical composition disclosed herein can be produced by the conventional methods in the pharmaceutical field. For example, the active ingredient can be mixed with one or more excipients, then to make the desired Formulation. The "pharmaceutically acceptable excipient" refers to conventional pharmaceutical carriers suitable for the desired pharmaceutical Formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "Cn-m" indicates a range which includes the endpoints, wherein n and m are integers and indicate the number of carbons. Examples include C1-8, C1-6, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from room temperature to the solvent's boiling temperature. A given reaction can be carried out in one solvent or mixture of solvents.

The selection of appropriate protecting group, can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ration used.

The compounds disclosed herein can be prepared by following Scheme I.

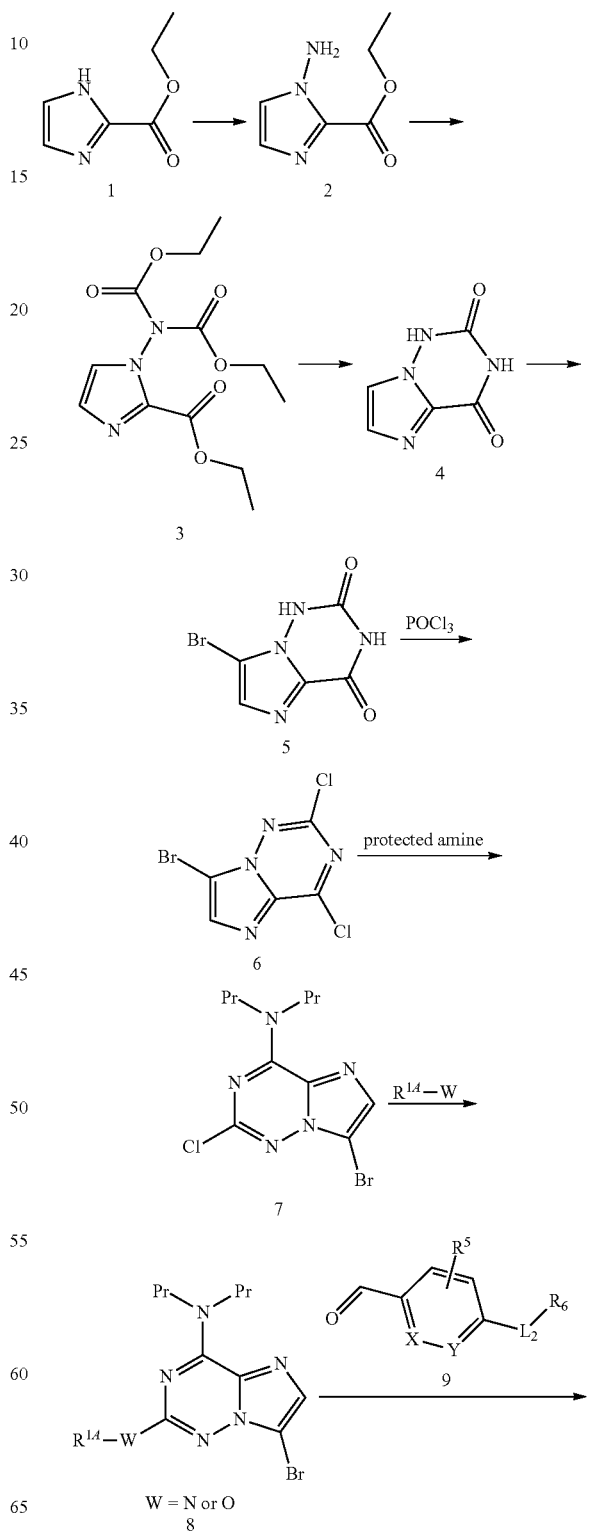

-continued

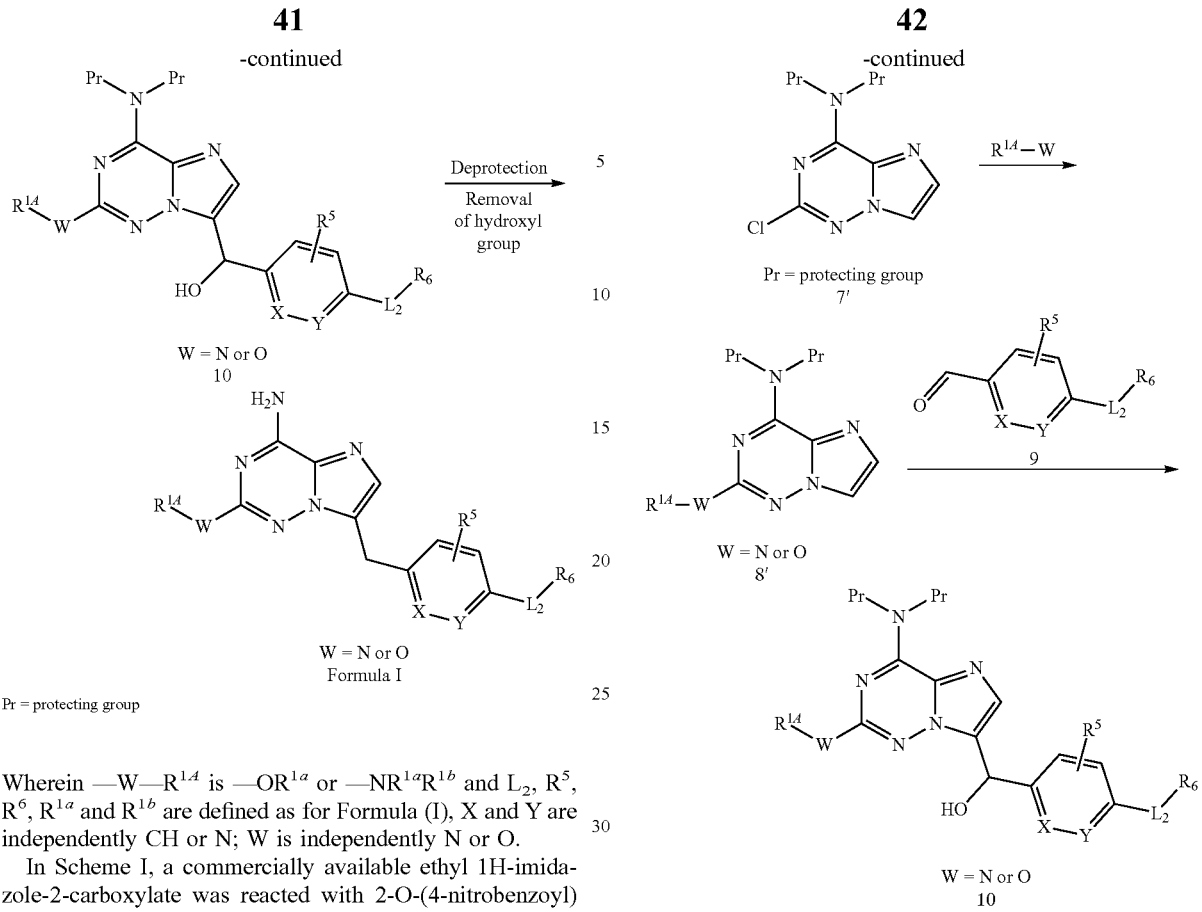

W = N or O
10

Formula I

Pr = protecting group

Wherein —W—R$^{1A}$ is —OR$^{1a}$ or —NR$^{1a}$R$^{1b}$ and L$_2$, R$^5$, R$^6$, R$^{1a}$ and R$^{1b}$ are defined as for Formula (I), X and Y are independently CH or N; W is independently N or O.

In Scheme I, a commercially available ethyl 1H-imidazole-2-carboxylate was reacted with 2-O-(4-nitrobenzoyl) hydroxylamine to form compound 2, which was reacted with ethyl carbonochloridate then the ring was closed in the presence of ammonium hydroxide to give imidazo[2,1-f][1,2,4]triazine-2,4(1H,3H)-dione. Intermediate 5 was obtained after introduction one Br atom using bromination reagent and then the dione was chloridized to form Intermediate 6. One chlorine atom was replaced by protected amine to obtain Intermediate 7, which was reacted with R$^{1A}$—W to give the key Intermediate 8, which subsequently was reacted with different aldehydes under basic condition to form Intermediate 10. The protected groups on the amine and the hydroxyl group were removed to give Formula I.

The Intermediate 10 also can be prepared by following Scheme II.

Scheme II

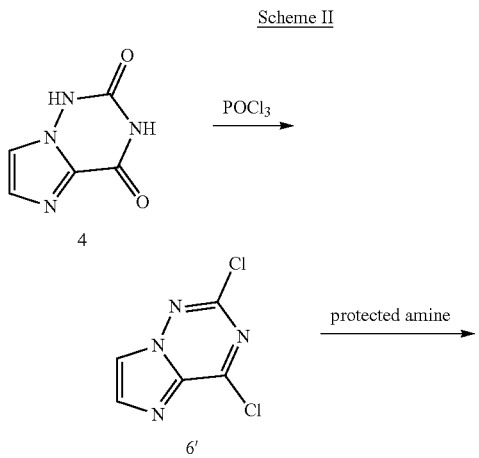

In Scheme II, Compound 4 was chloridized to form Intermediate 6'. One chlorine atom was replaced by protected amine to obtain Intermediate 7', which was reacted with R$^{1A}$—W give the key Intermediate 8', which subsequently was reacted with different aldehydes under basic condition to form Intermediate 10.

EXAMPLES

The examples below are intended to be purely exemplary and should not be considered to be limiting in any way. Unless otherwise specified, the experimental methods in the Examples described below are conventional methods. Unless otherwise specified, the reagents and materials are all commercially available. All solvents and chemicals employed are of analytical grade or chemical purity. Solvents are all redistilled before use. Anhydrous solvents are all prepared according to standard methods or reference methods. Silica gel (100-200 meshes) for column chromatography and silica gel (GF254) for thin-layer chromatography (TLC) are commercially available from Tsingdao Haiyang Chemical Co., Ltd. or Yantai Chemical Co., Ltd. of China; all are eluted with petroleum ether (60-90° C.)/ethyl acetate (v/v), and visualized by iodine or the solution of molybdphosphoric acid in ethanol unless otherwise specified. All extraction solvents, unless otherwise specified, are dried over anhydrous Na$_2$SO$_4$. $^1$H NMR spectra are recorded on Bruck-400 nuclear magnetic resonance spectrometer with TMS (tetramethylsilane) as the internal standard. LC/MS data are recorded by using Agilent1100 High Performance Liquid Chromatography-Ion Trap Mass Spectrometer (LC-MSD Trap) equipped with a diode array detector (DAD) detected at 214 nm and 254 nm, and an ion trap (ESI source). All compound names except the reagents were generated by ChemDraw®.

In the following examples, the following abbreviations are used:
AcOH Acetic acid
Aq. Aqueous
BINAP 2,2'-bis(diphenylphosphino)-1,1'-binaphthalene
Brine Saturated aqueous sodium chloride solution
Bn Benzyl
BnBr Benzyl Bromide
BPO Benzoyl peroxide
BSA N,O-Bis(trimethylsilyl)acetamide
$CH_2Cl_2$ or DCM Dichloromethane
DIAD Diisopropyl azodicarboxylate
DMF N,N-Dimethylformamide
Dppf 1,1'-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc or EA Ethyl acetate
EtOH Ethanol
$Et_2O$ or ether Diethyl ether
g Grams
h or hr Hour
HATU O-(7-Azabenzotriazol-1-yl)-N,N,N',N'-tetramethyluronium hexafluorophosphate
Hex Hexane
HCl Hydrochloric acid
HMDS Hexamethyldisilazane
HPLC High-performance liquid chromatography
IBX 2-Iodoxybenzoic acid
IPA Isopropyl alcohol
i-PrOH Isopropyl alcohol
LCMS Liquid chromatography-mass spectrometry
mg Milligrams
mL Milliliters
mmol Millimole
MeCN Acetonitrile
MeOH Methanol
Min Minutes
ms or MS Mass spectrum
MTBE methyl tert-butyl ether
$Na_2SO_4$ Sodium sulfate
NBS N-Bromosuccinimide
NMP N-Methyl Pyrrolidone
PE petroleum ether
PMB (4-methoxyphenyl)methanamine
prep Preparative
Rt or rt Room temperature
sat. Saturated
TBAF Tetra-butyl ammonium fluoride
TBSCl tert-Butyldimethylsilyl chloride
t-BuOK Potassium tert-butoxide
TFA Trifluoroacetic acid
THF Tetrahydrofuran
TLC thin layer chromatography
μL Microliters Synthesis of Intermediate-I 7-bromo-2-butoxy-N,N-bis(4-methoxybenzyl)imidazo[2,1-f][1,2,4]triazin-4-amine Step A: ethyl 1-amino-1H-imidazole-2-carboxylate hydrochloride To a stirred solution of ethyl 1H-imidazole-2-carboxylate (56 g, 0.4 mol) in NMP (1.2 L), t-BuOK (1M in THF, 440 ml, 0.44 mol) was added at 20~30° C. The mixture was stirred for 0.5 h. A solution of O-(4-nitrobenzoyl)hydroxylamine (80.08 g, 0.44 mol) in NMP (0.4 L) was added dropwise below 30° C. The solution was stirred at rt for 2 h. The solution was diluted with MTBE (500 ml). HCl (4M in EA, 100 ml) was added to quench the reaction. Diatomite (20 g) was added to the above mixture and then stirred for 0.5 h. The mixture was filtered. The filtrate was diluted with MTBE (2 L) and added HCl (4M in EA, 200 ml) dropwise. The suspension was stirred for 0.5 h and filtered. The filtration cake was rinsed with MTBE and dried in oven to afford the product (70 g, 91%). MS: M/e 156 (M+1)$^+$.

Step B: Mixture of ethyl 1-((ethoxycarbonyl)amino)-1H-imidazole-2-carboxylate and ethyl 1-(di(ethoxycarbonyl)amino)-1H-imidazole-2-carboxylate (1:1)

To a stirred solution of ethyl 1-amino-1H-imidazole-2-carboxylate hydrochloride (80 g, 0.42 mol) in THF (900 ml) and $H_2O$ (900 ml), $NaHCO_3$ (178.9 g, 2.1 mol) was added in several portions. Ethyl chloroformate (98.55 g, 0.9 mol) was added dropwise below 30° C. The mixture was stirred at rt for 4 h. The mixture was diluted with EA (1 L) and then separated. The aqueous layer was extracted with EA (800 ml). The collected organic layer was washed with brine, dried over $Na_2SO_4$, filtered and concentrated to afford the crude product (113 g) as a yellow oil, which was used directly for the next step without further purification. MS: M/e 228 (M+1)$^+$ & M/e 300 (M+1)$^+$.

Step C: imidazo[2,1-f][1,2,4]triazine-2,4(1H,3H)-dione

Into a sealed tube, a mixture of ethyl 1-((ethoxycarbonyl)amino)-1H-imidazole-2-carboxylate and ethyl 1-(di(ethoxycarbonyl)amino)-1H-imidazole-2-carboxylate (110 g) in ammonium hydroxide (400 ml, 3.6 V) and IPA (200 ml, 1.8 V) was charged. The mixture was stirred at 120° C. overnight. After cooling, the mixture was filtered. The filtration cake was rinsed with MeOH. The filtrate was concentrated under reduced pressure. The resulting residue was slurried in MeOH, filtered and rinsed with MeOH. The resulting filtration cake and the former filtration cake were mixed and dried in oven to afford the product (56 g) as a white solid. MS: M/e 153 (M+1)$^+$.

Step D: 7-bromoimidazo[2,1-f][1,2,4]triazine-2,4(1H,3H)-dione

To a solution of imidazo[2,1-f][1,2,4]triazine-2,4(1H,3H)-dione (30 g, 0.20 mol) in $H_2O$ (1.2 L), NBS (24.6 g, 0.14 mol) was added in several portions below 25° C. The mixture was stirred at rt for 1 h. The mixture was filtered. The filtrate was concentrated to remove solvent. The resulting residue and the former filtration cake was mixed and slurried in MeOH (20 V) and then MeOH:$H_2O$ (1:1, 20 V) to afford the product (30.4 g, 94%) as a white solid. MS: M/e 231 (M+1)$^+$.

Step E: 7-bromo-2,4-dichloroimidazo[2,1-f][1,2,4]triazine

Into a 350 ml sealed tube, 7-bromoimidazo[2,1-f][1,2,4]triazine-2,4(1H,3H)-dione (10 g, 43 mmol), triethylamine hydrochloride (12 g, 88 mmol) and $POCl_3$ (100 ml) were charged. The mixture was stirred at 120° C. overnight. The mixture was concentrated to remove POCl$_3$. The residue was diluted with EA (200 ml) and sat. NaHCO$_3$ (aq.) was added dropwise below 20° C. until pH value is higher than 7. The solution was separated. The organic layer was washed with H$_2$O, dried over Na$_2$SO$_4$, filtered and concentrated. The resulting residue was purified by column chromatography with 0-20% EA in PE to afford the product (8.5 g, 73%) as a white solid. MS: M/e 267 (M+1)$^+$.

Step F: 7-bromo-2-chloro-N,N-bis(4-methoxybenzyl)imidazo[2,1-f][1,2,4]triazin-4-amine To a stirred solution of 7-bromo-2,4-dichloroimidazo[2,1-f][1,2,4]triazine (30 g, 0.11 mol) in THF (500 ml), TEA (22.6 g, 0.22 mol) was added dropwise. The mixture was stirred at rt for 10 min. A solution of bis(4-methoxybenzyl)amine (31.6 g, 0.12 mol) in THF (80 ml) was added dropwise to the above solution. The mixture was stirred at rt for 2 h. The solution was quenched with H$_2$O (300 ml) and then extracted with EA (200 ml×2). The organic layer was washed with brine, dried over Na$_2$SO$_4$, filtered and concentrated. The resulting residue was slurried in PE (300 ml) and filtered to afford the product (41.4 g, 76%) as a white solid. MS: M/e 488 (M+1)$^+$.

Step G: 7-bromo-2-butoxy-N,N-bis(4-methoxybenzyl)imidazo[2,1-f][1,2,4]triazin-4-amine A mixture of 7-bromo-2-chloro-N,N-bis(4-methoxybenzyl)imidazo[2,1-f][1,2,4]triazin-4-amine (35 g, 71.6 mmol) and n-BuONa/n-BuOH (20%, 200 ml) was stirred at 80° C. under N$_2$ for 1 h. The solution was quenched with H$_2$O (200 ml). The aqueous solution was extracted with EA (150 ml×2). The collected organic layers were washed with brine, dried over Na$_2$SO$_4$, filtered and concentrated. The resulting residue was purified by column chromatography with 0-20% EA in PE to afford the product (33 g, 88%) as a colorless oil, which will be solidified after several hours. MS: M/e 526 (M+1)$^+$.

Compound A1: 2-butoxy-7-(4-(pyrrolidin-1-ylmethyl)benzyl)imidazo[2,1-f][1,2,4]triazin-4-amine Step A: 7-bromo-2-chloroimidazo[2,1-f][1,2,4]triazin-4-amine The reaction mixture of 7-bromo-2,4-dichloroimidazo[2,1-f][1,2,4]triazine (2.37 g, 8.84 mmol) and ammonium hydroxide (30 mL) was stirred at 80° C. overnight. The mixture was cooled to room temperature and the precipitated was filtered to give the crude product (1.7 g, 77%). MS: M/e 248 (M+1)$^+$.

Step B: 7-bromo-2-butoxyimidazo[2,1-f][1,2,4]triazin-4-amine

A mixture of the product of the step A (1.7 g, 6.84 mmol) and sodium butanolate (50 mL, 1M in 1-butanol) was stirred at 70° C. overnight. The mixture was evaporated and the residue was diluted with methanol. The precipitate was filtered to give the crude product (1 g, 51%). $^1$H NMR (400 MHz, DMSO-d$_6$) δ 8.31 (s, 1H), 8.24 (s, 1H), 7.60 (s, 1H), 4.24 (t, J=6.5 Hz, 2H), 1.81-1.62 (m, 2H), 1.53-1.34 (m, 2H), 0.94 (t, J=7.4 Hz, 3H) ppm. MS: M/e 286 (M+1)$^+$.

Step C: tert-butyl(7-bromo-2-butoxyimidazo[2,1-f][1,2,4]triazin-4-yl)(tert-butoxycarbonyl)carbamate To a solution of the product of the step B (525 mg, 1.84 mmol) and DMAP (224 mg, 1.84 mmol) in dichloromethane (20 mL) was added di-tert-butyl dicarbonate (1.2 g, 5.51 mmol). The resulting mixture was stirred at room temperature overnight. The mixture was diluted with dichloromethane (20 mL), washed with water and brine, dried over Na$_2$SO$_4$, filtered and evaporated to give the crude product (650 mg, 72%) which was used next step without further purification. MS: M/e 486 (M+1)$^+$.

Step D: tert-butyl (2-butoxy-7-(hydroxy(4-(pyrrolidin-1-ylmethyl)phenyl)methyl)imidazo[2,1-f][1,2,4]triazin-4-yl)(tert-butoxycarbonyl)carbamate To the solution of the product of the step C (650 mg, 1.33 mmol) in THF (30 mL) under nitrogen n-BuLi (0.8 mL, 2.00 mmol, 2.5M in hexane) was added at −78° C. and stirred for 0.5 hrs. After adding 4-(pyrrolidin-1-ylmethyl)benzaldehyde (378 mg, 2.00 mmol), the mixture was warmed to room temperature overnight. The reaction was quenched with an aqueous saturated solution of NH$_4$Cl and the resulting mixture was extracted with ethyl acetate (30 mL×3). The combined organic layers were dried over Na$_2$SO$_4$, filtered and evaporated in vacuo. The residue was purified by column chromatograph (eluent: MeOH/DCM=0.1% to 5%) to give the product (200 mg, 30%). MS: M/e 597 (M+1)$^+$.

Step E: 2-butoxy-7-(4-(pyrrolidin-1-ylmethyl)benzyl)imidazo[2,1-f][1,2,4]triazin-4-amine (Compound A1)

The reaction mixture of the product of the step D (140 mg, 0.28 mmol), trifluoroacetic acid (2 mL), triethylsilane (2 mL) and dichloromethane (1 mL) was stirred at 40° C. overnight. After complete, the mixture was evaporated and basified. The residue was purified by combi-flash (eluent: MeOH/DCM=0% to 10%) to give the product (50 mg, 47%). $^1$H NMR (400 MHz, DMSO-d$_6$) δ 8.15 (s, 1H), 8.04 (s, 1H), 7.30 (s, 1H), 7.29-7.18 (m, 4H), 4.19 (t, J=6.6 Hz, 2H), 4.11 (s, 2H), 3.59 (s, 2H), 2.49-2.33 (m, 4H), 1.70-1.61 (m, 6H), 1.50-1.32 (m, 2H), 0.92 (t, J=7.4 Hz, 3H) ppm. MS: M/e 381 (M+1)$^+$.

Compound A2: 2-butoxy-7-(4-(3-(dimethylamino)propoxy)benzyl)imidazo[2,1-f][1,2,4]triazin-4-amine Step A: 4-(3-(dimethylamino)propoxy)benzaldehyde DIAD (2.5 g, 12.3 mmol) was added dropwise to a solution of 4-hydroxy benzaldehyde (1 g, 8.2 mmol), 3-(dimethylamino)propan-1-ol (1.2 g, 12.3 mmol) and triphenylphosphane (3.2 g, 12.3 mmol) in THF (20 mL) at 0° C. under N$_2$ atmosphere. The mixture was warmed to rt and stirred for 6 hrs. The reaction was quenched with water (20 mL), extracted with ethyl acetate (20 mL) and washed with brine (10 mL). The organic layers were dried, concentrated and purified by CombiFlash to get the product (1.1 g, 65%) as a colorless oil. $^1$H NMR (400 MHz, CDCl$_3$) δ 9.88 (s, 1H), 7.82 (d, J=8.0 Hz, 2H), 7.00 (d, J=8.0 Hz, 2H), 4.11 (t, J=8.0 Hz, 2H), 2.46 (t, J=8.0 Hz, 2H), 2.26 (s, 6H), 2.02-1.96 (m, 2H) ppm. MS: M/e 208 (M+1)$^+$.

Step B: tert-butyl (2-butoxy-7-((4-(3-(dimethylamino)propoxy)phenyl)(hydroxy)methyl)imidazo[2,1-f][1,2,4]triazin-4-yl)(tert-butoxycarbonyl)carbamate A cooled solution of bromide (100 mg, 0.2 mmol) in THF (3 mL) at −78° C. was purged with N$_2$, and then n-BuLi (1.6

M, 0.3 mL) was added dropwise. After stirred at −78° C. for 30 mins, 4-(3-(dimethylamino)propoxy)benzaldehyde (83 mg, 0.4 mmol) in THF (1 mL) was added. The resulting mixture was stirred at this temperature for 30 mins, and then warmed to rt overnight. The solution was quenched with $NH_4Cl$ solution (5 mL), extracted with ethyl acetate (10 mL) and washed with brine (10 mL). The organic layers was dried with $Na_2SO_4$, filtered and concentrated to get the crude product, which was further purified by prep-TLC (DCM: MeOH=10:1) to get the pure product as a white solid (35 mg, 33%). MS: M/e 615 (M+1)$^+$.

Step C: 2-butoxy-7-(4-(3-(dimethylamino)propoxy) benzyl)imidazo[2,1-f][1,2,4]triazin-4-amine (Compound A2)

Triethylsilane (0.5 mL) and trifluoroacetic acid (0.5 mL) were added to a solution of the product step B (35 mg, 0.07 mmol) in DCM (2 mL). The mixture was heated at 40° C. for 1 hr and then concentrated. The residue was added with water (5 mL), extracted with ethyl acetate (5 mL), washed with $NaHCO_3$ (5 mL) and brine (5 mL). The organic layer was dried, concentrated and purified by prep-TLC (DCM: MeOH=6:1) to get the product (9 mg, 33%). $^1$H NMR (400 MHz, DMSO-d6) δ 9.75 (br.s, 1H), 8.12 (s, 1H), 8.04 (s, 1H), 7.25 (s, 1H), 7.23 (d, J=8.0 Hz, 2H), 6.86 (d, J=8.0 Hz, 2H), 4.20 (t, J=8.0 Hz, 2H), 4.07 (s, 2H), 3.99 (t, J=8.0 Hz, 2H), 3.11 (t, J=4.0 Hz, 2H), 2.74 (s, 6H), 2.10-2.03 (m, 2H), 1.71-1.64 (m, 2H), 1.45-1.36 (m, 2H), 0.93 (t, J=8.0 Hz, 3H) ppm. MS: M/e 399 (M+1)$^+$.

Compound A3: 2-butoxy-7-(4-(morpholinomethyl) benzyl)imidazo[2,1-f][1,2,4]triazin-4-amine Step A: 4-(bromomethyl)benzaldehyde To a stirred solution of 4-(hydroxymethyl)benzaldehyde (7 g, 50.7 mmol) in DCM (400 mL), NBS (17.8 g, 100 mmol) and $PPh_3$ (27.3 g, 104 mmol) were added. After the addition, the reaction mixture was stirred at rt for 4 hrs. The reaction mixture was washed by $H_2O$ (150 mL×3). The organic layers were washed with brine, dried over $Na_2SO_4$, concentrated and purified by column chromatography (petroleum ether/EtOAc=5:1) to give 4-(bromomethyl)benzaldehyde (9.5 g, 95%) as white solids. MS: M/e 199 (M+1)$^+$.

Step B: 4-(morpholinomethyl)benzaldehyde

To a stirred solution of 4-(bromomethyl)benzaldehyde (3 g, 15 mmol) in MeCN (40 mL) morpholine (1.39 g, 16 mmol) and $K_2CO_3$ (4.17 g, 30 mmol) were added. After the addition, the reaction mixture was stirred at Rt overnight. The mixture was filtered. The filtrate was poured into $H_2O$ and extracted with EtOAc (15 mL×3). The combined organic layers were washed with brine, dried over $Na_2SO_4$ and concentrated in vacuo. The crude product was purified by column chromatography (petroleum ether/EtOAc=1:1) to give 4-(morpholinomethyl)benzaldehyde (2 g, 66.7%) as a yellow oil. $^1$H NMR (400 MHz, DMSO-d6) δ 10.00 (s, 1H), 7.84 (d, J=8.2 Hz, 2H), 7.52 (d, J=8.2 Hz, 2H), 3.74-3.67 (m, 4H), 3.57 (s, 2H), 2.50-2.42 (m, 4H) ppm. MS: M/e 206 (M+1)$^+$.

Step C: (4-(bis(4-methoxybenzyl)amino)-2-butoxy-imidazo[2,1-f][1,2,4]triazin-7-yl)(4-(morpholinomethyl)phenyl)methanol To a stirred solution of 7-bromo-2-butoxy-N,N-bis(4-methoxybenzyl)imidazo[2,1-f][1,2,4]triazin-4-amine (150 mg, 0.3 mmol) in THF (10 mL), cooled to −78° C. under a nitrogen atmosphere was added n-BuLi (1.6 M in hexane, 0.75 mmol, 0.47 mL) dropwise. After stirring for 20 mins, a solution of 4-(morpholinomethyl)Benzaldehyde (114 mg, 0.45 mmol) in THF (2 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over $Na_2SO_4$, concentrated to give the title product (220 mg, 100%) which was used directly in next step without further purification. MS: M/e 653 (M+1)$^+$.

Step D: 2-butoxy-7-(4-(morpholinomethyl)benzyl) imidazo[2,1-f][1,2,4]triazin-4-amine (Compound A3)

A solution of (4-(bis(4-methoxybenzyl)amino)-2-butoxy-imidazo[2,1-f][1,2,4]triazin-7-yl)(4-(morpholinomethyl) phenyl)methanol (220 mg, 0.3 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by column chromatography (DCM/MeOH=5:1) to give the product (40 mg, 33.6%). $^1$H NMR (400 MHz, DMSO-d6) δ 8.13 (s, 1H), 8.04 (s, 1H), 7.57-7.25 (m, 5H), 4.23-4.15 (m, 2H), 3.83-3.65 (m, 2H), 3.62-3.49 (m, 4H), 2.43-2.29 (m, 4H). 1.71-1.57 (m, 2H), 1.47-1.33 (m, 2H), 0.90 (t, J=7.6 3H) ppm. MS: M/e 397 (M+1)$^+$.

Compound A4: $N^1$-(5-((4-amino-2-butoxyimidazo [2,1-f][1,2,4]triazin-7-yl)methyl)pyridin-2-yl)-$N^1$, $N^2$,$N^2$-trimethylethane-1,2-diamine Step A: 6-((2-(dimethylamino)ethyl)amino)nicotinaldehyde A mixture of 6-chloronicotinaldehyde (1 g, 7.1 mmol), $N^1$,$N^1$,$N^2$-trimethyl ethane-1,2-diamine (0.87 g, 8.5 mmol) and DIEA (1.8 g, 14.2 mmol) in DMSO (10 mL) was heated at 90° C. overnight. The solution was cooled and added with water (10 mL), extracted with ethyl acetate (10 mL) and washed with brine (10 mL). The organic layer was dried, concentrated and purified by CombiFlash (DCM: MeOH=4%) to get the product as a red oil (0.8 g, 57%). $^1$H NMR (400 MHz, CDCl$_3$) δ 9.76 (s, 1H), 8.54 (d, J=4.0 Hz, 1H), 7.90 (dd, J=8.0, 4.0 Hz, 1H), 6.55 (d, J=4.0 Hz, 1H), 3.77 (t, J=8.0 Hz, 2H), 3.17 (s, 3H), 2.53 (t, J=8.0 Hz, 2H), 2.30 (s, 6H) ppm. MS: M/e 208 (M+1)$^+$.

Step B: (4-(bis(4-methoxybenzyl)amino)-2-butoxy-imidazo[2,1-f][1,2,4]triazin-7-yl)(6-((2-(dimethyl-amino)ethyl)(methyl)amino)pyridin-3-yl)methanol To a cooled solution of 7-bromo-2-butoxy-N,N-bis(4-methoxybenzyl)imidazo[2,1-f][1,2,4]triazin-4-amine (150 mg, 0.29 mmol) in THF (8 mL) at −78° C. (purged with $N^2$), n-BuLi (1.6 M, 0.5 mL) was added dropwise. After stirred at −78° C. for 30 mins, 6-((2-(dimethylamino)ethyl)amino) nicotinaldehyde (88 mg, 0.43 mmol) in THF (2 mL) was added. The resulting mixture was stirred at this temperature for 30 mins, and then warmed to rt for 1 hour. The solution was quenched with $NH_4Cl$ solution (5 mL), extracted with ethyl acetate (10 mL) and washed with brine (10 mL). The organic layer was dried over $Na_2SO_4$, filtered and concentrated to get the crude product, which was further purified by Combiflash (DCM:MeOH=20%) to get the pure product as a white solid (130 mg, 70%). MS: M/e 655 (M+1)$^+$.

Step C: $N^1$-(5-((4-amino-2-butoxyimidazo[2,1-f][1,2,4]triazin-7-yl)methyl)pyridin-2-yl)-$N^1,N^2,N^2$-trimethylethane-1,2-diamine (Compound A4)

Triethylsilane (1 mL) and trifluoroacetic acid (1 mL) were added to a solution of (4-(bis(4-methoxybenzyl)amino)-2-butoxyimidazo[2,1-f][1,2,4]triazin-7-yl)(6-((2-(dimethylamino)ethyl)(methyl)amino)pyridin-3-yl)methanol (130 mg, 0.2 mmol) in DCM (2 mL). The mixture was heated at 80° C. overnight. The solvent was evaporated to get the residue, which was treated with NaHCO$_3$ (5 mL), extracted with ethyl acetate (5 mL), washed with brine (5 mL). The organic layers were dried, concentrated and purified by CombiFlash (DCM:MeOH=8:1) to get the product (28 mg, 35%). $^1$H NMR (400 MHz, DMSO-d6) δ 8.13-8.05 (m, 3H), 7.52 (dd, J=8.0, 4.0 Hz, 1H), 7.27 (s, 1H), 6.85 (d, J=8.0 Hz, 1H), 4.22 (t, J=8.0 Hz, 2H), 4.01 (s, 2H), 3.83 (t, J=8.0 Hz, 2H), 3.22 (s, 2H), 2.95 (s, 3H), 2.79 (s, 6H), 1.70-1.67 (m, 2H), 1.44-1.39 (m, 2H), 0.93 (t, J=8.0 Hz, 3H) ppm. MS: M/e 399 (M+1)$^+$.

Compound A5: 2-butoxy-7-(4-(piperidin-1-ylmethyl)benzyl)imidazo[2,1-f][1,2,4]triazin-4-amine Step A: 4-(piperidin-1-ylmethyl)benzaldehyde To a stirred solution of 4-(bromomethyl)benzaldehyde (3 g, 15 mmol) in MeCN (40 mL) was added piperidine (1.36 g, 16 mmol) and K$_2$CO$_3$ (4.17 g, 30 mmol). After the addition, the reaction mixture was stirred at Rt overnight. The mixture was filtered. The filtrate was poured into H$_2$O and extracted with EtOAc (15 mL×3). The combined organic layers were washed with brine, dried over Na$_2$SO$_4$ and concentrated in vacuo. The crude product was purified by column chromatography (petroleum ether/EtOAc=1:1) to give the title product (2.7 g, 88%) as a yellow oil. $^1$H NMR (400 MHz, DMSO-d6) δ 9.99 (s, 1H), 7.83 (d, J=7.9 Hz, 2H), 7.50 (d, J=7.9 Hz, 2H), 3.53 (s, 2H), 2.38 (s, 4H), 1.62-1.54 (m, 4H), 1.45 (d, J=4.9 Hz, 2H) ppm. MS: M/e 204 (M+1)$^+$.

Step B: (4-(bis(4-methoxybenzyl)amino)-2-butoxyimidazo[2,1-f][1,2,4]triazin-7-yl)(4-(piperidin-1-ylmethyl)phenyl)methanol To a stirred solution of 7-bromo-2-butoxy-N,N-bis(4-methoxybenzyl)imidazo[2,1-f][1,2,4]triazin-4-amine (150 mg, 0.3 mmol) in THF (10 mL), cooled to −78° C. and under a nitrogen atmosphere was added n-BuLi (1.6 M in hexane, 0.75 mmol, 0.47 mL) dropwise. After stirring for 20 mins, a solution of 4-(piperidin-1-ylmethyl)benzaldehyde (114 mg, 0.45 mmol) in THF (2 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over Na$_2$SO$_4$, concentrated to give the product (270 mg, 100%) which was used directly in next step without further purification. MS: M/e 651 (M+1)$^+$.

Step C: 2-butoxy-7-(4-(piperidin-1-ylmethyl)benzyl)imidazo[2,1-f][1,2,4]triazin-4-amine (Compound A5)

A solution of (4-(bis(4-methoxybenzyl)amino)-2-butoxyimidazo[2,1-f][1,2,4]triazin-7-yl)(4-(piperidin-1-ylmethyl)phenyl)methanol (270 mg, 0.3 mmol) in TFA (3 mL) and Et$_3$SiH (3 mL) was stirred at 80° C. for 2 h. The reaction mixture was concentrated in vacuo to remove TFA and Et$_3$SiH. The residue was added TFA (5 mL) and stirred at 85° C. overnight. The mixture was cooled down to rt and concentrated in vacuo. The crude product was purified by prep-HPLC to give the product (50 mg, 42%). $^1$H NMR (400 MHz, DMSO-d6) δ 8.12 (s, 1H), 8.03 (s, 1H), 7.30 (s, 1H), 7.24-7.17 (m, 4H), 4.19 (t, J=6.5 Hz, 2H), 4.11 (s, 2H), 3.35 (s, 2H), 2.31-2.21 (m, 4H), 1.70-1.61 (m, 2H), 1.45 (m, 4H), 1.42-1.31 (m, 4H), 0.91 (t, J=7.3 Hz, 3H) ppm. MS: M/e 395 (M+1)$^+$.

Compound A6: 2-butoxy-7-(4-((4-methylpiperazin-1-yl)methyl)benzyl)imidazo[2,1-f][1,2,4]triazin-4-amine Step A: 4-((4-methylpiperazin-1-yl)methyl)benzaldehyde To a stirred solution of 4-(bromomethyl)benzaldehyde (3 g, 15 mmol) in MeCN (40 mL) was added piperidine (1.6 g, 16 mmol) and K$_2$CO$_3$ (4.17 g, 30 mmol). After the addition, the reaction mixture was stirred at Rt overnight. The mixture was filtered. The filtrate was poured into H$_2$O and extracted with EtOAc (15 mL×3). The combined organic layers were washed with brine, dried over Na$_2$SO$_4$ and concentrated in vacuo. The crude product was purified by column chromatography (petroleum ether/EtOAc=1:1) to give 4-((4-methylpiperazin-1-yl)methyl)benzaldehyde (2.3 g, 71.8%) as a yellow oil. MS: M/e 219 (M+1)$^+$.

Step B: (4-(bis(4-methoxybenzyl)amino)-2-butoxyimidazo[2,1-f][1,2,4]triazin-7-yl)(4-((4-methylpiperazin-1-yl)methyl)phenyl)methanol To a stirred solution of 7-bromo-2-butoxy-N,N-bis(4-methoxybenzyl)imidazo[2,1-f][1,2,4]triazin-4-amine (150 mg, 0.3 mmol) in THF (10 mL), cooled to −78° C. and under a nitrogen atmosphere was added n-BuLi (1.6 M in hexane, 0.75 mmol, 0.47 mL) dropwise. After stirring for 20 mins, a solution of 4-((4-methylpiperazin-1-yl)methyl)benzaldehyde (122 mg, 0.45 mmol) in THF (2 mL) was added slowly. The reaction mixture was warmed up slowly to rt and stirred for 2 h. The reaction mixture was poured into saturated ammonium chloride solution and extracted by EtOAc (15 mL×3). The combined organic phase was washed with brine, dried over Na$_2$SO$_4$, concentrated to give the product (300 mg, 100%) which was used directly in next step without further purification. MS: M/e 666 (M+1)$^+$.

Step C: 2-butoxy-7-(4-((4-methylpiperazin-1-yl)methyl)benzyl)imidazo[2,1-f][1,2,4]triazin-4-amine (Compound A6)

A solution of (4-(bis(4-methoxybenzyl)amino)-2-butoxyimidazo[2,1-f][1,2,4]triazin-7-yl)(4-((4-methylpiperazin-1-yl)methyl)phenyl)methanol (300 mg, 0.3 mmol) in TFA (3 mL) and Et$_3$SiH (3 mL) was stirred at 80° C. for 2 h. The reaction mixture was concentrated in vacuo to remove TFA and Et$_3$SiH. The residue was added TFA (5 mL) and stirred at 85° C. overnight. The mixture was cooled down to rt and concentrated in vacuo. The crude product was purified by prep-HPLC to give the product (60 mg, 49.1%). $^1$H NMR (400 MHz, DMSO-d6)) δ 8.13 (s, 1H), 8.03 (s, 1H), 7.30 (s, 1H), 7.24 (d, J=7.9 Hz, 2H), 7.19 (d, J=7.9 Hz, 2H), 4.19 (t, J=6.5 Hz, 2H), 4.11 (s, 2H), 3.38 (s, 2H), 3.21-2.17 (m, 8H), 2.12 (s, 3H), 1.71-1.59 (m, 2H), 1.45-1.33 (m, 2H), 0.92 (t, J=7.4 Hz, 3H) ppm. MS: M/e 410 (M+1)⁺.

Compound A7: 2-butoxy-7-(3-(piperidin-1-ylmethyl)benzyl)imidazo[2,1-f][1,2,4]triazin-4-amine Step A: (4-(bis(4-methoxybenzyl)amino)-2-butoxyimidazo[2,1-f][1,2,4]triazin-7-yl)(3-(piperidin-1-ylmethyl)phenyl)methanol To a stirred solution of 7-bromo-2-butoxy-N,N-bis(4-methoxybenzyl)imidazo[2,1-f][1,2,4]triazin-4-amine (200 mg, 0.38 mmol) in THF (10 ml) at −78° C. under N₂ atmosphere, was added n-BuLi (1.6 M, 0.60 ml, 0.96 mmol). The solution was stirred at −78° C. for 30 min. 3-(piperidin-1-ylmethyl)benzaldehyde (116 mg, 0.57 mmol) in THF (2 ml) was added dropwise to the above solution. After addition, the solution was warmed to rt naturally and then stirred for 3 hr. After completing, the reaction mixture was quenched with H₂O (20 ml) and then extracted with DCM (20 ml×3). The organic phase was washed with H₂O (10 ml), dried and concentrated under reduced pressure to afford crude product as a yellow oil, which was used directly for the next step without further purification. MS: M/e 651 (M+1)⁻.

Step B: 2-butoxy-7-(3-(piperidin-1-ylmethyl)benzyl)imidazo[2,1-f][1,2,4]triazin-4-amine (Compound A7)

A solution of (4-(bis(4-methoxybenzyl)amino)-2-butoxyimidazo[2,1-f][1,2,4]triazin-7-yl)(3-(piperidin-1-ylmethyl)phenyl)methanol (crude) in TFA (2 ml) and triethylsilane (2 ml) was stirred at 80° C. for 15 hr. The solution was concentrated under reduced pressure to remove triethylsilane. The residue was dissolved in TFA (2 ml) and stirred at 80° C. overnight. After was completed, the reaction mixture was quenched with aq. NaHCO₃ (sat., 25 ml) and then extracted with DCM (20 ml×3). The organic phase was concentrated under reduced pressure and the resulting residue was purified by prep-TLC with DCM:MeOH (10:1) to afford the product (81.54 mg). ¹H NMR (400 MHz, DMSO-d6) δ 8.16 (s, 1H), 8.07 (s, 1H), 7.40 (d, J=8 Hz, 4H), 7.32 (s, 1H), 4.31-4.09 (m, 6H), 3.31-3.12 (m, 2H), 2.90-2.70 (m, 2H), 1.87-1.60 (m, 7H), 1.45-1.28 (m, 3H), 0.91 (t, J=8 Hz, 3H) ppm. MS: M/e 395 (M+1)⁺.

Compound A8: 2-butoxy-7-((2-isopropyl-1,2,3,4-tetrahydroisoquinolin-6-yl)methyl)imidazo[2,1-f][1,2,4]triazin-4-amine Step A: 6-bromo-2-isopropyl-1,2,3,4-tetrahydroisoquinoline To a solution of 6-bromo-1,2,3,4-tetrahydroisoquinoline (1.06 g, 5 mmol) in MeOH (3 mL) were added acetone (3 mL) and AcOH (10 drops). Then the mixture was stirred at 80° C. for 1.5 h. The mixture was cooled to room temperature, NaBH₃CN (0.93 g, 15 mmol) was added in some portions and the resulting mixture was stirred at room temperature for 3 h. The reaction was concentrated, diluted with water (30 mL), extracted with EtOAc (50 mL×2). The combined organic layers were washed with brine, dried over Na₂SO₄, filtered and concentrated. The residue was purified by combi flash to give target compound (450 mg, 36%) as oil. MS: M/e 254 (M+1)⁺.

Step B: 2-isopropyl-1,2,3,4-tetrahydroisoquinoline-6-carbaldehyde

To a solution of the product of Step A (450 mg, 1.77 mmol) in THF (5 mL) was added n-BuLi (2.2 mL, 1.6 mol/L, 3.54 mmol) dropwise maintaining the temperature between −75~−65° C. After 30 min, DMF (258 mg, 3.54 mmol) was added dropwise and the resulting mixture was stirred at −65° C. for 30 min. The reaction was quenched with saturated NH₄Cl solution, extracted with EtOAc (60 mL), washed with brine, dried over Na₂SO₄, filtered, and concentrated. The residue was purified by flash chromatography to give target compound (250 mg, 69%) as oil. ¹H NMR (400 MHz, CDCl₃) δ 9.94 (s, 1H), 7.68-7.60 (m, 2H), 7.20 (d, J=8.0 Hz, 1H), 3.90-3.78 (m, 2H), 3.11-2.95 (m, 3H), 2.90-2.80 (m, 2H), 1.18 (d, J=6.4 Hz, 6H) ppm. MS: M/e 204 (M+1)⁺.

Step C: (4-(bis(4-methoxybenzyl)amino)-2-butoxyimidazo[2,1-f][1,2,4]triazin-7-yl)(2-isopropyl-1,2,3,4-tetrahydroisoquinolin-6-yl)methanol To a solution of 7-bromo-2-butoxy-N,N-bis(4-methoxybenzyl)imidazo[2,1-f][1,2,4]triazin-4-amine (150 mg, 0.285 mmol) in THF (5 mL) was added n-BuLi (0.44 mL, 0.71 mmol) dropwise maintaining the temperature between −75~−65° C. After 30 min, a mixture of the product of Step B (87 mg, 0.423 mmol) in THF (4 mL) was added dropwise. The resulting mixture was stirred at −70° C. for 1 h and then warmed to room temperature for 1 h. The reaction was quenched with saturated NH₄Cl solution, extracted with EtOAc (80 mL), washed with brine, dried over Na₂SO₄, filtered, and concentrated. The residue was purified by column chromatography (DCM/MeOH=50/1) to give target compound (60 mg, 32%). MS: M/e 651 (M+1)⁺.

Step D: 2-butoxy-7-((2-isopropyl-1,2,3,4-tetrahydroisoquinolin-6-yl)methyl)imidazo[2,1-f][1,2,4]triazin-4-amine (Compound A8)

To a mixture of the product of Step C (60 mg, 0.092 mmol) in TFA (2 mL) was added Et₃SiH (2 mL). The reaction was heated at 80° C. for 2 h. The mixture was concentrated to dryness and the residue was treated with TFA (4 mL). The reaction was heated at 85° C. overnight. The mixture was concentrated and the residue was purified by prep-HPLC. The collected fraction was basified with NaHCO₃ solution, extracted with DCM (60 mL), washed with brine, dried over Na₂SO₄, filtered, and concentrated to give the product (20 mg, 55%). ¹H NMR (400 MHz, DMSO-d₆) δ 8.11 (s, 1H), 8.02 (s, 1H), 7.27 (s, 1H), 6.85-6.15 (m, 3H), 4.20 (t, J=6.4 Hz, 2H), 4.05 (s, 2H), 3.57 (s, 2H), 2.91-2.76 (m, 1H), 2.74-2.60 (m, 4H), 1.74-1.62 (m, 2H), 1.47-1.34 (m, 2H), 1.03 (d, J=5.6 Hz, 6H), 0.92 (t, J=7.2 Hz, 3H) ppm. MS: M/e 395 (M+1)⁺.

Compound A9: 2-butoxy-7-((2-isopropyl-1,2,3,4-tetrahydroisoquinolin-7-yl)methyl)imidazo[2,1-f][1,2,4]triazin-4-amine Step A: 7-bromo-2-isopropyl-1,2,3,4-tetrahydroisoquinoline To a solution of 7-bromo-1,2,3,4-tetrahydroisoquinoline (1.06 g, 5 mmol) in MeOH (3 mL) were added acetone (3 mL) and AcOH (10 drops). Then the mixture was stirred at 80° C. for 1.5 h. The mixture was cooled to room temperature, NaBH$_3$CN (0.93 g, 15 mmol) was added in some portions and the resulting mixture was stirred at room temperature for 3 h. The reaction was concentrated, diluted with water (30 mL), extracted with EtOAc (50 mL×2). The combined organic layers were washed with brine, dried over Na$_2$SO$_4$, filtered, concentrated and the residue was purified by flash chromatography to give target compound (930 mg, 73%) as oil. MS: M/e 254 (M+1)$^+$.

Step B: 2-isopropyl-1,2,3,4-tetrahydroisoquinoline-7-carbaldehyde

To a solution of the product of Step A (930 mg, 3.64 mmol) in THF (20 mL) was added a solution of n-BuLi (4.5 mL, 7.2 mmol) dropwise maintaining the temperature between −75~−65° C. After 30 min, DMF (532 mg, 7.3 mmol) was added dropwise and the resulting mixture was stirred at −65° C. for 30 min. The reaction was quenched with saturated NH$_4$Cl solution, extracted with EtOAc (60 mL), washed with brine, dried over Na$_2$SO$_4$, filtered, and concentrated. The residue was purified by flash chromatography to give target compound (80 mg, 11%) as oil. MS: M/e 204 (M+1)$^+$.

Step C: (4-(bis(4-methoxybenzyl)amino)-2-butoxy-imidazo[2,1-f][1,2,4]triazin-7-yl)(2-isopropyl-1,2,3,4-tetrahydroisoquinolin-7-yl)methanol To a solution of 7-bromo-2-butoxy-N,N-bis(4-methoxybenzyl)imidazo[2,1-f][1,2,4]triazin-4-amine (150 mg, 0.285 mmol) in THF (5 mL) was added a solution of n-BuLi (0.44 mL, 0.71 mmol) dropwise maintaining the temperature between −75~−65° C. After 30 min, a mixture of the product of Step B (80 mg, 0.42 mmol) in THF (4 mL) was added dropwise. The resulting mixture was stirred at −70° C. for 1 h and then warmed to room temperature for 1 h. The reaction was quenched with saturated NH$_4$Cl solution, extracted with EtOAc (80 mL), washed with brine, dried over Na$_2$SO$_4$, filtered, and concentrated. The residue was purified by column chromatography (DCM/MeOH=40/1) to give target compound (50 mg, crude). MS: M/e 651 (M+1)$^+$.

Step D: 2-butoxy-7-((2-isopropyl-1,2,3,4-tetrahydroisoquinolin-7-yl)methyl)imidazo[2,1-f][1,2,4]triazin-4-amine (Compound A9)

To a mixture of the product of Step C (50 mg, crude) in TFA (3 mL) was added Et$_3$SiH (1 mL). The reaction was heated at 85° C. overnight. The mixture was concentrated and the residue was purified by prep-HPLC. The collected fraction was basified with NaHCO$_3$ solution, extracted with DCM (60 mL), washed with brine, dried over Na$_2$SO$_4$, filtered, and concentrated to give the product (20 mg, 12% for two steps). $^1$H NMR (400 MHz, DMSO-d$_6$) δ 8.19-7.98 (m, 2H), 7.28 (s, 1H), 7.10-6.65 (m, 3H), 4.20 (t, J=6.4 Hz, 2H), 4.05 (s, 2H), 3.56 (s, 2H), 2.85-2.76 (m, 1H), 2.74-2.62 (m, 4H), 1.74-1.62 (m, 2H), 1.49-1.34 (m, 2H), 1.02 (d, J=6.4 Hz, 6H), 0.92 (t, J=7.6 Hz, 3H) ppm. MS: M/e 395 (M+1)$^+$.

Compound A10: 2-butoxy-7-(4-(piperazin-1-ylmethyl)benzyl)imidazo[2,1-f][1,2,4]triazin-4-amine Step A: tert-butyl 4-(4-formylbenzyl)piperazine-1-carboxylate To a stirred solution of 4-(bromomethyl)benzaldehyde (4 g, 20 mmol) in THF (40 mL) was added tert-butyl piperazine-1-carboxylate (4.6 g, 25 mmol) and DIEA (5.04 g, 40 mmol). After the addition, the reaction mixture was stirred at Rt overnight. The mixture was filtered. The filtrate was poured into H$_2$O and extracted with EtOAc (15 mL×3). The combined organic layers were washed with brine, dried over Na$_2$SO$_4$ and concentrated in vacuo. The crude product was purified by column chromatography (petroleum ether/EtOAc=1:1) to give tert-butyl 4-(4-formylbenzyl)piperazine-1-carboxylate (4.1 g, 68%) as a yellow oil. MS: M/e 305 (M+1)$^+$.

Step B: tert-butyl 4-(4-((4-(bis(4-methoxybenzyl)amino)-2-butoxyimidazo[2,1-f][1,2,4]triazin-7-yl)(hydroxy)methyl)benzyl)piperazine-1-carboxylate To a stirred solution of 7-bromo-2-butoxy-N,N-bis(4-methoxybenzyl)imidazo[2,1-f][1,2,4]triazin-4-amine (150 mg, 0.3 mmol) in THF (10 mL), cooled to −78° C. and under a nitrogen atmosphere was added n-BuLi (1.6 M in hexane, 0.75 mmol, 0.47 mL) dropwise. After stirring for 20 mins, a solution of 4-(4-formylbenzyl)piperazine-1-carboxylate (137 mg, 0.45 mmol) in THF (2 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over Na$_2$SO$_4$, concentrated to give the product (270 mg, 100%) which was used directly in next step without further purification. MS: M/e 752 (M+1)$^+$.

Step C: 2-butoxy-7-(4-(piperazin-1-ylmethyl)benzyl)imidazo[2,1-f][1,2,4]triazin-4-amine (Compound A10)

A solution of tert-butyl 4-(4-((4-(bis(4-methoxybenzyl)amino)-2-butoxyimidazo[2,1-f][1,2,4]triazin-7-yl)(hydroxy)methyl)benzyl)piperazine-1-carboxylate (270 mg, 0.3 mmol) in TFA (3 mL) and Et$_3$SiH (3 mL) was stirred at 80° C. for 2 h. The reaction mixture was concentrated in vacuo to remove TFA and Et$_3$SiH. The residue was added TFA (5 mL) and stirred at 85° C. overnight. The mixture was cooled down to rt and concentrated in vacuo. The crude product was purified by prep-HPLC to give the product (40 mg, 33.8%). $^1$H NMR (400 MHz, DMSO-d6) δ 8.13 (s, 1H), 8.03 (s, 1H), 7.30 (s, 1H), 7.24 (d, J=8 Hz, 2H), 7.19 (d, J=8 Hz, 2H), 4.19 (t, J=6.4 Hz, 2H), 4.11 (s, 2H), 3.40 (s, 2H), 2.71-2.61 (m, 4H), 2.32-2.28 (m, 4H), 1.65 (dd, J=14.2, 6.8 Hz, 2H), 1.42-1.36 (m, 2H), 0.92 (t, J=7.3 Hz, 3H) ppm. MS: M/e 396 (M+1)$^+$.

Compound A11: 2-butoxy-7-(3-(pyrrolidin-1-ylmethyl)benzyl)imidazo[2,1-f][1,2,4]triazin-4-amine Step A: (4-(bis(4-methoxybenzyl)amino)-2-butoxy-imidazo[2,1-f][1,2,4]triazin-7-yl)(3-(pyrrolidin-1-ylmethyl)phenyl)methanol To a stirred solution of 7-bromo-2-butoxy-N,N-bis(4-methoxybenzyl)imidazo[2,1-f][1,2,4]triazin-4-amine (170 mg, 0.32 mmol) in THF (10 ml) at −78° C. under N$_2$ atmosphere, was added n-BuLi (1.6 M, 0.51 ml, 0.82 mmol). The solution was stirred at −78° C. for 30 min. 3-(pyrrolidin-1-ylmethyl)benzaldehyde (92 mg, 0.49 mmol) in THF (2 ml) was added dropwise to the above solution. After addition, the solution was warmed to rt naturally and then stirred for 3 hr. After was completed, the reaction mixture was quenched with H$_2$O (20 ml) and then extracted with DCM (20 ml×3). The organic phase was washed with $H_2O$ (10 ml), dried and concentrated under reduced pressure. The residue was purified by prep-TLC with PE:EA (1:1) to afford the product (120 mg, 58%) as an off-white oil. MS: M/e 637 $(M+1)^+$.

Step B: 2-butoxy-7-(3-(pyrrolidin-1-ylmethyl)benzyl)imidazo[2,1-f][1,2,4]triazin-4-amine (Compound A11)

A solution of (4-(bis(4-methoxybenzyl)amino)-2-butoxyimidazo[2,1-f][1,2,4]triazin-7-yl)(3-(pyrrolidin-1-ylmethyl) phenyl)methanol (120 mg, 0.19 mmol) in TFA (2 ml) and triethylsilane (2 ml) was stirred at 80° C. for 15 hr. The solution was concentrated under reduced pressure to remove triethylsilane. The residue was dissolved in TFA (2 ml) and stirred at 80° C. overnight. After was completed, the reaction mixture was quenched with aq. $NaHCO_3$ (sat., 25 ml) and then extracted with DCM (20 ml×3). The organic phase was concentrated under reduced pressure and the resulting residue was purified by prep-TLC with DCM:MeOH (10:1) to afford the product (15.11 mg, 21%). $^1$H NMR (400 MHz, DMSO-d6) δ 8.11 (s, 1H), 8.02 (s, 1H), 7.43-7.11 (m, 5H), 4.26 (s, 2H), 4.18 (t, J=8 Hz, 2H), 3.65 (s, 2H), 2.40 (s, 4H), 1.73-1.60 (m, 6H), 1.42-1.35 (m, 2H), 0.91 (t, J=8 Hz, 3H) ppm. MS: M/e 381 $(M+1)^+$.

Compound A12: 2-butoxy-7-(3-(morpholinomethyl) benzyl)imidazo[2,1-f][1,2,4]triazin-4-amine Step A: (4-(bis(4-methoxybenzyl)amino)-2-butoxyimidazo[2,1-f][1,2,4]triazin-7-yl)(3-(morpholinomethyl)phenyl)methanol To a stirred solution of 7-bromo-2-butoxy-N,N-bis(4-methoxybenzyl)imidazo[2,1-f][1,2,4]triazin-4-amine (200 mg, 0.38 mmol) in THF (10 ml) at −78° C. under $N_2$ atmosphere, was added n-BuLi (1.6 M, 0.60 ml, 0.96 mmol). The solution was stirred at −78° C. for 30 min. 3-(morpholinomethyl)benzaldehyde (117 mg, 0.57 mmol) in THF (2 ml) was added dropwise to the above solution. After addition, the solution was warmed to rt naturally and then stirred for 3 hr. After was completed, the reaction mixture was quenched with $H_2O$ (20 ml) and then extracted with DCM (20 ml×3). The organic phase was washed with $H_2O$ (10 ml), dried and concentrated under reduced pressure to afford crude product as a yellow oil, which was used directly for the next step without further purification. MS: M/e 653 $(M+1)^-$.

Step B: 2-butoxy-7-(3-(morpholinomethyl)benzyl) imidazo[2,1-f][1,2,4]triazin-4-amine (Compound A12)

A solution of (4-(bis(4-methoxybenzyl)amino)-2-butoxyimidazo[2,1-f][1,2,4]triazin-7-yl)(3-(morpholinomethyl) phenyl)methanol (crude) in TFA (2 ml) and triethylsilane (2 ml) was stirred at 80° C. for 15 hr. The solution was concentrated under reduced pressure to remove triethylsilane. The residue was dissolved in TFA (2 ml) and stirred at 80° C. overnight. After was completed, the reaction mixture was quenched with aq. $NaHCO_3$ (sat., 25 ml) and then extracted with DCM (20 ml×3). The organic phase was concentrated under reduced pressure and the resulting residue was purified by prep-TLC with DCM:MeOH (10:1) to afford the product (59.43 mg). $^1$H NMR (400 MHz, DMSO-d6) δ 8.13 (s, 1H), 8.04 (s, 1H), 7.30-7.13 (m, 5H), 4.19 (t, J=8 Hz, 2H), 4.13 (s, 2H), 3.53 (s, 4H), 3.40 (s, 2H), 2.30 (s, 4H), 1.74-1.63 (m, 2H), 1.45-1.34 (m, 2H), 0.92 (t, J=8 Hz, 3H) ppm. MS: M/e 397 $(M+1)^+$.

Compound A13: 2-butoxy-7-(3-((4-methylpiperazin-1-yl)methyl)benzyl)imidazo[2,1-f][1,2,4]triazin-4-amine Step A: (4-(bis(4-methoxybenzyl)amino)-2-butoxyimidazo[2,1-f][1,2,4]triazin-7-yl)(3-((4-methylpiperazin-1-yl)methyl)phenyl)methanol To a stirred solution of 7-bromo-2-butoxy-N,N-bis(4-methoxybenzyl)imidazo[2,1-f][1,2,4]triazin-4-amine (200 mg, 0.38 mmol) in THF (10 ml) at −78° C. under $N_2$ atmosphere, was added n-BuLi (1.6 M, 0.60 ml, 0.96 mmol). The solution was stirred at −78° C. for 30 min. 3-((4-methylpiperazin-1-yl)methyl)benzaldehyde (124 mg, 0.57 mmol) in THF (2 ml) was added dropwise to the above solution. After added, the solution was warmed to rt naturally and then stirred for 3 hr. After was completed, the reaction mixture was quenched with $H_2O$ (20 ml) and then extracted with DCM (20 ml×3). The organic phase was washed with $H_2O$ (10 ml), dried and concentrated under reduced pressure to afford crude product as a green oil, which was used directly for the next step without further purification. MS: M/e 666 $(M+1)^+$.

Step B: 2-butoxy-7-(3-((4-methylpiperazin-1-yl) methyl)benzyl)imidazo[2,1-f][1,2,4]triazin-4-amine (Compound A13)

A solution of (4-(bis(4-methoxybenzyl)amino)-2-butoxyimidazo[2,1-f][1,2,4]triazine-7-yl)(3-((4-methylpiperazin-1-yl)methyl)phenyl)methanol (crude) in TFA (2 ml) and triethylsilane (2 ml) was stirred at 80° C. for 15 hr. The solution was concentrated under reduced pressure to remove triethylsilane. The residue was dissolved in TFA (2 ml) and stirred at 80° C. overnight. After was completed, the reaction mixture was quenched with aq. $NaHCO_3$ (sat., 25 ml) and then extracted with DCM (20 ml×3). The organic phase was concentrated under reduced pressure and the resulting residue was purified by prep-TLC with DCM:MeOH (10:1) to afford the product (49.03 mg). $^1$H NMR (400 MHz, DMSO-d6) δ 8.13 (s, 1H), 8.06 (s, 1H), 7.31-7.15 (m, 5H), 4.20 (t, J=8 Hz, 2H), 4.13 (s, 2H), 3.50 (s, 2H), 3.31-2.82 (m, 6H), 2.72 (s, 3H), 2.43-2.13 (m, 2H), 1.73-1.61 (m, 2H), 1.48-1.34 (m, 2H), 0.92 (t, J=8 Hz, 3H) ppm. MS: M/e 410 $(M+1)^+$.

Compound A14: 2-butoxy-7-(2-(morpholinomethyl) benzyl)imidazo[2,1-f][1,2,4]triazin-4-amine Step A: (4-(bis(4-methoxybenzyl)amino)-2-butoxyimidazo[2,1-f][1,2,4]triazine-7-yl)(2-(morpholinomethyl)phenyl)methanol To a solution of 7-bromo-2-butoxy-N,N-bis(4-methoxybenzyl)imidazo[2,1-f][1,2,4]triazine-4-amine (150 mg, 0.29 mmol) in THF (5 mL), n-Butyllithium (0.27 ml, 0.43 mmol) was added dropwise at −78° C. and stirred for 1 h. Then a solution of 2-(morpholinomethyl)benzaldehyde (88 mg, 0.43 mmol) in THF (2 mL) was added dropwise at −78° C., after addition, the mixture was stirred at 60° C. overnight. The mixture was quenched with saturated ammonium chloride solution (5 mL), extracted with DCM (30 mL×3). The combined organic layers were washed with brine, dried over Na₂SO₄, concentrated and purified by column chromatography (DCM/MeOH=20:1~5:1) to give the target product (83 mg, 44.6%) as yellow oil. MS: M/e 653 (M+1)⁺.

Step B: 2-butoxy-7-(2-(morpholinomethyl)benzyl)imidazo[2,1-f][1,2,4]triazine-4-amine (Compound A14)

A mixture of (4-(bis(4-methoxybenzyl)amino)-2-butoxyimidazo[2,1-f][1,2,4]triazin-7-yl)(2-(morpholinomethyl)phenyl)methanol (83 mg, 0.13 mmol) and triethylsilane (1 mL) in TFA (2 mL) was stirred at 90° C. overnight. The mixture was concentrated and purified with prep-HPLC to give the target product (23 mg, 46%). $^1$H NMR (400 MHz, DMSO-d6) δ 8.12 (s, 1H), 8.02 (s, 1H), 7.29-7.15 (m, 4H), 7.09 (s, 1H), 4.27 (s, 2H), 4.18 (t, J=6.6 Hz, 2H), 3.51 (s, 2H), 3.40 (s, 4H), 2.28 (s, 4H), 1.71-1.60 (m, 2H), 1.46-1.32 (m, 2H), 0.91 (t, J=7.4 Hz, 3H) ppm. MS: M/e 397 (M+1)⁺.

Compound A15: 2-butoxy-7-(2-(piperidin-1-ylmethyl)benzyl)imidazo[2,1-f][1,2,4]triazin-4-amine Step A: (4-(bis(4-methoxybenzyl)amino)-2-butoxyimidazo[2,1-f][1,2,4]triazin-7-yl)(2-(piperidin-1-ylmethyl)phenyl)methanol To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. and stirred for 1 h. Then a solution of 2-(piperidin-1-ylmethyl)benzaldehyde (87 mg, 0.43 mmol) in THF (2 mL) was added dropwise at −78° C., after addition, the mixture was stirred to 60° C. and stirred overnight. The mixture was quenched with saturated ammonium chloride solution (5 mL), extracted with DCM (30 mL×3). The combined organic layers were washed with brine, dried over Na₂SO₄, concentrated and purified by column chromatography (DCM/MeOH=20:1~5:1) to give the product (79 mg, 43%) as yellow oil. MS: M/e 651 (M+1)⁺.

Step B: 2-butoxy-7-(2-(piperidin-1-ylmethyl)benzyl)imidazo[2,1-f][1,2,4]triazin-4-amine (Compound A15)

A mixture of (4-(bis(4-methoxybenzyl)amino)-2-butoxyimidazo[2,1-f][1,2,4]triazin-7-yl)(2-(piperidin-1-ylmethyl)phenyl)methanol (79 mg, 0.12 mmol) and triethylsilane (1 mL) in TFA (2 mL) was stirred at 90° C. overnight. The mixture was concentrated and purified with prep-HPLC to give the target product (19 mg, 40%). $^1$H NMR (400 MHz, DMSO-d6) δ 8.10 (s, 1H), 8.01 (s, 1H), 7.25-7.15 (m, 4H), 7.09 (s, 1H), 4.26 (s, 2H), 4.18 (t, J=6.3 Hz, 2H), 3.45 (s, 2H), 2.28-2.13 (m, 4H), 1.70-1.62 (m, 2H), 1.47-1.30 (m, 8H), 0.91 (t, J=7.3 Hz, 3H) ppm. MS: M/e 395 (M+1)⁺.

Compound A16: 2-isobutoxy-7-(3-(pyrrolidin-1-ylmethyl)benzyl)imidazo[2,1-f][1,2,4]triazin-4-amine Step A: (4-(bis(4-methoxybenzyl)amino)-2-isobutoxyimidazo[2,1-f][1,2,4]triazin-7-yl)(3-(pyrrolidin-1-ylmethyl)phenyl)methanol To a stirred solution of 7-bromo-2-isobutoxy-N,N-bis(4-methoxybenzyl)imidazo[2,1-f][1,2,4]triazin-4-amine (180 mg, 0.34 mmol) in THF (10 ml) at −78° C. under N₂ atmosphere, was added n-BuLi (1.6 M, 0.54 ml, 0.86 mmol). The solution was stirred at −78° C. for 30 min. 3-(pyrrolidin-1-ylmethyl)benzaldehyde (97 mg, 0.51 mmol) in THF (2 ml) was added dropwise to the above solution. After added, the solution was warmed to rt naturally and then stirred for 3 hr. After was completed, the reaction mixture was quenched with H₂O (20 ml) and then extracted with DCM (20 ml×3). The organic phase was washed with H₂O (10 ml), dried and concentrated under reduced pressure to afford crude product as a yellow oil, which was used directly for the next step without further purification. MS: M/e 637 (M+1)⁻.

Step B: 2-isobutoxy-7-(3-(pyrrolidin-1-ylmethyl)benzyl)imidazo[2,1-f][1,2,4]triazin-4-amine (Compound A16)

A solution of (4-(bis(4-methoxybenzyl)amino)-2-isobutoxyimidazo[2,1-f][1,2,4]triazin-7-yl)(3-(pyrrolidin-1-ylmethyl)phenyl)methanol (crude) in TFA (2 ml) and triethylsilane (2 ml) was stirred at 80° C. for 15 hr. The solution was concentrated under reduced pressure to remove triethylsilane. The residue was dissolved in TFA (2 ml) and stirred at 80° C. overnight. After was completed, the reaction mixture was quenched with aq. NaHCO₃ (sat., 25 ml) and then extracted with DCM (20 ml×3). The organic phase was concentrated under reduced pressure and the resulting residue was purified by prep-TLC with DCM:MeOH (10:1) to afford the product (24.30 mg). $^1$H NMR (400 MHz, DMSO-d6) δ 8.12 (s, 1H), 8.03 (s, 1H), 7.32-7.14 (m, 5H), 4.27 (s, 2H), 3.96 (d, J=4 Hz, 2H), 3.67 (s, 2H), 2.41 (s, 4H), 2.05-1.94 (m, 1H), 1.63 (s, 4H), 0.96 (s, 3H), 0.94 (s, 3H) ppm. MS: M/e 381 (M+1)⁺.

Compound A17: 2-(2-methoxyethoxy)-7-(3-(pyrrolidin-1-ylmethyl)benzyl)imidazo[2,1-f][1,2,4]triazin-4-amine Step A: 7-bromo-N,N-bis(4-methoxybenzyl)-2-(2-methoxyethoxy)imidazo[2,1-f][1,2,4]triazin-4-amine To a solution of 2-methoxyethan-1-ol (6 g, 79 mmol) were added some small pieces of Na (about 0.6 g). To the resulting mixture (5 mL) was added 7-bromo-2-chloro-N,N-bis(4-methoxybenzyl)imidazo[2,1-f][1,2,4]triazin-4-amine (250 mg, 0.51 mmol). Then the mixture was stirred at 80° C. for 3 h. The mixture was concentrated, diluted with water (30 mL), extracted with EtOAc (80 mL), washed with brine, dried over Na₂SO₄, filtered, concentrated and the residue was purified by combi-flash to give target compound (200 mg, 75%). $^1$HNMR (400 MHz, CDCl₃) δ 7.47 (s, 1H), 7.20 (d, J=8.8 Hz, 2H), 7.17 (d, J=8.8 Hz, 2H), 6.85 (d, J=8.8 Hz, 4H), 5.60 (s, 1H), 4.86 (s, 2H), 4.52 (t, J=4.8 Hz, 2H), 3.80 (s, 6H), 3.77 (t, J=4.8 Hz, 2H), 3.42 (s, 3H) ppm. MS: M/e 528 (M+1)⁺.

Step B: (4-(bis(4-methoxybenzyl)amino)-2-(2-methoxyethoxy)imidazo[2,1-f][1,2,4]triazin-7-yl)(3-(pyrrolidin-1-ylmethyl)phenyl)methanol To a solution of the product of Step A (200 mg, 0.38 mmol) in THF (10 mL) was added a solution of n-BuLi (0.6 mL, 0.9 mmol) dropwise maintaining the temperature between −75~−65° C. After 1.5 h, a solution of 3-(pyrrolidin-1-ylmethyl)benzaldehyde (107 mg, 0.57 mmol) in THF (2 mL) was added dropwise. The resulting mixture was stirred at −70° C. for 1 h and then warmed to room temperature for 1 h. The reaction was quenched with saturated NH₄Cl solution, extracted with EtOAc (50 mL), washed with brine, dried over Na₂SO₄, filtered, and concentrated. The residue was purified by combi flash to give a solid (150 mg, 62%). MS: M/e 639 (M+1)⁺.

Step C: 2-(2-methoxyethoxy)-7-(3-(pyrrolidin-1-ylmethyl)benzyl)imidazo[2,1-f][1,2,4]triazin-4-amine (Compound A17)

To a mixture of the product of Step B (150 mg, 0.235 mmol) in TFA (6 mL) was added Et₃SiH (2 mL). The reaction was heated at 80° C. for 16 h. The mixture was concentrated to dryness and the residue was treated with TFA (6 mL). The reaction was heated at 85° C. overnight. The mixture was concentrated and the residue was purified by prep-HPLC. The collected fraction was basified with NaHCO₃ solution, extracted with DCM (60 mL), washed with brine, dried over Na₂SO₄, filtered, and concentrated to give the product (48 mg, 53%). ¹HNMR (400 MHz, CD3OD) δ 7.37 (t, J=6.0 Hz, 1H), 7.30-7.15 (m, 4H), 4.42 (t, J=4.8 Hz, 2H), 4.33 (s, 2H), 4.05-3.88 (m, 2H), 3.69 (t, J=4.8 Hz, 2H), 3.38 (s, 3H), 3.01-2.61 (m, 4H), 1.95-1.71 (m, 4H) ppm. MS: M/e 383 (M+1)⁺.

Compound A18: 7-(3-(pyrrolidin-1-ylmethyl)benzyl)-2-(4,4,4-trifluorobutoxy)imidazo[2,1-f][1,2,4]triazin-4-amine Step A: (4-(bis(4-methoxybenzyl)amino)-2-(4,4,4-trifluorobutoxy)imidazo[2,1-f][1,2,4]triazin-7-yl)(3-(pyrrolidin-1-ylmethyl)phenyl)methanol To a stirred solution of 7-bromo-N,N-bis(4-methoxybenzyl)-2-(4,4,4-trifluoro butoxy)imidazo[2,1-f][1,2,4]triazin-4-amine (130 mg, 0.22 mmol) in THF (10 ml) at −78° C. under N₂ atmosphere, was added n-BuLi (1.6 M, 0.35 ml, 0.56 mmol). The solution was stirred at −78° C. for 30 min. 3-(pyrrolidin-1-ylmethyl)benzaldehyde (64 mg, 0.34 mmol) in THF (2 ml) was added dropwise to the above solution. After was added, the solution was warmed to rt naturally and then stirred for 3 hr. After was completed, the reaction mixture was quenched with H₂O (20 ml) and then extracted with DCM (20 ml×3). The organic phase was washed with H₂O (10 ml), dried and concentrated under reduced pressure to afford crude product as a yellow oil, which was used directly for the next step without further purification. MS: M/e 691 (M+1)⁺.

Step B: 7-(3-(pyrrolidin-1-ylmethyl)benzyl)-2-(4,4,4-trifluorobutoxy)imidazo[2,1-f][1,2,4]triazin-4-amine (Compound A18)

A solution of (4-(bis(4-methoxybenzyl)amino)-2-(4,4,4-trifluorobutoxy)imidazo[2,1-f][1,2,4]triazin-7-yl)(3-(pyrrolidin-1-ylmethyl)phenyl)methanol (crude) in TFA (6 ml) and triethylsilane (2 ml) was stirred at 80° C. for 24 hr. After was completed, the reaction mixture was quenched with aq. NaHCO₃ (sat., 25 ml) and then extracted with DCM (20 ml×3). The organic phase was concentrated under reduced pressure and the resulting residue was purified by prep-TLC with DCM:MeOH (10:1) to afford the product (19.75 mg). ¹H NMR (400 MHz, DMSO-d6) δ 8.18 (s, 1H), 8.08 (s, 1H), 7.28-7.13 (m, 5H), 4.26 (s, 4H), 3.63 (s, 2H), 2.48-2.25 (m, 6H), 2.01-1.89 (m, 2H), 1.88-1.51 (m, 4H) ppm. MS: M/e 435 (M+1)⁺.

Compound A19: 2-butoxy-7-(2-(pyrrolidin-1-ylmethyl)benzyl)imidazo[2,1-f][1,2,4]triazin-4-amine Step A: (4-(bis(4-methoxybenzyl)amino)-2-butoxyimidazo[2,1-f][1,2,4]triazin-7-yl)(2-(pyrrolidin-1-ylmethyl)phenyl)methanol To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. and stirred for 1 h. Then a solution of 2-(pyrrolidin-1-ylmethyl)benzaldehyde (81 mg, 0.43 mmol) in THF (2 mL) was added dropwise at −78° C., after addition, the mixture was warmed to 60° C. and stirred overnight. The mixture was quenched with saturated ammonium chloride solution (5 mL), extracted with DCM (30 mL×3). The combined organic layers were washed with brine, dried over Na₂SO₄, concentrated and purified by column chromatography (DCM/MeOH=20:1~5:1) to give the target product (67 mg, 37%) as yellow oil. MS: M/e 637 (M+1)⁺.

Step B: 2-butoxy-7-(2-(pyrrolidin-1-ylmethyl)benzyl)imidazo[2,1-f][1,2,4]triazin-4-amine (Compound A19)

A mixture of (4-(bis(4-methoxybenzyl)amino)-2-butoxyimidazo[2,1-f][1,2,4]triazin-7-yl)(2-(pyrrolidin-1-ylmethyl)phenyl)methanol (67 mg, 0.11 mmol) and triethylsilane (1 mL) in TFA (2 mL) was stirred at 90° C. overnight. The mixture was concentrated and purified by prep-HPLC to give the target product (15 mg, 38%). ¹H NMR (400 MHz, DMSO-d6) δ 8.22-8.03 (m, 2H), 7.44-7.15 (m, 5H), 4.55 (s, 1H), 4.28 (s, 2H), 4.17 (t, J=6.6 Hz, 2H), 3.71-3.38 (m, 2H), 3.17 (s, 1H), 2.42-2.32 (m, 2H), 2.05-1.74 (m, 2H), 1.70-1.56 (m, 4H), 1.38 (dt, J=14.6, 7.4 Hz, 2H), 0.91 (t, J=7.4 Hz, 3H) ppm. MS: M/e 381 (M+1)⁺.

Compound A20: 2-butoxy-7-(2-fluoro-4-(pyrrolidin-1-ylmethyl)benzyl)imidazo[2,1-f][1,2,4]triazin-4-amine Step A: 2-fluoro-4-(pyrrolidin-1-ylmethyl)benzonitrile To a stirred solution of 2-fluoro-4-formylbenzonitrile (447 mg, 3 mmol) in MeOH (5 mL) was added pyrrolidine (234 mg, 3.3 mmol), then the mixture was stirred for 2 hours followed by NaBH₃CN (378 mg, 6 mmol). After the addition, the reaction mixture was concentrated to give the residue, which was purified by column chromatography (petroleum ether/EtOAc=2:1) to give the target compound (400 mg, 65.4%) as yellow oil. MS: M/e 205 (M+1)⁺.

Step B: 2-fluoro-4-(pyrrolidin-1-ylmethyl)benzaldehyde

To a stirred solution of the product of Step A (400 mg, 1.96 mmol) in dry THF (10 mL) was added DIBAL-H (1.2 M, 4 mL, 4.9 mmol) dropwise at −20° C. After the addition, the reaction was stirred for 3 hours at room temperature. The reaction was quenched with aq.NH₄Cl, extracted with EtOAc (20 mL×3) and filtered. The filtrate was washed with brine, dried over Na₂SO₄, concentrated and purified by column chromatography (petroleum ether/EtOAc=3:1~1:1) to give the target compound (182 mg, 44.3%) as light yellow oil. MS: M/e 208 (M+1)⁺.

Step C: (4-(bis(4-methoxybenzyl)amino)-2-butoxy-imidazo[2,1-f][1,2,4]triazin-7-yl)(2-fluoro-4-(pyrrolidin-1-ylmethyl)phenyl)methanol To a stirred solution of 7-bromo-2-butoxy-N,N-bis(4-methoxybenzyl)imidazo[2,1-f][1,2,4]triazin-4-amine (150 mg, 0.285 mmol) in THF (10 mL) was added n-BuLi (0.44 mL, 0.71 mmol) dropwise −78° C. After stirred for an hour, a solution of the product of Step B (88.7 mg, 0.428 mmol) in THF (2 mL) was added dropwise. The resulting mixture was stirred at −70° C. for 1 h and then warmed to room temperature for 1 h. The reaction was quenched with sat.aq.NH$_4$Cl solution, extracted with EtOAc (10 mL×3). The combined organic layers were washed with brine, dried over Na$_2$SO$_4$, filtered, and concentrated. The residue was purified by Pre-TLC (petroleum ether/EtOAc=1:1) to give target compound (60 mg, 32%). MS: M/e 655 (M+1)$^+$.

Step D: 2-butoxy-7-(2-fluoro-4-(pyrrolidin-1-ylmethyl)benzyl)imidazo[2,1-f][1,2,4]triazin-4-amine (Compound A20)

To a mixture of the product of Step C (60 mg, 0.092 mmol) in Et$_3$SiH/TFA (0.5 mL/2 mL) was stirred at 80° C. overnight. The reaction mixture was concentrated to give the residue, which was purified by prep-HPLC to give the target compound (23 mg, 62.8). $^1$H NMR (400 MHz, DMSO-d$_6$) δ 8.16 (s, 1H), 8.05 (s, 1H), 7.27 (s, 1H), 7.23-7.19 (m, 1H), 7.11-7.04 (m, 2H), 4.19-4.13 (m, 4H), 3.53 (s, 2H), 2.42-2.31 (m, 4H), 1.72-1.61 (m, 6H), 1.42-1.36 (m, 2H), 0.91 (t, J=7.6 Hz, 3H) ppm. MS: M/e 399 (M+1)$^+$.

Compound A21: 2-butoxy-7-(4-(3-(piperidin-1-yl)propoxy)benzyl)imidazo[2,1-f][1,2,4]triazin-4-amine Step A: 4-(3-bromopropoxy)benzaldehyde A solution of 4-hydroxybenzaldehyde (2 g, 16 mmol), 3-bromopropan-1-ol (2.3 g, 16 mmol) and triphenylphosphane (6.3 g, 24 mmol) in dry THF (60 mL) at 0° C. was treated with DTAD (5.5 g, 24 mmol) in portion-wise. The reaction mixture was warm up slowly to rt overnight. The solution was quenched with water (20 mL), extracted with ethyl acetate (20 mL) and washed with brine (20 mL). The organic layers was dried, concentrated and purified by CombiFlash (PE:EA=15:1) to get the product (1.3 g, 33%). $^1$H NMR (400 MHz, DMSO-d6) δ 9.88 (s, 1H), 7.88 (d, J=8.0 Hz, 2H), 7.16 (d, J=12.0 Hz, 2H), 4.21 (t, J=8.0 Hz, 2H), 3.68 (t, J=8.0 Hz, 2H), 2.32-2.27 (m, 2H) ppm. MS: M/e 243 (M+1)$^+$.

Step B: 4-(3-(piperidin-1-yl)propoxy)benzaldehyde

A mixture of 4-(3-bromopropoxy)benzaldehyde (200 mg, 0.8 mmol), piperidine (136 mg, 1.6 mmol), sodium carbonate (170 mg, 1.6 mmol) and potassium iodide (17 mg, 0.1 mmol) in n-BuOH (5 mL) was heated at 105° C. for 4 hrs. The solution was cooled, quenched with water (10 mL) and extracted with dichloromethane (10 mL). The organic layer was dried, concentrated and purified by CombiFlash (DCM: MeOH=8%) to get the product (190 mg, 93%). MS: M/e 248 (M+1)$^+$.

Step C: (4-(bis(4-methoxybenzyl)amino)-2-butoxy-imidazo[2,1-f][1,2,4]triazin-7-yl)(4-(3-(piperidin-1-yl)propoxy)phenyl)methanol To a cooled solution of 7-bromo-2-butoxy-N,N-bis(4-methoxybenzyl)imidazo[2,1-f][1,2,4]triazin-4-amine (200 mg, 0.4 mmol) in THF (8 mL) at −78° C. (purged with N$^2$), n-BuLi (1.6 M, 0.7 mL) was added dropwise. After stirring at −78° C. for 30 mins, 4-(3-(piperidin-1-yl)propoxy)benzaldehyde (148 mg, 0.6 mmol) in THF (2 mL) was added. The resulting mixture was stirred at this temperature for 30 mins, and then warmed to rt for 1 hour. The solution was quenched with NH$_4$Cl solution (5 mL), extracted with ethyl acetate (10 mL) and washed with brine (10 mL). The organic layers were dried with Na$_2$SO$_4$, filtered and concentrated to get the crude product, which was further purified by Combiflash (DCM:MeOH=5%) to get the pure product (140 mg, 37%). MS: M/e 695 (M+1)$^+$.

Step D: 2-butoxy-7-(4-(3-(piperidin-1-yl)propoxy) benzyl)imidazo[2,1-f][1,2,4]triazin-4-amine (Compound A21)

A solution of (4-(bis(4-methoxybenzyl)amino)-2-butoxy-imidazo[2,1-f][1,2,4]triazin-7-yl)(4-(3-(piperidin-1-yl)propoxy)phenyl)methanoltriethylsilane (140 mg, 0.2 mmol) in trifluoroacetic acid (3 mL) and triethylsilane (1 mL) was heated at 80° C. overnight. The solvent was evaporated to get the residue, Which was basified with NaHCO$_3$ solution, extracted with ethyl acetate (5 mL), washed with brine (5 mL). The organic layer was dried, concentrated and purified by CombiFlash (DCM:MeOH=8%) to get the product (35 mg, 40%). $^1$H NMR (400 MHz, DMSO-d6) δ 8.12 (s, 1H), 8.03 (s, 1H), 7.25 (s, 1H), 7.21 (d, J=8.0 Hz, 2H), 6.84 (d, J=8.0 Hz, 2H), 4.20 (t, J=8.0 Hz, 2H), 4.06 (s, 2H), 3.97-3.95 (m, 2H), 2.49-2.20 (m, 4H), 2.18-1.75 (m, 3H), 1.67-1.38 (m, 11H), 0.91 (t, J=7.6 Hz, 3H) ppm. MS: M/e 439 (M+1)$^+$.

Compound A22: 2-butoxy-7-(4-(3-morpholinopropoxy)benzyl)imidazo[2,1-f][1,2,4]triazin-4-amine Step A: 4-(3-morpholinopropoxy)benzaldehyde A mixture of 4-(3-bromopropoxy)benzaldehyde (300 mg, 1.2 mmol), morpholine (209 mg, 2.4 mmol) and potassium carbonate (193 mg, 2.4 mmol) in acetonitrile (10 mL) was heated at 80° C. overnight. The solution was cooled, concentrated, added with water (10 mL) and extracted with ethyl acetate (10 mL). The organic layer was dried, concentrated and purified by CombiFlash (DCM:MeOH=8%) to get the product as a colorless oil (260 mg, 84%). $^1$H NMR (400 MHz, DMSO-d6) δ 9.87 (s, 1H), 7.86 (d, J=8.0 Hz, 2H), 7.12 (d, J=8.0 Hz, 2H), 4.13 (t, J=8.0 Hz, 2H), 3.59-3.51 (m, 4H), 2.44-2.36 (m, 6H), 1.99-1.87 (m, 2H) ppm. MS: M/e 250 (M+1)$^+$.

Step B: (4-(bis(4-methoxybenzyl)amino)-2-butox-imidazo[2,1-f][1,2,4]triazin-7-yl)(4-(3-morpholinopropoxy)phenyl)methanol To a cooled solution of 7-bromo-2-butoxy-N,N-bis(4-methoxybenzyl)imidazo[2,1-f][1,2,4]triazin-4-amine (200 mg, 0.4 mmol) in THF (8 mL) at −78° C. (purged with N$^2$), n-BuLi (1.6 M, 0.7 mL) was added dropwise. After stirred at −78° C. for 30 mins, 4-(3-morpholinopropoxy)benzaldehyde (150 mg, 0.6 mmol) in THF (2 mL) was added. The resulting mixture was stirred at this temperature for 30 mins, and then warmed to rt for 1 hour. The solution was quenched with NH$_4$Cl solution (5 mL), extracted with ethyl acetate (10 mL) and washed with brine (10 mL). The organic layer was dried over Na$_2$SO$_4$, filtered and concentrated to get the crude product, which was further purified by Combiflash (DCM:MeOH=6%) to get the pure product (190 mg, 71%). MS: M/e 697 (M+1)$^+$.

Step C: 2-butoxy-7-(4-(3-morpholinopropoxy)benzyl)imidazo[2,1-f][1,2,4]triazin-4-amine (Compound A22)

A solution of (4-(bis(4-methoxybenzyl)amino)-2-butoxy-imidazo[2,1-f][1,2,4]triazin-7-yl)(4-(3-morpholinopropoxy)phenyl)methanol (190 mg, 0.27 mmol) in trifluoroacetic acid (2 mL) and triethylsilane (2 mL) was heated at 80° C. for 1 hour. After concentration, trifluoroacetic acid (2 mL) was added to the residue and the mixture was heated at 80° C. overnight. The solvent was evaporated to get the residue, Which was basified with NaHCO$_3$ solution, extracted with ethyl acetate (5 mL), washed with brine (5 mL). The organic layer was dried, concentrated and purified by CombiFlash (DCM:MeOH=8%) to get the product (84 mg, 70%). $^1$H NMR (400 MHz, DMSO-d6) δ 8.12 (s, 1H), 8.02 (s, 1H), 7.25 (s, 1H), 7.20 (d, J=8.0 Hz, 2H), 6.83 (d, J=8.0 Hz, 2H), 4.20 (t, J=8.0 Hz, 2H), 4.05 (s, 2H), 3.95 (t, J=8.0 Hz, 2H), 3.55 (t, J=4.0 Hz, 4H), 2.40-2.34 (m, 6H), 1.87-1.81 (m, 2H), 1.68-1.63 (m, 2H), 1.43-1.37 (m, 2H), 0.92 (t, J=8.0 Hz, 3H) ppm. MS: M/e 441 (M+1)$^+$.

Compound A23: 2-butoxy-7-(3-(3(dimethylamino)propoxy)benzyl)imidazo[2,1-f][1,2,4]triazin-4-amine Step A: (4-(bis(4-methoxybenzyl)amino)-2-butoxy-imidazo[2,1-f][1,2,4]triazin-7-yl)(3-(3-(dimethylamino)propoxy)phenyl)methanol To a stirred solution of 7-bromo-2-butoxy-N,N-bis(4-methoxybenzyl)imidazo[2,1-f][1,2,4]triazin-4-amine (180 mg, 0.34 mmol) in THF (10 ml) at −78° C. under N$_2$ atmosphere, was added n-BuLi (1.6 M, 0.54 ml, 0.86 mmol). The solution was stirred at −78° C. for 30 min. 3-(3-(dimethylamino)propoxy)benzaldehyde (71 mg, 0.34 mmol) in THF (2 ml) was added dropwise to the above solution. After was added, the solution was warmed to rt naturally and then stirred for 3 hr. After was completed, the reaction mixture was quenched with H$_2$O (20 ml) and then extracted with DCM (20 ml×3). The organic phase was washed with H$_2$O (10 ml), dried and concentrated under reduced pressure to afford crude product as a yellow oil, which was used directly for the next step without further purification. MS: M/e 655 (M+1)$^-$.

Step B: 2-butoxy-7-(3-(3-(dimethylamino)propoxy)benzyl)imidazo[2,1-f][1,2,4]triazin-4-amine A solution of (4-(bis(4-methoxybenzyl)amino)-2-butoxy-imidazo[2,1-f][1,2,4]triazin-7-yl)(3-(3-(dimethylamino)propoxy)phenyl)methanol (crude) in TFA (6 ml) and triethylsilane (2 ml) was stirred at 80° C. for 24 hr. After was completed, the reaction mixture was quenched with aq. NaHCO$_3$ (sat., 25 ml) and then extracted with DCM (20 ml×3). The organic phase was concentrated under reduced pressure and the resulting residue was purified by prep-TLC with DCM:MeOH (10:1) to afford the product (18.32 mg). $^1$H NMR (400 MHz, DMSO-d6) δ 8.15 (s, 1H), 8.08 (s, 1H), 7.31 (s, 1H), 7.23 (t, J=8 Hz, 1H), 6.91 (d, J=8 Hz, 1H), 6.85 (s, 1H), 6.80 (d, J=8 Hz, 1H), 4.21 (t, J=8 Hz, 2H), 4.12 (s, 2H), 4.00 (t, J=8 Hz, 2H), 3.17 (t, J=8 Hz, 2H), 2.78 (s, 6H), 2.13-2.03 (m, 2H), 1.72-1.64 (m, 2H), 1.45-1.36 (m, 2H), 0.93 (t, J=8 Hz, 3H) ppm. MS: M/e 399 (M+1)$^+$.

Compound A24: 2-butoxy-7-(3-(3-(dimethylamino)propoxy)-4-fluorobenzyl)imidazo[2,1-f][1,2,4]triazin-4-amine Step A: (4-(bis(4-methoxybenzyl)amino)-2-butoxy-imidazo[2,1-f][1,2,4]triazin-7-yl)(3-(3-(dimethylamino)propoxy)-4-fluorophenyl)methanol To a stirred solution of 7-bromo-2-butoxy-N,N-bis(4-methoxybenzyl)imidazo[2,1-f][1,2,4]triazin-4-amine (257 mg, 0.49 mmol) in THF (10 ml) at −78° C. under N$_2$ atmosphere, was added n-BuLi (1.6 M, 0.76 ml, 1.22 mmol). The solution was stirred at −78° C. for 30 min. 3-(3-(dimethylamino)propoxy)-4-fluorobenzaldehyde (110 mg, 0.49 mmol) in THF (2 ml) was added dropwise to the above solution. After added, the solution was warmed to rt naturally and then stirred for 3 hr. After was completed, the reaction mixture was quenched with H$_2$O (20 ml) and then extracted with DCM (20 ml×3). The organic phase was washed with H$_2$O (10 ml), dried and concentrated under reduced pressure to afford crude product as a yellow oil, which was used directly for the next step without further purification. MS: M/e 673 (M+1)$^+$.

Step B: 2-butoxy-7-(3-(3-(dimethylamino)propoxy)-4-fluorobenzyl)imidazo[2,1-f][1,2,4]triazin-4-amine (Compound A24)

A solution of (4-(bis(4-methoxybenzyl)amino)-2-butoxy-imidazo[2,1-f][1,2,4]triazin-7-yl)(3-(3-(dimethylamino)propoxy)-4-fluorophenyl)methanol (crude) in TFA (6 ml) and triethylsilane (2 ml) was stirred at 80° C. for 24 hr. After was completed, the reaction mixture was quenched with aq. NaHCO$_3$ (sat., 25 ml) and then extracted with DCM (20 ml×3). The organic phase was concentrated under reduced pressure and the resulting residue was purified by prep-TLC with DCM:MeOH (10:1) to afford the product (43.52 mg). $^1$H NMR (400 MHz, DMSO-d6) δ 8.14 (s, 1H), 8.06 (s, 1H), 7.29 (s, 1H), 7.22-7.08 (m, 2H), 6.92-6.83 (m, 1H), 4.20 (t, J=8 Hz, 2H), 4.11 (s, 2H), 4.08 (t, J=8 Hz, 2H), 3.15 (t, J=8 Hz, 2H), 2.75 (s, 6H), 2.18-2.06 (m, 2H), 1.72-1.61 (m, 2H), 1.45-1.34 (m, 2H), 0.92 (t, J=8 Hz, 3H) ppm. MS: M/e 417 (M+1)$^+$.

Compound A25: 2-butoxy-7-((4'-(pyrrolidin-1-ylmethyl)-[1,1'-biphenyl]-3-yl)methyl)imidazo[2,1-f][1,2,4]triazin-4-amine Step A: (4-(bis(4-methoxybenzyl)amino)-2-butoxy-imidazo[2,1-f][1,2,4]triazin-7-yl)(4'-(pyrrolidin-1-ylmethyl)-[1,1'-biphenyl]-3-yl)methanol To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. under N$_2$ and stirred for 1 h. Then a solution of 4'-(pyrrolidin-1-ylmethyl)-[1,1'-biphenyl]-3-carbaldehyde (114 mg, 0.4278 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over Na$_2$SO$_4$, concentrated and purified by column chromatography (DCM/MeOH=20:1~5:1) to give the title product (103 mg, 51%) as yellow oil. MS: M/e 713 (M+1)$^+$.

Step B: 2-butoxy-7-((4'-(pyrrolidin-1-ylmethyl)-[1,1'-biphenyl]-3-yl)methyl)imidazo[2,1-f][1,2,4]triazin-4-amine (Compound A25)

A mixture of (4-(bis(4-methoxybenzyl)amino)-2-butoxyimidazo[2,1-f][1,2,4]triazin-7-yl)(4'-(pyrrolidin-1-ylmethyl)-[1,1'-biphenyl]-3-yl)methanol (103 mg, 0.1447 mmol) and triethylsilane (1 mL) in TFA (2 mL) was stirred at 90° C. overnight. The mixture was concentrated and purified with prep-HPLC to give the target product (50 mg, 75.63%). $^1$H NMR (400 MHz, DMSO-d6) δ 9.80 (br.s, 1H), 8.13 (1H), 8.09 (s, 1H), 7.73-7.54 (m, 6H), 7.39-7.28 (m, 3H), 4.39 (d, J=5.5 Hz, 2H), 4.23 (s, 2H), 4.18 (t, J=6.5 Hz, 2H), 3.43-3.35 (m, 2H), 3.16-3.11 (m, 2H), 2.08-2.03 (m, 2H), 1.94-1.78 (m, 2H), 1.69-1.57 (m, 2H), 1.41-1.28 (m, 2H), 0.88 (t, J=7.4 Hz, 3H) ppm. MS: M/e 457 (M+1)$^+$.

Compound A26: 2-butoxy-7-(2-fluoro-5-(pyrrolidin-1-ylmethyl)benzyl)Imidazo[2,1-f][1,2,4]triazin-4-amine Step A: 2-fluoro-5-(pyrrolidin-1-ylmethyl)benzonitrile To a stirred solution of 2-fluoro-5-formylbenzonitrile (447 mg, 3 mmol) in MeOH (5 mL) was added pyrrolidine (234 mg, 3.3 mmol), then the mixture was stirred for 2 hours followed by NaBH$_3$CN (378 mg, 6 mmol). After the addition, the reaction mixture was concentrated to give the residue, which was purified by column chromatography (petroleum ether/EtOAc=2:1) to give the target compound (350 mg, 57.2%) as yellow oil. MS: M/e 205 (M+1)$^+$.

Step B: 2-fluoro-5-(pyrrolidin-1-ylmethyl)benzaldehyde

To a stirred solution of the product of Step A (350 mg, 1.7 mmol) in dry THF (10 mL) was added DIBAL-H (1.2 M, 3.57 mL, 4.3 mmol) dropwise at −20° C. After the addition, the reaction was stirred for 3 hours at room temperature. The reaction was quenched with aq.NH$_4$Cl, extracted with EtOAc (20 mL×3) and filtered. The filtrate was washed with brine, dried over Na$_2$SO$_4$, concentrated and purified by column chromatography (petroleum ether/EtOAc=3:1~2:1) to give the target compound (180 mg, 51.1%) as light yellow oil. MS: M/e 208 (M+1)$^+$.

Step C: (4-(bis(4-methoxybenzyl)amino)-2-butoxyimidazo[2,1-f][1,2,4]triazin-7-yl)(2-fluoro-5-(pyrrolidin-1-ylmethyl)phenyl)methanol To a solution of 7-bromo-2-butoxy-N,N-bis(4-methoxybenzyl)imidazo[2,1-f][1,2,4]triazin-4-amine (150 mg, 0.285 mmol) in THF (10 mL) was added n-BuLi (0.44 mL, 0.71 mmol) dropwise −78° C. After stirring for an hour, a solution of the product of Step B (88.7 mg, 0.428 mmol) in THF (2 mL) was added dropwise. The resulting mixture was stirred at −70° C. for 1 h and then warmed to room temperature for 1 h. The reaction was quenched with sat.aq.NH$_4$Cl solution, extracted with EtOAc (10 mL×3). The combined organic layers were washed with brine, dried over Na$_2$SO$_4$, filtered, and concentrated. The residue was purified by prep-TLC (petroleum ether/EtOAc=1:1) to give target compound (55 mg, 29.4%). MS: M/e 655 (M+1)$^+$.

Step D: 2-butoxy-7-(2-fluoro-5-(pyrrolidin-1-ylmethyl)benzyl)imidazo[2,1-f][1,2,4]triazin-4-amine (Compound A26)

To a mixture of the product of Step C (55 mg, 0.084 mmol) in Et$_3$SiH/TFA (0.5 mL/3 mL) was stirred at 85° C. overnight. The reaction mixture was concentrated to give the residue, which was purified by prep-HPLC to give the target compound (20 mg, 59.8%). $^1$H NMR (400 MHz, DMSO-d$_6$) δ 8.13 (s, 1H), 8.03 (s, 1H), 7.26 (s, 1H), 7.24-7.04 (m, 3H), 4.18-4.13 (m, 4H), 3.45 (s, 2H), 2.35-2.28 (m, 4H), 1.66-1.61 (m, 6H), 1.37-1.29 (m, 2H), 0.90 (t, J=7.2 Hz, 3H) ppm. MS: M/e 399 (M+1)$^+$.

Compound A27: 2-butoxy-7-(2-fluoro-5-(pyrrolidin-1-ylmethyl)benzyl)imidazo[2,1-f][1,2,4]triazin-4-amine Step A: 2-(3-(dimethylamino)propoxy)benzaldehyde A mixture of 2-hydroxybenzaldehyde (1.73 g, 10 mmol), 3-chloro-N,N-dimethylpropan-1-amine hydrochloride (1.74 g, 1.1 mmol) and K$_2$CO$_3$ (2.76 g, 20 mmol) in DMF (10 mL) was stirred at 60° C. overnight. The reaction mixture was poured into H$_2$O (50 mL) and extracted with EtOAc (20 mL×3). The combined organic layers were washed with brine, dried over Na$_2$SO$_4$, concentrated and purified by column chromatography (petroleum ether/EtOAc=5:1~100% EtOAc) to give the target compound (1.96 g, 76%) as light yellow oil. MS: M/e 208 (M+1)$^+$.

Step B: (4-(bis(4-methoxybenzyl)amino)-2-butoxyimidazo[2,1-f][1,2,4]triazin-7-yl)(2-(3-(dimethylamino)propoxy)phenyl)methanol To a solution of 7-bromo-2-butoxy-N,N-bis(4-methoxybenzyl)imidazo[2,1-f][1,2,4]triazin-4-amine (150 mg, 0.285 mmol) in THF (10 mL) was added n-BuLi (1.6 M, 0.44 mL, 0.71 mmol) dropwise at −78° C. After stirring for an hour, a solution of the product of Step A (88.7 mg, 0.428 mmol) in THF (2 mL) was added dropwise. The resulting mixture was stirred at −70° C. for 1 h and then warmed to room temperature for 1 h. The reaction was quenched with sat.aq. NH$_4$Cl solution, extracted with EtOAc (10 mL×3). The combined organic layers were washed with brine, dried over Na$_2$SO$_4$, filtered, and concentrated. The residue was purified by prep-TLC (CH$_2$Cl$_2$/MeOH=10:1) to give target compound (62 mg, 33%) as a white solid. MS: M/e 655 (M+1)$^+$.

Step C: 2-butoxy-7-(2-(3-(dimethylamino)propoxy)benzyl)imidazo[2,1-f][1,2,4]triazin-4-amine (Compound A27)

To a mixture of the product of Step B (62 mg, 0.095 mmol) in Et$_3$SiH/TFA (0.5 mL/3 mL) was stirred at 85° C. overnight. The reaction mixture was concentrated to give the residue, which was purified by prep-HPLC to give the target compound (24 mg, 63.4%). $^1$H NMR (400 MHz, DMSO-d$_6$) δ 8.09 (s, 1H), 8.00 (s, 1H), 7.22-7.18 (m, 2H), 7.10 (s, 1H), 6.95 (d, J=8.4 Hz, 1H), 6.85 (t, J=7.6 Hz, 1H), 4.21 (t, J=6.4 Hz, 2H), 4.07 (s, 2H), 3.96 (t, J=6.4 Hz, 2H), 2.23 (t, J=7.2 Hz, 2H), 2.08 (s, 6H), 1.85-1.61 (m, 4H), 1.48-1.35 (m, 2H), 0.92 (t, J=7.2 Hz, 3H) ppm. MS: Me 399 (M+1)$^+$.

Compound A28: 2-butoxy-7-(4-(3-(pyrrolidin-1-yl)propoxy)benzyl)imidazo[2,1-f][1,2,4]triazin-4-amine Step A: 4-(3-(pyrrolidin-1-yl)propoxy)benzaldehyde A solution of 4-(3-bromopropoxy)benzaldehyde (300 mg, 1.2 mmol), pyrrolidine (170 mg, 2.4 mmol), sodium carbonate (254 mg, 2.4 mmol) and potassium iodide (17 mg, 0.1 mmol) in acetonitrile (10 mL) was heated at 80° C. overnight. The solution was concentrated, treated with water (10 mL) and extracted with dichloromethane (10 mL). The organic layer was dried, concentrated and purified by CombiFlash (DCM:MeOH=8%) to get the product (200 mg, 70%) as a colorless oil. MS: M/e 234 (M+1)$^+$.

Step B: (4-(bis(4-methoxybenzyl)amino)-2-butoxy-imidazo[2,1-f][1,2,4]triazin-7-yl)(4-(3-(pyrrolidin-1-yl)propoxy)phenyl)methanol To a cooled solution of 7-bromo-2-butoxy-N,N-bis(4-methoxybenzyl)imidazo[2,1-f][1,2,4]triazin-4-amine (210 mg, 0.4 mmol) in THF (8 mL) at −78° C. (purged with N$^2$), n-BuLi (1.6 M, 0.7 mL) was added dropwise. After was stirred at −78° C. for 30 mins, 4-(3-(pyrrolidin-1-yl)propoxy)benzaldehyde (140 mg, 0.6 mmol) in THF (2 mL) was added. The resulting mixture was stirred at this temperature for 30 mins, and then warmed to rt for 1 hour. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by Combiflash (DCM:MeOH=7%) and prep-TLC (DCM:MeOH=6:1) to get the pure product (108 mg, 40%). MS: M/e 681 (M+1)$^+$.

Step C: 2-butoxy-7-(4-(3-(pyrrolidin-1-yl)propoxy)benzyl)imidazo[2,1-f][1,2,4]triazin-4-amine (Compound A28)

A solution of (4-(bis(4-methoxybenzyl)amino)-2-butoxy-imidazo[2,1-f][1,2,4]triazin-7-yl)(4-(3-(pyrrolidin-1-yl)propoxy)phenyl)methanol (108 mg, 0.16 mmol) in trifluoroacetic acid (2 mL) and triethylsilane (2 mL) was heated at 80° C. for 1 hour. After concentration, trifluoroacetic acid (1 mL) was added to the residue and the mixture was heated at 80° C. overnight. The solvent was evaporated to get the residue, which was basified with NaHCO$_3$, extracted with ethyl acetate (5 mL), washed with brine (5 mL). The organic layer was dried, concentrated and purified by CombiFlash (DCM:MeOH=18%) to get the product (25 mg, 37%). $^1$H NMR (400 MHz, DMSO-d6) δ 8.11 (s, 1H), 8.02 (s, 1H), 7.25 (s, 1H), 7.20 (d, J=8.0 Hz, 2H), 6.83 (d, J=8.0 Hz, 2H), 4.20 (t, J=8.0 Hz, 2H), 4.05 (s, 2H), 3.95 (t, J=8.0 Hz, 2H), 2.51 (s, 2H), 2.43 (s, 4H), 1.88-1.81 (m, 2H), 1.70-1.63 (m, 6H), 1.43-1.37 (m, 2H), 0.92 (t, J=8.0 Hz, 3H) ppm. MS: M/e 425 (M+1)$^+$.

Compound A29: 2-butoxy-7-(4-(3-(diethylamino)propoxy)benzyl)imidazo[2,1-f][1,2,4]triazin-4-amine Step A: 4-(3-(diethylamino)propoxy)benzaldehyde DEAD (1 g, 6 mmol) was added dropwise to a solution of 4-hydroxybenz-aldehyde (0.5 g, 4 mmol), 3-(diethylamino)propan-1-ol (0.5 g, 4 mmol) and triphenylphosphane (1.6 g, 6 mmol) in THF (10 mL) at 0° C. under N$_2$ atmosphere. The mixture was warmed to rt and stirred overnight. The solution was concentrated and purified by CombiFlash (PE:EA=80%) to get the product (0.4 g, 42%) as a colorless oil. MS: M/e 236 (M+1)$^+$.

Step B: (4-(bis(4-methoxybenzyl)amino)-2-butoxy-imidazo[2,1-f][1,2,4]triazin-7-yl)(4-(3-(diethylamino)propoxy)phenyl)methanol To a cooled solution of 7-bromo-2-butoxy-N,N-bis(4-methoxybenzyl)imidazo[2,1-f][1,2,4]triazin-4-amine (200 mg, 0.4 mmol) in THF (8 mL) at −78° C. (purged with N$^2$) n-BuLi (1.6 M, 0.6 mL) was added dropwise. After was stirred at −78° C. for 30 mins, 4-(3-(diethylamino)propoxy)benzaldehyde (134 mg, 0.6 mmol) in THF (2 mL) was added. The resulting mixture was stirred at this temperature for 30 mins, and then warmed to rt for 1 hour. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by Combiflash (DCM:MeOH=8%) and prep-TLC (DCM:MeOH=7:1) to get the pure product (150 mg, 58%). MS: M/e 683 (M+1)$^+$.

Step C: 2-butoxy-7-(4-(3-(diethylamino)propoxy)benzyl)imidazo[2,1-f][1,2,4]triazin-4-amine (Compound A29)

A solution of (4-(bis(4-methoxybenzyl)amino)-2-butoxy-imidazo[2,1-f][1,2,4]triazin-7-yl)(4-(3-(diethylamino)propoxy)phenyl)methanol (150 mg, 0.22 mmol) in trifluoroacetic acid (2 mL) and triethylsilane (2 mL) was heated at 80° C. for 1 hour. After concentration, trifluoroacetic acid (2 mL) was added to the residue and the mixture was heated at 80° C. overnight. The solvent was evaporated to get the residue, which was basified with NaHCO$_3$, extracted with ethyl acetate (5 mL), washed with brine (5 mL). The organic layer was dried, concentrated and purified by prep-TLC (DCM:MeOH=7:1) to get the product (50 mg, 54%). $^1$H NMR (400 MHz, DMSO-d6) δ 8.12 (s, 1H), 8.04 (s, 1H), 7.25 (s, 1H), 7.23 (d, J=8.0 Hz, 2H), 6.86 (d, J=12.0 Hz, 2H), 4.20 (t, J=8.0 Hz, 2H), 4.07 (s, 2H), 4.02 (t, J=8.0 Hz, 2H), 3.13 (s, 6H), 2.08 (br.s, 2H), 1.71-1.64 (m, 2H), 1.45-1.36 (m, 2H), 1.20 (t, J=8.0 Hz, 6H), 0.93 (t, J=8.0 Hz, 3H) ppm. MS: M/e 427 (M+1)$^+$.

Compound A30: 2-butoxy-7-((4'-(pyrrolidin-1-ylmethyl)-[1,1'-biphenyl]-4-yl)methyl)imidazo[2,1-f][1,2,4]triazin-4-amine Step A: (4-(bis(4-methoxybenzyl)amino)-2-butoxy-imidazo[2,1-f][1,2,4]triazin-7-yl)(4'-(pyrrolidin-1-ylmethyl)-[1,1'-biphenyl]-4-yl)methanol To a solution of 7-bromo-2-butoxy-N,N-bis(4-methoxybenzyl)imidazo[2,1-f][1,2,4]triazin-4-amine (150 mg, 0.23 mmol) in THF (5 mL), n-Butyllithium (0.27 ml, 0.43 mmol) was added dropwise at −78° C. and stirred for 1 h. Then a solution of 4'-(pyrrolidin-1-ylmethyl)-[1,1'-biphenyl]-4-carbaldehyde (114 mg, 0.43 mmol) in THF (2 mL) was added dropwise at −78° C., after addition, the mixture was warmed to rt and stirred for 3 h. The mixture was quenched with saturated ammonium chloride solution (5 mL), extracted with DCM (30 mL×3). The combined organic layers were washed with brine, dried over Na$_2$SO$_4$, concentrated and purified by column chromatography (DCM/MeOH=20:1~5:1) to give the title product (124 mg, 61%) as yellow oil. MS: M/e 713 (M+1)$^+$.

Step B: 2-butoxy-7-((4'-(pyrrolidin-1-ylmethyl)-[1,1'-biphenyl]-4-yl)methyl)imidazo[2,1-f][1,2,4]triazin-4-amine (Compound A30)

A mixture of (4-(bis(4-methoxybenzyl)amino)-2-butoxy-imidazo[2,1-f][1,2,4]triazin-7-yl)(4'-(pyrrolidin-1-ylmethyl)-[1,1'-biphenyl]-4-yl)methanol (124 mg, 0.17 mmol) and triethylsilane (1 mL) in TFA (2 mL) was stirred at 90° C. overnight. The mixture was concentrated and purified with prep-HPLC to give 2-butoxy-7-((4'-(pyrrolidin-1-ylmethyl)-[1,1'-biphenyl]-4-yl)methyl)imidazo[2,1-f][1,2,4]triazin-4-amine (58 mg, 73%). $^1$H NMR (400 MHz, DMSO-d6) δ 9.74 (br.s, 1H), 8.17 (s, 1H), 8.06 (s, 1H), 7.78-7.75 (m, 2H), 7.64-7.53 (m, 4H), 7.43-7.38 (m, 2H), 7.36 (s, 1H), 4.38 (d, J=5.7 Hz, 2H), 4.26-4.18 (m, 4H), 3.42-3.35 (m, 2H), 3.21-3.12 (m, 2H), 2.14-2.02 (m, 2H), 1.92-1.83 (m, 2H), 1.72-1.61 (m, 2H), 1.42-1.33 (m, 2H), 0.91 (t, J=7.4 Hz, 3H) ppm. MS: M/e 457 (M+1)$^+$.

Compound A31: 7-(4-(3-aminopropoxy)benzyl)-2-butoxyimidazo[2,1-f][1,2,4]triazin-4-amine Step A: tert-butyl (3-(4-formylphenoxy)propyl)carbamate To a solution of 4-hydroxybenzaldehyde (1.22 g, 10 mmol), tert-butyl (3-hydroxypropyl)carbamate (2.62 g, 15 mmol) and PPh$_3$ (3.93 g, 15 mmol) in THF (15 mL) was added DIAD (7.57 g, 15 mmol, 40% in toluene solution) dropwise. Then the mixture was stirred at room temperature for 5 hours. The mixture was diluted with water (50 mL), extracted with EtOAc (60 mL×2). The combined organic layers were washed with brine, dried over Na$_2$SO$_4$, filtered, concentrated and the residue was purified by combi flash to give the target compound (2.53 g, 90%). MS: M/e 224 (M+H-t-Bu)$^+$.

Step B: tert-butyl(3-(4-((4-(bis(4-methoxybenzyl)amino)-2-butoxyimidazo[2,1-f][1,2,4]triazin-7-yl)(hydroxy)methyl)phenoxy)propyl)carbamate To a solution of 7-bromo-2-butoxy-N,N-bis(4-methoxybenzyl)imidazo[2,1-f][1,2,4]triazin-4-amine (300 mg, 0.57 mmol) in THF (8 mL) was added a solution of n-BuLi (0.9 mL, 1.42 mmol) dropwise and maintaining the temperature between −75~−65° C. After 1 h, a mixture of the product of Step A (238 mg, 0.855 mmol) in THF (2 mL) was added dropwise. The resulting mixture was stirred at −70° C. for 0.5 h and then warmed to room temperature for 2 hours. The reaction was quenched with saturated NH$_4$Cl solution, extracted with EtOAc (50 mL), washed with brine, dried over Na$_2$SO$_4$, filtered, and concentrated. The residue was purified by prep-TLC (EA/PE=1/3) to give the target compound (100 mg, crude). MS: M/e 727 (M+1)$^+$.

Step C: 7-(4-(3-aminopropoxy)benzyl)-2-butoxyimidazo[2,1-f][1,2,4]triazin-4-amine (Compound A31)

To a mixture of the product of Step B (100 mg, crude) in TFA (3 mL) was added Et$_3$SiH (1 mL). The reaction was heated at 85° C. overnight. The mixture was cooled to room temperature and concentrated to dryness. To the residue was added TFA (3 mL) and the resulting mixture was heated at 85° C. overnight. The mixture was concentrated to dryness and the residue was purified by prep-HPLC. The collected fraction was basified with NaHCO$_3$ solution, extracted with DCM (50 mL×2), washed with brine, dried over Na$_2$SO$_4$, filtered, and concentrated to give the target compound (30 mg, 15% for two steps). $^1$HNMR (400 MHz, DMSO-d$_6$) δ 8.11 (s, 1H), 8.02 (s, 1H), 7.25 (s, 1H), 7.20 (d, J=8.8 Hz, 2H), 6.84 (d, J=8.4 Hz, 2H), 4.20 (t, J=6.0 Hz, 2H), 4.05 (s, 2H), 3.97 (t, J=6.4 Hz, 2H), 3.05-2.90 (m, 2H), 2.68 (t, J=7.2 Hz, 2H), 1.86-1.59 (m, 4H), 1.49-1.35 (m, 2H), 0.92 (t, J=7.6 Hz, 3H) ppm. MS: M/e 371 (M+1)$^+$.

Compound A32: 2-butoxy-7-((6-(3-(dimethylamino) propoxy)53yridine-3-yl) methyl)imidazo[2,1-f][1,2,4]53yridine-4-amine Step A: 6-(3-(dimethylamino)propoxy)nicotinaldehyde DEAD (2.1 g, 12 mmol) was added dropwise to a solution of 6-hydroxy nicotin aldehyde (1 g, 8.1 mmol), 3-(dimethylamino)propan-1-ol (837 mg, 8.1 mmol) and triphenylphosphane (3.1 g, 12 mmol) in THF (20 mL) at 0° C. under N$_2$ atmosphere. The mixture was warmed to rt and stirred overnight. The solution was quenched with water (20 mL), extracted with ethyl acetate (20 mL) and washed with brine (10 mL). The organic layer was dried, concentrated and purified by CombiFlash (EA to DCM:MeOH=10%) to get the product (0.5 g, 30%) as a colorless oil. $^1$H NMR (400 MHz, DMSO-d6) δ 9.95 (s, 1H), 8.74 (d, J=4.0 Hz, 1H), 8.10 (dd, J=8.0, 4.0 Hz, 1H), 6.96 (d, J=8.0 Hz, 1H), 4.40 (t, J=8.0 Hz, 2H), 2.37-2.35 (m, 2H), 2.13 (s, 6H), 1.88-1.85 (m, 2H) ppm. MS: M/e 209 (M+1)$^+$.

Step B: (4-(bis(4-methoxybenzyl)amino)-2-butoxyimidazo[2,1-f][1,2,4]triazin-7-yl)(6-(3-(dimethylamino)propoxy)pyridin-3-yl)methanol To a cooled solution of 7-bromo-2-butoxy-N,N-bis(4-methoxybenzyl)imidazo[2,1-f][1,2,4]triazin-4-amine (420 mg, 0.8 mmol) in THF (12 mL) at −78° C. (purged with N$^2$), n-BuLi (1.6 M, 1.3 mL) was added dropwise. After stirred at −78° C. for 30 mins, 6-(3-(dimethylamino)propoxy)nicotinaldehyde (250 mg, 1.2 mmol) in THF (3 mL) was added. The resulting mixture was stirred at this temperature for 30 mins, and then warmed to rt overnight. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by Combiflash (DCM:MeOH=8%) to get the pure product as a white solid (133 mg, 46%). MS: M/e 656 (M+1)$^+$.

Step C: 2-butoxy-7-((6-(3-(dimethylamino)propoxy) pyridin-3-yl)methyl)imidazo[2,1-f][1,2,4]triazin-4-amine (Compound A32)

A solution of (4-(bis(4-methoxybenzyl)amino)-2-butoxy-imidazo[2,1-f][1,2,4]triazin-7-yl)(6-(3-(dimethylamino) propoxy)pyridin-3-yl)methanol (78 mg, 0.12 mmol) in trifluoroacetic acid (2 mL) and triethylsilane (2 mL) was heated at 80° C. for 1 hour. After concentration, trifluoroacetic acid (2 mL) was added to the residue and the mixture was heated at 80° C. overnight. The solvent was evaporated to get the residue, which was basified with NaHCO$_3$, extracted with ethyl acetate (5 mL), washed with brine (5 mL). The organic layer was dried, concentrated and purified by prep-TLC (DCM:MeOH=8:1) to get the product (10 mg, 21%). $^1$H NMR (400 MHz, DMSO-d6) δ 8.13 (s, 2H), 8.06 (s, 1H), 7.65 (d, J=8.0 Hz, 1H), 7.30 (s, 1H), 6.75 (d, J=8.0 Hz, 1H), 4.27 (t, J=8.0 Hz, 2H), 4.20 (t, J=8.0 Hz, 2H), 4.09 (s, 2H), 3.14 (t, J=8.0 Hz, 2H), 2.74 (s, 6H), 2.12-2.05 (m, 2H), 1.71-1.64 (m, 2H), 1.45-1.36 (m, 2H), 0.93 (t, J=8.0 Hz, 3H) ppm. MS: M/e 400 (M+1)$^+$.

Compound A33: 2-butoxy-7-(4-(piperidin-4-ylmethyl)benzyl)imidazo[2,1-f][1,2,4]triazin-4-amine Step A: methyl 4-((diethoxyphosphoryl)methyl)benzoate A solution of methyl 4-(bromomethyl)benzoate (5.5 g, 24 mmol) in triethyl phosphite (15 mL) was stirred at 115° C. for 4 h. The mixture was cooled to room temperature, concentrated and the residue was purified by combi flash to give the target compound (6.16 g, 90%). MS: M/e 287 (M+1)$^+$.

Step B: tert-butyl 4-(4-(methoxycarbonyl)benzylidene)piperidine-1-carboxylate

To a solution of the product of Step A (6.16 g, 21.54 mmol) in THF (60 mL) was added LDA (12 mL, 23.69 mmol) dropwise at −70° C. After being stirred at this temperature for 30 min, a solution of tert-butyl 4-oxopiperidine-1-carboxylate (4.7 g, 23.69 mmol) in THF (10 mL) was added. The resulting mixture was warmed slowly to room temperature overnight. The reaction was quenched with saturated NH$_4$Cl solution, extracted with EtOAc (80 mL×2). The combined organic layers were washed with brine, dried over Na$_2$SO$_4$, filtered, and concentrated. The residue was purified by combi flash to give the target compound (4.5 g, 63%). MS: M/e 276 (M+H-tBu)$^+$.

Step C: tert-butyl 4-(4-(methoxycarbonyl)benzyl)piperidine-1-carboxylate

To a solution of the product of Step B (4.5 g, 13.6 mmol) in MeOH (40 mL) was added 10% Pd/C (450 mg). The reaction was stirred at room temperature under H$_2$ atmosphere (balloon) for 4 h. The catalyst was filtered off and the filtrate was concentrated to give the target compound (4 g, 88%). MS: M/e 278 (M+H-tBu)$^+$.

Step D: tert-butyl 4-(4-(hydroxymethyl)benzyl)piperidine-1-carboxylate

To a solution of LiAlH$_4$ (273 mg, 7.2 mmol) in THF (10 mL) was added the product of Step C (2 g, 6 mmol) in THF (10 mL) dropwise at 0° C. After addition the resulting mixture was warmed slowly to room temperature overnight. The reaction was quenched with saturated water (0.3 mL), 10% NaOH solution (0.3 mL) and water (0.9 mL). The resulting mixture was filtered and the filtrate was concentrated to give the target compound (1.65 g, 90%). $^1$HNMR (400 MHz, CD$_3$Cl) δ 7.28 (d, J=7.6 Hz, 2H), 7.13 (d, J=8.4 Hz, 2H), 4.66 (s, 2H), 4.06 (d, J=12.8 Hz, 2H), 2.71-2.57 (m, 2H), 2.53 (d, J=6.4 Hz, 2H), 1.73-1.54 (m, 5H), 1.44 (s, 9H) ppm.

Step E: tert-butyl 4-(4-formylbenzyl)piperidine-1-carboxylate

To a solution of the product of Step D (1.65 g, 5.4 mmol) in THF (30 mL) was added Dess-Martin reagent (4.58 g, 10.8 mmol) at 0° C. in some portions. The mixture was stirred at room temperature for 1 h. The reaction was quenched with saturated K$_2$CO$_3$ solution, filtered through a pad of Celite, washed with EA (50 mL). The filtrate was washed with water and brine, dried over Na$_2$SO$_4$, filtered, and concentrated. The residue was purified by combi flash to give the target compound (475 mg, 29%). MS: M/e 248 (M+H-tBu)$^+$.

Step F: tert-butyl 4-(4-((4-(bis(4-methoxybenzyl)amino)-2-butoxyimidazo[2,1-f][1,2,4]triazin-7-yl)(hydroxy)methyl)benzyl)piperidine-1-carboxylate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.6 mL, 0.95 mmol) dropwise maintaining the temperature between −75~−65° C. After 1 h, a mixture of the product of Step E (172 mg, 0.57 mmol) in THF (2 mL) was added dropwise. The resulting mixture was stirred at −70° C. for 0.5 h and then warmed to room temperature overnight. The reaction was quenched with saturated NH$_4$Cl solution, extracted with EtOAc (50 mL), washed with brine, dried over Na$_2$SO$_4$, filtered, and concentrated. The residue was purified by prep-TLC (EA/PE=1/2) to give the target compound (60 mg, crude). MS: M/e 751 (M+1)$^+$.

Step G: 2-butoxy-7-(4-(piperidin-4-ylmethyl)benzyl)imidazo[2,1-f][1,2,4]triazin-4-amine (Compound A33)

To a mixture of the product of Step F (60 mg, 0.08 mmol) in TFA (3 mL) was added Et$_3$SiH (0.5 mL). The reaction was heated at 85° C. overnight. The mixture was concentrated to dryness and the residue was purified by prep-HPLC. The collected fraction was basified with NaHCO$_3$ solution, extracted with DCM (60 mL), washed with brine, dried over Na$_2$SO$_4$, filtered, and concentrated to give the target compound (4 mg, 3% for two steps). $^1$HNMR (400 MHz, DMSO-d$_6$) δ 8.12 (s, 1H), 8.03 (s, 1H), 7.29 (s, 1H), 7.21 (d, J=8.0 Hz, 2H), 7.07 (d, J=8.0 Hz, 2H), 4.19 (t, J=6.0 Hz, 2H), 4.09 (s, 2H), 3.00 (d, J=12.0 Hz, 2H), 2.53-2.49 (m, 2H), 2.44 (d, J=7.2 Hz, 2H), 1.75-1.49 (m, 5H), 1.48-1.34 (m, 2H), 1.18-1.04 (m, 2H), 0.92 (t, J=7.2 Hz, 3H) ppm. MS: M/e 395 (M+1)$^+$.

Compound A34: 2-butoxy-7-((5-chloro-6-(3-(dimethylamino)propoxy)pyridin-3-yl)methyl)imidazo[2,1-f][1,2,4]triazin-4-amine Step A: 5-chloro-6-(3-(dimethylamino)propoxy)nicotinaldehyde To a solution of 5,6-dichloronicotinaldehyde (1.76 g, 10 mmol) and K$_2$CO$_3$ (1.65 g, 12 mmol) in DMF (20 mL) was added 3-(dimethylamino)propan-1-ol (1.13 g, 11 mmol). Then the mixture was stirred at 80° C. overnight under N$_2$. The mixture was cooled to room temperature, diluted with water (50 mL), extracted with EtOAc (50 mL×2). The combined organic layers were washed with brine, dried over Na$_2$SO$_4$, filtered, concentrated and the residue was purified by flash chromatograph to give the target compound (0.5 g, 21%). $^1$HNMR (400 MHz, CDCl$_3$) δ 9.93 (s, 1H), 8.50 (d, J=2.2 Hz, 1H), 8.11 (d, J=2.2 Hz, 1H), 4.56 (t, J=6.0 Hz, 2H), 2.56 (t, J=7.6 Hz, 2H), 2.33 (s, 6H), 2.15-2.03 (m, 2H) ppm. MS: M/e 243 (M+1)$^+$.

Step B: (4-(bis(4-methoxybenzyl)amino)-2-butoxy-imidazo[2,1-f][1,2,4]triazin-7-yl)(5-chloro-6-(3-(dimethylamino)propoxy)pyridin-3-yl)methanol To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.6 mL, 0.95 mmol) dropwise maintaining the temperature between −75∼−65° C. After 1 h, a mixture of the product of Step A (138 mg, 0.57 mmol) in THF (2 mL) was added dropwise. The resulting mixture was stirred at −70° C. for 1 h and then warmed to room temperature overnight. The reaction was quenched with saturated $NH_4Cl$ solution, extracted with EtOAc (50 mL×2), washed with brine, dried over $Na_2SO_4$, filtered, and concentrated. The residue was purified by prep-TLC (DCM/MeOH=10/1) to give the target compound (60 mg, crude). MS: M/e 690 (M+1)$^+$.

Step C: 2-butoxy-7-((5-chloro-6-(3-(dimethylamino)propoxy)pyridin-3-yl)methyl)imidazo[2,1-f][1,2,4]triazin-4-amine (Compound A34)

To a mixture of the product of Step B (60 mg, crude) in TFA (3 mL) was added $Et_3SiH$ (0.5 mL) and the resulting mixture was heated at 80° C. overnight. The mixture was cooled to room temperature and concentrated to dryness. To the residue was added TFA (3 mL) and the resulting mixture was heated at 85° C. overnight. The mixture was concentrated to dryness and the residue was purified by prep-HPLC. The collected fraction was basified with $NaHCO_3$ solution, extracted with DCM (50 mL×2), washed with brine, dried over $Na_2SO_4$, filtered, and concentrated to give the target compound (8 mg, 5% for two steps). $^1$HNMR (400 MHz, $CD_3OD$) δ 8.02 (d, J=2.0 Hz, 1H), 7.75 (d, J=2.0 Hz, 1H), 7.36 (s, 1H), 4.38 (t, J=6.0 Hz, 2H), 4.28 (t, J=6.4 Hz, 2H), 4.15 (s, 2H), 2.59 (t, J=8.0 Hz, 2H), 2.32 (s, 6H), 2.05-1.94 (m, 2H), 1.82-1.70 (m, 2H), 1.56-1.43 (m, 2H), 0.98 (t, J=7.2 Hz, 3H) ppm. MS: M/e 434 (M+1)$^+$.

Compound A35: 2-butoxy-7-(4-(3-(dimethylamino)propoxy)-3-fluorobenzyl)imidazo[2,1-f][1,2,4]triazin-4-amine Step A: (4-(bis(4-methoxybenzyl)amino)-2-butoxy-imidazo[2,1-f][1,2,4]triazin-7-yl)(4-(3-(dimethyl-amino)propoxy)-3-fluorophenyl)methanol To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. under $N_2$ and stirred for 1 h. Then a solution of 4-(3-(dimethylamino)propoxy)-3-fluorobenzaldehyde (96 mg, 0.43 mmol) in THF (2 mL) was added dropwise at −78° C., then the mixture was warmed to rt and stirred for 3 h. The mixture was quenched with a saturated of ammonium chloride solution (5 mL), extracted with DCM (30 mL×3). The combined organic layers were washed with brine, dried over $Na_2SO_4$, concentrated and purified by column chromatography (DCM/MeOH=20:1∼5:1) to give the product (136 mg, 70.86%) as yellow oil. MS: M/e 673 (M+1)$^+$.

Step B: 2-butoxy-7-(4-(3-(dimethylamino)propoxy)-3-fluorobenzyl)imidazo[2,1-f][1,2,4]triazin-4-amine (Compound A35)

A mixture of (4-(bis(4-methoxybenzyl)amino)-2-butoxy-imidazo[2,1-f][1,2,4]triazin-7-yl)(4-(3-(dimethylamino)propoxy)-3-fluorophenyl)methanol (136 mg, 0.2 mmol) and triethylsilane (1 mL) in TFA (2 mL) was stirred at 90° C. overnight. The mixture was concentrated and purified with prep-HPLC to give product (34 mg, 40%). $^1$H NMR (400 MHz, DMSO-d6) δ 9.36 (br.s, 1H), 8.14 (s, 1H), 8.07 (s, 1H), 7.30 (s, 1H), 7.19 (d, J=12.6 Hz, 1H), 7.13-7.02 (m, 2H), 4.20 (t, J=6.5 Hz, 2H), 4.11-4.02 (m, 4H), 3.20 (dd, J=15.2, 5.5 Hz, 2H), 2.81 (d, J=4.8 Hz, 6H), 2.09 (dt, J=12.3, 6.1 Hz, 2H), 1.76-1.57 (m, 2H), 1.47-1.33 (m, 2H), 0.92 (t, J=7.4 Hz, 3H) ppm. MS: M/e 417 (M+1)$^+$.

Compound A36: 2-butoxy-7-(4-(3-(dimethylamino)propoxy)-2-fluorobenzyl)imidazo[2,1-f][1,2,4]triazin-4-amine Step A: (4-(bis(4-methoxybenzyl)amino)-2-butoxy-imidazo[2,1-f][1,2,4]triazin-7-yl)(4-(3-(dimethyl-amino)propoxy)-2-fluorophenyl)methanol To a solution of 7-bromo-2-butoxy-N,N-bis(4-methoxybenzyl)imidazo[2,1-f][1,2,4]triazin-4-amine (150 mg, 0.29 mmol) in THF (5 mL), n-Butyllithium (0.27 ml, 0.43 mmol) was added dropwise at −78° C. and stirred for 1 h. Then a solution of 4-(3-(dimethylamino)propoxy)-2-fluorobenzaldehyde (96 mg, 0.43 mmol) in THF (2 mL) was added dropwise at −78° C., after addition, the mixture was warmed to rt and stirred for 3 hrs. The mixture was quenched with saturated ammonium chloride solution (5 mL), extracted with DCM (30 mL×3). The combined organic layers were washed with brine, dried over $Na_2SO_4$, concentrated and purified by column chromatography (DCM/MeOH=20:1∼5:1) to give the product (107 mg, 55.8%) as yellow oil. MS: M/e 673 (M+1)$^+$.

Step B: 2-butoxy-7-(4-(3-(dimethylamino)propoxy)-2-fluorobenzyl)imidazo[2,1-f][1,2,4]triazin-4-amine (Compound A36)

A mixture of (4-(bis(4-methoxybenzyl)amino)-2-butoxy-imidazo[2,1-f][1,2,4]triazin-7-yl)(4-(3-(dimethylamino)propoxy)-2-fluorophenyl)methanol (107 mg, 0.16 mmol) and triethylsilane (1 mL) in TFA (2 mL) was stirred at 90° C. overnight. The mixture was concentrated and purified with prep-HPLC to give the title product (48 mg, 72.6%). $^1$H NMR (400 MHz, DMSO-d6) δ 9.32 (s, 1H), 8.14 (s, 1H), 8.06 (s, 1H), 7.37-7.07 (m, 2H), 6.82 (dd, J=11.9, 2.1 Hz, 1H), 6.72 (d, J=8.4 Hz, 1H), 4.19 (t, J=6.5 Hz, 2H), 4.08 (s, 2H), 4.02 (t, J=5.9 Hz, 2H), 3.25-3.17 (m, 2H), 2.80 (s, 6H), 2.12-2.00 (m, 2H), 1.74-1.59 (m, 2H), 1.47-1.34 (m, 2H), 0.92 (t, J=7.4 Hz, 3H) ppm. MS: M/e 417 (M+1)$^+$.

Compound A37: 7-((6-(2-aminoethoxy)pyridin-3-yl)methyl)-2-butoxyimidazo[2,1-f][1,2,4]triazin-4-amine Step A: tert-butyl (2-((5-formylpyridin-2-yl)oxy)ethyl)carbamate $K_2CO_3$ (2.76 g, 20 mmol) was added to a solution of 6-chloronicotinaldehyde (1.41 g, 10 mmol) and tert-butyl (2-hydroxyethyl)carbamate (1.61 g, 10 mmol) in DMA (20 mL), the reaction mixture was stirred at 80° C. overnight, was cooled to room temperature. The solution was quenched with $H_2O$ (10 ml). The aqueous solution was extracted with EA (20 ml×4). The collected organic layers were washed with brine, dried over $Na_2SO_4$, filtered and concentrated.

The resulting residue was purified by column chromatography to afford the product (120 mg, 4%). MS: M/e 267 (M+1)$^+$.

Step B: tert-butyl (2-((5-((4-(bis(4-methoxybenzyl) amino)-2-butoxyimidazo[2,1-f][1,2,4]triazin-7-yl) (hydroxy)methyl)pyridin-2-yl)oxy)ethyl)carbamate To a solution of 7-bromo-2-butoxy-N,N-bis(4-methoxybenzyl)imidazo[2,1-f][1,2,4]triazin-4-amine (158 mg, 0.3 mmol) in THF (2 mL) was added dropwise a solution of n-BuLi (0.38 mL, 0.6 mmol) maintaining the temperature between −75~−65° C. After 10 min, a solution of product of Step A (120 mg, 0.45 mmol) in THF (3 mL) was added dropwise. The resulting mixture was stirred at −70° C. for 20 min. The reaction was quenched with saturated NH$_4$Cl solution, extracted with EtOAc (5 mL×3), washed with brine, dried over Na$_2$SO$_4$, filtered, and concentrated. The residue was purified by column chromatography to give target compound (80 mg, 37%). MS: M/e 714 (M+1)$^+$.

Step C: 7-((6-(2-aminoethoxy)pyridin-3-yl)methyl)-2-butoxyimidazo[2,1-f][1,2,4]triazin-4-amine (Compound A37)

To a mixture of the product of Step B (80 mg, 0.11 mmol) in TFA (1 mL) was added Et$_3$SiH (1 mL). The reaction was heated at 80° C. for 3 h. The mixture was concentrated to dryness and the residue was treated with TFA (2 mL). The reaction was heated at 80° C. overnight. The mixture was concentrated and the residue was purified by prep-HPLC. The collected fraction was basified with NaHCO$_3$ solution, extracted with DCM (30 mL), washed with brine, dried over Na$_2$SO$_4$, filtered, and concentrated to give the title product (12 mg, 33%). $^1$H NMR (400 MHz, CDCl3) δ 8.12 (s, 1H) 7.51 (d, J=8.0 Hz, 1H), 7.25 (s, 1H), 6.70 (d, J=8.0 Hz, 1H), 4.35-4.21 (m, 4H), 4.11 (s, 2H), 3.06 (t, J=6.0 Hz, 2H), 1.62-1.51 (m, 2H), 1.47-1.35 (m, 4H), 0.98 (t, J=8.0 Hz, 3H) ppm. MS: M/e 358 (M+1)$^+$.

Compound A38: 7-(4-(((1R,5S)-8-azabicyclo[3.2.1]octan-3-yl)oxy)-2-fluorobenzyl)-2-butoxyimidazo[2,1-f][1,2,4]triazin-4-amine

Step A: tert-butyl (1R,5S)-3-(3-fluoro-4-formylphenoxy)-8-azabicyclo [3.2.1] octane-8-carboxylate DIAD (3.8 mL, 7.2 mmol) was added dropwise to a solution of 2-fluoro-4-hydroxybenzaldehyde (500 mg, 3.6 mmol), tert-butyl(1R,5S)-3-hydroxy-8-azabicyclo[3.2.1]octane-8-carboxylate (817 mg, 3.6 mmol) and triphenylphosphane (1.8 g, 7.2 mmol) in THF (20 mL) at 0° C. under N$_2$ atmosphere. The mixture was warmed to rt and stirred overnight. The solution was quenched with water (20 mL), extracted with ethyl acetate (20 mL) and washed with brine (10 mL). The organic layer was dried, concentrated and purified by CombiFlash (PE:EA=10%) to get the product (330 mg, 27%) as a colorless oil. $^1$H NMR (400 MHz, CDCl$_3$) δ 10.21 (s, 1H), 7.83 (t, J=8.0 Hz, 1H), 6.72 (dd, J=8.0, 4.0 Hz, 1H), 6.57 (dd, J=12, 4.0 Hz, 1H), 4.70 (t, J=4.0 Hz, 1H), 4.24 (s, 2H), 2.20 (d, J=12.0 Hz, 2H), 2.08-1.94 (m, 6H), 1.49 (s, 9H) ppm. MS: M/e 350 (M+1)$^+$.

Step B: tert-butyl(1R,5S)-3-(4-((4-(bis(4-methoxybenzyl)amino)-2-butoxyimidazo[2,1-f][1,2,4]triazin-7-yl)(hydroxy)methyl)-3-fluorophenoxy)-8-azabicyclo[3.2.1]octane-8-carboxylate To a cooled solution of 7-bromo-2-butoxy-N,N-bis(4-methoxybenzyl)imidazo[2,1-f][1,2,4]triazin-4-amine (200 mg, 0.38 mmol) in THF (8 mL) at −78° C. (purged with N$^2$), n-BuLi (1.6 M, 0.6 mL) was added dropwise. After stirred at −78° C. for 30 mins, tert-butyl (1R,5S)-3-(3-fluoro-4-formylphenoxy)-8-azabicyclo[3.2.1]octane-8-carboxylate (199 mg, 0.57 mmol) in THF (2 mL) was added. The resulting mixture was stirred at this temperature for 30 mins, and then warmed to rt overnight. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by CombiFlash (PE: EA=30%) to get the pure product as a red oil (190 mg, 63%). MS: M/e 797 (M+1)$^+$.

Step C: 7-(4-(((1R,5S)-8-azabicyclo[3.2.1]octan-3-yl)oxy)-2-fluorobenzyl)-2-butoxyimidazo[2,1-f][1,2,4]triazin-4-amine (Compound A38)

A mixture of tert-butyl (1R,5S)-3-(4-((4-(bis(4-methoxybenzyl)amino)-2-butoxyimidazo[2,1-f][1,2,4]triazin-7-yl) (hydroxy)methyl)-3-fluorophenoxy)-8-azabicyclo[3.2.1]octane-8-carboxylateTriethylsilane (190 mg, 0.24 mmol) in triethylsilane (3 mL) and trifluoroacetic acid (3 mL) was heated at 80° C. for 2 hrs. The solution was concentrated, added with trifluoroacetic acid (2 mL) and heated at 80° C. overnight. The solvent was evaporated to get the residue, which was basified with NaHCO$_3$ water (5 mL), extracted with ethyl acetate (5 mL), washed with brine (5 mL). The organic layer was dried, concentrated and purified by prep-HPLC to get the product (30 mg, 33%). $^1$H NMR (400 MHz, DMSO-d6) δ 8.14 (s, 1H), 8.04 (s, 1H), 7.25 (s, 1H), 7.18 (t, J=8.0 Hz, 1H), 6.72 (d, J=12.0 Hz, 1H), 6.62 (d, J=8.0 Hz, 1H), 4.59 (s, 1H), 4.19 (t, J=8.0 Hz, 2H), 4.06 (s, 2H), 3.37 (s, 2H), 1.99-1.91 (m, 4H), 1.77 (s, 1H), 1.74 (s, 1H), 1.68-1.64 (m, 4H), 1.44-1.35 (m, 2H), 0.92 (t, J=8.0 Hz, 3H) ppm. MS: M/e 441 (M+1)$^+$.

Compound A39: 1-(4-(4-((4-amino-2-butoxyimidazo[2,1-f][1,2,4]triazin-7-yl)methyl)benzyl)piperazin-1-yl)-2-(dimethylamino)ethan-1-one To a mixture of 2-butoxy-7-(4-(piperazin-1-ylmethyl) benzyl)imidazo[2,1-f][1,2,4]triazin-4-amine (20 mg, 0.052 mmol), dimethylglycine (5 mg, 0.05 mmol) and DIEA (12 mg, 0.1 mmol) in THF (4 mL) was added HATU (19 mg, 0.05 mmol). The reaction was stirred at room temperature overnight. The reaction was diluted with water, extracted with DCM (20 mL×2), washed with brine, dried over Na$_2$SO$_4$, filtered, and concentrated. The residue was purified by prep-TLC to give the target compound (2 mg, 8.3%). $^1$HNMR (400 MHz, CD$_3$OD) δ 7.34-7.24 (m, 5H), 4.28 (t, J=6.4 Hz, 2H), 4.19 (s, 2H), 4.09 (s, 2H), 3.66-3.58 (m, 2H), 3.54 (s, 2H), 3.43-3.36 (m, 2H), 2.84 (s, 6H), 2.55-2.40 (m, 4H), 1.83-1.70 (m, 2H), 1.55-1.45 (m, 2H), 0.98 (t, J=7.6 Hz, 3H) ppm. MS: M/e 481 (M+1)$^+$.

Compound A40: 2-butoxy-7-((5-chloro-6-(piperidin-4-yloxy)pyridin-3-yl)methyl)imidazo[2,1-f][1,2,4] triazin-4-amine

Step A: tert-butyl 4-((5-bromo-3-chloropyridin-2-yl) oxy)piperidine-1-carboxylate To a solution of NaH (0.6 g, 15 mmol) in DMA (15 mL) was added tert-butyl 4-hydroxypiperidine-1-carboxylate (2.2 g, 11 mmol). The mixture was stirred at room temperature for 1 h. Then a solution of 5-bromo-2,3-dichloropyridine (2.26 g, 10 mmol) in DMA (5 mL) was added and the resulting mixture was stirred at 80° C. overnight under N₂ protect. The mixture was cooled to room temperature, diluted with water (50 mL), extracted with EtOAc (60 mL×2). The combined organic layers were washed with brine, dried over Na₂SO₄, filtered, concentrated and the residue was purified by combi-flash to give the target compound (2.23 g, 57%). MS: M/e 335 (M+H-t-Bu)⁺.

Step B: tert-butyl 4-((3-chloro-5-formylpyridin-2-yl)oxy)piperidine-1-carboxylate To a solution of the product of Step A (2.23 g, 5.7 mmol) in THF (15 mL) was added a solution of n-BuLi (5.3 mL, 8.55 mmol) dropwise maintaining the temperature between −75~−65° C. After 1 h, DMF (500 mg, 6.3 mmol) was added dropwise and the resulting mixture was stirred at −70° C. for 2 h. The reaction was quenched with saturated NH₄Cl solution, extracted with EtOAc (40 mL×2), washed with brine, dried over Na₂SO₄, filtered, and concentrated. The residue was purified by combi-flash to give the target compound (350 mg, 18%) as oil. ¹H NMR (400 MHz, CDCl₃) δ 9.93 (s, 1H), 8.49 (d, J=2.0 Hz, 1H), 8.12 (d, J=2.0 Hz, 1H), 5.49-5.41 (m, 1H), 3.79-3.65 (m, 2H), 3.49-3.38 (m, 2H), 2.05-1.92 (m, 2H), 1.91-1.78 (m, 2H), 1.47 (s, 9H) ppm. MS: M/e 341 (M+1)⁺.

Step C: tert-butyl 4-((5-((4-(bis(4-methoxybenzyl)amino)-2-butoxyimidazo[2,1-f][1,2,4]triazin-7-yl)(hydroxy)methyl)-3-chloropyridin-2-yl)oxy)piperidine-1-carboxylate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.6 mL, 0.95 mmol) dropwise maintaining the temperature between −75~−65° C. After 1 h, a mixture of the product of Step B (155 mg, 0.456 mmol) in THF (2 mL) was added dropwise. The resulting mixture was stirred at −70° C. for 1 h and then warmed to room temperature for 5 h. The reaction was quenched with saturated NH₄Cl solution, extracted with EtOAc (60 mL), washed with brine, dried over Na₂SO₄, filtered, and concentrated. The residue was purified by prep-TLC (EA/PE=1/2) to give the target compound (80 mg, crude). MS: M/e 788 (M+1)⁺.

Step D: 2-butoxy-7-((5-chloro-6-(piperidin-4-yloxy)pyridin-3-yl)methyl)imidazo[2,1-f][1,2,4]triazin-4-amine (Compound A40)

To a mixture of the product of Step C (80 mg, crude) in TFA (3 mL) was added Et₃SiH (0.5 mL) and the resulting mixture was stirred at 85° C. overnight. The mixture was cooled to room temperature and concentrated to dryness. The residue was purified by prep-HPLC. The collected fractions were basified with NaHCO₃ solution, extracted with DCM (50 mL), washed with brine, dried over Na₂SO₄, filtered, and concentrated to give the target compound (20 mg, 45% for two steps). ¹HNMR (400 MHz, DMSO-d₆) δ 8.15 (s, 1H), 8.10-8.01 (m, 2H), 7.84 (d, J=2.0 Hz, 1H), 7.34 (s, 1H), 5.15-5.04 (m, 1H), 4.19 (t, J=6.4 Hz, 2H), 4.09 (s, 2H), 3.02-2.90 (m, 2H), 2.64-2.53 (m, 2H), 1.98-1.86 (m, 2H), 1.72-1.60 (m, 2H), 1.59-1.46 (m, 2H), 1.44-1.32 (m, 2H), 0.92 (t, J=7.2 Hz, 3H) ppm. MS: M/e 432 (M+1)⁺.

Compound A41: 7-(4-(((1S,4S)-2,5-diazabicyclo[2.2.1]heptan-2-yl)methyl)benzyl)-2-butoxyimidazo[2,1-f][1,2,4]triazin-4-amine Step A: tert-butyl (1S,4S)-5-(4-formylbenzyl)-2,5-diazabicyclo[2.2.1]heptane-2-carboxylate The mixture of 4-(chloromethyl)benzaldehyde (2 g, 12.9 mmol), tert-butyl (1S,4S)-2,5-diazabicyclo[2.2.1]heptane-2-carboxylate (3.06 g, 15.5 mmol) and K₂CO₃ (3.56 g, 25.8 mmol) in CH₃CN (30 mL) was stirred at 50° C. overnight. The reaction was cooled to room temperature. The mixture was diluted with water (50 mL) and extracted with EA (30 mL×3). The combined organic phase was washed with brine, dried over Na₂SO₄ and concentrated under reduced pressure. The residue was purified by combiflash to obtain the title compound (3.8 g, yield: 93.1%) as a brown oil. ¹H NMR (400 MHz, DMSO-d6) δ9.98 (s, 1H), 7.86 (d, J=8.0 Hz, 2H), 7.56 (d, J=8.0 Hz, 2H), 3.79 (s, 2H), 3.42-3.37 (m, 2H), 3.19-3.00 (m, 1H), 2.83-2.70 (m, 1H), 2.53-2.38 (m, 1H), 1.85-1.75 (m, 1H), 1.72-1.55 (m, 1H), 1.48-1.32 (m, 10H) ppm. MS: M/e 317 (M+1)⁺.

Step B: tert-butyl (1S,4S)-5-(4-((4-(bis(4-methoxybenzyl)amino)-2-butoxyImidazo[2,1-f][1,2,4]triazin-7-yl)(hydroxy)methyl)benzyl)-2,5-diazabicyclo[2.2.1]heptane-2-carboxylate To a stirred solution of 7-bromo-2-butoxy-N,N-bis(4-methoxybenzyl)imidazo[2,1-f][1,2,4]triazin-4-amine (150 mg, 0.29 mmol) in THF (10 mL) was added n-BuLi (1.6 M, 0.45 mL) at −78° C. under N₂ atmosphere. The mixture was stirred at −78° C. for 1 hour. Then the product of Step A (135 mg, 0.43 mmol) in THF (0.5 mL) was added to the system at −78° C. The reaction was warmed to room temperature and stirred overnight. The reaction was quenched with saturated NH₄Cl aqueous at room temperature. The mixture was extracted with EA (20 mL×3). The combined organic phase was washed with brine, dried over Na₂SO₄ and concentrated under reduced pressure. The residue was purified by combiflash to afford the title compound (140 mg, yield: 63.3%) as a yellow oil. MS: M/e 764 (M+1)⁺.

Step C: 7-(4-(((1S,4S)-2,5-diazabicyclo[2.2.1]heptan-2-yl)methyl)benzyl)-2-butoxyimidazo[2,1-f][1,2,4]triazin-4-amine (Compound A41)

To a stirred solution of the product of Step B (140 mg, 0.18 mmol) in Et₃SiH (4 mL) was added CF₃COOH (4 mL) at room temperature. The mixture was stirred at 80° C. for 1 hour. The reaction was cooled to room temperature and concentrated under reduced pressure. The residue was dissolved into CF₃COOH (4 mL). And the mixture was stirred at 80° C. overnight. The reaction was cooled to room temperature. The mixture was concentrated under reduced pressure. The residue was purified by prep-HPLC to afford the title compound (12 mg, yield: 16.1%). ¹H NMR (400 MHz, DMSO-d6) δ8.19-7.97 (m, 2H), 7.30 (s, 1H), 7.25-7.19 (m, 4H), 4.20 (t, J=6.4 Hz, 2H), 4.11 (s, 2H), 3.67-3.55 (m, 2H), 3.31-3.18 (m, 2H), 3.03 (d, J=9.6 Hz, 1H), 2.68 (t, J=8.4 Hz, 2H), 2.36 (d, J=9.6 Hz, 1H), 1.77-1.60 (m, 3H), 1.49-1.33 (m, 3H), 0.92 (t, J=7.2 Hz, 3H) ppm. MS: M/e 408 (M+1)⁺.

Compound A42: 2-butoxy-7-(4-(2-(pyrrolidin-1-yl)ethyl)benzyl)imidazo[2,1-f][1,2,4]triazin-4-amine

Step A: 4-bromophenethyl 4-methylbenzenesulfonate

To a stirred solution of 2-(4-bromophenyl)ethan-1-ol (4 g, 20 mmol) in DCM (40 mL) was added 4-Methylbenzenesulfonyl chloride (4.12 g, 20.14 mmol) and $Et_3N$ (2.18 g, 20.14 mmol). The reaction mixture was stirred at rt overnight. The mixture was added 1N HCl aqueous solution (40 mL) and extracted with DCM (20 ml×3). The combined organic phase was washed with brine, dried over $Na_2SO_4$ and concentrated in vacuo to give the product (7.7 g, 100%) as a yellow oil. and was used in next step without further purification.

Step B: 1-(4-bromophenethyl)pyrrolidine

To a stirred solution of 4-bromophenethyl 4-methylbenzenesulfonate (7 g, 20 mmol) in MeCN (50 mL) was added pyrrole (5.6 g, 77 mmol) and $Et_3N$ (8 g, 80 mmol). The reaction mixture was stirred at rt overnight. The mixture was concentrated in vacuo. The residue was added $H_2O$ (40 mL) and extracted with DCM (20 ml×3). The combined organic phase was washed with brine, dried over $Na_2SO_4$ and concentrated in vacuo. The crude product was purified by column chromatography to give the product (4.3 g, 86%) as a yellow oil. MS: M/e 254 $(M+1)^+$.

Step C: 4-(2-(pyrrolidin-1-yl)ethyl)benzaldehyde

To a stirred solution of 1-(4-bromophenethyl)pyrrolidine (1 g, 4 mmol) in THF (20 mL), cooled to −78° C. and under atmosphere of nitrogen was added n-BuLi (1.6 M in hexane, 4.4 mmol, 2.7 mL) dropwise. After stirring for 60 mins, a solution of DMF (876 mg, 12 mmol) in THF (3 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over $Na_2SO_4$, concentrated in vacuo. The crude product was purified by column chromatography to give the title product (600 mg, 73.8%). MS: M/e 204 $(M+1)^+$.

Step D: (4-(bis(4-methoxybenzyl)amino)-2-butoxyimidazo[2,1-f][1,2,4]triazin-7-yl)(4-(2-(pyrrolidin-1-yl)ethyl)phenyl)methanol To a stirred solution of 7-bromo-2-butoxy-N,N-bis(4-methoxybenzyl)imidazo[2,1-f][1,2,4]triazin-4-amine (150 mg, 0.29 mmol) in THF (10 mL), cooled to −78° C. under atmosphere of nitrogen was added n-BuLi (1.6 M in hexane, 0.71 mmol, 0.47 mL) dropwise. After stirring for 20 mins, a solution of 4-(2-(pyrrolidin-1-yl)ethyl)benzaldehyde (87.5 mg, 0.43 mmol) in THF (2 mL) was added slowly. The reaction mixture was warmed up slowly to rt and stirred overnight. The reaction mixture was poured into saturated ammonium chloride solution and extracted with EtOAc (15 mL×3). The combined organic phase was washed with brine, dried over $Na_2SO_4$, concentrated in vacuo. The crude product was purified by column chromatography to give the title product (80 mg, 43%). MS: M/e 651 $(M+1)^+$.

Step E: 2-butoxy-7-(4-(2-(pyrrolidin-1-yl)ethyl)benzyl)imidazo[2,1-f][1,2,4]triazin-4-amine (Compound A42)

A solution of (4-(bis(4-methoxybenzyl)amino)-2-butoxyimidazo[2,1-f][1,2,4]triazin-7-yl)(4-(2-(pyrrolidin-1-yl)ethyl)phenyl)methanol (80 mg, 0.123 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (14 mg, 29%). $^1H$ NMR (400 MHz, DMSO-d6)) δ 8.12 (s, 1H), 8.03 (s, 1H), 7.28 (s, 1H), 7.21 (d, J=7.8 Hz, 2H), 7.13 (d, J=7.8 Hz, 2H), 4.20 (t, J=6.5 Hz, 2H), 4.09 (s, 2H), 2.71-2.59 (m, 2H), 2.65 (s, 2H), 2.50 (s, 4H), 1.68-1.57 (m, 6H), 1.45-1.36 (m, 2H), 0.92 (t, J=7.3 Hz, 3H) ppm. MS: M/e 395 $(M+1)^+$.

Compound A43: 7-(4-((4-aminopiperidin-1-yl)methyl)benzyl)-2-butoxyimidazo[2,1-f][1,2,4]triazin-4-amine

Step A: tert-butyl (1-(4-formylbenzyl)piperidin-4-yl)carbamate

To a solution of 4-(bromomethyl)benzaldehyde (0.4 g, 2 mmol), and DIEA (0.52 g, 4 mmol) in THF (10 mL) was added tert-butyl piperidin-4-ylcarbamate (0.44 g, 2.2 mmol). Then the mixture was stirred at room temperature overnight. The mixture was diluted with water (50 mL), extracted with EtOAc (80 mL), washed with brine, dried over $Na_2SO_4$, filtered, concentrated and the residue was purified by combiflash to give the target compound (0.6 g, 94%). MS: M/e 319 $(M+1)^+$

Step B: tert-butyl (1-(4-((4-(bis(4-methoxybenzyl)amino)-2-butoxyimidazo[2,1-f][1,2,4]triazin-7-yl)(hydroxy)methyl)benzyl)piperidin-4-yl)carbamate To a solution of 7-bromo-2-butoxy-N,N-bis(4-methoxybenzyl)imidazo[2,1-f][1,2,4]triazin-4-amine (380 mg, 0.72 mmol) in THF (12 mL) was added a solution of n-BuLi (1 mL, 1.6 mmol) dropwise maintaining the temperature between −75~−65° C. After 1 h, a mixture of the product of Step A (276 mg, 0.868 mmol) in THF (3 mL) was added dropwise. The resulting mixture was stirred at −70° C. for 1 h and then warmed to room temperature overnight. The reaction was quenched with saturated $NH_4Cl$ solution, extracted with EtOAc (50 mL), washed with brine, dried over $Na_2SO_4$, filtered, and concentrated. The residue was purified by prep-TLC to give target compound (60 mg, crude). MS: M/e 766 $(M+1)^+$.

Step C: 7-(4-((4-aminopiperidin-1-yl)methyl)benzyl)-2-butoxyimidazo[2,1-f][1,2,4]triazin-4-amine (Compound A43)

To a mixture of the product of Step B (60 mg, crude) in TFA (3 mL) was added $Et_3SiH$ (0.5 mL). The resulting mixture was heated at 85° C. overnight. The mixture was concentrated to dryness and the residue was purified by prep-HPLC. The collected fraction was basified with $NaHCO_3$ solution, extracted with DCM (50 mL), washed with brine, dried over $Na_2SO_4$, filtered, and concentrated to give the target compound (7 mg, 2.3% for two steps). $^1HNMR$ (400 MHz, DMSO-$d_6$) δ 8.12 (s, 1H), 8.03 (s, 1H), 7.30 (s, 1H), 7.23 (d, J=7.6 Hz, 2H), 7.18 (d, J=7.6 Hz, 2H), 4.19 (t, J=6.0 Hz, 2H), 4.11 (s, 2H), 3.36 (s, 2H), 3.15-2.80 (m, 2H), 2.74-2.61 (m, 2H), 2.60-2.51 (m, 1H), 1.89 (t, J=10.4 Hz, 2H), 1.72-1.58 (m, 4H), 1.49-1.34 (m, 2H), 1.29-1.15 (m, 2H), 0.92 (t, J=7.6 Hz, 3H) ppm. MS: M/e 410 (M+1)$^+$.

Compound A44: 2-butoxy-7-(4-((3-(dimethylamino)pyrrolidin-1-yl)methyl)benzyl)imidazo[2,1-f][1,2,4]triazin-4-amine

Step A: 4-((3-(dimethylamino)pyrrolidin-1-yl)methyl)benzaldehyde

To a stirred solution of 4-(bromomethyl)benzaldehyde (459 mg, 2.3 mmol) in MeCN (15 mL) was added N,N-dimethylpyrrolidin-3-amine (319 mg, 2.8 mmol) and Et$_3$N (929 mg, 9.2 mmol). The reaction mixture was stirred at rt overnight. The mixture was concentrated in vacuo. The residue purified by prep-HPLC to give the product (100 mg, 18.7%) as a yellow oil. MS: M/e 233 (M+1)$^+$.

Step B: (4-(bis(4-methoxybenzyl)amino)-2-butoxyimidazo[2,1-f][1,2,4]triazin-7-yl)(4-((3-(dimethylamino)pyrrolidin-1-yl)methyl)phenyl)methanol To a stirred solution of 4-((4-(bis(4-methoxybenzyl)amino)-7-bromoimidazo[2,1-f][1,2,4]triazin-2-yl)oxy)butan-2-ylium (150 mg, 0.28 mmol) in THF (10 mL), cooled to −78° C. under atmosphere of nitrogen was added n-BuLi (1.6 M in hexane, 0.7 mmol, 0.43 mL) dropwise. After stirring for 60 mins, a solution of 4-((3-(dimethylamino)pyrrolidin-1-yl)methyl)benzaldehyde (80 mg, 0.34 mmol) in THF (2 mL) was added slowly. The reaction mixture was warmed up slowly to rt and stirred for 2 h. The reaction mixture was poured into saturated ammonium chloride solution and extracted by EtOAc (15 mL×3). The combined organic phase was washed with brine, dried over Na$_2$SO$_4$, concentrated in vacuo to give the crude product (110 mg, 57.8%) which was used directly in next step without further purification. MS: M/e 680 (M+1)$^+$.

Step C: 2-butoxy-7-(4-((3-(dimethylamino)pyrrolidin-1-yl)methyl)benzyl)imidazo[2,1-f][1,2,4]triazin-4-amine (Compound A44)

A solution of (4-(bis(4-methoxybenzyl)amino)-2-butoxyimidazo[2,1-f][1,2,4]triazin-7-yl)(4-((3-(dimethylamino)pyrrolidin-1-yl)methyl)phenyl)methanol (110 mg, 0.162 mmol) in TFA (3 mL) and Et$_3$SiH (3 mL) was stirred at 80° C. for 2 h. The reaction mixture was concentrated in vacuo to remove TFA and Et$_3$SiH. The residue was added TFA (5 mL) and stirred at 85° C. overnight. The mixture was cooled down to rt and concentrated in vacuo. The crude product was purified by prep-HPLC to give the product (30 mg, 43.5%). $^1$H NMR (400 MHz, DMSO-d6)) δ 8.12 (s, 1H), 8.03 (s, 1H), 7.30 (s, 1H), 7.25-7.19 (m, 4H), 4.19 (t, J=6.5 Hz, 2H), 4.11 (s, 2H), 3.52-3.38 (m, 2H), 2.74-2.65 (m, 1H), 2.61 (t, J=8.0 Hz, 1H), 2.53 (d, J=8.4 Hz, 1H), 2.38 (dd, J=14.7, 8.5 Hz, 1H), 2.27-2.16 (m, 1H), 2.07 (s, 6H), 1.81 (dd, J=13.3, 6.0 Hz, 1H), 1.72-1.53 (m, 3H), 1.42-1.33 (m, 2H), 0.91 (t, J=7.4 Hz, 3H) ppm. MS: M/e 424 (M+1)$^+$.

Compound A45: 2-butoxy-7-((5-chloro-6-(3-(dimethylamino)-2,2-dimethylpropoxy)pyridin-3-yl)methyl)imidazo[2,1-f][1,2,4]triazin-4-amine

Step A: 3-((5-bromo-3-chloropyridin-2-yl)oxy)-N,N,2,2-tetramethylpropan-1-amine To a stirred suspension of NaH (60%, 600 mg, 15 mmol) in DMA (15 mL) was added a solution of 3-(dimethylamino)-2,2-dimethylpropan-1-ol (1.44 g, 1.1 mmol) in DMA (2 mL). After stirred for 30 min, a solution of 5-bromo-2,3-dichloropyridine (2.26 g, 10 mmol) in DMA (2 mL) was added. After the addition, the reaction was stirred at 80° C. overnight. The reaction was quenched with H$_2$O (10 mL) and extracted with EtOAc (20 mL×3). The combined organic layers were washed with brine, dried over Na$_2$SO$_4$, concentrated and purified by column chromatography (petroleum ether/EtOAc=20:1~5:1) to give the target compound (2.3 g, 71.5%) as colorless oil. MS: M/e 321 (M+1)$^+$.

Step B: 5-chloro-6-(3-(dimethylamino)-2,2-dimethylpropoxy)nicotinaldehyde

To a stirred solution of the product of Step A (961.5 mg, 3 mmol) in dry THF (10 mL) was added dropwise n-BuLi (1.6 M, 2.8 mL, 4.5 mL) at −78° C. After stirring for 30 min, DMF (337 mg, 4.5 mmol) was added and stirred for 2 hours. The reaction was quenched with aq.NH$_4$Cl and extracted with EtOAc (10 mL×3). The combined organic layers were washed with brine, dried over Na$_2$SO$_4$, concentrated and purified by column chromatography (petroleum ether/EtOAc=5: 11: 1) to give target compound (550 mg, 68%) as colorless oil. MS: M/e 271 (M+1)$^+$.

Step C: (4-(bis(4-methoxybenzyl)amino)-2-butoxyimidazo[2,1-f][1,2,4]triazin-7-yl)(5-chloro-6-(3-(dimethylamino)-2,2-dimethylpropoxy)pyridin-3-yl)methanol To a solution of 7-bromo-2-butoxy-N,N-bis(4-methoxybenzyl)imidazo[2,1-f][1,2,4]triazin-4-amine (150 mg, 0.286 mmol) in THF (10 mL) was added n-BuLi (1.6 M, 0.44 mL, 0.71 mmol) dropwise −78° C. After stirring for 1 hour, a solution of the product of Step B (115 mg, 0.428 mmol) in THF (2 mL) was added dropwise. The resulting mixture was stirred overnight. The reaction was quenched with sat.aq.NH$_4$Cl solution, extracted with EtOAc (10 mL×3). The combined organic layers were washed with brine, dried over Na$_2$SO$_4$, filtered, and concentrated. The residue was purified by prep-TLC (100% EtOAc) to give target compound (60 mg, 29.3%). MS: M/e 718 (M+1)$^+$.

Step D: 2-butoxy-7-((5-chloro-6-(3-(dimethylamino)-2,2-dimethylpropoxy)pyridin-3-yl)methyl)imidazo[2,1-f][1,2,4]triazin-4-amine (Compound A45)

To a mixture of the product of Step C (70 mg, 0.095 mmol) in Et$_3$SiH/TFA (0.5 mL/3 mL) was stirred at 85° C. overnight. The reaction mixture was concentrated to give the residue, which was purified by prep-HPLC to give the target compound (20 mg, 54.1%). $^1$H NMR (400 MHz, DMSO-d$_6$) δ 8.15 (s, 1H), 8.07 (s, 2H), 7.85 (d, J=2.0 Hz, 1H), 7.34 (s, 1H), 4.19 (t, J=6.4 Hz, 2H), 4.10 (s, 2H), 4.04 (s, 2H), 2.30-2.15 (m, 8H), 1.73-1.61 (m, 2H), 1.44-1.35 (m, 2H), 0.98-0.88 (m, 9H) ppm. MS: M/e 462 (M+1)$^+$.

Compound A46: 7-(4-(aminomethyl)benzyl)-2-butoxyimidazo[2,1-f][1,2,4]triazin-4-amine

Step A: tert-butyl (4-((4-(bis(4-methoxybenzyl)amino)-2-butoxyimidazo[2,1-f][1,2,4]triazin-7-yl)(hydroxy)methyl)benzyl)carbamate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.5 mL, 0.76 mmol) dropwise maintaining the temperature between −75~−65° C. After 1.5 h, a solution of tert-butyl (4-formylbenzyl)carbamate (107 mg, 0.456 mmol) in THF (1 mL) was added dropwise. The resulting mixture was stirred at −70° C. for 1 h and then warmed to room temperature for 1 h. The reaction was quenched with saturated NH$_4$Cl solution, extracted with EtOAc (50 mL), washed with brine, dried over Na$_2$SO$_4$, filtered, and concentrated. The residue was purified by prep-TLC to give the target compound (90 mg, crude). MS: M/e 683 (M+1)$^+$.

Step B: 7-(4-(aminomethyl)benzyl)-2-butoxyimidazo[2,1-f][1,2,4]triazin-4-amine (Compound A46)

To a mixture of the product of Step A (90 mg, crude) in TFA (3 mL) was added Et$_3$SiH (0.5 mL). The reaction was heated at 85° C. overnight. The mixture was concentrated to dryness and the residue was purified by prep-HPLC. The collected fraction was basified with NaHCO$_3$ solution, extracted with DCM (60 mL), washed with brine, dried over Na$_2$SO$_4$, filtered, and concentrated to afford the product (10 mg, 10% for two steps). $^1$HNMR (400 MHz, DMSO-d$_6$) δ 8.11 (s, 1H), 8.03 (s, 1H), 7.27 (s, 1H), 7.25-7.22 (m, 4H), 4.42 (t, J=6.4 Hz, 2H), 4.10 (s, 2H), 3.67 (s, 2H), 1.75-1.60 (m, 2H), 1.50-1.30 (m, 2H), 0.93 (t, J=7.6 Hz, 3H) ppm. MS: M/e 327 (M+1)$^+$.

Compound A47: 2-butoxy-7-(4-((4-phenoxypiperidin-1-yl)methyl)benzyl)imidazo[2,1-f][1,2,4]triazin-4-amine Step A: 4-((4-phenoxypiperidin-1-yl)methyl)benzaldehyde To a solution of 4-(bromomethyl)benzaldehyde (0.4 g, 2 mmol) and DIPEA (0.36 g, 3 mmol) in THF (10 mL) was added 4-phenoxypiperidine (0.35 g, 2 mmol). Then the mixture was stirred at room temperature overnight. The reaction was diluted with water (50 mL), extracted with EtOAc (60 mL), washed with brine, dried over Na$_2$SO$_4$, filtered, concentrated and the residue was purified by flash chromatograph to give the target compound (0.22 g, 37%). MS: M/e 296 (M+1)$^+$.

Step B: tert-butyl (4-(bis(4-methoxybenzyl)amino)-2-butoxyimidazo[2,1-f][1,2,4]triazin-7-yl)(4-((4-phenoxypiperidin-1-yl)methyl)phenyl)methanol To a solution of 7-bromo-2-butoxy-N,N-bis(4-methoxybenzyl)imidazo[2,1-f][1,2,4]triazin-4-amine (150 mg, 0.285 mmol) in THF (5 mL) was added a solution of n-BuLi (0.4 mL, 0.64 mmol) dropwise maintaining the temperature between −75~−65° C. After 1 h, a mixture of the product of Step A (100 mg, 0.34 mmol) in THF (1 mL) was added dropwise. The resulting mixture was stirred at −70° C. for 2 h and then warmed to room temperature overnight. The reaction was quenched with saturated NH$_4$Cl solution, extracted with EtOAc (50 mL), washed with brine, dried over Na$_2$SO$_4$, filtered, and concentrated. The residue was purified by prep-TLC (EA/PE=1/1) to give the target compound (95 mg, crude). MS: M/e 743 (M+1)$^+$.

Step C: 2-butoxy-7-(4-((4-phenoxypiperidin-1-yl)methyl)benzyl)imidazo[2,1-f][1,2,4]triazin-4-amine (Compound A47)

To a mixture of the product of Step B (95 mg, crude) in TFA (3 mL) was added Et$_3$SiH (1 mL) and the resulting mixture was stirred at 85° C. overnight. The mixture was cooled to room temperature and concentrated to dryness. To the residue was added TFA (3 mL) and the resulting mixture was heated at 85° C. overnight. The mixture was concentrated to dryness and the residue was purified by prep-HPLC. The collected fraction was basified with NaHCO$_3$ solution, extracted with DCM (60 mL), washed with brine, dried over Na$_2$SO$_4$, filtered, and concentrated to give the target compound (15 mg, 11% for two steps). $^1$HNMR (400 MHz, DMSO-d$_6$) δ 8.13 (s, 1H), 8.03 (s, 1H), 7.31 (s, 1H), 7.29-7.18 (m, 6H), 6.96-6.85 (m, 3H), 4.42-4.28 (m, 1H), 4.19 (t, J=6.4 Hz, 2H), 4.12 (s, 2H), 3.43 (s, 2H), 2.70-2.58 (m, 2H), 2.25-2.10 (m, 2H), 1.98-1.82 (m, 2H), 1.72-1.50 (m, 4H), 1.46-1.32 (m, 2H), 0.91 (t, J=7.8 Hz, 3H) ppm. MS: M/e 487 (M+1)$^+$.

Compound A48: 2-((5-methylisoxazol-3-yl)methoxy)-7-(4-(pyrrolidin-1-ylmethyl)benzyl)imidazo[2,1-f][1,2,4]triazin-4-amine Step A: 7-bromo-N,N-bis(4-methoxybenzyl)-2-((5-methylisoxazol-3-yl)methoxy)imidazo[2,1-f][1,2,4]triazin-4-amine To a suspension of NaH (80 mg, 2 mmol) in THF (5 mL) was added (5-methylisoxazol-3-yl)methanol (226 mg, 2 mmol). After stirring at room temperature for 30 min, a solution of 7-bromo-2-chloro-N,N-bis(4-methoxybenzyl)imidazo[2,1-f][1,2,4]triazin-4-amine (240 mg, 0.5 mmol) in THF (2 mL) was added. Then the mixture was stirred at 80° C. for 6 h. The mixture was cooled to room temperature, diluted with water (30 mL), extracted with EtOAc (60 mL), washed with brine, dried over Na$_2$SO$_4$, filtered, concentrated and the residue was purified by combi-flash to give the target compound (200 mg, 71%). $^1$HNMR (400 MHz, CDCl$_3$) δ 7.50 (s, 1H), 7.18 (d, J=8.4 Hz, 4H), 6.88-6.82 (m, 4H), 6.18 (s, 1H), 5.61 (s, 2H), 5.43 (s, 2H), 4.85 (s, 2H), 3.80 (s, 6H), 2.40 (s, 3H) ppm. MS: M/e 565 (M+1)$^+$.

Step B: (4-(bis(4-methoxybenzyl)amino)-2-((5-methylisoxazol-3-yl)methoxy)imidazo[2,1-f][1,2,4]triazin-7-yl)(4-(pyrrolidin-1-ylmethyl)phenyl)methanol To a solution of the product of Step A (100 mg, 0.177 mmol) in THF (3 mL) was added a solution of n-BuLi (0.3 mL, 0.44 mmol) dropwise maintaining the temperature between −75~−65° C. After 1 h, a solution of 4-(pyrrolidin-1-ylmethyl)benzaldehyde (80 mg, 0.424 mmol) in THF (1 mL) was added dropwise. The resulting mixture was stirred at −70° C. for 1 h and then warmed to room temperature for 4 h. The reaction was quenched with saturated NH$_4$Cl solution, extracted with EtOAc (50 mL), washed with brine, dried over Na$_2$SO$_4$, filtered, and concentrated. The residue was purified by prep-TLC to give the target compound (50 mg, crude). MS: M/e 676 (M+1)$^+$.

Step C: 2-((5-methylisoxazol-3-yl)methoxy)-7-(4-(pyrrolidin-1-ylmethyl)benzyl)imidazo[2,1-f][1,2,4]triazin-4-amine (Compound A48)

To a mixture of the product of Step B (50 mg, crude) in TFA (3 mL) was added Et$_3$SiH (0.5 mL). The reaction was heated at 85° C. for 16 h. The mixture was concentrated to dryness and the residue was treated with TFA (3 mL). The reaction was heated at 85° C. overnight. The mixture was concentrated and the residue was purified by prep-HPLC.

The collected fraction was basified with NaHCO₃ solution, extracted with DCM (60 mL), washed with brine, dried over Na₂SO₄, filtered, and concentrated to give the target compound (10 mg, 13% for two steps). ¹H NMR (400 MHz, DMSO-d₆) δ 8.28 (s, 1H), 8.19 (s, 1H), 7.34 (s, 1H), 7.30-7.15 (m, 4H), 6.27 (s, 1H), 5.31 (s, 2H), 4.12 (s, 2H), 3.51 (s, 2H), 2.44-2.33 (m, 7H), 1.75-1.62 (m, 4H) ppm. MS: M/e 420 (M+1)⁺.

Compound A49: 2-butoxy-7-(4-(((1R,5S)-8-ethyl-8-azabicyclo[3.2.1] octan-3-yl)oxy)-2-fluorobenzyl) imidazo[2,1-f][1,2,4]triazin-4-amine Step A: 4-(((1R,5S)-8-azabicyclo[3.2.1]octan-3-yl) oxy)-2-fluorobenzaldehyde hydrochloride A solution of tert-butyl (1R,5S)-3-(3-fluoro-4-formylphenoxy)-8-azabicyclo [3.2.1]octane-8-carboxylate (330 mg, 1 mmol) in HCl/dioxane (4M, 4 mL) was stirred rt overnight. The solution was concentrated to get the product of HCl salt as a white solid (250 mg, 92%). MS: M/e 252 (M+1)⁺.

Step B: 4-(((1R,5S)-8-ethyl-8-azabicyclo[3.2.1]octan-3-yl)oxy)-2-fluorobenzaldehyde Iodoethane (156 mg, 1 mmol) was added to a solution of 4-(((1R,5S)-8-azabicyclo[3.2.1]octan-3-yl)oxy)-2-fluorobenzaldehyde hydrochloride (150 mg, 0.5 mmol) and K₂CO₃ (138 mg, 1 mmol) in THF (3 mL) and DMF (3 mL). The solution was stirred at rt overnight, added with water (10 mL), extracted with ethyl acetate (10 mL) and washed with brine (10 mL). The organic layer was dried over Na₂SO₄, filtered and concentrated to get the crude product, which was further purified by prep-TLC (DCM:MeOH=7:1) to get the pure product (60 mg, 41%). MS: M/e 278 (M+1)⁺.

Step C: (4-(bis(4-methoxybenzyl)amino)-2-butoxy-imidazo[2,1-f][1,2,4]triazin-7-yl)(4-(((1R,5S)-8-ethyl-8-azabicyclo[3.2.1]octan-3-yl)oxy)-2-fluorophenyl)methanol To a cooled solution of 7-bromo-2-butoxy-N,N-bis(4-methoxybenzyl)imidazo[2,1-f][1,2,4]triazin-4-amine (100 mg, 0.19 mmol) in THF (8 mL) at −78° C. (purged with N²), n-BuLi (1.6 M, 0.3 mL) was added dropwise. After stirring at −78° C. for 30 mins, 4-(((1R,5S)-8-ethyl-8-azabicyclo [3.2.1]octan-3-yl)oxy)-2-fluorobenzalde hyde (58 mg, 0.21 mmol) in THF (2 mL) was added. The resulting mixture was stirred at this temperature for 30 mins, and then warmed to rt for 2 hrs. The solution was quenched with NH₄Cl solution (5 mL), extracted with ethyl acetate (5 mL) and washed with brine (5 mL). The organic layer was dried with Na₂SO₄, filtered and concentrated to get the crude product, which was further purified by prep-TLC (DCM:MeOH=8:1) to get the product (30 mg, 22%). MS: M/e 725 (M+1)⁺.

Step D: 2-butoxy-7-(4-(((1R,5S)-8-ethyl-8-azabicyclo[3.2.1]octan-3-yl)oxy)-2-fluorobenzyl)imidazo[2,1-f][1,2,4]triazin-4-amine (Compound A49)

A solution of (4-(bis(4-methoxybenzyl)amino)-2-butoxy-imidazo[2,1-f][1,2,4]triazin-7-yl)(4-(((1R,5S)-8-ethyl-8-azabicyclo[3.2.1]octan-3-yl)oxy)-2-fluorophenyl)methanol (28 mg, 0.04 mmol) in triethylsilane (2 mL) and trifluoroacetic acid (2 mL) was heated at 80° C. overnight. The solvent was evaporated to get the residue, which was purified by prep-HPLC to get the product (15 mg, 83%). ¹H NMR (400 MHz, DMSO-d6) δ 9.22 (s, 1H), 8.16 (s, 1H), 8.09 (s, 1H), 7.28 (s, 1H), 7.24 (t, J=8.0 Hz, 1H), 6.91 (dd, J=12.0, J=4.0 Hz, 1H), 6.75 (d, J=8.0 Hz, 1H), 4.71 (s, 1H), 4.20 (t, J=8.0 Hz, 2H), 4.08 (s, 2H), 3.96 (s, 2H), 3.03-2.96 (m, 2H), 2.34-2.30 (m, 2H), 2.21-2.08 (m, 6H), 1.70-1.63 (m, 2H), 1.45-1.36 (m, 2H), 1.24-1.21 (m, 3H), 0.92 (t, J=8.0 Hz, 3H) ppm. MS: M/e 469 (M+1)⁺.

Compound A50: 2-butoxy-7-((5-methoxypyridin-2-yl)methyl)imidazo[2,1-f][1,2,4]triazin-4-amine Step A: (4-(bis(4-methoxybenzyl)amino)-2-butoxy-imidazo[2,1-f][1,2,4]triazin-7-yl)(5-methoxypyridin-2-yl)methanol To a stirred solution of 7-bromo-2-butoxy-N,N-bis(4-methoxybenzyl)imidazo[2,1-f][1,2,4]triazin-4-amine (150 mg, 0.28 mmol) in THF (10 mL), cooled to −78° C. and under atmosphere of nitrogen was added n-BuLi (1.6 M in hexane, 0.7 mmol, 0.43 mL) dropwise. After stirring for 60 mins, a solution of 5-methoxypicolinaldehyde (50 mg, 0.34 mmol) in THF (2 mL) was added slowly. The reaction mixture was slowly warmed up to rt and stirred for 2 h. The reaction mixture was poured into saturated ammonium chloride solution and extracted by EtOAc (15 mL×3). The combined organic phase was washed with brine, dried over Na₂SO₄, concentrated in vacuo to give the title product (200 mg, 100%) which was used directly in next step without further purification. MS: M/e 585 (M+1)⁺.

Step B: 2-butoxy-7-((5-methoxypyridin-2-yl) methyl)imidazo[2,1-f][1,2,4]triazin-4-amine (Compound A50)

A solution of (4-(bis(4-methoxybenzyl)amino)-2-butoxy-imidazo[2,1-f][1,2,4]triazin-7-yl)(5-methoxypyridin-2-yl) methanol (200 mg, 0.28 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (10 mg, 10.8%). ¹H NMR (400 MHz, DMSO-d6)) δ 8.18 (d, J=2.8 Hz, 1H), 8.13 (s, 1H), 8.03 (s, 1H), 7.31 (dd, J=8.5, 2.8 Hz, 1H), 7.28 (s, 1H), 7.24 (d, J=8.6 Hz, 1H), 4.23 (s, 2H), 4.15 (t, J=6.5 Hz, 2H), 3.78 (s, 3H), 1.68-1.57 (m, 2H), 1.43-1.30 (m, 2H), 0.90 (t, J=7.4 Hz, 3H) ppm. MS: M/e 329 (M+1)⁺.

Compound A51: 2-butoxy-7-((6-methoxypyridin-2-yl)methyl)imidazo[2,1-f][1,2,4]triazin-4-amine Step A: (4-(bis(4-methoxybenzyl)amino)-2-butoxy-imidazo[2,1-f][1,2,4]triazin-7-yl)(6-methoxypyridin-2-yl)methanol To a stirred solution of 7-bromo-2-butoxy-N,N-bis(4-methoxybenzyl)imidazo[2,1-f][1,2,4]triazin-4-amine (150 mg, 0.28 mmol) in THF (10 mL), cooled to −78° C. and under a nitrogen atmosphere was added n-BuLi (1.6 M in hexane, 0.7 mmol, 0.43 mL) dropwise. After stirring for 60 mins, a solution of 6-methoxypicolinaldehyde (50 mg, 0.34 mmol) in THF (2 mL) was added slowly. The reaction mixture was warmed up slowly to rt and stirred for 2 h. The reaction mixture was poured into saturated ammonium chloride solution and extracted by EtOAc (15 mL×3). The combined organic phase was washed with brine, dried over Na₂SO₄, concentrated in vacuo to give the title product (250 mg, 100%) which was used directly in next step without further purification. MS: M/e 585 (M+1)⁺.

Step B: 2-butoxy-7-((6-methoxypyridin-2-yl) methyl)imidazo[2,1-f][1,2,4]triazin-4-amine (Compound A51)

A solution of (4-(bis(4-methoxybenzyl)amino)-2-butoxy-imidazo[2,1-f][1,2,4]triazin-7-yl)(6-methoxypyridin-2-yl) methanol (250 mg, 0.28 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (25 mg, 27.2%). $^1$H NMR (400 MHz, DMSO-d6)) δ 8.15 (s, 1H), 8.05 (s, 1H), 7.60 (t, J=7.8 Hz, 1H), 7.35 (s, 1H), 6.80 (d, J=7.3 Hz, 1H), 6.65 (d, J=8.2 Hz, 1H), 4.21 (s, 2H), 4.15 (t, J=6.5 Hz, 2H), 3.79 (s, 3H), 1.68-1.56 (m, 2H), 1.37 (dd, J=15.0, 7.5 Hz, 2H), 0.90 (t, J=7.4 Hz, 3H) ppm. MS: M/e 329 (M+1)⁺.

Compound A52: 7-(4-(pyrrolidin-1-ylmethyl)benzyl)imidazo[2,1-f] [1,2,4]triazine-2,4-diamine Step A: 7-bromo-N2-(furan-2-ylmethyl)-N4,N4-bis (4-methoxybenzyl)imidazo[2,1-f][1,2,4]triazine-2,4-diamine A solution of 7-bromo-2-chloro-N,N-bis(4-methoxybenzyl)imidazo[2,1-f][1,2,4]triazin-4-amine (200 mg, 0.41 mmol), furan-2-ylmethanamine (80 mg, 0.28 mmol) and DIEA (106 mg, 0.82 mmol) in n-BuOH (5 mL) was heated at 120° C. in a sealed tube for 48 hrs. The solution was cooled down, concentrated and further purified by prep-TLC (PE:EA=2:1) to get the pure product (70 mg, 31%). MS: M/e 549 (M+1)⁺.

Step B: (4-(bis(4-methoxybenzyl)amino)-2-((furan-2-ylmethyl)amino)imidazo[2,1-f][1,2,4]triazin-7-yl) (4-(pyrrolidin-1-ylmethyl)phenyl)methanol To a cooled solution of (4-(bis(4-methoxybenzyl)amino)-2-((furan-2-ylmethyl)amino)imidazo[2,1-f][1,2,4]triazin-7-yl)(4-(pyrrolidin-1-ylmethyl)phenyl)methanol (70 mg, 0.13 mmol) in THF (5 mL) at −78° C. (purged with N²), n-BuLi (1.6 M, 0.2 mL) was added dropwise. After stirring at −78° C. for 30 mins, 4-(pyrrolidin-1-ylmethyl)benzaldehyde (37 mg, 0.20 mmol) in THF (1 mL) was added. The resulting mixture was stirred at this temperature for 30 mins, and then warmed to rt overnight. The solution was quenched with NH₄Cl solution (2 mL), extracted with ethyl acetate (10 mL) and washed with brine (10 mL). The organic layer was dried with Na₂SO₄, filtered and concentrated to get the crude product, which was further purified by prep-TLC (DCM: MeOH=7:1) to get the product (15 mg, 18%). MS: M/e 660 (M+1)⁺.

Step C: 7-(4-(pyrrolidin-1-ylmethyl)benzyl)imidazo [2,1-f][1,2,4]triazine-2,4-diamine (Compound A52)

A solution of (4-(bis(4-methoxybenzyl)amino)-2-((furan-2-ylmethyl)amino)imidazo[2,1-f][1,2,4]triazin-7-yl)(4-(pyrrolidin-1-ylmethyl)phenyl)methanol (15 mg, 0.02 mmol) in triethylsilane (2 mL) and trifluoroacetic acid (2 mL) was heated at 80° C. overnight. The solution was evaporated to get the residue, which was purified by prep-HPLC to get the product (5 mg, 50%). $^1$H NMR (400 MHz, DMSO-d6) δ 9.86 (br.s, 1H), 7.86 (br.s, 1H), 7.44 (d, J=8.0 Hz, 2H), 7.35 (d, J=8.0 Hz, 2H), 7.31 (s, 1H), 4.31 (d, J=8.0 Hz, 2H), 4.15 (s, 2H), 3.35-3.31 (m, 2H), 3.12-3.05 (m, 2H), 2.05-2.02 (m, 2H), 1.86-1.81 (m, 2H) ppm. MS: M/e 324 (M+1)⁺.

Compound A53: 2-butoxy-7-((6-(3-(dimethylamino)-2,2-dimethylpropoxy)pyridin-3-yl)methyl) imidazo[2,1-f][1,2,4]triazin-4-amine Step A: 6-(3-(dimethylamino)-2,2-dimethylpropoxy) nicotinonitrile To a stirred suspension of NaH (60%, 600 mg, 15 mmol) in DMA (15 mL) was added a solution of 3-(dimethylamino)-2,2-dimethylpropan-1-ol (1.44 g, 1.1 mmol) in DMA (2 mL). After stirring for 30 min, a solution of 6-chloronicotinonitrile (1.38 g, 10 mmol) in DMA (2 mL) was added. After the addition, the reaction was stirred at 80° C. overnight. The reaction was quenched with aq.NH₄Cl and extracted with EtOAc (20 mL×3). The combined organic layers were washed with brine, dried over Na₂SO₄, concentrated and purified by column chromatography (petroleum ether/EtOAc=20:1) to give the target compound (240 mg, 10.3%) as a white solid. MS: M/e 234 (M+1)⁺.

Step B: 6-(3-(dimethylamino)-2,2-dimethylpropoxy) nicotinaldehyde

To a stirred solution of the product of Step A (233 mg, 1 mmol) in dry THF (10 mL) was added dropwise DIBAL-H (1.2 M, 2 mL, 2.5 mmol) at −20° C. After the addition, the reaction was stirred for 3 hours. The reaction was quenched with aq.NH₄Cl and extracted with EtOAc (10 mL×3). The combined organic layers were washed with brine, dried over Na₂SO₄, concentrated and purified by column chromatography (petroleum ether/EtOAc=10:1~2:1) to give target compound (120 mg, 50.8%) as a white solid. MS: M/e 237 (M+1)⁺.

Step C: (4-(bis(4-methoxybenzyl)amino)-2-butoxy-imidazo[2,1-f][1,2,4]triazin-7-yl)(6-(3-(dimethylamino)-2,2-dimethylpropoxy)pyridin-3-yl)methanol To a solution of 7-bromo-2-butoxy-N,N-bis(4-methoxybenzyl)imidazo[2,1-f][1,2,4]triazin-4-amine (150 mg, 0.286 mmol) in THF (10 mL) was added n-BuLi (1.6 M, 0.44 mL, 0.71 mmol) dropwise −78° C. After stirring for an hour, a solution of the product of Step B (115 mg, 0.428 mmol) in THF (2 mL) was added dropwise. The resulting mixture was stirred overnight. The reaction was quenched with sat.aq.NH₄Cl solution, extracted with EtOAc (10 mL×3). The combined organic layers were washed with brine, dried over Na₂SO₄, filtered, and concentrated. The residue was purified by prep-TLC (100% EtOAc) to give target compound (45 mg, 23%) as colorless oil. MS: M/e 684 (M+1)⁺.

Step D: 2-butoxy-7-((5-chloro-6-(3-(dimethyl-amino)-2,2-dimethylpropoxy)pyridin-3-yl)methyl) imidazo[2,1-f][1,2,4]triazin-4-amine (Compound A53)

To a mixture of the product of Step C (45 mg, 0.066 mmol) in Et₃SiH/TFA (0.5 mL/3 mL) was stirred at 85° C. overnight. The reaction mixture was concentrated to give the residue, which was purified by prep-HPLC to give the target compound (10 mg, 35.4%). ¹H NMR (400 MHz, DMSO-d₆) δ 8.14 (s, 1H), 8.11 (s, 1H), 8.05 (s, 1H), 7.59 (dd, J=8.4, 2.4 Hz, 1H), 7.30 (s, 1H), 6.73 (d, J=8.4 Hz, 1H), 4.19 (t, J=6.5 Hz, 2H), 4.07 (s, 2H), 3.94 (s, 2H), 2.18 (s, 8H), 1.72-1.59 (m, 2H), 1.47-1.34 (m, 2H), 0.96-0.86 (m, 9H) ppm. MS: M/e 428 (M+1)⁺.

Compound A54: 2-isobutoxy-7-(4-(pyrrolidin-1-ylmethyl)benzyl)imidazo[2,1-f][1,2,4]triazin-4-amine Step A: 7-bromo-2-isobutoxy-N,N-bis(4-methoxybenzyl)imidazo[2,1-f][1,2,4]triazin-4-amine Sodium (1 g) was added to a stirred 2-methylpropan-1-ol (10 g) in several portions. The mixture was stirred at 80° C. for 2 h. the above clear solution was added into 7-bromo-2-chloro-N,N-bis(4-methoxybenzyl)imidazo[2,1-f][1,2,4]triazin-4-amine (0.25 g, 0.51 mmol). The mixture was heated to 80° C. and stirred for 1 h. After was completed, the mixture was quenched with H₂O (20 ml) and then extracted with DCM (20 ml×3). The organic phase was washed with H₂O (10 ml), dried and concentrated under reduced pressure. The resulting residue was purified by flash column chromatography with 0-20% EA in PE to afford the product (0.18 g, 67%) as a white solid. MS: M/e 526 (M+1)⁺.

Step B: (4-(bis(4-methoxybenzyl)amino)-2-isobutoxyimidazo[2,1-f][1,2,4]triazin-7-yl)(4-(pyrrolidin-1-ylmethyl)phenyl)methanol To a stirred solution of 7-bromo-2-isobutoxy-N,N-bis(4-methoxybenzyl)imidazo[2,1-f][1,2,4]triazin-4-amine (180 mg, 0.34 mmol) in THF (10 ml) at −78° C. under N₂ atmosphere, was added n-BuLi (1.6 M, 0.54 ml, 0.86 mmol). The solution was stirred at −78° C. for 30 min. 4-(pyrrolidin-1-ylmethyl)benzaldehyde (97 mg, 0.51 mmol) in THF (2 ml) was added dropwise to the above solution. After added, the solution was warmed to rt naturally and then stirred for 3 hr. After was completed, the reaction mixture was quenched with H₂O (20 ml) and then extracted with DCM (20 ml×3). The organic phase was washed with H₂O (10 ml), dried and concentrated under reduced pressure to afford crude product as a yellow oil, which was used directly for the next step without further purification. MS: M/e 637 (M+1)⁻.

Step C: 2-isobutoxy-7-(4-(pyrrolidin-1-ylmethyl)benzyl)imidazo[2,1-f][1,2,4]triazin-4-amine (Compound A54)

A solution of (4-(bis(4-methoxybenzyl)amino)-2-isobutoxyimidazo[2,1-f][1,2,4]triazin-7-yl)(4-(pyrrolidin-1-ylmethyl)phenyl)methanol (crude) in TFA (6 ml) and triethylsilane (2 ml) was stirred at 80° C. for 24 h. After was completed, the reaction mixture was concentrated under reduced pressure. The residue was dissolved in EA (30 ml) and washed with aq. NaHCO₃ (sat., 25 ml) and brine (20 ml). The organic phase was dried over Na₂SO₄, filtered and concentrated. The resulting residue was purified by prep-TLC with DCM:MeOH (10:1) to afford the product (13.83 mg). ¹H NMR (400 MHz, CD3OD) δ 7.49-7.42 (m, 4H), 7.33 (s, 1H), 4.65 (s, 1H), 4.38-4.34 (m, 1H), 4.33 (s, 2H), 4.26 (s, 2H), 4.04 (d, J=4 Hz, 2H), 2.16-1.98 (m, 7H), 1.02 (d, J=8 Hz, 6H) ppm. MS: M/e 381 (M+1)⁺.

Compound A55: 2-butoxy-7-((3-methoxypyridin-2-yl)methyl)imidazo[2,1-f][1,2,4]triazin-4-amine Step A: tert-butyl (2-butoxy-7-(hydroxy(3-methoxypyridin-2-yl)methyl)imidazo[2,1-f][1,2,4]triazin-4-yl)(tert-butoxycarbonyl)carbamate To a solution of tert-butyl (2-butoxy-7-(hydroxy(3-methoxypyridin-2-yl)methyl)imidazo[2,1-f][1,2,4]triazin-4-yl)(tert-butoxycarbonyl)carbamate (150 mg, 0.3 mmol) in THF (5 mL) was added a solution of n-BuLi (0.4 mL, 0.6 mmol) dropwise maintaining the temperature between −75~−65° C. After 1 h, a solution of 3-methoxypicolinaldehyde (55 mg, 0.45 mmol) in THF (1 mL) was added dropwise. The resulting mixture was stirred at −70° C. for 1 h and then warmed to room temperature overnight. The reaction was quenched with saturated NH₄Cl solution, extracted with EtOAc (60 mL), washed with brine, dried over Na₂SO₄, filtered, and concentrated. The residue was purified by prep-TLC to give the target compound (20 mg, crude). MS: M/e 545 (M+1)⁺.

Step B: 2-butoxy-7-((3-methoxypyridin-2-yl)methyl)imidazo[2,1-f][1,2,4]triazin-4-amine (Compound A55)

To a mixture of the product of Step A (20 mg, crude) in TFA (3 mL) was added Et₃SiH (0.5 mL). The reaction was heated at 85° C. overnight. The mixture was concentrated to dryness and the residue was purified by prep-HPLC to give the title product (8 mg, 6% for two steps). ¹HNMR (400 MHz, CD₃OD) δ 8.23 (d, J=5.4 Hz, 1H), 8.04 (d, J=8.0 Hz, 1H), 7.80 (dd, J=8.0, 5.4, Hz, 1H), 7.54 (s, 1H), 4.60 (s, 2H), 4.14 (t, J=6.4 Hz, 2H), 4.03 (s, 3H), 175-1.62 (m, 2H), 1.50-1.38 (m, 2H), 0.96 (t, J=7.6 Hz, 3H) ppm. MS: M/e 329 (M+1)⁺.

Compound A56: (4-amino-2-butoxyimidazo[2,1-f][1,2,4]triazin-7-yl)(3-methoxypyridin-2-yl)methanol To a mixture of tert-butyl (2-butoxy-7-(hydroxy(3-methoxypyridin-2-yl)methyl)imidazo[2,1-f][1,2,4]triazin-4-yl)(tert-butoxycarbonyl)carbamate (35 mg, crude) in DCM (3 mL) were TFA (1 mL) and Et₃SiH (1 mL). The reaction was heated at 40° C. overnight. The mixture was concentrated to dryness and the residue was purified by prep-HPLC to give the title product (20 mg, 68%). ¹HNMR (400 MHz, DMSO-d₆) δ 8.25 (d, J=4.0 Hz, 1H), 8.20 (s, 1H), 8.14 (s, 1H), 7.81 (d, J=6.0 Hz, 1H), 7.66 (d, J=3.2 Hz, 1H), 7.43 (s, 1H), 6.43 (s, 1H), 4.10-3.98 (m, 1H), 3.96-3.86 (m, 1H), 3.82 (s, 3H), 1.66-1.52 (m, 2H), 1.45-1.26 (m, 2H), 0.91 (t, J=7.6 Hz, 3H) ppm. MS: M/e 345 (M+1)⁺.

Compound A57: methyl 5-((4-amino-2-butoxyimidazo[2,1-f][1,2,4]triazin-7-yl)methyl)-2-(3-(dimethylamino)propoxy)benzoate Step A: methyl 2-(3-(dimethylamino)propoxy)-5-formylbenzoate A mixture of methyl 5-formyl-2-hydroxybenzoate (500 mg, 2.7 mmol), 3-chloro-N,N-dimethylpropan-1-amine hydrochloride (512 mg, 3.2 mmol) and Cs₂CO₃ (1.7 g, 5.4 mmol) in DMF (20 mL) was heated at 80° C. overnight. The solution was eluted with water (20 mL), extracted with ethyl acetate (20 mL) and washed with brine (10 mL). The organic layer was dried, concentrated and purified by CombiFlash (DCM:MeOH=10%, with 10% of NH$_3$·MeOH) to get the product (400 mg, 54%). $^1$H NMR (400 MHz, DMSO-d6) δ 9.91 (s, 1H), 8.20 (s, 1H), 8.06 (dd, J=8.0, 4.0 Hz, 1H), 7.35 (d, J=12.0 Hz, 1H), 4.20 (t, J=8.0 Hz, 2H), 3.84 (s, 3H), 2.42 (t, J=8.0 Hz, 2H), 2.16 (s, 6H), 1.91-1.85 (m, 2H) ppm. MS: M/e 266 (M+1)$^+$.

Step B: methyl 5-((4-(bis(4-methoxybenzyl)amino)-2-butoxyimidazo[2,1-f][1,2,4]triazin-7-yl)(hydroxy)methyl)-2-(3-(dimethylamino)propoxy)benzoate To a cooled solution of 7-bromo-2-butoxy-N,N-bis(4-methoxybenzyl)imidazo[2,1-f][1,2,4]triazin-4-amine (150 mg, 0.29 mmol) in THF (8 mL) at −78° C. (purged with N$^2$), n-BuLi (1.6 M, 0.5 mL) was added dropwise. After stirring at −78° C. for 30 mins, methyl 2-(3-(dimethylamino)propoxy)-5-formylbenzoate (115 mg, 0.44 mmol) in THF (2 mL) was added. The resulting mixture was stirred at this temperature for 30 mins, and then warmed to rt for 2 hrs. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by prep-TLC (DCM:MeOH=7:1) to get the product (54 mg, 27%). MS: M/e 713 (M+1)+

Step C: methyl 5-((4-amino-2-butoxyimidazo[2,1-f][1,2,4]triazin-7-yl)methyl)-2-(3-(dimethylamino)propoxy)benzoate (Compound A57)

A solution of methyl 5-((4-(bis(4-methoxybenzyl)amino)-2-butoxyimidazo[2,1-f][1,2,4]triazin-7-yl)(hydroxy)methyl)-2-(3-(dimethylamino)propoxy)benzoate (54 mg, 0.08 mmol) in triethylsilane (2 mL) and trifluoroacetic acid (2 mL) was heated at 80° C. overnight. The solvent was evaporated to get the residue, which was purified by prep-HPLC to get the product (23 mg, 67%). $^1$H NMR (400 MHz, DMSO-d6) δ 9.50 (br.s, 1H), 8.14 (s, 1H), 8.06 (s, 1H), 7.73 (s, 1H), 7.50 (d, J=8.0 Hz, 1H), 7.33 (s, 1H), 7.10 (d, J=8.0 Hz, 1H), 4.20 (t, J=8.0 Hz, 2H), 4.12-4.09 (m, 4H), 3.80 (s, 3H), 3.27-3.23 (m, 2H), 2.82 (d, J=4.0 Hz, 6H), 2.14-2.10 (m, 2H), 1.70-1.65 (m, 2H), 1.43-1.38 (m, 2H), 0.92 (t, J=8.0 Hz, 3H) ppm. MS: M/e 457 (M+1)$^+$.

Compound A58: 2-butoxy-7-((6-(2-(methylamino)ethoxy)pyridin-3-yl)methyl)imidazo[2,1-f][1,2,4]triazin-4-amine Step A tert-butyl (2-((5-formylpyridin-2-yl)oxy)ethyl)(methyl)carbamate K$_2$CO$_3$ (5.52 g, 40 mmol) was added to a solution of 6-chloronicotinaldehyde (2.82 g, 20 mmol) tert-butyl (2-hydroxyethyl)(methyl)carbamate (4.2 g, 24 mmol) in DMA (40 mL), the reaction mixture was heated at 80° C. overnight, was cooled to room temperature. The solution was quenched with H$_2$O (40 ml). The aqueous solution was extracted with EA (40 ml×3). The collected organic layers were washed with brine, dried over Na$_2$SO$_4$, filtered and concentrated. The resulting residue was purified by column chromatography to afford the product (560 mg, 10%) MS: M/e 281 (M+1)+

Step B: tert-butyl (2-((5-((4-(bis(4-methoxybenzyl)amino)-2-butoxyimidazo[2,1-f][1,2,4]triazin-7-yl)(hydroxy)methyl)pyridin-2-yl)oxy)ethyl)(methyl)carbamate To a solution of 7-bromo-2-butoxy-N,N-bis(4-methoxybenzyl)imidazo[2,1-f][1,2,4]triazin-4-amine (158 mg, 0.3 mmol) in THF (1 mL) was added dropwise a solution of n-BuLi (0.28 mL, 0.45 mmol) maintaining the temperature between −75~−65° C. After 10 min, a solution of product of Step A (126 mg, 0.45 mmol) in THF (1 mL) was added dropwise. The resulting mixture was stirred at −70° C. for 30 min. The reaction was quenched with saturated NH$_4$Cl solution, extracted with EtOAc (10 mL×3), washed with brine, dried over Na$_2$SO$_4$, filtered, and concentrated. The residue was purified by column chromatography to give target compound (200 mg, 91%). MS: M/e 728 (M+1)$^+$.

Step C: 2-butoxy-7-((6-(2-(methylamino)ethoxy)pyridin-3-yl)methyl)imidazo[2,1-f][1,2,4]triazin-4-amine (Compound A58)

To a mixture of the product of Step B (180 mg, 0.25 mmol) in TFA (1 mL) was added Et$_3$SiH (1 mL). The reaction was heated at 80° C. overnight. The mixture was concentrated to dryness and the residue was treated with TFA (1 mL). The reaction was heated at 80° C. overnight. The mixture was concentrated and the residue was purified by prep-HPLC. The collected fraction was basified with NaHCO$_3$ solution, extracted with DCM (30 mL), washed with brine, dried over Na$_2$SO$_4$, filtered, and concentrated to give the title product (20 mg, 22%). $^1$H NMR (400 MHz, CDCl3) δ 8.11 (s, 1H) 7.52 (d, J=8.0 Hz, 1H), 7.25 (s, 1H), 6.70 (d, J=8.0 Hz, 1H), 4.40 (t, J=6.0 Hz, 2H), 4.28 (t, J=6.0 Hz, 2H), 4.11 (s, 2H), 2.99 (t, J=8.3 Hz, 2H), 2.52 (s, 3H), 1.82-1.71 (m, 4H), 1.53-1.42 (m, 2H), 0.98 (t, J=6.2 Hz, 3H) ppm. MS: M/e 372 (M+1)$^+$.

Compound A59: N-(2-((5-((4-amino-2-butoxyimidazo[2,1-f][1,2,4]triazin-7-yl)methyl)pyridin-2-yl)oxy)ethyl)-N-methylacetamide Ac$_2$O (4 mg, 0.04 mmol) was added to a solution of 2-butoxy-7-((6-(2-(methylamino)ethoxy)pyridin-3-yl)methyl)imidazo[2,1-f][1,2,4]triazin-4-amine (11 mg, 0.03 mmol) and Et$_3$N in DCM (0.5 mL), the reaction mixture was stirred at 0° C. for 2 hours. The mixture was concentrated and the residue was purified by prep-HPLC. The collected fraction were basified with NaHCO$_3$ solution, extracted with DCM (30 mL), washed with brine, dried over Na$_2$SO$_4$, filtered, and concentrated to give the title product (10 mg, 80%). $^1$H NMR (400 MHz, CDCl3) δ 8.11 (s, 1H) 7.50 (d, J=8.2 Hz, 1H), 7.31 (s, 1H), 6.69 (d, J=8.2 Hz, 1H), 4.45 (t, J=6.4 Hz, 2H), 4.33 (t, J=8.0 Hz, 2H), 4.15 (s, 2H), 3.74-3.68 (m, 2H), 3.11 (s, 2H), 2.99 (s, 2H), 2.15-2.10 (m, 3H), 1.78-1.69 (m, 2H), 1.39-1.26 (m, 2H), 0.98 (t, J=6.0 Hz, 3H) ppm. MS: M/e 414 (M+1)$^+$.

Compound A60: 2-butoxy-7-(4-((1-ethylpyrrolidin-3-yl)oxy)-2-fluoro benzyl)imidazo[2,1-f][1,2,4]triazin-4-amine Step A:
2-fluoro-4-(pyrrolidin-3-yloxy)benzaldehyde hydrochloride A solution of tert-butyl 3-(3-fluoro-4-formylphenoxy)pyrrolidine-1-carboxylate (500 mg, 1.6 mmol) in HCl/dioxane (4M, 3 mL) was stirred rt overnight. The solution was concentrated to get the product of HCl salt as a white solid (400 mg, 100%). MS: M/e 210 (M+1)$^+$.

Step B: 4-((1-ethylpyrrolidin-3-yl)oxy)-2-fluorobenzaldehyde

Iodoethane (500 mg, 1.6 mmol) was added to a mixture of 2-fluoro-4-(pyrrolidin-3-yloxy)benzaldehyde hydrochloride (400 mg, 1.6 mmol) and K$_2$CO$_3$ (442 mg, 3.2 mmol) in DMF (10 mL). The solution was stirred at rt overnight, eluted with water (10 mL), extracted with ethyl acetate (10 mL) and washed with brine (10 mL). The organic layer was dried with Na$_2$SO$_4$, filtered and concentrated to get the crude product, which was further purified by CombiFlash (PE:EA=1:1 to EA) to get the pure product (133 mg, 34%). MS: M/e 238 (M+1)$^+$.

Step C: (4-(bis(4-methoxybenzyl)amino)-2-butoxy-imidazo[2,1-f][1,2,4]triazin-7-yl)(4-((1-ethylpyrrolidin-3-yl)oxy)-2-fluorophenyl)methanol To a cooled solution of 7-bromo-2-butoxy-N,N-bis(4-methoxybenzyl)imidazo[2,1-f][1,2,4]triazin-4-amine (100 mg, 0.2 mmol) in THF (8 mL) at −78° C. (purged with N2), n-BuLi (1.6 M, 0.3 mL) was added dropwise. After stirring at −78° C. for 30 mins, 4-((1-ethylpyrrolidin-3-yl)oxy)-2-fluorobenzaldehyde (68 mg, 0.3 mmol) in THF (2 mL) was added. The resulting mixture was stirred at this temperature for 30 mins, and then warmed to rt for 2 hrs. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by prep-TLC (DCM:MeOH=8:1) to get the product (78 mg, 60%). MS: M/e 685 (M+1)$^+$.

Step D: 2-butoxy-7-(4-((1-ethylpyrrolidin-3-yl)oxy)-2-fluorobenzyl)imidazo[2,1-f][1,2,4]triazin-4-amine (Compound A60)

A solution of (4-(bis(4-methoxybenzyl)amino)-2-butoxy-imidazo[2,1-f][1,2,4]triazin-7-yl)(4-((1-ethylpyrrolidin-3-yl)oxy)-2-fluorophenyl)methanol (78 mg, 0.1 mmol) in triethylsilane (2 mL) and trifluoroacetic acid (2 mL) was heated at 80° C. overnight. The solvent was evaporated to get the residue, which was purified by prep-TLC (DCM:MeOH=8:1) to get the product (18 mg, 38%). $^1$H NMR (400 MHz, DMSO-d6) δ 8.15 (s, 1H), 8.05 (s, 1H), 7.24 (s, 1H), 7.18 (t, J=8.0 Hz, 1H), 6.75 (dd, J=12.0 Hz, J$_2$=4.0 Hz, 1H), 6.66 (d, J=8.0 Hz, 1H), 4.84 (s, 1H), 4.19 (t, J=8.0 Hz, 2H), 4.07 (s, 2H), 2.79 (s, 1H), 2.71-2.65 (m, 2H), 2.44-2.30 (m, 3H), 2.29-2.21 (m, 1H), 1.75-1.63 (m, 3H), 1.44-1.35 (m, 2H), 1.02 (t, J=8.0 Hz, 3H), 0.92 (t, J=8.0 Hz, 3H) ppm. MS: M/e 429 (M+1)$^+$.

Compound A61: 2-butoxy-7-(2-fluoro-4-(pyrrolidin-3-yloxy)benzyl)imidazo[2,1-f][1,2,4]triazin-4-amine Step A: tert-butyl 3-(3-fluoro-4-formylphenoxy)pyrrolidine-1-carboxylate A solution of 2-fluoro-4-hydroxybenzaldehyde (1 g, 7.1 mmol), tert-butyl 3-bromopyrrolidine-1-carboxylate (2.7 g, 10.7 mmol) and Cs$_2$CO$_3$ (4.6 g, 14.2 mmol) in DMF (20 mL) was heated at 80° C. overnight. The solution was filtered and the filtrate was added with water (10 mL), extracted with ethyl acetate (20 mL) and washed with brine (10 mL). The organic layer was dried, concentrated and purified by CombiFlash (PE:EA=20%) to get the product as a colorless oil (1.1 g, 50%). $^1$H NMR (400 MHz, CDCl$_3$) δ 10.21 (s, 1H), 7.83 (t, J=8.0 Hz, 1H), 6.75 (dd, J=8.0, 4.0 Hz, 1H), 6.62 (dd, J=12.0, 4.0 Hz, 1H), 4.95 (s, 1H), 3.67-3.50 (m, 4H), 2.20 (d, J=8.0 Hz, 2H), 1.48 (s, 9H) ppm. M/e 310 (M+1)$^+$.

Step B: tert-butyl 3-(4-((4-(bis(4-methoxybenzyl)amino)-2-butoxyimidazo[2,1-f][1,2,4]triazin-7-yl)(hydroxy)methyl)-3-fluorophenoxy)pyrrolidine-1-carboxylate To a cooled solution of 7-bromo-2-butoxy-N,N-bis(4-methoxybenzyl)imidazo[2,1-f][1,2,4]triazin-4-amine (150 mg, 0.29 mmol) in THF (8 mL) at −78° C. (purged with N$^2$), n-BuLi (1.6 M, 0.5 mL) was added dropwise. After stirred at −78° C. for 30 mins, tert-butyl 3-(3-fluoro-4-formylphenoxy)pyrrolidine-1-carboxylate (132 mg, 0.43 mmol) in THF (2 mL) was added. The resulting mixture was stirred at this temperature for 30 mins, and then warmed to rt overnight. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by CombiFlash (PE:EA=1:1) to get the product (110 mg, 51%). MS: M/e 757 (M+1)$^+$.

Step C: 2-butoxy-7-(2-fluoro-4-(pyrrolidin-3-yloxy)benzyl)imidazo[2,1-f][1,2,4]triazin-4-amine (Compound A61)

A solution of tert-butyl 3-(4-((4-(bis(4-methoxybenzyl)amino)-2-butoxy imidazo[2,1-f][1,2,4]triazin-7-yl)(hydroxy)methyl)-3-fluorophenoxy)pyrrolidine-1-carboxylate (110 mg, 0.15 mmol) in triethylsilane (2 mL) and trifluoroacetic acid (2 mL) was heated at 80° C. overnight. The solvent was evaporated to get the residue, which was purified by prep-HPLC to get the product (33 mg, 57%). $^1$H NMR (400 MHz, DMSO-d6) δ 8.15 (s, 1H), 8.04 (s, 1H), 7.23 (s, 1H), 7.18 (t, J=8.0 Hz, 1H), 6.77-6.66 (m, 2H), 4.81 (s, 1H), 4.19 (t, J=8.0 Hz, 2H), 4.06 (s, 2H), 3.04-3.01 (m, 1H), 2.82-2.71 (m, 3H), 1.98-1.95 (m, 1H), 1.72-1.63 (m, 3H), 1.41-1.37 (m, 2H), 0.92 (t, J=8.0 Hz, 3H) ppm. MS: M/e 401 (M+1)$^+$.

Compound A62: 7-(4-((1H-1,2,4-triazol-1-yl)methyl)benzyl)-2-butoxyimidazo[2,1-f][1,2,4]triazin-4-amine Step A: 4-((1H-1,2,4-triazol-1-yl)methyl)benzaldehyde To a solution of 4-(bromomethyl)benzaldehyde (200 mg, 1 mmol), and K$_2$CO$_3$ (200 mg, 1.5 mmol) in acetone (5 mL) was added 1H-1,2,4-triazole (75 mg, 2.2 mmol). Then the mixture was stirred at room temperature overnight. The mixture was diluted with water (50 mL), extracted with EtOAc (60 mL), washed with brine, dried over Na$_2$SO$_4$, filtered, concentrated and the residue was purified by combiflash to give the target compound (130 mg, 69%). MS: M/e 188 (M+1)$^+$.

Step B: (4-((1H-1,2,4-triazol-1-yl)methyl)phenyl)(4-(bis(4-methoxybenzyl)amino)-2-butoxyimidazo[2,1-f][1,2,4]triazin-7-yl)methanol To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.48 mL, 1.6 mmol) dropwise maintaining the temperature between −75~−65° C. After 1 h, a mixture of the product of Step A (107 mg, 0.57 mmol) in THF (1 mL) was added dropwise. The resulting mixture was stirred at −70° C. for 1 h and then warmed to room temperature overnight. The reaction was quenched with saturated NH$_4$Cl solution, extracted with EtOAc (40 mL×2), washed with brine, dried over Na$_2$SO$_4$, filtered, and concentrated. The residue was purified by prep-TLC to give target compound (130 mg, crude). MS: M/e 635 (M+1)$^+$.

Step C: 7-(4-((1H-1,2,4-triazol-1-yl)methyl)benzyl)-2-butoxyimidazo[2,1-f][1,2,4]triazin-4-amine (Compound A62)

To a mixture of the product of Step B (60 mg, crude) in TFA (3 mL) was added Et$_3$SiH (0.5 mL). The resulting mixture was heated at 85° C. overnight. The mixture was concentrated to dryness and the residue was purified by prep-HPLC. The collected fraction was basified with NaHCO$_3$ solution, extracted with DCM (50 mL), washed with brine, dried over Na$_2$SO$_4$, filtered, and concentrated to give the target compound (25 mg, 17% for two steps). $^1$HNMR (400 MHz, DMSO-d$_6$) δ 8.62 (s, 1H), 8.13 (s, 1H), 8.03 (s, 1H), 7.95 (s, 1H), 7.34-7.27 (m, 3H), 7.19 (d, J=8.4 Hz, 2H), 5.36 (s, 2H), 4.17 (t, J=6.4 Hz, 2H), 4.12 (s, 2H), 1.72-1.59 (m, 2H), 1.46-1.30 (m, 2H), 0.91 (t, J=7.2 Hz, 3H) ppm. MS: M/e 379 (M+1)$^+$.

Compound A63: 2-butoxy-7-(4-(3-(methylamino)propoxy)benzyl)imidazo[2,1-f][1,2,4]triazin-4-amine Step A: tert-butyl (3-(4-formylphenoxy)propyl)(methyl)carbamate To a solution of 4-hydroxybenzaldehyde (0.61 g, 5 mmol), tert-butyl (3-hydroxypropyl)(methyl)carbamate (0.95 g, 5 mmol) and PPh$_3$ (1.96 g, 7.5 mmol) in THF (8 mL) was added 40% DIAD in toluene solution (3.7 g, 7.5 mmol) dropwise. Then the mixture was stirred at room temperature overnight. The mixture was diluted with water (50 mL), extracted with EtOAc (40 mL×2). The combined organic layers were washed with brine, dried over Na$_2$SO$_4$, filtered, concentrated and the residue was purified by combi flash to give the target compound (0.71 g, 48%). MS: M/e 238 (M+H-t-Bu)$^+$.

Step B: tert-butyl(3-(4-((4-(bis(4-methoxybenzyl)amino)-2-butoxyimidazo[2,1-f][1,2,4]triazin-7-yl)(hydroxy)methyl)phenoxy)propyl)(methyl)carbamate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.4 mL, 0.57 mmol) dropwise maintaining the temperature between −75~−65° C. After 1 h, a mixture of the product of Step A (168 mg, 0.57 mmol) in THF (1 mL) was added dropwise. The resulting mixture was stirred at −70° C. for 0.5 h and then warmed to room temperature overnight. The reaction was quenched with saturated NH$_4$Cl solution, extracted with EtOAc (50 mL), washed with brine, dried over Na$_2$SO$_4$, filtered, and concentrated. The residue was purified by prep-TLC (EA/PE=1/2) to give the target compound (130 mg, crude). MS: M/e 741 (M+1)$^+$.

Step C: 2-butoxy-7-(4-(3-(methylamino)propoxy)benzyl)imidazo[2,1-f][1,2,4]triazin-4-amine (Compound A63)

To a mixture of the product of Step B (130 mg, crude) in TFA (3 mL) was added Et$_3$SiH (1 mL). The reaction was heated at 85° C. overnight. The mixture was cooled to room temperature and concentrated to dryness. The residue was purified by prep-HPLC. The collected fraction was basified with NaHCO$_3$ solution, extracted with DCM (60 mL×2), washed with brine, dried over Na$_2$SO$_4$, filtered, and concentrated to give the target compound (36 mg, 25% for two steps). $^1$HNMR (400 MHz, DMSO-d$_6$) δ 8.12 (s, 1H), 8.02 (s, 1H), 7.25 (s, 1H), 7.20 (d, J=8.4 Hz, 2H), 6.83 (d, J=8.4 Hz, 2H), 4.20 (t, J=6.4 Hz, 2H), 4.05 (s, 2H), 3.96 (t, J=6.4 Hz, 2H), 2.63 (t, J=7.2 Hz, 2H), 2.30 (s, 3H), 1.90-1.79 (m, 2H), 1.73-1.62 (m, 2H), 1.46-1.34 (m, 2H), 0.92 (t, J=7.6 Hz, 3H) ppm. MS: M/e 385 (M+1)$^+$.

Compound A64: N$^2$-(furan-2-ylmethyl)-7-(4-(pyrrolidin-1-ylmethyl)benzyl)imidazo[2,1-f][1,2,4]triazine-2,4-diamine Step A: 7-bromo-N$^2$-(furan-2-ylmethyl)imidazo[2,1-f][1,2,4]triazine-2,4-diamine A solution of 7-bromo-2-chloroimidazo[2,1-f][1,2,4]triazin-4-amine (500 mg, 2 mmol), furan-2-ylmethanamine (388 mg, 4 mmol) and DIEA (516 mg, 4 mmol) in n-BuOH (10 mL) in a sealed tube was heated at 120° C. overnight. After concentrating in reduced pressure, the residue was diluted with water (10 mL) and extracted with ethyl acetate (10 mL). The organic layer was dried, concentrated and purified by CombiFlash (PE:EA=50%) to get the product (180 mg, 29%). $^1$H NMR (400 MHz, DMSO-d6) δ 7.86 (br.s, 2H), 7.54 (s, 1H), 7.44 (s, 1H), 7.02 (t, J=8.0 Hz, 1H), 6.37 (d, J=4.0 Hz, 1H), 6.30 (d, J=4.0 Hz, 1H), 4.38 (d, J=4.0 Hz, 2H) ppm. MS: M/e 309 (M+1)$^+$ Step B: tert-butyl (7-bromo-2-((tert-butoxycarbonyl)(furan-2-ylmethyl)amino)imidazo[2,1-f][1,2,4]triazin-4-yl)(tert-butoxycarbonyl)carbamate A solution of 7-bromo-N$^2$-(furan-2-ylmethyl)imidazo[2,1-f][1,2,4]triazine-2,4-diamine (150 mg, 0.5 mmol), (Boc)$_2$O (327 mg, 1.5 mmol) and DMAP (31 mg, 0.25 mmol) in DCM (10 mL) was stirred at rt overnight. The solution was concentrated and purified by CombiFlash (PE:EA=20%) to get the pure product (270 mg, 91%). MS: M/e 609 (M+1)$^+$.

Step C: tert-butyl (tert-butoxycarbonyl)(2-((furan-2-ylmethyl)amino)-7-(hydroxy(4-(pyrrolidin-1-ylmethyl)phenyl)methyl)imidazo[2,1-f][1,2,4]triazin-4-yl)carbamate To a cooled solution of tert-butyl (7-bromo-2-((tert-butoxycarbonyl)(furan-2-ylmethyl)amino)imidazo[2,1-f][1,2,4]triazin-4-yl)(tert-butoxycarbonyl)carbamate (150 mg, 0.25 mmol) in THF (8 mL) at −78° C. (purged with N$^2$), n-BuLi (1.6 M, 0.4 mL) was added dropwise. After stirring at −78° C. for 30 mins, 4-(pyrrolidin-1-ylmethyl)benzaldehyde (70 mg, 0.37 mmol) in THF (2 mL) was added. The resulting mixture was stirred at this temperature for 30 mins, and then warmed to rt overnight. The solution was quenched with NH$_4$Cl solution (5 mL), extracted with ethyl acetate (10 mL) and washed with brine (10 mL). The organic layer was dried with Na$_2$SO$_4$, filtered and concentrated to get the crude product, which was further purified by CombiFlash (DCM:MeOH=7:1) to get the pure product (15 mg, 10%). MS: M/e 620 (M+1)$^+$.

Step D: N²-(furan-2-ylmethyl)-7-(4-(pyrrolidin-1-ylmethyl)benzyl)imidazo[2,1-f][1,2,4]triazine-2,4-diamine (Compound A64)

Triethylsilane (0.5 mL) and trifluoroacetic acid (0.5 mL) were added to a mixture of tert-butyl(tert-butoxycarbonyl)(2-((furan-2-ylmethyl)amino)-7-(hydroxyl (4-(pyrrolidin-1-ylmethyl)phenyl)methyl)imidazo[2,1-f][1,2,4]triazin-4-yl)carbamate (15 mg, 0.02 mmol) in DCM (1 mL) and it was heated at 40° C. for 2 hrs. The solvent was evaporated to get the residue, which was purified by prep-HPLC to get the product (3 mg, 31%). ¹H NMR (400 MHz, CD₃OD) δ 7.47-7.41 (m, 6H), 6.32 (d, J=4.0 Hz, 1H), 6.21 (d, J=4.0 Hz, 1H), 4.46 (s, 2H), 4.33 (s, 2H), 4.26 (s, 2H), 3.19-3.44 (m, 2H), 3.17-3.13 (m, 2H), 2.22-2.15 (m, 2H), 2.02-1.93 (m, 2H) ppm. MS: M/e 404 (M+1)⁺.

Compound A65: 4-amino-7-(4-(pyrrolidin-1-ylmethyl)benzyl)imidazo[2,1-f][1,2,4]triazin-2-ol

Step A: 7-bromo-2-(furan-2-ylmethoxy)-N,N-bis(4-methoxybenzyl)imidazo[2,1-f][1,2,4]triazin-4-amine To a stirred solution of furan-2-ylmethanol (73 mg, 0.75 mmol) in THF (20 mL) was added NaH (80 mg, 2 mmol, 60% in oil) at 0° C. The reaction mixture was stirred at 0° C. for 0.5 h. 7-bromo-2-chloro-N,N-bis(4-methoxybenzyl)imidazo[2,1-f][1,2,4]triazin-4-amine (243 mg, 0.5 mmol) was added to the mixture and the reaction mixture was stirred at 70° C. for 6 h. The mixture was diluted H₂O (20 mL) and extracted with EtOAc (10 ml×3). The combined organic phase was washed with brine, dried over Na₂SO₄ and concentrated in vacuo. The crude product was purified by column chromatography to give the product (150 mg, 57.4%) as white solids. MS: M/e 550 (M+1)⁺.

Step B: (4-(bis(4-methoxybenzyl)amino)-2-(furan-2-ylmethoxy)imidazo[2,1-f][1,2,4]triazin-7-yl)(4-(pyrrolidin-1-ylmethyl)phenyl)methanol To a stirred solution of 7-bromo-2-(furan-2-ylmethoxy)-N,N-bis(4-methoxybenzyl)imidazo[2,1-f][1,2,4]triazin-4-amine (120 mg, 0.22 mmol) in THF (10 mL), cooled to −78° C. and under a nitrogen atmosphere was added n-BuLi (1.6 M in hexane, 0.55 mmol, 0.34 mL) dropwise. After stirring for 50 mins, a solution of 4-(pyrrolidin-1-ylmethyl)benzaldehyde (66 mg, 0.33 mmol) in THF (2 mL) was added slowly. The reaction mixture was warmed up slowly to rt and stirred for 2 h. The reaction mixture was poured into saturated ammonium chloride solution and extracted with EtOAc (15 mL×3). The combined organic phase was washed with brine, dried over Na₂SO₄, concentrated in vacuo. The crude product was purified by column chromatography to give the title product (30 mg, 20.6%). MS: M/e 661 (M+1)⁺.

Step C: 4-amino-7-(4-(pyrrolidin-1-ylmethyl)benzyl)imidazo[2,1-f][1,2,4]triazin-2-ol A solution of (4-(bis(4-methoxybenzyl)amino)-2-(furan-2-ylmethoxy)imidazo[2,1-f][1,2,4]triazin-7-yl)(4-(pyrrolidin-1-ylmethyl)phenyl)methanol (30 mg, 0.045 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (13 mg, 88%). ¹H NMR (400 MHz, DMSO-d6) δ 9.83 (s, 1H), 8.08 (s, 1H), 7.95 (s, 1H), 7.44 (d, J=7.6 Hz, 2H), 7.34 (d, J=7.6 Hz, 2H), 7.26 (s, 1H), 4.32 (s, 2H), 4.17 (s, 2H), 3.34 (s, 2H), 3.07 (s, 2H), 1.96-1.91 (m, 2H), 1.86-1.75 (m, 2H) ppm. MS: M/e 325 (M+1)⁺.

Compound A66: 2-butoxy-7-(4-(1-methylpyrrolidin-3-yl)benzyl)imidazo[2,1-f][1,2,4]triazin-4-amine

Step A: (4-(bis(4-methoxybenzyl)amino)-2-butoxyimidazo[2,1-f][1,2,4]triazin-7-yl)(4-(1-methylpyrrolidin-3-yl)phenyl)methanol To a stirred solution of 7-bromo-2-butoxy-N,N-bis(4-methoxybenzyl)Imidazo[2,1-f][1,2,4]triazin-4-amine (105 mg, 0.2 mmol) in THF (10 mL), cooled to −78° C. under a nitrogen atmosphere was added n-BuLi (1.6 M in hexane, 0.5 mmol, 0.31 mL) dropwise. After stirring for 50 mins, a solution of 4-(1-methylpyrrolidin-3-yl)benzaldehyde (43 mg, 0.2 mmol) in THF (2 mL) was added slowly. The reaction mixture was warmed up slowly to rt and stirred for 2 h. The reaction mixture was poured into saturated ammonium chloride solution and extracted by EtOAc (15 mL×3). The combined organic phase was washed with brine, dried over Na₂SO₄, concentrated in vacuo to give the product (30 mg, 23.5%). MS: M/e 638 (M+1)⁺.

Step B: 2-butoxy-7-(4-(1-methylpyrrolidin-3-yl)benzyl)imidazo[2,1-f][1,2,4]triazin-4-amine (Compound A66)

A solution of (4-(bis(4-methoxybenzyl)amino)-2-butoxyimidazo[2,1-f][1,2,4]triazin-7-yl)(4-(1-methylpyrrolidin-3-yl)phenyl)methanol (30 mg, 0.047 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (5 mg, 28%). ¹H NMR (400 MHz, DMSO-d6)) δ 8.12 (s, 1H), 8.03 (s, 1H), 7.29 (s, 1H), 7.25-7.19 (m, 4H), 4.20 (t, J=6.4 Hz, 2H), 4.09 (s, 2H), 3.11-2.95 (m, 1H), 2.82-2.75 (m, 2H), 2.59-5.52 (m, 2H), 2.44 (s, 3H), 2.26-2.18 (m, 1H), 1.79-1.61 (m, 3H), 1.42-1.37 (m, 2H), 0.92 (t, J=7.4 Hz, 3H) ppm. MS: M/e 381 (M+1)⁺.

Compound A67: N2-butyl-7-(4-(pyrrolidin-1-ylmethyl)benzyl)imidazo[2,1-f][1,2,4]triazine-2,4-diamine

Step A: (4-(bis(4-methoxybenzyl)amino)-2-(butylamino)imidazo[2,1-f][1,2,4]triazin-7-yl)(4-(pyrrolidin-1-ylmethyl)phenyl)methanol To a stirred solution of 7-bromo-N2-butyl-N4,N4-bis(4-methoxybenzyl)imidazo[2,1-f][1,2,4]triazine-2,4-diamine (150 mg, 0.285 mmol) in THF (10 mL) was added dropwise n-BuLi (1.6 M, 0.35 mL, 0.428 mmol) at −78° C. After stirring for an hour under N₂, a solution of 4-(pyrrolidin-1-ylmethyl)benzaldehyde (87.4 mg, 0.428 mmol) in THF (2 mL) was added dropwise at −78° C. After the addition, the reaction was stirred for 3 hours. The reaction was quenched with aq.NH₄Cl, extracted with EtOAc (10 mL×3). The combined organic layers were washed with brine, dried over Na₂SO₄, concentrated and purified by prep-TLC (CH₂Cl₂:

MeOH=10:1) to give the target compound (65 mg, 35.8%) as a white solid. MS: M/e 636 (M+1)$^+$.

Step B: N2-butyl-7-(4-(pyrrolidin-1-ylmethyl)benzyl)imidazo[2,1-f][1,2,4]triazine-2,4-diamine To a mixture of the product of Step A (65 mg, 0.102 mmol) in Et$_3$SiH/TFA (0.5 mL/3 mL) was stirred at 85° C. overnight. The reaction mixture was concentrated to give the residue, which was purified by prep-HPLC to give the target compound (26 mg, 67.1%). $^1$H NMR (400 MHz, DMSO-d$_6$) δ 9.72 (br.s, 1H), 7.69 (s, 2H), 7.46-7.37 (m, 4H), 7.36-7.28 (m, 1H), 6.45 (s, 1H), 4.30 (d, J=5.6 Hz, 2H), 4.14 (s, 2H), 3.38-3.26 (m, 2H), 3.16 (t, J=6.8 Hz, 2H), 3.15-3.02 (m, 2H), 2.05-1.96 (m, 2H), 1.90-1.76 (m, 2H), 1.56-1.45 (m, 2H), 1.39-1.26 (m, 2H), 0.89 (t, J=7.2 Hz, 3H) ppm. MS: M/e 380 (M+1)$^+$.

Compound A68: 2-(pyridin-3-ylmethoxy)-7-(4-(pyrrolidin-1-ylmethyl)benzyl)imidazo[2,1-f][1,2,4]triazin-4-amine Step A: 7-bromo-N,N-bis(4-methoxybenzyl)-2-(pyridin-3-ylmethoxy)imidazo[2,1-f][1,2,4]triazin-4-amine To a suspension of NaH (80 mg, 2 mmol) in THF (8 mL), pyridin-3-ylmethanol (218 mg, 2 mmol) was added. After stirring at room temperature for 30 min, a solution of 7-bromo-2-chloro-N,N-bis(4-methoxybenzyl)imidazo[2,1-f][1,2,4]triazin-4-amine (240 mg, 0.5 mmol) in THF (2 mL) was added. Then the mixture was stirred at 80° C. for 4 h. The mixture was cooled to room temperature, diluted with water (30 mL), extracted with EtOAc (50 mL×2), washed with brine, dried over Na$_2$SO$_4$, filtered, concentrated and the residue was purified by combi-flash to give the target compound (250 mg, 89%). $^1$H NMR (400 MHz, CDCl$_3$) δ 8.84 (s, 1H), 8.59 (d, J=2.4 Hz, 1H), 8.07 (d, J=6.8 Hz, 1H), 7.51-7.45 (m, 2H), 7.17 (d, J=8.4 Hz, 4H), 6.85 (d, J=8.0 Hz 4H), 5.60 (s, 2H), 5.46 (s, 2H), 4.83 (s, 2H), 3.81 (s, 3H), 3.80 (s, 3H) ppm. MS: M/e 561 (M+1)$^+$.

Step B: (4-(bis(4-methoxybenzyl)amino)-2-(pyridin-3-ylmethoxy)imidazo[2,1-f][1,2,4]triazin-7-yl)(4-(pyrrolidin-1-ylmethyl)phenyl)methanol To a solution of the product of Step A (250 mg, 0.44 mmol) in THF (8 mL) was added a solution of n-BuLi (0.41 mL, 0.66 mmol) dropwise maintaining the temperature between −75~−65° C. After 1 h, a solution of 4-(pyrrolidin-1-ylmethyl)benzaldehyde (100 mg, 0.53 mmol) in THF (1 mL) was added dropwise. The resulting mixture was stirred at −70° C. for 1 h and then warmed to room temperature for 5 h. The reaction was quenched with saturated NH$_4$Cl solution, extracted with EtOAc (50 mL), washed with brine, dried over Na$_2$SO$_4$, filtered, and concentrated. The residue was purified by prep-TLC to give the target compound (80 mg, crude). MS: M/e 672 (M+1)$^+$.

Step C: 2-(pyridin-3-ylmethoxy)-7-(4-(pyrrolidin-1ylmethyl)benzyl)imidazo[2,1-f][1,2,4]triazin-4-amine (Compound A68)

To a mixture of the product of Step B (80 mg, crude) in TFA (3 mL) was added Et$_3$SiH (1 mL). The reaction was heated at 85° C. overnight. The mixture was concentrated and the residue was purified by prep-HPLC. The collected fraction was basified with NaHCO$_3$ solution, extracted with DCM (60 mL), washed with brine, dried over Na$_2$SO$_4$, filtered, and concentrated to give the target compound (8 mg, 5% for two steps). $^1$HNMR (400 MHz, CD$_3$OD) δ 8.66 (s, 1H), 8.49 (d, J=4.4 Hz, 1H), 7.94 (d, J=8.4 Hz, 1H), 7.50-7.39 (m, 1H), 7.37-7.20 (m, 5H), 5.39 (s, 2H), 4.21 (s, 2H), 3.67 (s, 2H), 2.71-2.50 (m, 4H), 1.91-1.75 (m, 4H) ppm. MS: M/e 416 (M+1)$^+$.

Compound A69: 7-(4-(pyrrolidin-1-ylmethyl)benzyl)-2-(4,4,4-trifluorobutoxy)imidazo[2,1-f][1,2,4]triazin-4-amine Step A: 7-bromo-N,N-bis(4-methoxybenzyl)-2-(4,4,4-trifluorobutoxy)imidazo[2,1-f][1,2,4]triazin-4-amine Sodium (0.4 g) was added to a stirred 4,4,4-trifluorobutan-1-ol (5 g) in several portions. The mixture was stirred at 80° C. for 2 hrs. Took the above clear solution and added 7-bromo-2-chloro-N,N-bis(4-methoxybenzyl)imidazo[2,1-f][1,2,4]triazin-4-amine (0.3 g, 0.61 mmol). The mixture was heated to 80° C. and stirred for 1 h. After was completed, the mixture was quenched with H$_2$O (20 ml) and then extracted with DCM (20 ml×3). The organic phase was washed with H$_2$O (10 ml), dried and concentrated under reduced pressure. The resulting residue was purified by flash column chromatography with 0-15% EA in PE to afford the product (0.2 g, 56%) as a light yellow solid. MS: M/e 580 (M+1)$^+$.

Step B: (4-(bis(4-methoxybenzyl)amino)-2-(4,4,4-trifluorobutoxy)imidazo[2,1-f][1,2,4]triazin-7-yl)(4-(pyrrolidin-1-ylmethyl)phenyl)methanol To a stirred solution of 7-bromo-N,N-bis(4-methoxybenzyl)-2-(4,4,4-trifluorobutoxy)imidazo[2,1-f][1,2,4]triazin-4-amine (200 mg, 0.34 mmol) in THF (15 ml) at −78° C. under N$_2$ atmosphere, was added n-BuLi (1.6 M, 0.54 ml, 0.86 mmol). The solution was stirred at −78° C. for 30 min. 4-(pyrrolidin-1-ylmethyl)benzaldehyde (97 mg, 0.51 mmol) in THF (2 ml) was added dropwise to the above solution. After was added, the solution was warmed to rt naturally and then stirred for 3 hrs. After was completed, the reaction mixture was quenched with H$_2$O (20 ml) and then extracted with DCM (20 ml×3). The organic phase was washed with H$_2$O (10 ml), dried and concentrated under reduced pressure to afford crude product as a yellow oil, which was used directly for the next step without further purification. MS: M/e 691 (M+1)$^+$.

Step C: 7-(4-(pyrrolidin-1-ylmethyl)benzyl)-2-(4,4,4-trifluorobutoxy)imidazo[2,1-f][1,2,4]triazin-4-amine (Compound A69)

A solution of (4-(bis(4-methoxybenzyl)amino)-2-(4,4,4-trifluorobutoxy)imidazo[2,1-f][1,2,4]triazin-7-yl)(4-(pyrrolidin-1-ylmethyl)phenyl)methanol (crude) in TFA (6 ml) and triethylsilane (2 ml) was stirred at 80° C. for 24 hrs. After was completed, the reaction mixture was concentrated under reduced pressure. The residue was dissolved in EA (30 ml) and washed with aq. NaHCO$_3$ (sat., 25 ml) and brine (20 ml). The organic phase was dried over Na$_2$SO$_4$, filtered and concentrated. The resulting residue was purified by prep-TLC with DCM:MeOH (10:1) to afford the product (15.11 mg). $^1$H NMR (400 MHz, DMSO-d6) δ 8.21 (s, 1H), 8.11

(s, 1H), 7.55-7.30 (m, 5H), 4.47-3.86 (m, 6H), 3.30-2.70 (m, 4H), 2.46-2.32 (m, 2H), 2.03-1.71 (m, 6H) ppm. MS: M/e 435 (M+1)$^+$.

Compound A70: 7-(3-(aminomethyl)benzyl)-2-butoxyimidazo[2,1-f][1,2,4]triazin-4-amine Step A: 3-((4-(bis(4-methoxybenzyl)amino)-2-butoxyimidazo[2,1f][1,2,4]triazin-7-yl)(hydroxy)methyl)benzonitrile To a stirred solution of 7-bromo-2-butoxy-N,N-bis(4-methoxybenzyl)imidazo[2,1-f][1,2,4]triazin-4-amine (150 mg, 0.29 mmol) in THF (15 ml) at −78° C. under N$_2$ atmosphere, was added n-BuLi (1.6 M, 0.22 ml, 0.35 mmol). The solution was stirred at −78° C. for 30 min. 3-formylbenzonitrile (37.4 mg, 0.29 mmol) in THF (2 ml) was added dropwise to the above solution. After addition, the solution was warmed to rt naturally and then stirred for 3 hr. After was completed, the reaction mixture was quenched with H$_2$O (20 ml) and then extracted with DCM (20 ml×3). The organic phase was washed with H$_2$O (10 ml), dried over Na$_2$SO$_4$, filtered and concentrated under reduced pressure to afford crude product as an off-white semi-solid (180 mg), which was used directly for the next step without further purification. MS: M/e 579 (M+1)$^+$.

Step B: (3-(aminomethyl)phenyl)(4-(bis(4-methoxybenzyl)amino)-2-butoxyimidazo[2,1-f][1,2,4]triazin-7-yl)methanol To a stirred solution of 3-((4-(bis(4-methoxybenzyl)amino)-2-butoxyimidazo[2,1-f][1,2,4]triazin-7-yl)(hydroxy)methyl)benzonitrile (180 mg, 0.31 mmol) in THF (15 ml) was added LiAlH$_4$ (24 mg, 0.63 mmol). The mixture was stirred at 66° C. overnight. After was completed, the reaction mixture was poured into ice-water and then extracted with EA (15 ml×2). The organic layers were washed with brine, dried over Na$_2$SO$_4$, filtered and concentrated to afford crude product as a light-yellow semi-solid, which was used directly for the next step without further purification. MS: M/e 583 (M+1)$^+$.

Step C: 7-(3-(aminomethyl)benzyl)-2-butoxyimidazo[2,1-f][1,2,4]triazin-4-amine (Compound A70)

A solution of (3-(aminomethyl)phenyl)(4-(bis(4-methoxybenzyl)amino)-2-butoxyimidazo[2,1-f][1,2,4]triazin-7-yl)methanol (crude) in TFA (6 ml) and triethylsilane (2 ml) was stirred at 80° C. for 24 h. After was completed, the reaction mixture was concentrated under reduced pressure. The residue was dissolved in EA (30 ml) and washed with aq. NaHCO$_3$ (sat., 25 ml) and brine (20 ml). The organic phase was dried over Na$_2$SO$_4$, filtered and concentrated. The resulting residue was purified by prep-TLC with DCM:MeOH (10:1) and then prep-HPLC to afford the product (5.04 mg). $^1$H NMR (400 MHz, DMSO-d6) δ 8.25-7.98 (m, 4H), 7.41-7.27 (m, 5H), 4.20 (t, J=8 Hz, 2H), 4.16 (s, 2H), 4.02-3.94 (m, 2H), 1.72-1.53 (m, 2H), 1.47-1.28 (m, 2H), 0.97-0.84 (m, 3H) ppm. MS: M/e 327 (M+1)$^+$.

Compound A71: 3-(4-(4-((4-amino-2-butoxyimidazo[2,1-f][1,2,4]triazin-7-yl)methyl)benzyl)piperazin-1-yl)propan-1-ol Step A: ethyl tert-butyl 4-(4-formylbenzyl)piperazine-1-carboxylate The mixture of 4-(chloromethyl)benzaldehyde (1.8 g, 11.6 mmol), tert-butyl piperazine-1-carboxylate (2.6 g, 13.9 mmol) and K$_2$CO$_3$ (3.2 g, 23.2 mmol) in CH$_3$CN (50 mL) was stirred at 50° C. overnight. The reaction was cooled to room temperature. The mixture was diluted with water (100 mL) and extracted with EA (80 mL×3). The combined organic phase was washed with brine, dried over Na$_2$SO$_4$ and concentrated under reduced pressure. The residue was purified by combiflash to obtain the title compound (2 g, yield: 56.7%) as a yellow oil. MS: M/e 305 (M+1)$^+$.

Step B: 4-(piperazin-1-ylmethyl)benzaldehyde hydrogen chloride salt

The product of Step A (2 g, 6.6 mmol) was dissolved into HCl/EA (4M, 20 mL) at room temperature. The mixture was stirred at room temperature for 3 hours. The mixture was concentrated under reduced pressure. The residue (2HCl salt) as yellow solid was used into next step directly. MS: M/e 205 (M+1)$^+$.

Step C: 4-((4-(3-((tert-butyldimethylsilyl)oxy)propyl)piperazin-1-yl)methyl)benzaldehyde The mixture of the product of Step B (508 mg, 1.84 mmol), tert-butyl(3-chloropropoxy)dimethylsilane (574 mg, 2.76 mmol), K$_2$CO$_3$ (1.02 g, 7.36 mmol) and KI (61 mg, 0.37 mmol) in DMF (10 mL) was stirred at 100° C. for 12 hours. The reaction was cooled to room temperature. The mixture was quenched with water (20 mL) and extracted with EA (20 mL×3). The combined organic phase was washed with brine, dried over Na$_2$SO$_4$ and concentrated under reduced pressure. The residue was purified by combiflash to afford the title compound (440 mg, yield: 63.6%) as yellow oil. MS: M/e 377 (M+1)$^+$.

Step D: (4-(bis(4-methoxybenzyl)amino)-2-butoxyimidazo[2,1-f][1,2,4]triazin-7-yl)(4-((4-(3-((tert-butyldimethylsilyl)oxy)propyl)piperazin-1-yl)methyl)phenyl)methanol To a stirred solution of 7-bromo-2-butoxy-N,N-bis(4-methoxybenzyl)imidazo[2,1-f][1,2,4]triazin-4-amine (140 mg, 0.27 mmol) in THF (2 mL) was added n-BuLi (1.6 M, 0.21 mL) at −78° C. under N$_2$ atmosphere. The mixture was stirred at −78° C. for 1 hour. Then the product of Step C (150 mg, 0.40 mmol) in THF (0.3 mL) was added to the system at −78° C. The reaction was stirred at −78° C. for 0.5 hour. The reaction was warmed to room temperature and stirred overnight. The reaction was quenched with saturated NH$_4$Cl aqueous at room temperature. The mixture was extracted with EA (10 mL×3). The combined organic phase was washed with brine, dried over Na$_2$SO$_4$ and concentrated under reduced pressure. The residue was purified by combiflash to afford the title compound (160 mg, yield: 72.1%) as a yellow oil. MS: M/e 824 (M+1)$^+$.

Step E: 3-(4-(4-((4-amino-2-butoxyimidazo[2,1-f][1,2,4]triazin-7-yl)methyl)benzyl)piperazin-1-yl)propan-1-ol (Compound A71)

The product of Step D (80 mg, 0.10 mmol) was dissolved into Et$_3$SiH (0.5 mL) and CF$_3$COOH (0.1 mL). The mixture was stirred at room temperature overnight. The mixture was concentrated under reduced pressure. The residue was dissolved into CF$_3$COOH (0.5 mL) at room temperature. The mixture was stirred at 80° C. for 3 hours. The reaction was cooled to room temperature. The mixture was concentrated under reduced pressure. The residue was purified by prep- HPLC to afford the title compound (6.5 mg, yield: 14.4%). $^1$H NMR (400 MHz, DMSO-d6) δ 8.25-7.95 (m, 2H), 7.36-7.13 (m, 5H), 4.31-4.17 (m, 2H), 4.12 (s, 2H), 3.51-3.41 (m, 4H), 2.50-2.28 (m, 8H), 1.73-1.54 (m, 4H), 1.46-1.34 (m, 2H), 1.29-1.06 (m, 2H), 0.92 (t, J=7.2 Hz, 3H) ppm. MS: M/e 454 (M+1)$^+$.

Compound A72: 2-butoxy-7-((5-methyl-6-(piperidin-4-yloxy)pyridin-3-yl)methyl)imidazo[2,1-f][1,2,4]triazin-4-amine Step A: tert-butyl 4-((5-bromo-3-methylpyridin-2-yl)oxy)piperidine-1-carboxylate To a solution of NaH (0.3 g, 7.5 mmol) in DMA (15 mL) was added tert-butyl 4-hydroxypiperidine-1-carboxylate (1.1 g, 5.5 mmol). The mixture was stirred at room temperature for 1 h. Then a solution of 5-bromo-2-chloro-3-methylpyridine (1.1 g, 5 mmol) in DMA (5 mL) was added and the resulting mixture was stirred at 80° C. overnight under N$_2$ protect. The mixture was cooled to room temperature, diluted with water (50 mL), extracted with EtOAc (60 mL×2). The combined organic layers were washed with brine, dried over Na$_2$SO$_4$, filtered, concentrated and the residue was purified by combi-flash to give the target compound (1.3 g, 70%). MS: M/e 371 (M+H)$^+$.

Step B: tert-butyl 4-((5-formyl-3-methylpyridin-2-yl)oxy)piperidine-1-carboxylate To a stirred solution of the product of Step A (1.1 g, 3 mmol) in THF (15 mL) was added a solution of n-BuLi (2.81 mL, 4.5 mmol) dropwise maintaining the temperature between −75~−65° C. After 1 h, a solution of DMF (266 mg, 3.6 mmol) in THF (1 mL) was added dropwise and the resulting mixture was stirred at −70° C. for 2 h. The reaction was quenched with saturated NH$_4$Cl solution, extracted with EtOAc (60 mL), washed with brine, dried over Na$_2$SO$_4$, filtered, and concentrated. The residue was purified by combi-flash to give the target compound (900 mg, 93%). MS: M/e 321 (M+H)$^+$.

Step C: tert-butyl4-((5-((4-(bis(4-methoxybenzyl)amino)-2-butoxyimidazo[2,1-f][1,2,4]triazin-7-yl)(hydroxy)methyl)-3-methylpyridin-2-yl)oxy)piperidine-1-carboxylate To a solution of 7-bromo-2-butoxy-N,N-bis(4-methoxybenzyl)imidazo[2,1-f][1,2,4]triazin-4-amine (200 mg, 0.38 mmol) in THF (8 mL) was added a solution of n-BuLi (0.6 mL, 0.95 mmol) dropwise maintaining the temperature between −75~−65° C. After 1 h, a mixture of the product of Step B (150 mg, 0.456 mmol) in THF (1 mL) was added dropwise. The resulting mixture was stirred at −70° C. for 1 h and then warmed to room temperature for 5 h. The reaction was quenched with saturated NH$_4$Cl solution, extracted with EtOAc (50 mL), washed with brine, dried over Na$_2$SO$_4$, filtered, and concentrated. The residue was purified by combi-flash to give the target compound (180 mg, crude). MS: M/e 768 (M+1)$^+$.

Step D: 2-butoxy-7-((5-methyl-6-(piperidin-4-yloxy)pyridin-3-yl)methyl)imidazo[2,1-f][1,2,4]triazin-4-amine (Compound A72)

To a mixture of the product of Step C (180 mg, crude) in TFA (12 mL) was added Et$_3$SiH (4 mL) and the resulting mixture was stirred at 85° C. overnight. The mixture was cooled to room temperature and concentrated to dryness. To the residue was added TFA (8 mL) and the resulting mixture was stirred at 85° C. overnight. The mixture was cooled to room temperature and concentrated to dryness. The residue was purified by prep-HPLC to give the target compound (120 mg, 60% for two steps). $^1$HNMR (400 MHz, DMSO-d$_6$) δ 8.71-8.35 (m, 2H), 8.17 (s, 2H), 7.94 (d, J=1.6 Hz, 1H), 7.51 (s, 1H), 7.45-7.30 (m, 1H), 5.31-5.16 (m, 1H), 4.21 (t, J=6.4 Hz, 2H), 4.06 (s, 2H), 3.35-3.05 (m, 4H), 2.11 (s, 3H), 2.11-2.01 (m, 2H), 1.95-1.80 (m, 2H), 1.74-1.60 (m, 2H), 1.44-1.32 (m, 2H), 0.92 (t, J=7.6 Hz, 3H) ppm. MS: M/e 412 (M+1)$^+$.

Compound A73: (4-amino-2-butoxyimidazo[2,1-f][1,2,4]triazin-7-yl)(4-methoxypyridin-2-yl)methanol Step A: (4-(bis(4-methoxybenzyl)amino)-2-butoxyimidazo[2,1-f][1,2,4]triazin-7-yl)(4-methoxypyridin-2-yl)methanol To a stirred solution of 7-bromo-2-butoxy-N,N-bis(4-methoxybenzyl)Imidazo[2,1-f][1,2,4]triazin-4-amine (150 mg, 0.286 mmol) in THF (10 mL) was added dropwise n-BuLi (1.6 M, 0.45 mL, 0.715 mmol) at −78° C. After stirred for an hour under N$_2$, a solution of 4-methoxypicolinaldehyde (58.6 mg, 0.48 mmol) in THF (2 mL) was added dropwise at −78° C. and the reaction was stirred for 4 hours. The reaction was quenched with aq.NH$_4$Cl, extracted with EtOAc (10 mL×3). The combined organic layers were washed with brine, dried over Na$_2$SO$_4$, concentrated and purified by prep-TLC (petroleum ether/EtOAc=2:1) to give the target compound (42 mg, 25%) as colorless oil. MS: M/e 585 (M+1)$^+$.

Step B: (4-amino-2-butoxyimidazo[2,1-f][1,2,4]triazin-7-yl)(4-methoxypyridin-2-yl)methanol (Compound A73)

A mixture of the product of Step A (42 mg, 0.072 mmol) in TFA/Et$_3$SiH (3 mL/0.5 mL) was stirred at 85° C. overnight. The reaction mixture was concentrated to give the residue, which was purified by prep-HPLC to give the target compound (5 mg, 20%). $^1$H NMR (400 MHz, DMSO-d$_6$) δ 8.25 (d, J=5.6 Hz, 1H), 8.16 (s, 1H), 8.06 (s, 1H), 7.26 (d, J=2.4 Hz, 1H), 7.21 (s, 1H), 6.88-6.86 (m, 1H), 6.14 (d, J=5.6 Hz, 1H), 6.02 (d, J=5.6 Hz, 1H), 4.18-4.04 (m, 2H), 3.85 (s, 3H), 1.71-1.53 (m, 2H), 1.43-1.31 (m, 2H), 0.91 (t, J=7.2 Hz, 3H) ppm. MS: M/e 345 (M+1)$^+$.

Compound A74: (4-amino-2-butoxyimidazo[2,1-f][1,2,4]triazin-7-yl)(pyridin-2-yl)methanol Step A: (4-(bis(4-methoxybenzyl)amino)-2-butoxyimidazo[2,1-f][1,2,4]triazin-7-yl)(pyridin-2-yl)methanol To a stirred solution of 7-bromo-2-butoxy-N,N-bis(4-methoxybenzyl)imidazo[2,1-f][1,2,4]triazin-4-amine (300 mg, 0.572 mmol) in THF (15 mL) was added dropwise n-BuLi (1.6 M, 0.9 mL, 1.43 mmol) at −78° C. After stirred for an hour under N$_2$, a solution of picolinaldehyde (92 mg, 0.856 mmol) in THF (2 mL) was added dropwise at −78° C. and the reaction was stirred for 3 hours. The reaction was quenched with aq.NH$_4$Cl, extracted with EtOAc (30 mL×2). The combined organic layers were washed with brine, dried over Na$_2$SO$_4$, concentrated and purified by column chromatography (petroleum ether/EtOAc=3:1) to give the target compound (240 mg, 75.7%) as colorless syrup. MS: M/e 585 (M+1)$^+$.

Step B: (4-amino-2-butoxyimidazo[2,1-f][1,2,4]triazin-7-yl)(pyridin-2-yl)methanol (Compound A74)

A mixture of the product of Step A (100 mg, 0.18 mmol) in TFA/Et$_3$SiH (3 mL/0.5 mL) was stirred at 85° C. overnight. The reaction mixture was concentrated to give the residue, which was purified by prep-HPLC to give the target compound (6 mg, 10.6%). $^1$H NMR (400 MHz, DMSO-d$_6$) 8.45 (d, J=4.4 Hz, 1H), 8.17-8.09 (m, 2H), 7.84 (t, J=7.6 Hz, 1H), 7.68 (d, J=7.6 Hz, 1H), 7.31-7.25 (m, 1H), 7.22 (s, 1H), 6.17 (d, J=5.6 Hz, 1H), 6.06 (d, J=5.6 Hz, 1H), 4.16-4.02 (m, 2H), 1.69-1.52 (m, 2H), 1.47-1.29 (m, 2H), 0.91 (t, J=7.4 Hz, 3H) ppm. MS: M/e 315 (M+1)$^+$.

Compound A75: 2-butoxy-7-(1-(4-(pyrrolidin-1-ylmethyl)phenyl)ethyl)imidazo[2,1-f][1,2,4]triazin-4-amine

Step A: (4-(bis(4-methoxybenzyl)amino)-2-butoxy-imidazo[2,1-f][1,2,4]triazin-7-yl)(4-(pyrrolidin-1-ylmethyl)phenyl)methanol To a cooled solution of 7-bromo-2-butoxy-N,N-bis(4-methoxybenzyl)imidazo[2,1-f][1,2,4]triazin-4-amine (200 mg, 0.38 mmol) in THF (8 mL) at −78° C. (purged with N$^2$), n-BuLi (1.6 M, 0.6 mL) was added dropwise. After stirring at −78° C. for 30 mins, 4-(pyrrolidin-1-ylmethyl)benzaldehyde (100 mg, 0.57 mmol) in THF (2 mL) was added. The resulting mixture was stirred at this temperature for 30 mins, and then warmed to rt for 2 hrs. The reaction was quenched with NH$_4$Cl solution (2 mL), extracted with ethyl acetate (10 mL) and washed with brine (10 mL). The organic layer was dried over Na$_2$SO$_4$, filtered and concentrated to get the crude product, which was further purified by Combi-Flash (DCM: MeOH=6%) to get the pure product (170 mg, 70%). MS: M/e 637 (M+1)$^+$.

Step B: (4-(bis(4-methoxybenzyl)amino)-2-butoxy-imidazo[2,1-f][1,2,4]triazin-7-yl)(4-(pyrrolidin-1-ylmethyl)phenyl)methanone Dess-martin reagent (229 mg, 0.54 mmol) was added in portionwise to a solution of the product of Step A (170 mg, 0.27 mmol) in THF (3 mL) at 0° C. After stirring at rt for 4 hrs, TLC showed the reaction was complete. The solution was quenched with NH$_4$Cl solution (5 mL) and extracted with ethyl acetate (10 mL). The organic layer was dried over Na$_2$SO$_4$, filtered and concentrated to get the crude product, which was further purified by CombiFlash (DCM: MeOH=5%) to get the product (130 mg, 76%). MS: M/e 635 (M+1)$^+$.

Step C: 1-(4-(bis(4-methoxybenzyl)amino)-2-butoxyimidazo[2,1-f][1,2,4]triazin-7-yl)-1-(4-(pyrrolidin-1-ylmethyl)phenyl)ethan-1-ol A solution of product of Step B (30 mg, 0.05 mmol) in THF (3 mL) at 0° C. under N$_2$ atmosphere was treated with CH$_3$MgBr (3M in ether, 0.2 mL) dropwise. The reaction mixture was stirred at rt for 3 hrs, and then quenched with NH$_4$Cl solution (5 mL). The solution was extracted with ethyl acetate (10 mL), washed with brine (10 mL), dried and concentrated to get the crude product, which was used in the next step directly without further purification. MS: M/e 651 (M+1)$^+$.

Step D: 2-butoxy-7-(1-(4-(pyrrolidin-1-ylmethyl)phenyl)ethyl)imidazo[2,1-f][1,2,4]triazin-4-amine (Compound A75)

A solution of 1-(4-(bis(4-methoxybenzyl)amino)-2-butoxyimidazo[2,1-f][1,2,4]triazin-7-yl)-1-(4-(pyrrolidin-1-ylmethyl)phenyl)ethan-1-ol (25 mg, 0.04 mmol) in triethylsilane (1 mL) and trifluoroacetic acid (1 mL) was heated at 80° C. for 1 hr. The solution was concentrated, added with trifluoroacetic acid (1 mL) and heated at 80° C. overnight. The solvent was evaporated to get the residue, which was basified with NaHCO$_3$, extracted with ethyl acetate (5 mL), washed with brine (5 mL). The organic layer was dried, concentrated and purified by prep-HPLC to get the product (6 mg, 40%). $^1$H NMR (400 MHz, DMSO-d6) δ 9.74 (br.s, 1H), 8.15 (s, 1H), 8.06 (s, 1H), 7.46-7.37 (m, 5H), 4.48 (q, J=8.0 Hz, 1H), 4.29 (s, 2H), 4.14-4.08 (m, 2H), 3.33 (s, 2H), 3.07-3.04 (m, 2H), 2.03-2.01 (m, 2H), 1.85-1.82 (m, 2H), 1.68-1.59 (m, 5H), 1.42-1.32 (m, 2H), 0.91 (t, J=8.0 Hz, 3H) ppm. MS: M/e 395 (M+1)$^+$.

Compound A76: 2-butoxy-7-((1-(piperidin-3-ylmethyl)-1H-pyrazol-4-yl)methyl)imidazo[2,1-f][1,2,4]triazin-4-amine

Step A: tert-butyl 3-(bromomethyl)piperidine-1-carboxylate

Tert-butyl 3-(hydroxymethyl)piperidine-1-carboxylate (2.15 g, 10 mmol) and CBr$_4$ (4.98 g, 15 mmol) were dissolved in CH$_2$Cl$_2$ (50 mL) was added PPh$_3$ (3.1 g, 12 mmol) at room temperature. After the addition, the reaction mixture was concentrated to give the residue, which was purified by column chromatography (petroleum ether/EtOAc=20:1) to give the target compound (2.3 g, 82.7%) as colorless oil. MS: M/e 278 (M+1)$^+$.

Step B: tert-butyl 3-((4-formyl-1H-pyrazol-1-yl)methyl)piperidine-1-carboxylate To a stirred suspension of NaH (60%, 0.6 g, 5 mmol) in DMF (5 mL) was added a solution of 1H-pyrazole-4-carbaldehyde (0.32 g, 3.3 mmol) in DMF (3 mL) at 0° C. After stirring for 30 min, was added a solution of the product of Step A (1.1 g, 4 mmol) in DMF (3 mL). Then the mixture was stirred overnight. The reaction mixture was quenched with H$_2$O (20 mL) and extracted with EtOAc (20 mL×3). The combined organic layers were washed with brine, dried over Na$_2$SO$_4$, concentrated and purified by column chromatography (petroleum ether/EtOAc=10: 1-1:1) to give the target compound (420 mg, 43.4%) as colorless oil. MS: M/e 294 (M+1)$^+$.

Step C: tert-butyl 3-((4-((4-(bis(4-methoxybenzyl)amino)-2-butoxyimidazo[2,1-f][1,2,4]triazin-7-yl)(hydroxy)methyl)-1H-pyrazol-1-yl)methyl)piperidine-1-carboxylate To a solution of 7-bromo-2-butoxy-N,N-bis(4-methoxybenzyl)imidazo[2,1-f][1,2,4]triazin-4-amine (150 mg, 0.286 mmol) in THF (10 mL) was added n-BuLi (1.6 M, 0.44 mL, 0.71 mmol) dropwise −78° C. After stirring for an hour, a solution of the product of Step B (125 mg, 0.428 mmol) in THF (2 mL) was added dropwise. The resulting mixture was stirred at −70° C. for 1 h and then warmed to room temperature for 1 h. The reaction was quenched with sat.aq.NH$_4$Cl solution, extracted with EtOAc (10 mL×3). The combined organic layers were washed with brine, dried over Na$_2$SO$_4$, filtered, and concentrated. The residue was purified by prep-TLC (petroleum ether/EtOAc=2:1) to give target compound (70 mg, 33%) as an off-white solid. MS: M/e 741 (M+1)$^+$.

Step D: 2-butoxy-7-((1-(piperidin-3-ylmethyl)-1H-pyrazol-4-yl)methyl)imidazo[2,1-f][1,2,4]triazin-4-amine (Compound A76)

To a mixture of the product of Step C (70 mg, 0.095 mmol) in Et$_3$SiH/TFA (0.5 mL/3 mL) was stirred at 85° C. overnight. The reaction mixture was concentrated to give the residue, which was purified by prep-HPLC to give the target compound (24 mg, 63.4%). $^1$H NMR (400 MHz, DMSO-d$_6$) δ 8.10 (s, 1H), 8.02 (s, 1H), 7.55 (s, 1H), 7.34 (s, 1H), 7.21 (s, 1H), 4.22 (t, J=6.4 Hz, 2H), 3.93 (s, 2H), 3.88 (d, J=7.2 Hz, 2H), 2.80-2.76 (m, 1H), 2.70-2.66 (m, 1H), 2.44-2.34 (m, 1H), 2.23-2.13 (m, 1H), 1.92-1.83 (m, 1H), 1.75-1.63 (m, 2H), 1.56-1.46 (m, 2H), 1.48-1.36 (m, 2H), 1.33-1.22 (m, 1H), 1.06-0.96 (m, 1H), 0.93 (t, J=7.2 Hz, 3H) ppm. MS: M/e 385 (M+1)$^+$.

Compound A77: 7-((6-(2-(methylamino)ethoxy)pyridin-3-yl)methyl)-2-(pentan-2-yloxy)imidazo[2,1-f][1,2,4]triazin-4-amine Step A: tert-butyl (2-((5-((4-(bis(4-methoxybenzyl)amino)-2-(pentan-2-yloxy)imidazo[2,1-f][1,2,4]triazin-7-yl)(hydroxy)methyl)pyridin-2-yl)oxy)ethyl)(methyl)carbamate To a stirred solution of N,N-bis(4-methoxybenzyl)-2-(pentan-2-yloxy)imidazo[2,1-f][1,2,4]triazin-4-amine (754 mg, 1.64 mmol) in dry THF (15 mL) was added dropwise n-BuLi (2.05 mL, 3.28 mmol) at −78° C. After stirred for half an hour, a solution of tert-butyl (2-((5-formylpyridin-2-yl)oxy)ethyl)(methyl)carbamate (550 mg, 1.96 mmol) in THF (5 mL) was added dropwise. After the addition, the reaction was stirred for 2 hours. The reaction was quenched with aq.NH$_4$Cl, extracted with EtOAc (30 mL×2). The combined organic layers were washed with brine, dried over Na$_2$SO$_4$, concentrated and purified by column chromatography (petroleum ether/EtOAc=2:1) to give the target compound (256 mg, 21%) as brown syrup. MS: M/e 742 (M+1)$^+$.

Step B: 7-((6-(2-(methylamino)ethoxy)pyridin-3-yl)methyl)-2-(pentan-2-yloxy)imidazo[2,1-f][1,2,4]triazin-4-amine (Compound A77)

A mixture of the product of step A (256 mg, 0.345 mmol) in TFA/Et$_3$SiH (3 mL/3 mL) was stirred at 90° C. overnight. The reaction mixture was concentrated to give the residue, which was purified by Prep-HPLC to give the target compound (20 mg). $^1$H NMR (400 MHz, DMSO-d$_6$) δ 8.21-7.94 (m, 4H), 7.65 (dd, J=8.5, 2.0 Hz, 1H), 7.31 (s, 1H), 6.78 (d, J=8.4 Hz, 1H), 5.03-4.89 (m, 1H), 4.41 (t, J=5.2 Hz, 2H), 4.09 (s, 2H), 3.24-3.12 (m, 2H), 2.55 (s, 3H), 1.70-1.47 (m, 2H), 1.43-1.29 (m, 2H), 1.25 (d, J=6.0 Hz, 3H), 0.89 (t, J=7.2 Hz, 3H) ppm. MS: M/e 386 (M+1)$^+$.

Compound A78: 7-((5-methyl-6-(2-(methylamino)ethoxy)pyridin-3-yl)methyl)-2-(pentan-2-yloxy)imidazo[2,1-f][1,2,4]triazin-4-amine Step A: tert-butyl (2-((5-((4-(bis(4-methoxybenzyl)amino)-2-(pentan-2-yloxy)imidazo[2,1-f][1,2,4]triazin-7-yl)(hydroxy)methyl)-3-methylpyridin-2-yl)oxy)ethyl)(methyl)carbamate To a stirred solution of N,N-bis(4-methoxybenzyl)-2-(pentan-2-yloxy)imidazo[2,1-f][1,2,4]triazin-4-amine (461 mg, 1 mmol) in dry THF (10 mL) was added dropwise n-BuLi (1.25 mL, 2 mmol) at −78° C. After stirred for half an hour, a solution of tert-butyl (2-((5-formyl-3-methylpyridin-2-yl)oxy)ethyl)(methyl)carbamate (353 mg, 1.2 mmol) in THF (2 mL) was added dropwise. After the addition, the reaction was stirred overnight. The reaction was quenched with aq.NH$_4$Cl, extracted with EtOAc (30 mL×2). The combined organic layers were washed with brine, dried over Na$_2$SO$_4$, concentrated and purified by column chromatography (petroleum ether/EtOAc=5:1-2:1) to give the target compound (340 mg, 45%) as brown syrup. MS: M/e 756 (M+1)$^+$.

Step B: 7-((5-methyl-6-(2-(methylamino)ethoxy)pyridin-3-yl)methyl)-2-(pentan-2-yloxy)imidazo[2,1-f][1,2,4]triazin-4-amine (Compound A78)

A mixture of the product of step A (340 mg, 0.45 mmol) in TFA/Et$_3$SiH (3 mL/3 mL) was stirred at 90° C. overnight. The reaction mixture was concentrated to give the residue, which was purified by Prep-HPLC to give the target compound (42 mg). $^1$H NMR (400 MHz, DMSO-d$_6$) δ 8.58 (br.s, 2H), 8.16 (s, 1H), 8.11 (s, 11H), 7.95 (d, J=1.6 Hz, 1H), 7.51 (d, J=1.4 Hz, 1H), 7.37 (s, 1H), 5.03-4.94 (m, 1H), 4.49-4.44 (m, 2H), 4.07 (s, 2H), 3.38-3.29 (m, 2H), 2.64 (t, J=5.6 Hz, 3H), 2.15 (s, 3H), 1.71-1.48 (m, 2H), 1.45-1.30 (m, 2H), 1.26 (d, J=6.0 Hz, 3H), 0.89 (t, J=7.2 Hz, 3H) ppm. MS: M/e 400 (M+1)$^+$.

Compound A79: 3-((4-amino-7-((6-(2-(methylamino)ethoxy)pyridin-3 yl)methyl) imidazo[2,1-f][1,2,4]triazin-2-yl)oxy)hexan-1-ol Step A: hexane-1,3-diol To a stirred suspension of LAH (0.76 g, 20 mmol) in THF (10 mL) was added dropwise a solution of methyl 3-hydroxyhexanoate (1.46 g, 10 mmol) in THF (5 mL) at 0° C. After the addition, the reaction was stirred for 2 hours. The reaction was quenched with H$_2$O (0.76 mL), aq.NaOH (15%, 0.76 mL), followed by H$_2$O (2.28 mL), then filtered. The filtrate was concentrated and purified by column chromatography (petroleum ether/EtOAc=2:1~1:1) to give the target compound (634 mg, 53.7%) as colorless oil.

Step B: 1-((tert-butyldimethylsilyl)oxy)hexan-3-ol

To a stirred solution of the product of step A (634 mg, 5.37 mmol) in CH$_2$Cl$_2$ (15 mL) was added Imidazole (730 mg, 10.74 mmol), then a solution of TBS-Cl (730 mg, 4.83 mmol) in CH$_2$Cl$_2$ (3 mL) was added dropwise at 0° C. After the addition, the reaction mixture was stirred for 2 hours. The reaction mixture was concentrated to give the residue, which was purified by column chromatography (petroleum ether/EtOAc=1:1) to give the target compound (1.1 g, 88.2%) as colorless oil.

Step C: 7-bromo-2-((1-((tert-butyldimethylsilyl)oxy)hexan-3-yl)oxy)-N,N-bis(4-methoxybenzyl)imidazo[2,1-f][1,2,4]triazin-4-amine To a stirred solution of the product of step B (464 mg, 2 mmol) in THF (10 mL) was added NaH (60%, 80 mg). After stirred for 30 min, 7-bromo-2-chloro-N,N-bis(4-methoxybenzyl)imidazo[2,1-f][1,2,4]triazin-4-amine (488 mg, 1 mmol) was added. After the addition, the reaction was stirred at 60° C. overnight. The reaction mixture was treated with $H_2O$ (20 mL), extracted with EtOAc (15 mL×2). The combined organic layers were washed with brine, dried over $Na_2SO_4$, concentrated and purified by column chromatography (petroleum ether/EtOAc=10:1) to give the target compound (530 mg, 77.5%) as colorless oil. MS: M/e 684 $(M+1)^+$.

Step D: tert-butyl (2-((5-((4-(bis(3,4-dimethoxylbenzyl)amino)-2-((1-((tert-butyldimethylsilyl)oxy)hexan-3-yl)oxy)imidazo[2,1-f][1,2,4]triazin-7-yl)(hydroxy)methyl)pyridin-2-yl)oxy)ethyl)(methyl)carbamate To a solution of 7-bromo-2-((1-((tert-butyldimethylsilyl)oxy)hexan-3-yl)oxy)-N,N-bis(2,4-dimethoxybenzyl)imidazo[2,1-f][1,2,4]triazin-4-amine (700 mg, 0.939 mmol) in THF (10 mL) was added n-BuLi (1.8 mL, 2.88 mmol) under $N_2$ at −78° C. After stirring for 0.5 h at −78° C., tert-butyl (2-((5-formylpyridin-2-yl)oxy)ethyl)(methyl)carbamate (400 mg, 1.429 mmol) was added. The reaction mixture was stirred for 2.5 h at −78° C. After completed, the reaction mixture was quenched with aq $NH_4Cl$ (30 mL) and extracted with DCM (3×30 mL). The combined organic layers was dried over $Na_2SO_4$ and concentrated under vacuum to get a residue. The residue was purified by column chromatography on silica gel eluting with ethyl acetate in petroleum ether (60%) to afford the title compound (590 mg, 66%). MS: M/e 946 $(M+1)^+$.

Step E: 3-((4-amino-7-(hydroxy(6-(2-(methylamino)ethoxy)pyridin-3-yl)methyl)imidazo[2,1-f][1,2,4]triazin-2-yl)oxy)hexan-1-ol The product of Step D (800 mg, 0.846 mmol) was dissolved in TFA (9 mL) and $H_2O$ (1 mL) under $N_2$. The reaction mixture was stirred for 12 h at 35° C. After completed, the solvent was removed by in vacuo. The residue was diluted with water (20 mL) and DCM (20 mL) and the aqueous phase was acid with 1 N HCl to adjust PH=2~3. The aqueous phase was washed with DCM (3×30 mL) and based with 2 N NaOH to adjust pH=13~14 and extracted with DCM/i-PrOH (5/1, 3×100 mL). The combined organic layers was dried over $Na_2SO_4$ and concentrated under vacuum to afford the title compound (320 mg, crude). MS: M/e 432 $(M+1)^+$.

Step F: 3-((4-amino-7-((6-(2-(methylamino)ethoxy)pyridin-3 yl)methyl) imidazo[2,1-f][1,2,4]triazin-2-yl)oxy)hexan-1-ol (Compound A79)

The product of step E (320 mg) was dissolved in TFA (5 mL) and $Et_3SiH$ (5 mL) under $N_2$. The reaction mixture was stirred for 12 h at 90° C. After completed, the solvent was removed by in vacuo. The residue was diluted with water (20 mL) and DCM (20 mL) and the aqueous phase was acid with 1 N HCl to adjust pH=2~3. The aqueous phase was washed with DCM (3×20 mL) and based with 2 N NaOH to adjust pH=13~14 and extracted with DCM/i-PrOH (5/1, 3×60 mL). The combined organic layers was dried over $Na_2SO_4$ and concentrated under vacuum to get a residue. The residue was purified by prep-HPLC to afford the title compound (15 mg). $^1$H NMR (400 MHz, $CD_3OD$) δ 8.09 (s, 1H), 7.62 (d, J=8.4 Hz, 1H), 7.33 (s, 1H), 6.77 (d, J=8.4 Hz, 1H), 5.24-5.10 (m, 1H), 4.37 (s, 2H), 4.15 (s, 2H), 3.70-3.56 (m, 2H), 2.99 (s, 2H), 2.47 (s, 3H), 1.98-1.79 (m, 2H), 1.77-1.53 (m, 2H), 1.50-1.33 (m, 2H), 0.91 (t, J=7.2 Hz, 3H) ppm. MS: M/e 416 $(M+1)^+$.

Compound A80: 7-((6-(2-(methylamino)ethoxy)pyridin-3-yl)methyl)-2-((tetrahydrofuran-3-yl)methoxy)imidazo[2,1-f][1,2,4]triazin-4-amine

Step A: tert-butyl (2-((5-((4-(bis(4-methoxybenzyl)amino)-2-((tetrahydrofuran-3-yl)methoxy)imidazo[2,1-f][1,2,4]triazin-7-yl)(hydroxy)methyl)pyridin-2-yl)oxy)ethyl)(methyl)carbamate To a solution of 7-bromo-N,N-bis(4-methoxybenzyl)-2-((tetrahydrofuran-3-yl)methoxy)imidazo[2,1-f][1,2,4]triazin-4-amine (134 mg, 0.24 mmol) in THF (8 mL) was added a solution of n-BuLi (1.6 M, 0.3 mL, 0.48 mmol) drop wise maintaining the temperature between −75~−65° C. After 1 h, a suspension of tert-butyl (2-((5-formylpyridin-2-yl)oxy)ethyl)(methyl)carbamate (100 mg, 0.36 mmol) in THF (2 mL) was added dropwise. The resulted mixture was stirred at −70° C. for 2 h and then warmed to room temperature for overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (160 mg, 88%). MS: M/e 756.9 $(M+1)^+$.

Step B: 7-((6-(2-(methylamino)ethoxy)pyridin-3-yl)methyl)-2-((tetrahydrofuran-3-yl)methoxy)imidazo[2,1-f][1,2,4]triazin-4-amine (Compound A80)

To a mixture of the product of step A (160 mg, 0.21 mmol) in TFA (4 mL) was added $Et_3SiH$ (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated and the residue was purified by prep-HPLC to give the target compound (19 mg, 22.6%). 1H NMR (400 MHz, DMSO-d6) δ 8.18 (s, 1H), 8.12 (s, 1H), 8.08 (s, 1H), 7.63 (d, J=8.3 Hz, 1H), 7.29 (s, 1H), 6.74 (d, J=8.4 Hz, 1H), 4.27 (t, J=5.5 Hz, 2H), 4.23-4.16 (m, 1H), 4.13-4.08 (m, 3H), 3.77 (t, J=7.6 Hz, 2H), 3.68-3.61 (m, 1H), 3.54-3.48 (m, 1H), 2.86 (d, J=5.3 Hz, 2H), 2.64 (dd, J=13.6, 6.9 Hz, 1H), 2.34 (s, 3H), 2.03-1.95 (m, 1H), 1.66-1.61 (m, 1H) ppm. MS: M/e 400 $(M+1)^+$.

Compound A81 and Compound A82: (R or S) 3-((4-amino-7-((6-(2-(methylamino)ethoxy)pyridin-3-yl)methyl)imidazo[2,1-f][1,2,4]triazin-2-yl)oxy)hexan-1-ol, and (S or R) 3-((4-amino-7-((6-(2-(methylamino)ethoxy)pyridin-3-yl)methyl)imidazo[2,1-f][1,2,4]triazin-2-yl)oxy)hexan-1-ol Compound A79 3-((4-amino-7-((6-(2-(methylamino)ethoxy)pyridin-3-yl)methyl)imidazo[2,1-f][1,2,4]triazin-2-yl)oxy)hexan-1-ol (70 mg, 0.168 mmol) was separated into two optical isomers Compound A81 and Compound A82 by prep-SFC to afford Compound A 81 (18 mg), and Compound A82 (38 mg). The condition of prep-SFC was below.

| | |
|---|---|
| Column | Chiral PAK AD-H |
| Column size | 3 cm × 25 cm, 5 μm |
| Mobile phase | hexane (2 mM $NH_3$—MeOH):IPA = 75:25 |
| Flow rate | 45 mL/min |
| Wavelength | UV: 220 mn |
| Temperature | 25° C. |

Compound A 81 (R or S optical isomer 1): $^1$H NMR (400 MHz, $CD_3OD$) δ 8.09 (s, 1H), 7.62 (d, J=8.4 Hz, 1H), 7.33 (s, 1H), 6.77 (d, J=8.4 Hz, 1H), 5.24-5.08 (m, 1H), 4.37 (t, J=5.2 Hz, 2H), 4.15 (s, 2H), 3.65 (d, J=4.8 Hz, 2H), 2.99 (s, 2H), 2.45 (s, 3H), 1.95-1.82 (m, 2H), 1.78-1.56 (m, 2H), 1.49-1.32 (m, 2H), 0.91 (t, J=7.2 Hz, 3H) ppm. MS: M/e 416 $(M+1)^+$.

Compound A82 (S or R optical isomer 2): $^1$H NMR (400 MHz, $CD_3OD$) δ 8.09 (s, 1H), 7.62 (d, J=8.4 Hz, 1H), 7.33 (s, 1H), 6.77 (d, J=8.4 Hz, 1H), 5.22-5.13 (m, 1H), 4.36 (t, J=5.2 Hz, 2H), 4.15 (s, 2H), 3.66 (d, J=4.8 Hz, 2H), 2.96 (s, 2H), 2.45 (s, 3H), 1.97-1.77 (m, 2H), 1.77-1.54 (m, 2H), 1.49-1.32 (m, 2H), 0.91 (t, J=7.2 Hz, 3H) ppm. MS: M/e 416 $(M+1)^+$.

Compound A83: 7-((6-(2-(methylamino)ethoxy) pyridin-3-yl)methyl)-2-(pentan-3-yloxy)imidazo[2,1-f][1,2,4]triazin-4-amine

Step A: N,N-bis(4-methoxybenzyl)-2-(pentan-3-yloxy)imidazo[2,1-f][1,2,4]triazin-4-amine To a solution of pentan-3-ol (88 mg, 1 mmol) in THF (10 mL) was added NaH (60%, 80 mg, 2 mmol) at 0 degrees. The reaction mixture was stirred at room temperature for 20 mins. 2-chloro-N,N-bis(4-methoxybenzyl)imidazo[2,1-f][1,2,4]triazin-4-amine (204 mg, 0.5 mmol) was added to the mixture. The reaction mixture was stirred at 70 degrees for overnight. An aqueous ammonium chloride solution was added and the mixture was extracted with ethyl acetate. The combined organic extracts were dried over sodium sulfate, filtered and evaporated. The crude product was purified by column chromatography to give the title product (220 mg, 95.6%). MS: m/e: 462 $(M+1)^+$.

Step B: tert-butyl (2-((5-((4-(bis(4-methoxybenzyl)amino)-2-(pentan-3-yloxy)imidazo[2,1-f][1,2,4]triazin-7-yl)(hydroxy)methyl)pyridin-2-yl)oxy)ethyl)(methyl)carbamate To a solution of N,N-bis(4-methoxybenzyl)-2-(pentan-3-yloxy)imidazo[2,1-f][1,2,4]triazin-4-amine (220 mg, 0.48 mmol) in THF (8 mL) was added a solution of n-BuLi (1.6 M, 0.44 mL, 0.72 mmol) drop wise maintaining the temperature between −75~−65° C. After 1 h, a suspension of tert-butyl (2-((5-formylpyridin-2-yl)oxy)ethyl)(methyl)carbamate (200 mg, 0.72 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (120 mg, 47%). MS: M/e 742 $(M+1)^+$.

Step C: 7-((6-(2-(methylamino)ethoxy)pyridin-3-yl)methyl)-2-(pentan-3-yloxy)imidazo[2,1-f][1,2,4]triazin-4-amine (Compound A83)

To a mixture of the product of step B (120 mg, 0.161 mmol) in TFA (4 mL) was added $Et_3SiH$ (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (25 mg, 38.6%). 1H NMR (400 MHz, DMSO-d6) δ 8.11 (s, 2H), 8.00 (s, 1H), 7.60 (d, J=8.5 Hz, 1H), 7.30 (s, 1H), 6.74 (d, J=8.4 Hz, 1H), 4.82-4.74 (m, 1H), 4.28 (t, J=5.5 Hz, 2H), 4.07 (s, 2H), 2.89 (t, J=5.4 Hz, 2H), 2.37 (s, 3H), 1.64-1.58 (m, 4H), 0.87 (t, J=7.3 Hz, 6H) ppm. MS: M/e 386 $(M+1)^+$.

Compound A84: 2-(hexan-3-yloxy)-7-((6-(2-(methylamino)ethoxy)pyridin-3-yl)methyl)imidazo[2,1-f][1,2,4]triazin-4-amine

Step A: 2-(hexan-3-yloxy)-N,N-bis(4-methoxybenzyl)imidazo[2,1-f][1,2,4]triazin-4-amine To a solution of hexan-3-ol (102 mg, 1 mmol) in THF (10 mL) was added NaH (60%, 80 mg, 2 mmol) at 0 degrees. The reaction mixture was stirred at room temperature for 20 mins. 2-chloro-N,N-bis(4-methoxybenzyl)imidazo[2,1-f][1,2,4]triazin-4-amine (204 mg, 0.5 mmol) was added to the mixture. The reaction mixture was stirred at 70 degrees for overnight. An aqueous ammonium chloride solution was added and the mixture was extracted with ethyl acetate. The combined organic extracts were dried over sodium sulfate, filtered and evaporated. The crude product was purified by column chromatography to give the title product (260 mg, 100%). MS: m/e: 476 $(M+1)^+$.

Step B: tert-butyl (2-((5-((4-(bis(4-methoxybenzyl)amino)-2-(hexan-3-yloxy)imidazo[2,1-f][1,2,4]triazin-7-yl)(hydroxy)methyl)pyridin-2-yl)oxy)ethyl)(methyl)carbamate To a solution of 2-(hexan-3-yloxy)-N,N-bis(4-methoxybenzyl)imidazo[2,1-f][1,2,4]triazin-4-amine (260 mg, 0.5 mmol) in THF (8 mL) was added a solution of n-BuLi (1.6 M, 0.44 mL, 0.72 mmol) drop wise maintaining the temperature between −75~−65° C. After 1 h, a suspension of tert-butyl (2-((5-formylpyridin-2-yl)oxy)ethyl)(methyl)carbamate (200 mg, 0.72 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (130 mg, 34.4%). MS: M/e 756 $(M+1)^+$.

Step C: 2-(hexan-3-yloxy)-7-((6-(2-(methylamino)ethoxy)pyridin-3-yl)methyl)imidazo[2,1-f][1,2,4]triazin-4-amine (Compound A84)

To a mixture of the product of step B (130 mg, 0.172 mmol) in TFA (4 mL) was added $Et_3SiH$ (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (12 mg, 16.9%). 1H NMR (400 MHz, DMSO-d6) δ 8.11 (s, 2H), 8.00 (s, 1H), 7.60 (d, J=8.4 Hz, 1H), 7.31 (s, 1H), 6.74 (d, J=8.6 Hz, 1H), 4.89-4.83 (m, 1H), 4.30 (t, J=5.5 Hz, 2H), 4.07 (s, 2H), 2.94 (s, 2H), 2.39 (s, 3H), 1.61-1.54 (m, 4H), 1.38-1.26 (m, 2H), 0.87 (t, J=6.9 Hz, 6H) ppm. MS: M/e 400 (M+1)$^+$.

Compound A85: 3-((4-amino-7-(4-(2-(methylamino) ethoxy)benzyl)imidazo [2,1-f][1,2,4]triazin-2-yl) oxy)hexan-1-ol Step A:
2-((tert-butoxycarbonyl)(methyl)amino)ethyl methanesulfonate To a 0° C. solution of tert-butyl (2-hydroxyethyl)(methyl) carbamate (3.5 g, 20 mmol) in THF (40 mL) was added DIEA (7.8 g, 60 mmol) and followed by MsCl (3.4 g, 30 mmol) in drops. The resulted mixture was stirred at rt for 2 hrs. The suspension was filtered, and the filtrate was diluted with EA (100 mL), washed with brine (100 mL×3), dried over Na$_2$SO$_4$ and concentrated under reduced pressure. The residue was purified by column chromatography (PE/EA=3:1) to obtain the title compound (3.1 g, crude). MS: M/e 254 (M+1)$^+$.

Step B: tert-butyl
(2-(4-formylphenoxy)ethyl)(methyl)carbamate

A mixture of 2-((tert-butoxycarbonyl)(methyl)amino) ethyl methanesulfonate (1.5 g, crude), 4-hydroxybenzaldehyde (800 mg, 6.5 mmol) and K$_2$CO$_3$ (2.5 g, 18.1 mmol) in DMF (10 mL) was stirred at 60° C. for 16 hrs. The mixture was diluted with EA (50 mL), filtered. The filtrate was washed with brine (20 mL×3), dried over Na$_2$SO$_4$ and concentrated under reduced pressure. The residue was purified by column chromatography (PE/EA=4:1) to obtain the title compound (105 mg, yield: 4% for 2 steps). MS: M/e 280 (M+1)$^+$.

Step C: tert-butyl (2-(4-((2-((1-(benzyloxy)hexan-3-yl)oxy)-4-(bis(2,4-dimethoxybenzyl)amino)imidazo [2,1-f][1,2,4]triazin-7-yl)(hydroxy)methyl)phenoxy) ethyl)(methyl)carbamate To a solution of 2-((1-(benzyloxy)hexan-3-yl)oxy)-N,N-bis(2,4-dimethoxybenzyl)imidazo[2,1-f][1,2,4]triazin-4-amine (156 mg, 0.24 mmol) in THF (2 mL) was added n-BuLi (1.6 M, 0.3 mL, 0.48 mmol) at −78° C. in N$_2$ atmosphere. The mixture was stirred at −78° C. for 20 min. Then the solution of tert-butyl (2-(4-formylphenoxy)ethyl) (methyl)carbamate (102 mg, 0.36 mmol) in THF (2 mL) was added to the system at −78° C. The reaction was stirred for 30 min, and then warmed to room temperature and stirred for 2 hrs. The reaction was quenched with saturated NH$_4$Cl (20 mL) at room temperature and extracted with EA (10 mL×3). The combined organic phase was washed with brine (10 mL×3), dried over Na$_2$SO$_4$ and concentrated under reduced pressure. The residue was purified by column chromatography to obtain the title compound (80 mg, yield: 36%). MS: M/e 921 (M+1)$^+$.

Step D: tert-butyl (2-(4-((4-(bis(2,4-dimethoxybenzyl)amino)-2-((1-(benzyloxy)hexan-3-yl)oxy)imidazo[2,1-f][1,2,4]triazin-7-yl)methyl)phenoxy)ethyl) (methyl)carbamate A mixture of tert-butyl (2-(4-((2-((1-(benzyloxy)hexan-3-yl)oxy)-4-(bis(2,4-dimethoxybenzyl)amino)imidazo[2,1-f] [1,2,4]triazin-7-yl)(hydroxy)methyl)phenoxy) ethyl) (methyl)carbamate (60 mg, 0.065 mmol) and Pd/C (wet, 60 mg) in MeOH (2 mL) was stirred under H$_2$ at rt for 2 days. The mixture was filtered and the filtrate was concentrated to obtain the title product (50 mg, yield: 94%). MS: M/e 815 (M+1)$^+$.

Step E: 3-((4-amino-7-(4-(2-(methylamino)ethoxy) benzyl)imidazo[2,1-f][1,2,4]triazin-2-yl)oxy)hexan-1-ol (Compound A85)

tert-butyl (2-(4-((4-(bis(2,4-dimethoxybenzyl)amino)-2-((1-hydroxyhexan-3-yl)oxy)imidazo[2,1-f][1,2,4]triazin-7-yl)methyl)phenoxy)ethyl)(methyl)carbamate (50 mg, 0.06 mmol) in TFA/H$_2$O (9:1, 5 mL) was stirred at rt for 16 hrs. The reaction was concentrated under reduced pressure. 2 mL H$_2$O was added. The mixture was stirred at RT for 20 min then was filtered. The filtrate was extracted with DCM (20 mL×2) to remove the impurities. The aqueous layer was basified by aq. NaOH (4M) to pH>10, extracted with DCM/IPA (5:1, 3 mL×5). The combined extracts were washed with brine (5 mL×3), dried over Na$_2$SO$_4$, concentrated and purified by prep-TLC (DCM/MeOH(NH$_3$)=10:1) to obtain the title compound (5 mg, yield: 12%). $^1$H NMR (400 MHz, CD$_3$OD) δ 7.32-7.23 (m, 3H), 6.94 (d, J=8.8 Hz, 2H), 5.26-5.11 (m, 1H), 4.26-4.19 (m, 2H), 4.18-4.11 (m, 2H), 3.75-3.54 (m, 2H), 3.46-3.37 (m, 2H), 2.77 (s, 3H), 1.95-1.82 (m, 2H), 1.77-1.61 (m, 2H), 1.49-1.37 (m, 2H), 0.92 (t, J=7.2 Hz, 3H) ppm. MS: M/e 415 (M+1)$^+$.

Compound A86: 3-((4-amino-7-((6-(3-(methylamino)propoxy)pyridin-3-yl)methyl)imidazo[2,1-f] [1,2,4]triazin-2-yl)oxy)hexan-1-ol Step A: tert-butyl (3-((5-formylpyridin-2-yl)oxy) propyl)(methyl)carbamate A mixture of 6-chloronicotinaldehyde (400 mg, 2.84 mmol), tert-butyl (3-hydroxypropyl)(methyl)carbamate (600 mg, 3.17 mmol), Pd$_2$(dba)$_3$ (180 mg, 0.20 mmol), RuPhos (187 mmol, 0.40 mmol) and Cs$_2$CO$_3$ (2.3 g, 7.0 mmol) in Dioxane (5 mL) was stirred at 100° C. for 4 hrs. The mixture was treated with 20 mL of EA and 20 mL of H$_2$O. The mixture was filtered through a celite pad. The aqueous layer was extracted with EA (20 mL×2). The combined organics was washed with brine (30 mL×3), dried over Na$_2$SO$_4$ and concentrated under reduced pressure. The residue was purified by column chromatography (PE/EA=2:1) to obtain the title compound (490 mg, yield: 59%). MS: M/e 295 (M+1)$^+$.

Step B: tert-butyl (3-((5-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)pyridin-2-yl)oxy)propyl)(methyl)carbamate To a solution of 2-((1-(benzyloxy)hexan-3-yl)oxy)-N,N-bis(2,4-dimethoxybenzyl)imidazo[2,1-f][1,2,4]triazin-4-amine (642 mg, 1.0 mmol) in THF (5 mL) was added n-BuLi (1.6 M, 1.5 mL, 2.4 mmol) at −78° C. in N$_2$ atmosphere. The mixture was stirred at −78° C. for 20 min. Then the solution of tert-butyl (3-((5-formylpyridin-2-yl)oxy)propyl)(methyl) carbamate (480 mg, 1.6 mmol) in THF (3 mL) was added to the system at −78° C. The reaction was stirred for 30 min, and then warmed to room temperature and stirred for 2 hrs. The reaction mixture was quenched with saturated NH$_4$Cl (20 mL) at room temperature and extracted with EA (10 mL×3). The combined organic phase was washed with brine (10 mL×3), dried over $Na_2SO_4$ and concentrated under reduced pressure. The residue was purified by column chromatography to obtain the title compound (510 mg, yield: 54%). MS: M/e 936 (M+1)+.

Step C: tert-butyl (3-((5-((4-(bis(2,4-dimethoxybenzyl)amino)-2-((1-hydroxyhexan-3-yl)oxy)imidazo[2,1-f][1,2,4]triazin-7-yl)(hydroxy)methyl)pyridin-2-yl)oxy)propyl)(methyl)carbamate A mixture of tert-butyl (3-((5-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)pyridin-2-yl)oxy)propyl)(methyl)carbamate (120 mg, 0.128 mmol) and Pd/C (wet, 120 mg) in MeOH (4 mL) was stirred under $H_2$ at rt for 5 days. The mixture was filtered and the filtrate was concentrated to obtain the title product (100 mg, crude) which was used for the next step directly. MS: M/e 846 (M+1)+.

Step D: 3-((4-amino-7-(hydroxy(6-(3-(methylamino)propoxy)pyridin-3-yl)methyl)imidazo[2,1-f][1,2,4]triazin-2-yl)oxy)hexan-1-ol tert-butyl (3-((5-((4-(bis(2,4-dimethoxybenzyl)amino)-2-((1-hydroxyhexan-3-yl)oxy)imidazo[2,1-f][1,2,4]triazin-7-yl)(hydroxy)methyl)pyridin-2-yl)oxy)propyl)(methyl)carbamate (100 mg, crude) in TFA/H2O (9:1, 5 mL) was stirred at rt for 16 hrs. The reaction mixture was concentrated under reduced pressure. 2 mL H2O was added. The mixture was stirred at RT for 30 min then was filtered. The filtrate was extracted with DCM (5 mL×2) to remove the impurities. The aqueous layer was basified by aq. NaOH (4M) to pH>10, extracted with DCM/IPA (5:1, 10 mL×3). The combined extracts were washed with brine (10 mL×3), dried over $Na_2SO_4$, concentrated to obtain the title compound (45 mg, crude). MS: M/e 446 (M+1)+.

Step E: 3-((4-amino-7-((6-(3-(methylamino)propoxy)pyridin-3-yl)methyl)imidazo[2,1-f][1,2,4]triazin-2-yl)oxy)hexan-1-ol (Compound A86)

A mixture of 3-((4-amino-7-(hydroxy(6-(3-(methylamino)propoxy)pyridin-3-yl)methyl)imidazo[2,1-f][1,2,4]triazin-2-yl)oxy)hexan-1-ol (45 mg, crude), TFA (2.5 mL) and $Et_3SiH$ (2.5 mL) was stirred at 70° C. for 20 hrs. The reaction mixture was concentrated under reduced pressure. The residue was dissolved into $H_2O$ (2 mL) and extracted with DCM (2 mL×2). The organic phase was discarded. The inorganic phase was basified by aq. NaOH (4 M) to pH>10. The mixture was extracted with DCM/iPrOH (5:1, 3 mL×3). The combined organic phase was washed with brine (5 mL×2), dried over $Na_2SO_4$ and concentrated. The residue was purified by prep-TLC (DCM/MeOH(NH$_3$)=9:1) to obtain the title compound (3.2 mg, yield: 6% for 3 steps). $^1$H NMR (400 MHz, CD$_3$OD) δ 8.12 (s, 1H), 7.66 (d, J=8.0 Hz, 1H), 7.36 (s, 1H), 6.78 (d, J=8.8 Hz, 1H), 5.23-5.11 (m, 1H), 4.37 (t, J=5.6 Hz, 2H), 4.16 (s, 2H), 3.69-3.60 (m, 2H), 3.20-3.12 (m, 2H), 2.71 (s, 3H), 2.21-2.10 (m, 2H), 1.95-1.83 (m, 2H), 1.76-1.62 (m, 2H), 1.49-1.36 (m, 2H), 0.92 (t, J=7.6 Hz, 3H) ppm. MS: M/e 430 (M+1)+.

Compound A87: 2-(heptan-4-yloxy)-7-((6-(2-(methylamino)ethyl)pyridin-3-yl)methyl)imidazo[2,1-f][1,2,4]triazin-4-amine Step A: 2-(heptan-4-yloxy)-N,N-bis(4-methoxybenzyl)imidazo[2,1-f][1,2,4]triazin-4-amine To a solution of heptan-4-ol (116 mg, 1 mmol) in THF (10 mL) was added NaH (60%, 80 mg, 2 mmol) at 0 degrees. The reaction mixture was stirred at room temperature for 20 mins. 2-chloro-N,N-bis(4-methoxybenzyl)imidazo[2,1-f][1,2,4]triazin-4-amine (204 mg, 0.5 mmol) was added to the mixture. The reaction mixture was stirred at 70 degrees for overnight. An aqueous ammonium chloride solution was added and the mixture was extracted with ethyl acetate. The combined organic extracts were dried over sodium sulfate, filtered and evaporated. The crude product was purified by column chromatography to give the title product (160 mg, 65.5%). MS: m/e: 490 (M+1)+.

Step B: tert-butyl (2-((5-((4-(bis(4-methoxybenzyl)amino)-2-(heptan-4-yloxy)imidazo[2,1-f][1,2,4]triazin-7-yl)(hydroxy)methyl)pyridin-2-yl)oxy)ethyl)(methyl)carbamate To a solution of 2-(heptan-4-yloxy)-N,N-bis(4-methoxybenzyl)imidazo[2,1-f][1,2,4]triazin-4-amine (160 mg, 0.327 mmol) in THF (8 mL) was added a solution of n-BuLi (1.6 M, 0.31 mL, 0.5 mmol) drop wise maintaining the temperature between −75~−65° C. After 1 h, a suspension of tert-butyl (2-((5-formylpyridin-2-yl)oxy)ethyl)(methyl)carbamate (130 mg, 0.46 mmol) in THF (2 mL) was added dropwise. The resulted mixture was stirred at −70° C. for 2 h and then warmed to room temperature for overnight. The reaction was quenched with saturated NH$_4$Cl solution, extracted with EtOAc (20 mL×3), washed with brine, dried over $Na_2SO_4$, filtered, and concentrated. The residue was purified by prep-TLC to give the target compound (100 mg, 39.8%). MS: M/e 770 (M+1)+.

Step C: 2-(heptan-4-yloxy)-7-((6-(2-(methylamino)ethoxy)pyridin-3-yl)methyl)imidazo[2,1-f][1,2,4]triazin-4-amine (Compound A87)

To a mixture of the product of step B (100 mg, 0.13 mmol) in TFA (4 mL) was added Et$_3$SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (3 mg, 5.4%). 1H NMR (400 MHz, DMSO-d6) δ 8.69 (s, 2H), 8.13 (s, 2H), 8.01 (s, 1H), 7.65 (d, J=8.3 Hz, 1H), 7.31 (s, 1H), 6.78 (d, J=8.6 Hz, 1H), 5.04-4.92 (m, 1H), 4.44 (s, 2H), 4.09 (s, 2H), 2.98 (s, 2H), 2.60 (s, 3H), 1.61-1.54 (m, 4H), 1.42-1.33 (m, 4H), 0.87 (t, J=7.3 Hz, 6H) ppm. MS: M/e 414 (M+1)+.

Compound A88: 7-((6-(2-(methylamino)ethoxy)pyridin-3-yl)methyl)-2-((tetrahydrofuran-2-yl)methoxy)imidazo[2,1-f][1,2,4]triazin-4-amine Step A: 7-bromo-N,N-bis(4-methoxybenzyl)-2-((tetrahydrofuran-2-yl)methoxy)imidazo[2,1-f][1,2,4]triazin-4-amine To a solution of (tetrahydrofuran-2-yl)methanol (204 mg, 2 mmol) in THF (10 mL) was added NaH (60%, 160 mg, 4 mmol) at 0 degrees. The reaction mixture was stirred at room temperature for 20 mins. 7-bromo-2-chloro-N,N-bis(4-methoxybenzyl)imidazo[2,1-f][1,2,4]triazin-4-amine (487 mg, 1 mmol) was added to the mixture. The reaction mixture was stirred at 70 degrees for overnight. An aqueous ammonium chloride solution was added and the mixture was extracted with ethyl acetate. The combined organic extracts were dried over sodium sulfate, filtered and evaporated. The crude product was purified by column chromatography to give the title product (440 mg, 79.4%). MS: m/e: 554 (M+1)$^+$.

Step B: tert-butyl (2-((5-((4-(bis(4-methoxybenzyl) amino)-2-((tetrahydrofuran-2-yl)methoxy)imidazo[2, 1-f][1,2,4]triazin-7-yl)(hydroxy)methyl)pyridin-2-yl) oxy)ethyl)(methyl)carbamate To a solution of 7-bromo-N,N-bis(4-methoxybenzyl)-2-((tetrahydrofuran-2-yl)methoxy)imidazo[2,1-f][1,2,4]triazin-4-amine (220 mg, 0.39 mmol) in THF (8 mL) was added a solution of n-BuLi (1.6 M, 0.45 mL, 0.72 mmol) drop wise maintaining the temperature between −75~−65° C. After 1 h, a suspension of tert-butyl (2-((5-formylpyridin-2-yl)oxy)ethyl)(methyl)carbamate (151 mg, 0.54 mmol) in THF (2 mL) was added dropwise. The resulted mixture was stirred at −70° C. for 2 h and then warmed to room temperature for overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (130 mg, 44.2%). MS: M/e 756 (M+1)$^+$.

Step C: 7-((6-(2-(methylamino)ethoxy)pyridin-3-yl) methyl)-2-((tetrahydrofuran-2-yl)methoxy)imidazo [2,1-f][1,2,4]triazin-4-amine (Compound A88)

To a mixture of the product of step B (130 mg, 0.172 mmol) in TFA (4 mL) was added Et$_3$SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated and the residue was purified by prep-HPLC to give the target compound (5 mg, 7.2%). 1H NMR (400 MHz, DMSO-d6) δ 8.18 (s, 1H), 8.14 (s, 1H), 8.10 (s, 1H), 7.66 (d, J=8.2 Hz, 1H), 7.30 (s, 1H), 6.78 (d, J=8.5 Hz, 1H), 4.38 (t, J=4.9 Hz, 2H), 4.17 (t, J=8.3 Hz, 2H), 4.14 (s, 1H), 4.10 (s, 2H), 3.76 (t, J=7.3 Hz, 1H), 3.72-3.62 (m, 1H), 3.14 (s, 2H), 2.51 (s, 3H), 1.99 (s, 1H), 1.84 (dd, J=13.9, 6.8 Hz, 2H), 1.66 (d, J=8.0 Hz, 1H) ppm. MS: M/e 400 (M+1)$^+$.

Compound A89: (S)-2-(sec-butoxy)-7-((6-(2-(methylamino)ethoxy)pyridin-3-yl)methyl)imidazo[2,1-f] [1,2,4]triazin-4-amine Step A: 2-chloro-N,N-bis(2,4-dimethoxybenzyl) imidazo[2,1-f][1,2,4]triazin-4-amine To a mixture of imidazo[2,1-f][1,2,4]triazine-2,4(1H,3H)-dione (10 g, 65.8 mmol), POCl$_3$ (50 g, 0.33 mol) and toluene (60 mL) was added DIPEA (25.5 g, 0.20 mmol) during 30 min at 60° C. At which time an exotherm was noted and the temperature was rising to 90° C. (Solid was dissolved gradually). After addition completed, the reaction was warmed to 100° C. (inner temperature was about 95° C.) and stirred overnight. Then the reaction was cooled to room temperature. The mixture was concentrated under reduced pressure. The residue was dissolved into THF (100 mL), then DIPEA (25.5 g, 0.20 mmol) was added to the mixture dropwisely. This mixture was added to the solution of bis(2,4-dimethoxybenzyl)amine (31.3 g, 0.10 mol), K$_2$CO$_3$ (18 g, 1.32 mol), THF (260 mL) and water (260 mL) at 0° C. during 1 hour. After addition completed, the mixture was extracted with EA (300 mL×3). The combined organic phase was washed with brine, dried over Na$_2$SO$_4$ and concentrated under reduced pressure. The residue was dissolved into EA (400 mL), the mixture was stirred at reflux for 1 hour and filtered at this temperature. The filtrate was concentrated under reduced pressure. The EA was swapped to MeOH and the mixture was stirred at room temperature overnight. The mixture was filtered and the solid (off-white) was collected. The product was used into next step directly (20 g, HPLC: 98.87%, Yield: 54.4%).

Step B: (S)-2-(sec-butoxy)-N,N-bis(2,4-dimethoxybenzyl)imidazo[2,1-f][1,2,4]triazin-4-amine To a solution of (S)-butan-2-ol (236 mg, 3.19 mmol) in THF (20 mL) was added NaH (128 mg, 3.2 mmol) under N$_2$ at 0° C. After stirring for 0.5 h at 25° C., 2-chloro-N,N-bis (2,4-dimethoxybenzyl)imidazo[2,1-f][1,2,4]triazin-4-amine (500 mg, 1.06 mmol) was added. The reaction mixture was stirred for 6 h at 70° C. After completed, the reaction mixture was quenched with water (20 mL) and extracted with EtOAc (3×30 mL). The combined organic layers was dried over Na$_2$SO$_4$ and concentrated under vacuum to get a residue. The residue was purified by column chromatography on silica gel eluting with ethyl acetate in petroleum ether (40%) to afford the title compound (540 mg, crude). MS: M/e 508 (M+1)$^+$.

Step C: tert-butyl (2-((5-((4-(bis(2,4-dimethoxybenzyl)amino)-2-((R)-sec-butoxy)imidazo[2,1-f][1,2,4] triazin-7-yl)(hydroxy)methyl)pyridin-2-yl)oxy)ethyl) (methyl)carbamate To a solution of the product of step B (540 mg, 1.06 mmol) in THF (15 mL) was added n-BuLi (1.4 mL, 2.24 mmol) under N$_2$ at −78° C. After stirring for 0.5 h at −78° C., tert-butyl (2-((5-formylpyridin-2-yl)oxy)ethyl)(methyl) carbamate (445 mg, 1.59 mmol) was added. The reaction mixture was stirred for 2.5 h at −78° C. After completed, the reaction mixture was quenched with aq NH$_4$Cl (30 mL) and extracted with DCM (3×30 mL). The combined organic layers was dried over Na$_2$SO$_4$ and concentrated under vacuum to get a residue. The residue was purified by column chromatography on silica gel eluting with ethyl acetate in petroleum ether (70%) to afford the title compound (340 mg, 41%). MS: M/e 788 (M+1)$^+$.

Step D: (4-amino-2-((S)-sec-butoxy)imidazo[2,1-f] [1,2,4]triazin-7-yl)(6-(2-(methylamino)ethoxy)pyridin-3-yl)methanol The product of step C (340 mg, 0.431 mmol) was dissolved in TFA (6 mL) and H$_2$O (0.6 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust PH=13~14 and extracted with DCM/i-PrOH (5/1, 3×100 mL). The combined organic layers was dried over Na$_2$SO$_4$ and concentrated under vacuum to afford the title compound (120 mg, crude). MS: M/e 388 (M+1)$^+$.

Step E: (S)-2-(sec-butoxy)-7-((6-(2-(methylamino) ethoxy)pyridin-3 yl)methyl)imidazo [2,1-f][1,2,4] triazin-4-amine (Compound A89)

The product of step D (120 mg, 0.31 mmol) was dissolved in TFA (4 mL) and Et$_3$SiH (4 mL) under N$_2$. The reaction mixture was stirred for 12 h at 90° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust pH=13~14 and extracted with DCM/i-PrOH (5/1, 3×100 mL). The combined organic layers was dried over $Na_2SO_4$ and concentrated under vacuum to get a residue. The residue was purified by Prep-TLC (DCM/$CH_3OH$ ($NH_3$)=15/1) to afford the title compound (17 mg). $^1H$ NMR (400 MHz, $CD_3OD$) δ 8.13 (s, 1H), 7.67 (d, J=8.4 Hz, 1H), 7.34 (s, 1H), 6.82 (d, J=8.4 Hz, 1H), 4.99-4.94 (m, 1H), 4.55-4.44 (m, 2H), 4.16 (s, 2H), 3.32 (s, 2H), 2.68 (s, 3H), 1.80-1.59 (m, 2H), 1.31 (d, J=6.0 Hz, 3H), 0.97 (t, J=7.2 Hz, 3H) ppm. MS: M/e 372 (M+1)$^+$.

Compound A90: (S)-7-((6-(2-(methylamino)ethoxy)pyridin-3-yl)methyl)-2-(pentan-2-yloxy)imidazo[2,1-f][1,2,4]triazin-4-amine Step A: tert-butyl (2-((5-((4-(bis(2,4-dimethoxybenzyl)amino)-2-(((R)-pentan-2-yl)oxy)imidazo[2,1-f][1,2,4]triazin-7-yl)(hydroxy)methyl)pyridin-2 yl)oxy)ethyl) (methyl)carbamate To a solution of (S)—N,N-bis(2,4-dimethoxybenzyl)-2-(pentan-2-yloxy)imidazo[2,1-f][1,2,4]triazin-4-amine (600 mg, 1.15 mmol) in THF (10 mL) was added n-BuLi (1.4 mL, 2.24 mmol) under $N_2$ at −78° C. After stirring for 0.5 h at −78° C., tert-butyl (2-((5-formylpyridin-2-yl)oxy)ethyl) (methyl)carbamate (480 mg, 1.71 mmol) was added. The reaction mixture was stirred for 2.5 h at −78° C. After completed, the reaction mixture was quenched with aq $NH_4Cl$ (30 mL) and extracted with DCM (3×30 mL). The combined organic layers was dried over $Na_2SO_4$ and concentrated under vacuum to get a residue. The residue was purified by column chromatography on silica gel eluting with ethyl acetate in petroleum ether (40%) to afford the title compound (720 mg, 78%). MS: M/e 802 (M+1)$^+$.

Step B: (4-amino-2-(((S)-pentan-2-yl)oxy)imidazo[2,1-f][1,2,4]triazin-7-yl)(6-(2-(methylamino)ethoxy)pyridin-3-yl)methanol tert-butyl (2-((5-((4-(bis(2,4-dimethoxybenzyl)amino)-2-(((R)-pentan-2-yl)oxy)imidazo[2,1-f][1,2,4]triazin-7-yl)(hydroxy)methyl)pyridin-2 yl)oxy)ethyl) (methyl)carbamate (720 mg, 0.898 mmol) was dissolved in TFA (9 mL) and $H_2O$ (1 mL) under $N_2$. The reaction mixture was stirred for 12 h at 40° C. After completed, the solvent was removed by in vacuo. The residue was diluted with water (20 mL) and DCM (30 mL) and the aqueous phase was acid with 1 N HCl to adjust pH=1-2. The aqueous phase was washed with DCM (3×20 mL) and based with 2 N NaOH to adjust pH=13~14 and extracted with DCM/i-PrOH (5/1, 3×120 mL). The combined organic layers was dried over $Na_2SO_4$ and concentrated under vacuum to afford the title compound (290 mg, crude). MS: M/e 402 (M+1)$^+$.

Step C: (S)-7-((6-(2-(methylamino)ethoxy)pyridin-3-yl)methyl)-2-(pentan-2-yloxy)imidazo [2,1-f][1,2,4]triazin-4-amine (Compound A90)

(4-amino-2-(((S)-pentan-2-yl)oxy)imidazo[2,1-f][1,2,4]triazin-7-yl)(6-(2-(methylamino)ethoxy)pyridin-3-yl) methanol (290 mg, crude) was dissolved in TFA (5 mL) and $Et_3SiH$ (5 mL) under $N_2$. The reaction mixture was stirred for 12 h at 90° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust pH=13~14 and extracted with DCM/i-PrOH (5/1, 3×120 mL). The combined organic layers was dried over $Na_2SO_4$ and concentrated under vacuum to get a residue. The residue was purified by Prep-TLC (DCM/$CH_3OH$ ($NH_3$)=20/1 to 15/1) to afford the title compound (70 mg). $^1H$ NMR (400 MHz, $CD_3OD$) δ 8.01 (s, 1H), 7.54 (d, J=8.4 Hz, 1H), 7.24 (s, 1H), 6.69 (d, J=8.4 Hz, 1H), 4.95 (qt, J=12.0, 6.4 Hz, 1H), 4.37-4.27 (m, 2H), 4.05 (s, 2H), 3.08-2.98 (m, 2H), 2.47 (s, 3H), 1.71-1.55 (m, 1H), 1.54-1.25 (m, 3H), 1.21 (d, J=6.0 Hz, 3H), 0.84 (t, J=7.2 Hz, 3H) ppm. MS: M/e 386 (M+1)$^+$.

Compound A91: 3-((4-amino-7-(3-fluoro-4-(2-(methylamino)ethoxy)benzyl)imidazo[2,1-f][1,2,4]triazin-2-yl)oxy)hexan-1-ol Step A: tert-butyl (2-(2-fluoro-4-formylphenoxy)ethyl)(methyl)carbamate To a solution of 3-fluoro-4-hydroxybenzaldehyde (280 mg, 2 mmol) in THF (10 mL) was added tert-butyl (2-hydroxyethyl)(methyl)carbamate (350 mg, 2 mmol) and PPh3 (628 mg, 2.4 mmol), The mixture was protected by nitrogen and cooled down to 0 degrees. A solution of DIAD (552 mg, 2.4 mmol) in THE (2 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (400 mg, 67.3%). MS: m/e: 298 (M+1)$^+$.

Step B: tert-butyl (2-(4-((2-((1-(benzyloxy)hexan-3-yl)oxy)-4-(bis(4-methoxybenzyl)amino)imidazo[2,1-f][1,2,4]triazin-7-yl)(hydroxy)methyl)-2-fluorophenoxy)ethyl)(methyl)carbamate To a solution of 2-((1-(benzyloxy)hexan-3-yl)oxy)-N,N-bis(4-methoxybenzyl)imidazo[2,1-f][1,2,4]triazin-4-amine (291 mg, 0.5 mmol) in THF (8 mL) was added a solution of n-BuLi (1.6 M, 0.44 mL, 0.72 mmol) drop wise maintaining the temperature between −75~−65° C. After 1 h, a suspension of tert-butyl (2-(2-fluoro-4-formylphenoxy)ethyl) (methyl)carbamate (400 mg, 1.3 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (340 mg, 77%). MS: M/e 879 (M+1)$^+$.

Step C: tert-butyl (2-(4-((4-(bis(4-methoxybenzyl)amino)-2-((1-hydroxyhexan-3-yl)oxy)imidazo[2,1-f][1,2,4]triazin-7-yl)(hydroxy)methyl)-2-fluorophenoxy)ethyl)(methyl)carbamate To a solution of the product of step B (340 mg, 0.38 mmol) in MeOH (20 mL) was added Pd/C (800 mg). The mixture was protected by hydrogen and stirred at room temperature for overnight. The mixture was filtered and the filtrate was concentrated in vacuo. The crude product was purified by column chromatography to give the title product (230 mg, 75.4%). MS: m/e: 789 (M+1)$^+$.

Step D: 3-((4-amino-7-(3-fluoro-4-(2-(methylamino) ethoxy)benzyl)imidazo[2,1-f][1,2,4]triazin-2-yl)oxy) hexan-1-ol (Compound A91)

To a mixture of the product of step C (230 mg, 0.291 mmol) in TFA (4 mL) was added Et$_3$SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (8 mg, 6.4%). 1H NMR (400 MHz, DMSO-d6) δ 8.13 (s, 1H), 8.02 (s, 1H), 7.31 (s, 1H), 7.19 (d, J=12.2 Hz, 1H), 7.08 (d, J=8.5 Hz, 2H), 5.04 (d, J=5.3 Hz, 1H), 4.17 (d, J=4.8 Hz, 2H), 4.08 (s, 2H), 3.55-3.39 (m, 5H), 3.11 (s, 2H), 1.82-1.70 (m, 2H), 1.61 (d, J=6.2 Hz, 2H), 1.31 (dd, J=14.8, 7.3 Hz, 2H), 1.23 (s, 1H), 0.86 (t, J=7.2 Hz, 3H) ppm. MS: M/e 433 (M+1)$^+$.

Compound A92 and Compound A93: (R or S) 3-((4-amino-7-(4-(2-(methylamino)ethoxy)benzyl) imidazo[2,1-f][1,2,4]triazin-2-yl)oxy)hexan-1-ol, and (S or R) 3-((4-amino-7-(4-(2-(methylamino) ethoxy)benzyl)imidazo[2,1-f][1,2,4]triazin-2-yl)oxy) hexan-1-ol Compound A85 3-((4-amino-7-(4-(2-(methylamino) ethoxy)benzyl)imidazo[2,1-f][1,2,4]triazin-2-yl)oxy)hexan-1-ol (1.1 g, 2.66 mmol) was separated into two optical isomers Compound A92 (441 mg) and Compound A93 (410 mg) by prep-SFC. The condition of prep-SFC was below.

| Column | CHIRAL ART Amylose-C NEO |
|---|---|
| Column size | 3 cm × 25 cm, 5 um |
| Injection | 3.0 mL |
| Mobile phase | CO2:IPA(2 mM NH3—MeOH) = 60:40 |
| Flow rate | 50 mL/min |
| Wavelength | UV 220 nm |
| Temperature | 35° C. |
| Sample solution | 19.6 mg/ml in IPA:MeOH = 3:1 |

Compound A92 (R or S optical isomer 1): $^1$H NMR (400 MHz, CD$_3$OD) δ 7.25 (s, 1H), 7.20 (d, J=8.8 Hz, 2H), 6.87 (d, J=8.4 Hz, 2H), 5.27-5.08 (m, 1H), 4.12 (s, 2H), 4.04 (t, J=5.2 Hz, 2H), 3.65 (t, J=6.0 Hz, 2H), 2.92 (t, J=5.2 Hz, 2H), 2.43 (s, 3H), 1.98-1.81 (m, 2H), 1.78-1.57 (m, 2H), 1.51-1.32 (m, 2H), 0.91 (t, J=7.2 Hz, 3H) ppm. MS: M/e 415 (M+1)$^+$.

Compound A93: (S or R optical isomer 2): $^1$H NMR (400 MHz, CD$_3$OD) δ 7.25 (s, 1H), 7.20 (d, J=8.4 Hz, 2H), 6.87 (d, J=8.4 Hz, 2H), 5.24-5.09 (m, 1H), 4.12 (s, 2H), 4.05 (t, J=5.2 Hz, 2H), 3.65 (t, J=6.4 Hz, 2H), 2.92 (t, J=5.2 Hz, 2H), 2.44 (s, 3H), 2.00-1.82 (m, 2H), 1.80-1.58 (m, 2H), 1.50-1.31 (m, 2H), 0.91 (t, J=7.2 Hz, 3H) ppm. MS: M/e 415 (M+1)$^+$.

Compound A94:3-((4-amino-7-(4-(methyl(2-(methylamino)ethyl)amino)benzyl)imidazo[2,1-f][1,2,4] triazin-2-yl)oxy)hexan-1-ol Step A: tert-butyl (2-((4-formylphenyl)(methyl) amino)ethyl)(methyl)carbamate To a solution of 4-chlorobenzaldehyde (500 mg, 3.57 mmol), tert-butyl methyl(2-(methylamino)ethyl)carbamate (740 mg, 3.94 mmol) in dioxane (10 mL) were added Pd(OAc)$_2$ (100 mg, 0.446 mmol), BINAP (350 mg, 0.562 mmol) and Cs$_2$CO$_3$ (2.4 g, 7.36 mmol) under N$_2$. The reaction mixture was stirred for 1 h at 90° C. After completed, the reaction mixture was quenched with water (30 mL) and extracted with EtOAc (3×30 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (510 mg, 49%). MS: M/e 293. (M+H)$^+$.

Step B: tert-butyl (2-((4-((2-((1-(benzyloxy)hexan-3-yl)oxy)-4-(bis(2,4-dimethoxybenzyl)amino)imidazo[2,1-f][1,2,4]triazin-7 yl)(hydroxy)methyl)phenyl) (methyl)amino)ethyl)(methyl)carbamate To a solution of 2-((1-(benzyloxy)hexan-3-yl)oxy)-N,N-bis(2,4-dimethoxybenzyl)imidazo[2,1-f][1,2,4]triazin-4-amine (480 mg, 0.748 mmol) in THF (20 mL) was added n-BuLi (0.7 mL, 1.12 mmol) under N$_2$ at −78° C. After stirring for 0.5 h at −78° C., a solution of tert-butyl (2-((4-formylphenyl)(methyl)amino)ethyl)(methyl) carbamate (260 mg, 0.89 mmol) in THF (5 mL) was added dropwise. The reaction mixture was stirred for 2.5 h at −78° C. After completed, the reaction mixture was quenched with aq NH$_4$Cl (30 mL) and extracted with DCM (3×30 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (470 mg, 67%). MS: M/e 934 (M+1)$^+$.

Step C: tert-butyl (2-((4-((4-(bis(2,4-dimethoxybenzyl)amino)-2-((1-hydroxyhexan-3-yl)oxy)imidazo[2, 1-f][1,2,4]triazin-7 yl)methyl)phenyl)(methyl) amino)ethyl)(methyl)carbamate To a solution of tert-butyl (2-((4-((2-((1-(benzyloxy) hexan-3-yl)oxy)-4-(bis(2,4-dimethoxybenzyl)amino)imidazo[2,1-f][1,2,4]triazin-7 yl)(hydroxy)methyl)phenyl) (methyl)amino)ethyl)(methyl)carbamate (470 mg, 0.503 mmol) in MeOH (20 mL) was added Pd/C (500 mg). The reaction mixture was stirred for 48 h at 40° C. under H$_2$ (1 atm). The mixture was filtered and the filtrate was combined together and concentrated in vacuo. The residue was purified by column chromatography on silica gel eluting with ethyl acetate in petroleum ether (80%) to afford the title compound (90 mg, 22%). MS: M/e 828 (M+1)$^+$.

Step D: 3-((4-amino-7-(4-(methyl(2 (methylamino) ethyl)amino)benzyl)imidazo [2,1-f][1,2,4]triazin-2-yl)oxy)hexan-1-ol (Compound A94)

tert-butyl (2-((4-((4-(bis(2,4-dimethoxybenzyl)amino)-2-((1-hydroxyhexan-3-yl)oxy)imidazo[2,1-f][1,2,4]triazin-7-yl)methyl)phenyl)(methyl) amino)ethyl)(methyl) carbamate (90 mg, 0.109 mmol) was dissolved in TFA (4 mL) and H$_2$O (0.4 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×30 mL) and based with 2 N NaOH to adjust PH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=20/1 to 10/1) to afford the title compound (16 mg, 35%). $^1$H NMR (400 MHz, CD$_3$OD) δ 7.23 (s, 1H), 7.14 (d, J=8.4 Hz, 2H), 6.74 (d, J=8.4 Hz, 2H), 5.25-5.13 (m, 1H), 4.07 (s, 2H), 3.65 (t, J=6.4 Hz, 2H), 3.44 (t, J=6.8 Hz, 2H), 2.90 (s, 3H), 2.83 (t, J=6.8 Hz, 2H), 2.46 (s, 3H), 1.95-1.84 (m, 2H), 1.79-1.59 (m, 2H), 1.51-1.32 (m, 2H), 0.92 (t, J=7.2 Hz, 3H) ppm. MS: M/e 428 (M+1)$^+$.

Compound A95:3-((4-amino-7-(4-(2-(methylamino) ethyl)benzyl)imidazo[2,1-f][1,2,4]triazin-2-yl)oxy) hexan-1-ol Step A: methyl 4-(2-((tert-butoxycarbonyl)(methyl) amino)ethyl)benzoate To a solution of 4-(2-((tert-butoxycarbonyl)amino)ethyl) benzoic acid (2.5 g, 9.43 mmol) in DMF (30 mL) were added NaH (1.5 g, 37.5 mmol) under N$_2$ at 0° C. After stirring for 0.5 h at 25° C., CH$_3$I (5.4 g, 38.03 mmol) in DMF (10 mL) was added dropwise. The reaction mixture was stirred for 16 h at 25° C. After completed, the reaction mixture was quenched with ice water (50 mL) at 0° C. and extracted with EtOAc (3×100 mL). The combined organic layers were washed with water (3×50 mL), brine (3×50 mL), dried over Na$_2$SO$_4$ and concentrated under vacuum to get a crude product (2.2 g). $^1$H NMR (400 MHz, CDCl$_3$) δ 7.96 (d, J=8.0 Hz, 2H), 7.25 (d, J=8.0 Hz, 2H), 3.91 (s, 3H), 3.45 (t, J=7.2 Hz, 2H), 2.87 (t, J=7.2 Hz, 2H), 2.80 (s, 3H), 1.41 (s, 9H) ppm. MS: M/e 316. (M+H)$^+$.

Step B: tert-butyl (4-(hydroxymethyl)phenethyl)(methyl)carbamate

To a solution of methyl 4-(2-((tert-butoxycarbonyl) (methyl)amino)ethyl)benzoate (2.1 g, 7.17 mmol) in THF (20 mL) were added LiAlH$_4$ (1.1 g, 28.94 mmol) under N$_2$ at 0° C. The reaction mixture was stirred for 0.5 h at 25° C. After completed, the reaction mixture was quenched with water (1.1 mL), 15% NaOH (1.1 mL) and water (3.3 mL) at 0° C. and Na$_2$SO$_4$ was added. The mixture was filtered and the filtrate was combined together and concentrated in vacuo to get crude product (2.2 g). MS: M/e 288. (M+Na)$^+$.

Step C: tert-butyl (4-formylphenethyl)(methyl)carbamate

To a solution of tert-butyl (4-(hydroxymethyl)phenethyl) (methyl)carbamate (2.15 g, 8.11 mmol) in DCM (20 mL) were added DMP (4.1 g, 9.67 mmol) under N$_2$ at 0° C. The reaction mixture was stirred for 1 h at 25° C. After completed, the reaction mixture was quenched with aq Na$_2$S$_2$O$_3$ (50 mL) and extracted with DCM (3×50 mL). The combined organic layers were washed with aq NaHCO$_3$ (50 mL), brine (50 mL) and dried over Na$_2$SO$_4$ and concentrated under vacuum to get a residue. The residue was purified by column chromatography on silica gel eluting with ethyl acetate in petroleum ether (40%) to afford the title compound (1.1 g, 44% for three steps). $^1$H NMR (400 MHz, DMSO) δ 9.97 (s, 1H), 7.84 (d, J=7.6 Hz, 2H), 7.43 (d, J=6.8 Hz, 2H), 3.43 (t, J=6.0 Hz, 2H), 2.86 (t, J=7.2 Hz, 2H), 2.74 (s, 3H), 1.43-1.16 (m, 9H) ppm.

Step D: tert-butyl (4-((2-((1-(benzyloxy)hexan-3-yl) oxy)-4-(bis(2,4-dimethoxybenzyl)amino)imidazo[2, 1-f][1,2,4]triazin-7-yl)(hydroxy)methyl)phenethyl) (methyl)carbamate To a solution of 2-((1-(benzyloxy)hexan-3-yl)oxy)-N,N-bis(2,4-dimethoxybenzyl)imidazo[2,1-f][1,2,4]triazin-4-amine (500 mg, 0.78 mmol) in THF (15 mL) was added n-BuLi (0.73 mL, 1.17 mmol) under N$_2$ at −78° C. After stirring for 0.5 h at −78° C., a solution of tert-butyl (4-(form-ylphenethyl)(methyl)carbamate (246 mg, 0.935 mmol) in THF (5 mL) was added dropwise. The reaction mixture was stirred for 2.5 h at −78° C. After completed, the reaction mixture was quenched with aq NH$_4$Cl (50 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (430 mg, 61%). MS: M/e 905 (M+1)$^+$.

Step E: tert-butyl (4-((4-(bis(2,4-dimethoxybenzyl) amino)-2-((1-hydroxyhexan-3-yl)oxy)imidazo[2,1-f] [1,2,4]triazin-7-yl)methyl)phenethyl)(methyl)car-bamate To a solution of tert-butyl (4-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)phenethyl) (methyl) carbamate (430 mg, 0.475 mmol) in MeOH (20 mL) was added Pd/C (500 mg). The reaction mixture was stirred for 16 h at 40° C. under H$_2$ (1 atm). The mixture was filtered and the filtrate was combined together and concentrated in vacuo. The residue was purified by column chromatography on silica gel eluting with ethyl acetate in petroleum ether (80%) to afford the title compound (190 mg, 50%). MS: M/e 799 (M+1)$^+$.

Step F: 3-((4-amino-7-(4-(2-(methylamino)ethyl) benzyl)imidazo[2,1-f][1,2,4]triazin-2-yl)oxy)hexan-1-ol (Compound A95)

Tert-butyl (4-((4-(bis(2,4-dimethoxybenzyl)amino)-2-((1-hydroxyhexan-3-yl)oxy)imidazo[2,1-f][1,2,4]triazin-7-yl)methyl)phenethyl)(methyl)carbamate (190 mg, 0.238 mmol) was dissolved in TFA (4 mL) and H$_2$O (0.4 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust pH=1~2. The aqueous phase was washed with DCM (3×30 mL) and based with 2 N NaOH to adjust pH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=20/1 to 15/1) to afford the title compound (50 mg, 53%). $^1$H NMR (400 MHz, CD$_3$OD) δ 7.31-7.25 (m, 3H), 7.18 (d, J=7.6 Hz, 2H), 5.24-5.11 (m, 1H), 4.18 (s, 2H), 3.68-3.58 (m, 2H), 3.00 (d, J=7.6 Hz, 2H), 2.86 (t, J=7.6 Hz, 2H), 2.54 (s, 3H), 1.95-1.88 (m, 2H), 1.78-1.56 (m, 2H), 1.51-1.31 (m, 2H), 0.92 (t, J=7.2 Hz, 3H) ppm. MS: M/e 399 (M+1)$^+$.

Compound A96: 3-((4-amino-7-(4-(2-(methylamino) ethoxy)benzyl)imidazo [2,1-f][1,2,4]triazin-2-yl) oxy)hexan-1-ol Step A: tert-butyl (2-((5-((2-((1-(benzyloxy)hexan-3-yl)oxy)-4-(bis(2,4-dimethoxybenzyl)amino)imi-dazo[2,1-f][1,2,4]triazin-7-yl)(hydroxy)methyl)-6-methoxypyridin-2-yl)oxy)ethyl)(methyl)carbamate To a solution of 2-((1-(benzyloxy)hexan-3-yl)oxy)-N,N-bis(2,4-dimethoxybenzyl)imidazo[2,1-f][1,2,4]triazin-4- amine (250 mg, 0.39 mmol) in THF (3 mL) was added n-BuLi (1.6 M, 1.0 mL, 1.6 mmol) at −78° C. in $N_2$ atmosphere. The mixture was stirred at −78° C. for 30 min. Then the solution of tert-butyl (2-((5-formyl-6-methoxypyridin-2-yl)oxy)ethyl)(methyl)carbamate (170 mg, 0.55 mmol) in THF (2 mL) was added to the system at −78° C. The reaction was stirred for 30 min, and then warmed to room temperature and stirred for 16 hrs. The reaction was quenched with saturated $NH_4Cl$ (10 mL) at room temperature and extracted with EA (10 mL×3). The combined organic phase was washed with brine (10 mL×2), dried over $Na_2SO_4$ and concentrated under reduced pressure. The residue was purified by column chromatography to obtain the title compound (120 mg, yield: 32%). MS: M/e 952 (M+1)+.

Step B: tert-butyl (2-((5-((4-(bis(2,4-dimethoxybenzyl)amino)-2-((1-hydroxyhexan-3-yl)oxy)imidazo[2,1-f][1,2,4]triazin-7-yl)methyl)-6-methoxypyridin-2-yl)oxy)ethyl) (methyl)carbamate A mixture of tert-butyl (2-((5-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)-6-methoxypyridin-2-yl)oxy)ethyl)(methyl)carbamate (120 mg, 0.126 mmol) and Pd/C (wet, 200 mg) in MeOH (5 mL) was stirred under $H_2$ at rt for 16 hrs. The mixture was filtered and the filtrate was concentrated. The resulted residue was purified by prep-TLC (PE/EA=1:1) to obtain the title product (65 mg, yield: 60%). MS: M/e 846 (M+1)+.

Step C: 3-((4-amino-7-((2-methoxy-6-(2-(methylamino)ethoxy)pyridin-3-yl)methyl)imidazo[2,1-f][1,2,4]triazin-2-yl)oxy)hexan-1-ol (Compound A96)

Tert-butyl (2-((5-((4-(bis(2,4-dimethoxybenzyl)amino)-2-((1-hydroxyhexan-3-yl)oxy)imidazo[2,1-f][1,2,4]triazin-7-yl)methyl)-6-methoxypyridin-2-yl)oxy)ethyl) (methyl) carbamate (65 mg, 0.077 mmol) in TFA (2 mL) was stirred at rt for 24 hrs. The reaction mixture was concentrated under reduced pressure. The residue was treated with NaOH (2 mL, 4M), extracted with DCM/IPA (5:1, 3 mL×3). The combined organics was washed with brine (5 mL×3), dried over $Na_2SO_4$, concentrated and purified by prep-TLC (DCM/MeOH($NH_3$)=8:1) to obtain the title compound (5 mg, yield: 15%). $^1H$ NMR (400 MHz, $CD_3OD$) δ 7.51 (d, J=8.0 Hz, 1H), 7.24 (s, 1H), 6.37 (d, J=8.0 Hz, 1H), 5.24-5.15 (m, 1H), 4.60-4.54 (m, 2H), 4.07 (s, 2H), 3.96 (s, 3H), 3.68-3.61 (m, 2H), 3.46-3.42 (m, 2H), 2.76 (s, 3H), 2.07-1.98 (m, 2H), 1.96-1.82 (m, 2H), 1.75-1.64 (m, 2H), 0.94-0.89 (m, 3H) ppm. MS: M/e 446 (M+1)+.

Compound A97: 3-((4-amino-7-(2-fluoro-4-(2-(methylamino)ethoxy)benzyl)imidazo[2,1-f][1,2,4]triazin-2-yl)oxy)hexan-1-ol Step A: tert-butyl (2-(3-fluoro-4-formylphenoxy)ethyl)(methyl)carbamate To a solution of 2-fluoro-4-hydroxybenzaldehyde (1.4 g, 10 mmol) in THF (20 mL) was added tert-butyl (2-hydroxyethyl)(methyl)carbamate (1.75 g, 10 mmol) and $PPh_3$ (3.1 g, 12 mmol), The mixture was protected by nitrogen and cooled down to 0 degrees. A solution of DIAD (2.4 g, 12 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (867 mg, 29.2%). MS: m/e: 298 (M+1)+.

Step B: tert-butyl (2-(4-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)-3-fluorophenoxy)ethyl)(methyl)carbamate To a solution of 2-((1-(benzyloxy)hexan-3-yl)oxy)-N,N-bis(2,4-dimethoxybenzyl)imidazo[2,1-f][1,2,4]triazin-4-amine (867 mg, 1.35 mmol) in THF (10 mL) was added a solution of n-BuLi (1.6 M, 2.1 mL, 3.3 mmol) dropwise maintaining the temperature between −75~−65° C. After 1 h, a suspension of tert-butyl (2-(3-fluoro-4-formylphenoxy)ethyl)(methyl)carbamate (400 mg, 1.34 mmol) in THF (2 mL) was added dropwise. The resulted mixture was stirred at −70° C. for 2 h and then warmed to room temperature overnight. The reaction was quenched with saturated $NH_4Cl$ solution, extracted with EtOAc (20 mL×3), washed with brine, dried over $Na_2SO_4$, filtered, and concentrated. The residue was purified by prep-TLC to give the target compound (670 mg, 52.9%). MS: M/e 939 (M+1)+.

Step C: tert-butyl (2-(4-((4-(bis(2,4-dimethoxybenzyl)amino)-2-((1-hydroxyhexan-3-yl)oxy)imidazo[2,1-f][1,2,4]triazin-7-yl)methyl)-3-fluorophenoxy)ethyl)(methyl)carbamate To a solution of tert-butyl (2-(4-((2-((1-(benzyloxy)hexan-3-yl)oxy)-4-(bis(2,4-dimethoxybenzyl)amino)imidazo[2,1-f][1,2,4]triazin-7-yl)(hydroxy)methyl)-3-fluorophenoxy)ethyl)(methyl)carbamate (670 mg, 0.71 mmol) in MeOH (20 mL) was added Pd/C (600 mg). The mixture was protected by hydrogen and stirred at room temperature for overnight. The mixture was filtered and the filtrate was concentrated in vacuo. The crude product was purified by column chromatography to give the title product (100 mg, 16.9%). MS: m/e: 834 (M+1)+.

Step D: 3-((4-amino-7-(2-fluoro-4-(2-(methylamino)ethoxy)benzyl)imidazo[2,1-f][1,2,4]triazin-2-yl)oxy)hexan-1-ol (Compound A97)

To a mixture of the product of step C (100 mg, 0.12 mmol) in TFA (9 mL) was added $H_2O$ (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over $Na_2SO_4$ and concentrated in vacuo. The crude product was purified by prep-HPLC to give the target compound (10 mg, 19.2%). 1H NMR (400 MHz, DMSO-d6) δ 8.11 (s, 1H), 8.00 (s, 1H), 7.29-7.14 (m, 2H), 6.82 (d, J=11.7 Hz, 1H), 6.71 (d, J=8.0 Hz, 1H), 5.04 (s, 1H), 4.43 (s, 1H), 4.03 (dd, J=14.1, 8.4 Hz, 4H), 3.48 (d, J=6.0 Hz, 2H), 2.89 (s, 2H), 2.37 (s, 3H), 1.77 (d, J=6.1 Hz, 2H), 1.59 (s, 2H), 1.37-1.26 (m, 2H), 0.86 (t, J=7.3 Hz, 3H) ppm. MS: M/e 433 (M+1)+.

Compound A98: 3-((4-amino-7-(3-methoxy-4-(2-(methylamino)ethoxy)benzyl)imidazo[2,1-f][1,2,4]triazin-2-yl)oxy)hexan-1-ol Step A: tert-butyl (2-(4-formyl-2-methoxyphenoxy)ethyl)(methyl)carbamate To a solution of 4-hydroxy-3-methoxybenzaldehyde (1.52 g, 10 mmol) in THF (20 mL) was added tert-butyl (2-hydroxyethyl)(methyl)carbamate (1.75 g, 10 mmol) and PPh$_3$ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1.6 g, 51.7%). MS: m/e: 310 (M+1)$^+$.

Step B: tert-butyl (2-(4-((2-((1-(benzyloxy)hexan-3-yl)oxy)-4-(bis(2,4-dimethoxybenzyl)amino)imidazo [2,1-f][1,2,4]triazin-7-yl)(hydroxy)methyl)-2-methoxyphenoxy)ethyl)(methyl)carbamate To a solution of 2-((1-(benzyloxy)hexan-3-yl)oxy)-N,N-bis(2,4-dimethoxybenzyl)imidazo[2,1-f][1,2,4]triazin-4-amine (867 mg, 1.35 mmol) in THF (10 mL) was added a solution of n-BuLi (1.6 M, 2.1 mL, 3.3 mmol) drop wise maintaining the temperature between −75~−65° C. After 1 h, a suspension of tert-butyl (2-(4-formyl-2-methoxyphenoxy) ethyl)(methyl)carbamate (618 mg, 2 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by HPLC to give the target compound (650 mg, 50.7%). MS: M/e 951 (M+1)$^+$.

Step C: tert-butyl (2-(4-((4-(bis(2,4-dimethoxybenzyl)amino)-2-((1-hydroxyhexan-3-yl)oxy)imidazo[2,1-f][1,2,4]triazin-7-yl)methyl)-2-methoxyphenoxy) ethyl)(methyl)carbamate To a solution of tert-butyl (2-(4-((2-((1-(benzyloxy) hexan-3-yl)oxy)-4-(bis(2,4-dimethoxybenzyl)amino)imi-dazo[2,1-f][1,2,4]triazin-7-yl)(hydroxy)methyl)-2-methoxyphenoxy)ethyl)(methyl)carbamate (650 mg, 0.68 mmol) in MeOH (20 mL) was added Pd/C (600 mg). The mixture was protected by hydrogen and stirred at room temperature for overnight. The mixture was filtered and the filtrate was concentrated in vacuo. The crude product was purified by column chromatography to give the title product (200 mg, 34.7%). MS: m/e: 845 (M+1)$^+$.

Step D: 3-((4-amino-7-(3-methoxy-4-(2-(methyl-amino)ethoxy)benzyl)imidazo[2,1-f][1,2,4]triazin-2-yl)oxy)hexan-1-ol (Compound A98)

To a mixture of the product of step C (200 mg, 0.24 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (50 mg, 47.6%). 1H NMR (400 MHz, DMSO-d6) δ 8.09 (s, 1H), 7.97 (s, 1H), 7.27 (s, 1H), 6.95 (s, 1H), 6.86 (d, J=8.4 Hz, 1H), 6.78 (d, J=7.9 Hz, 1H), 5.06-5.01 (m, 1H), 4.44 (s, 1H), 4.05 (s, 2H), 3.95 (t, J=5.5 Hz, 2H), 3.72 (s, 3H), 3.48 (s, 2H), 2.82 (s, 2H), 2.34 (s, 3H), 1.78 (d, J=6.5 Hz, 2H), 1.60 (s, 2H), 1.41-1.26 (m, 2H), 0.86 (t, J=7.3 Hz, 3H) ppm. MS: M/e 445 (M+1)$^+$.

Compound A99: (S)-7-(3-fluoro-4-(2-(methylamino) ethoxy)benzyl)-2-(pentan-2-yloxy)imidazo[2,1-f][1, 2,4]triazin-4-amine Step A: tert-butyl (2-(4-((4-(bis(4-methoxybenzyl) amino)-2-(((S)-pentan-2-yl)oxy)imidazo[2,1-f][1,2, 4]triazin-7-yl)(hydroxy)methyl)-2-fluorophenoxy) ethyl)(methyl)carbamate To a solution of (S)—N,N-bis(4-methoxybenzyl)-2-(pen-tan-2-yloxy)imidazo[2,1-f][1,2,4]triazin-4-amine (234 mg, 0.5 mmol) in THF (10 mL) was added a solution of n-BuLi (1.6 M, 0.9 mL, 1.5 mmol) dropwise maintaining the temperature between −75~−65° C. After 1 h, a suspension of tert-butyl (2-(2-fluoro-4-formylphenoxy)ethyl)(methyl)car-bamate (297 mg, 1 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (120 mg, 31.6%). MS: M/e 759 (M+1)$^+$.

Step B: (S)-7-(3-fluoro-4-(2-(methylamino)ethoxy) benzyl)-2-(pentan-2-yloxy)imidazo[2,1-f][1,2,4] triazin-4-amine (Compound A99)

To a mixture of the product of step C (120 mg, 0.158 mmol) in TFA (4 mL) was added Et$_3$SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (22 mg, 34.9%). 1H NMR (400 MHz, DMSO-d6) δ 8.11 (s, 1H), 7.99 (s, 1H), 7.30 (s, 1H), 7.16 (m, 1H), 7.09 (t, J=8.5 Hz, 1H), 7.02 (d, J=8.2 Hz, 1H), 5.03-4.88 (m, 1H), 4.07 (s, 4H), 2.90 (t, J=5.3 Hz, 2H), 2.38 (s, 3H), 1.62 (d, J=6.8 Hz, 1H), 1.51 (d, J=5.9 Hz, 1H), 1.35 (dd, J=14.8, 7.5 Hz, 2H), 1.24 (d, J=6.0 Hz, 3H), 0.88 (t, J=7.2 Hz, 3H) ppm. MS: M/e 403 (M+1)$^+$.

Compound A100: (S)-7-(4-(2-(methylamino)ethoxy) benzyl)-2-(pentan-2-yloxy)imidazo[2,1-f][1,2,4] triazin-4-amine Step A: tert-butyl (2-(4-((4-(bis(2,4-dimethoxyben-zyl)amino)-2-(((S)-pentan-2-yl)oxy)imidazo[2,1-f] [1,2,4]triazin-7-yl)(hydroxy)methyl)phenoxy)ethyl) (methyl)carbamate To a solution of (S)—N,N-bis(2,4-dimethoxybenzyl)-2-(pentan-2-yloxy)imidazo[2,1-f][1,2,4]triazin-4-amine (521 mg, 1.0 mmol) in THF (5 mL) was added n-BuLi (1.6 M, 3.1 mL, 5.0 mmol) at −78° C. in N$_2$ atmosphere. The mixture was stirred at −78° C. for 30 min. Then the solution of tert-butyl (2-(4-formylphenoxy)ethyl)(methyl)carbamate (500 mg, 2.0 mmol) in THF (5 mL) was added to the system at −78° C. The reaction was stirred for 30 min, and then warmed to room temperature and stirred for 16 hrs. The reaction was quenched with saturated NH$_4$Cl (10 mL) at room temperature and extracted with EA (10 mL×3). The combined organic phase was washed with brine (10 mL×3), dried over Na$_2$SO$_4$ and concentrated under reduced pressure. The residue was purified by column chromatography to obtain the title compound (265 mg, yield: 33%). MS: M/e 801 (M+1)$^+$.

Step B: tert-butyl (S)-(2-(4-((4-(bis(2,4-dimethoxybenzyl)amino)-2-(pentan-2-yloxy)imidazo[2,1-f][1,2,4]triazin-7-yl)methyl)phenoxy)ethyl)(methyl)carbamate A mixture of tert-butyl (2-(4-((4-(bis(2,4-dimethoxybenzyl)amino)-2-(((S)-pentan-2-yl)oxy)imidazo[2,1-f][1,2,4]triazin-7-yl)(hydroxy)methyl)phenoxy)ethyl)(methyl) carbamate (210 mg, 0.26 mmol), Pd/C (wet, 200 mg) and AcOH (0.5 mL) in MeOH (20 mL) was stirred under H2 at rt for 24 hrs. The mixture was filtered and the filtrate was concentrated under high vacuum to obtain the title product (205 mg, crude). MS: M/e 785 (M+1)$^+$.

Step C: (S)-7-(4-(2-(methylamino)ethoxy)benzyl)-2-(pentan-2-yloxy)imidazo[2,1-f][1,2,4]triazin-4-amine (Compound A100)

tert-butyl (S)-(2-(4-((4-(bis(2,4-dimethoxybenzyl)amino)-2-(pentan-2-yloxy)imidazo[2,1-f][1,2,4]triazin-7-yl)methyl)phenoxy)ethyl)(methyl)carbamate (205 mg, 0.26 mmol) in TFA (5 mL) was stirred at rt for 16 hrs. The reaction mixture was concentrated under reduced pressure. The residue was treated with NaOH (2 mL, 4M), extracted with DCM/IPA (5:1, 3 mL×3). The combined organics was washed with brine (5 mL×3), dried over Na$_2$SO$_4$, concentrated and purified by prep-TLC (DCM/MeOH(NH$_3$)=10:1) to obtain the title compound (5 mg, yield: 15%). $^1$H NMR (400 MHz, CD$_3$OD) δ 7.26 (s, 1H), 7.20 (d, J=8.0 Hz, 2H), 6.87 (d, J=8.0 Hz, 2H), 5.13-4.99 (m, 1H), 4.12 (s, 2H), 4.05 (t, J=4.8 Hz, 2H), 2.98-2.88 (m, 2H), 2.44 (s, 3H), 1.80-1.66 (m, 1H), 1.64-1.50 (m, 1H), 1.50-1.35 (m, 2H), 1.30 (d, J=6.0 Hz, 3H), 0.93 (t, J=7.2 Hz, 3H) ppm. MS: M/e 385 (M+1)$^+$.

Compound A101: (R or S)-3-((4-amino-7-(2-methoxy-4-(2-(methylamino)ethoxy)benzyl)imidazo[2,1-f][1,2,4]triazin-2-yl)oxy)hexan-1-ol Step A: (R or S)-2-(2-(benzyloxy)ethyl)oxirane Set up a reactor R-1 with an agitator. (Note: the reactor R-1: 500 mL bottle), Charged NaH (19.1 g, 0.54× by weight, 60% purity) into reactor R-1. Charged THF (210 mL, 6.00× by volume) into reactor R-1. Charged (R or S)-2-(oxiran-2-yl)ethan-1-ol (35.0 g, 1.00× by weight) into reactor R-1 at 0° C. Stirred the mixture at 0° C. for 0.5 h. Charged BnBr (81.5 g, 2.33× by weight) and TBAI (14.7 g, 0.42× by weight) into reactor R-1 at 0° C. Stirred the mixture at 25° C. for 16 h. TLC (petroleum ether/ethyl acetate=3/1, R$^f$=0.42) showed the reaction was completed. Added H$_2$O (150 mL, 4.29× by volume) to the mixture. Extracted the mixture with EtOAc (200 mL×2, 11.4× by volume). Combined the organic layer and washed the organic layer with brine. Dried the organic layer with Na$_2$SO$_4$. Concentrated the organic layer to get the crude product. The residue was purified by column chromatography (SiO$_2$, petroleum ether/ethyl acetate=50/1 to 5/1). To afford the target compound (40.0 g, 56.5% yield) as a yellow oil. $^1$HNMR: 400 MHz CDCl$_3$: δ 7.30-7.36 (m, 5H), 4.55 (s, 2H), 3.62-3.66 (m, 2H), 3.08-3.09 (m, 1H), 2.78-2.81 (m, 1H), 2.53-2.55 (m, 1H), 1.90-1.92 (m, 1H), 1.81-1.82 (m, 1H) ppm.

Step B: (R or S)-1-(benzyloxy)hexan-3-ol

Set up a reactor R-1 with an agitator. (Note: the reactor R-1:1 L bottle), Charged EtMgBr (150 mL, 3.75× by volume) into reactor R-1. Charged THF (240 mL, 6.00× by volume) into reactor R-1. Charged CuI (0.85 g, 0.02× by weight) into reactor R-1 at 0° C. Stirred the mixture at 0° C. for 0.5 h. Charged (R or S)-2-(2-(benzyloxy)ethyl)oxirane (40.0 g, 1.00× by weight) into reactor R-1. Stirred the mixture at 25° C. for 1 h. TLC (petroleum ether/ethyl acetate=3/1, R$_f$=0.35) showed the reaction was completed. Added aq.NH$_4$Cl (200 mL, 5.00× by volume) to the mixture. Extracted the mixture with EtOAc (200 mL×2, 10.0× by volume). Combined the organic layer and washed the organic layer with brine. Dried the organic layer with Na$_2$SO$_4$. Concentrated the organic layer to get the crude product. The residue was purified by column chromatography (SiO$_2$, petroleum ether/ethyl acetate=50/1 to 5/1). Target (22.7 g, 47.1% yield, 97.0% purity) as a yellow oil. $^1$HNMR: 400 MHz CDCl$_3$: δ 7.30-7.38 (m, 5H), 4.54 (s, 2H), 3.74-3.83 (m, 1H), 3.69-3.73 (m, 1H), 3.65-3.67 (m, 1H), 2.87 (s, 1H), 1.75-1.77 (m, 2H), 1.36-1.48 (m, 4H), 0.92-0.95 (m, 3H) ppm.

Step C: (R or S)-2-((1-(benzyloxy)hexan-3-yl)oxy)-N,N-bis(2,4-dimethoxybenzyl)imidazo[2,1-f][1,2,4]triazin-4-amine To a solution of (R or S)-1-(benzyloxy)hexan-3-ol (10.0 g, 48.07 mmol) in DMF (100 mL) was added NaH (3.8 g, 95.0 mmol) under N$_2$ at 0° C. After stirring for 0.5 h at 25° C., 2-chloro-N,N-bis(2,4-dimethoxybenzyl)imidazo[2,1-f][1,2,4]triazin-4-amine (18.8 g, 40.0 mmol) was added. The reaction mixture was stirred for 0.5 h at 80° C. After completed, the reaction mixture was quenched with aq NH$_4$Cl (80 mL) and extracted with EtOAc (3×100 mL). The combined organic layers was washed with water (3×50 mL), brine (3×50 mL), dried over Na$_2$SO$_4$ and concentrated under vacuum to get a residue. The residue was purified by column chromatography on silica gel eluting with ethyl acetate in petroleum ether (50%) to afford the title compound (24.9 g, 97%). MS: M/e 642 (M+1)$^+$.

Step D: tert-butyl (2-(4-formyl-3-methoxyphenoxy)ethyl)(methyl)carbamate

To a solution of 4-hydroxy-2-methoxybenzaldehyde (304 g, 2 mmol) in THF (20 mL) was added tert-butyl (2-hydroxyethyl)(methyl)carbamate (350 g, 2 mmol) and PPh$_3$ (665 g, 2.5 mmol), The mixture was protected by nitrogen and cooled down to 0 degrees. A solution of DIAD (505 mg, 2.5 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (300 mg, 48.5%). MS: m/e: 310 (M+1)$^+$.

Step E: tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-3-methoxyphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]

triazin-4-amine (237 mg, 0.37 mmol) in THF (10 mL) was added a solution of n-BuLi (1.6 M, 0.7 mL, 1.1 mmol) drop wise maintaining the temperature between −75~−65° C. After 1 h, a suspension of tert-butyl (2-(4-formyl-3-methoxyphenoxy)ethyl)(methyl)carbamate (340 mg, 1 mmol) in THF (2 mL) was added dropwise. The resulted mixture was stirred at −70° C. for 2 h and then warmed to room temperature overnight. The reaction was quenched with saturated NH₄Cl solution, extracted with EtOAc (20 mL×3), washed with brine, dried over Na₂SO₄, filtered, and concentrated. The residue was purified by prep-TLC to give the target compound (100 mg, 28.4%). MS: M/e 951 (M+1)⁺.

Step F: tert-butyl (R or S)-(2-(4-((4-(bis(2,4-dimethoxybenzyl)amino)-2-((1-hydroxyhexan-3-yl)oxy)imidazo[2,1-f][1,2,4]triazin-7-yl)methyl)-3-methoxyphenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-3-methoxyphenoxy)ethyl)(methyl)carbamate (100 mg, 0.105 mmol) in MeOH (20 mL) was added Pd/C (200 mg). The mixture was protected by hydrogen and stirred at room temperature for overnight. The mixture was filtered and the filtrate was concentrated in vacuo. The crude product was purified by column chromatography to give the title product (60 mg, 67.6%). MS: m/e: 845 (M+1)⁺.

Step G: (R or S)-3-((4-amino-7-(2-methoxy-4-(2-(methylamino)ethoxy)benzyl)imidazo[2,1-f][1,2,4]triazin-2-yl)oxy)hexan-1-ol (Compound A101)

To a mixture of the product of step F (60 mg, 0.071 mmol) in TFA (9 mL) was added H₂O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na₂SO₄ and concentrated in vacuo. The crude product was purified by prep-HPLC to give the target compound (8 mg, 25.3%). 1H NMR (400 MHz, DMSO-d6) δ 8.88 (br.s, 2H), 8.38 (s, 1H), 8.25 (s, 1H), 7.35 (s, 1H), 7.10 (d, J=8.1 Hz, 1H), 6.61 (s, 1H), 6.49 (d, J=8.2 Hz, 1H), 5.08 (m, 1H), 4.21 (s, 2H), 4.00 (s, 2H), 3.80 (s, 3H), 3.49 (d, J=6.0 Hz, 2H), 3.30 (s, 2H), 2.62 (s, 3H), 1.78 (s, 2H), 1.62 (s, 2H), 1.41-1.28 (m, 2H), 0.87 (t, J=7.1 Hz, 3H) ppm. MS: M/e 445 (M+1)⁺.

Compound A102: 3-((4-amino-7-(3-chloro-4-(2-(methylamino)ethoxy)benzyl)imidazo[2,1-f][1,2,4]triazin-2-yl)oxy)hexan-1-ol Step A: tert-butyl (2-(2-chloro-4-formylphenoxy)ethyl)(methyl)carbamate To a solution of 3-chloro-4-hydroxybenzaldehyde (1.56 g, 10 mmol) in THF (20 mL) was added tert-butyl (2-hydroxyethyl)(methyl)carbamate (1.75 g, 10 mmol) and PPh₃ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1.6 g, 49.8%). MS: m/e: 314 (M+1)⁺.

Step B: tert-butyl (2-(4-((2-((1-(benzyloxy)hexan-3-yl)oxy)-4-(bis(4-methoxybenzyl)amino)imidazo[2,1-f][1,2,4]triazin-7-yl)(hydroxy)methyl)-2-chlorophenoxy)ethyl)(methyl)carbamate To a solution of 2-((1-(benzyloxy)hexan-3-yl)oxy)-N,N-bis(4-methoxybenzyl)imidazo[2,1-f][1,2,4]triazin-4-amine (288 mg, 0.5 mmol) in THF (10 mL) was added a solution of n-BuLi (1.6 M, 1.25 mL, 2 mmol) drop wise maintaining the temperature between −75~−65° C. After 1 h, a suspension of tert-butyl (2-(2-chloro-4-formylphenoxy)ethyl)(methyl)carbamate (313 mg, 1 mmol) in THF (2 mL) was added dropwise. The resulted mixture was stirred at −70° C. for 2 h and then warmed to room temperature overnight. The reaction was quenched with saturated NH₄Cl solution, extracted with EtOAc (20 mL×3), washed with brine, dried over Na₂SO₄, filtered, and concentrated. The residue was purified by prep-TLC to give the target compound (320 mg, 71.8%). MS: M/e 896 (M+1)⁺.

Step C: 3-((4-amino-7-(3-chloro-4-(2-(methylamino)ethoxy)benzyl)imidazo[2,1-f][1,2,4]triazin-2-yl)oxy)hexan-1-ol (Compound A102)

To a mixture of the product of step C (320 mg, 0.357 mmol) in TFA (4 mL) was added Et₃SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (25 mg, 15.6%). 1H NMR (400 MHz, DMSO-d6) δ 8.12 (s, 1H), 8.00 (s, 1H), 7.38 (s, 1H), 7.32 (s, 1H), 7.21 (d, J=8.2 Hz, 1H), 7.07 (d, J=8.2 Hz, 1H), 5.07-5.01 (m, 1H), 4.44 (s, 1H), 4.07 (s, 4H), 3.49 (s, 2H), 2.93 (d, J=4.5 Hz, 2H), 2.41 (s, 3H), 1.83-1.71 (m, 2H), 1.60 (d, J=6.3 Hz, 2H), 1.38-1.25 (m, 2H), 0.85 (t, J=7.1 Hz, 3H) ppm. MS: M/e 449 (M+1)⁺.

Compound A103: (R or S)-3-((4-amino-7-(3-methyl-4-(2-(methylamino)ethoxy)benzyl)imidazo[2,1-f][1,2,4]triazin-2-yl)oxy)hexan-1-ol Step A: tert-butyl (2-(4-formyl-2-methylphenoxy)ethyl)(methyl)carbamate To a solution of 4-hydroxy-3-methylbenzaldehyde (1.36 g, 10 mmol) in THF (20 mL) was added tert-butyl (2-hydroxyethyl)(methyl)carbamate (1.75 g, 10 mmol) and PPh₃ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1.7 g, 58%). MS: m/e: 294 (M+1)⁺.

Step B: tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2-methylphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]

triazin-4-amine (384 mg, 0.6 mmol) in THF (10 mL) was added a solution of n-BuLi (1.6 M, 0.75 mL, 1.2 mmol) drop wise maintaining the temperature between −75~−65° C. After 1 h, a suspension of tert-butyl (2-(4-formyl-2-methylphenoxy)ethyl)(methyl)carbamate (300 mg, 1 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by HPLC to give the target compound (400 mg, 71.4%). MS: M/e 935 (M+1)$^+$.

Step C: tert-butyl (R or S)-(2-(4-((4-(bis(2,4-dimethoxybenzyl)amino)-2-((1-hydroxyhexan-3-yl)oxy) imidazo[2,1-f][1,2,4]triazin-7-yl)methyl)-2-methylphenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino) imidazo[2,1-f][1,2,4]triazin-7-yl)(hydroxy)methyl)-2-methylphenoxy)ethyl)(methyl)carbamate (400 mg, 0.428 mmol) in MeOH (20 mL) was added Pd/C (400 mg). The mixture was protected by hydrogen and stirred at room temperature for overnight. The mixture was filtered and the filtrate was concentrated in vacuo. The crude product was purified by column chromatography to give the title product (200 mg, 56.4%). MS: m/e: 829 (M+1)$^+$.

Step D: (R or S)-3-((4-amino-7-(3-methyl-4-(2-(methylamino)ethoxy)benzyl)imidazo[2,1-f][1,2,4]triazin-2-yl)oxy)hexan-1-ol (Compound A103)

To a mixture of the product of step C (200 mg, 0.24 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (40 mg, 38.8%). 1H NMR (400 MHz, DMSO-d6) δ 8.08 (s, 1H), 7.97 (s, 1H), 7.26 (s, 1H), 7.07 (d, J=10.3 Hz, 2H), 6.82 (d, J=8.1 Hz, 1H), 5.11-5.02 (m, 1H), 4.45 (s, 1H), 4.01 (s, 2H), 3.96 (t, J=5.5 Hz, 2H), 3.49 (d, J=5.0 Hz, 2H), 2.84 (t, J=5.5 Hz, 2H), 2.35 (s, 3H), 2.10 (s, 3H), 1.79 (dd, J=12.5, 6.1 Hz, 2H), 1.65-1.58 (m, 2H), 1.33 (dt, J=14.5, 7.1 Hz, 2H), 0.86 (t, J=7.3 Hz, 3H) ppm. MS: M/e 429 (M+1)$^+$.

Compound A104: (R or S)-3-((4-amino-7-(3-(2-(methylamino)ethoxy)benzyl)imidazo[2,1-f][1,2,4]triazin-2-yl)oxy)hexan-1-ol Step A: tert-butyl (2-(3-formylphenoxy)ethyl)(methyl)carbamate To a solution of 3-hydroxybenzaldehyde (2 g, 16.39 mmol), tert-butyl (2-hydroxyethyl)(methyl)carbamate (2.9 g, 16.57 mmol) and PPh$_3$ (6.4 g, 24.4 mmol) in THF (60 mL) was added a solution of DTAD (4.1 g, 17.83 mmol) in THF (20 mL) under N$_2$ at 0° C. The reaction mixture was stirred for 16 h at 25° C. After completed, the reaction mixture was quenched with water (50 mL) and extracted with EtOAc (3×80 mL). The combined organic layers were washed with aq NaHCO$_3$ (3×50 mL), brine (50 mL), dried over Na$_2$SO$_4$ and concentrated under vacuum to get a residue. The residue was purified by column chromatography on silica gel eluting with ethyl acetate in petroleum ether (20%) to afford the title compound (4.3 g, crude). MS: M/e 302 (M+Na)$^+$.

Step B: tert-butyl (2-(3-((2-(((R or S)-1-(benzyloxy) hexan-3-yl)oxy)-4-(bis(2,4-dimethoxybenzyl)amino) imidazo[2,1-f][1,2,4]triazin-7 yl)(hydroxy)methyl) phenoxy) ethyl)(methyl)carbamate To a solution of (R or S)-2-((1-(benzyloxy)hexan-3-yl) oxy)-N,N-bis(2,4-dimethoxybenzyl)imidazo[2,1-f][1,2,4] triazin-4-amine (500 mg, 0.78 mmol) in THF (20 mL) was added n-BuLi (2 mL, 3.2 mmol) under N$_2$ at −78° C. After stirring for 0.5 h at −78° C., tert-butyl (2-(3-formylphenoxy) ethyl)(methyl)carbamate (870 mg, crude) was added. The reaction mixture was stirred for 2.5 h at −78° C. After completed, the reaction mixture was quenched with aq NH$_4$Cl (30 mL) and extracted with DCM (3×30 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (150 mg, 21%). MS: M/e 921 (M+1)$^+$.

Step C: tert-butyl (R or S)-(2-(3-((4-(bis(2,4-dimethoxybenzyl)amino)-2-((1-hydroxyhexan-3-yl)oxy) imidazo[2,1-f][1,2,4]triazin-7-yl)methyl)phenoxy) ethyl) (methyl)carbamate To a solution of tert-butyl (2-(3-((2-(((R or S)-1-(benzyloxy)hexan-3-yl)oxy)-4-(bis(2,4-dimethoxybenzyl)amino) imidazo[2,1-f][1,2,4]triazin-7 yl)(hydroxy)methyl) phenoxy) ethyl)(methyl)carbamate (150 mg, 0.163 mmol) in MeOH (20 mL) was added Pd/C (150 mg) and AcOH (0.1 mL). The reaction mixture was stirred for 24 h at 40° C. under H$_2$ (1 atm). The mixture was filtered and the filtrate was combined together and concentrated in vacuo. The residue was purified by column chromatography on silica gel eluting with ethyl acetate in petroleum ether (90%) to afford the title compound (120 mg, 90%). MS: M/e 815 (M+1)$^+$.

Step D: (R or S)-3-((4-amino-7-(3-(2 (methylamino)ethoxy)benzyl)imidazo[2,1,f][1,2,4]triazin-2-yl)oxy)hexan-1-ol (Compound A104)

Tert-butyl (R or S)-(2-(3-((4-(bis(2,4-dimethoxybenzyl) amino)-2-((1-hydroxyhexan-3-yl)oxy)imidazo[2,1-f][1,2,4] triazin-7-yl)methyl)phenoxy)ethyl) (methyl)carbamate (120 mg, 0.147 mmol) was dissolved in TFA (3 mL) and H$_2$O (0.3 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×30 mL) and based with 2 N NaOH to adjust PH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=15/1 to 10/1) to afford the title compound (30 mg). $^1$H NMR (400 MHz, CD$_3$OD) δ 7.29 (s, 1H), 7.23 (t, J=7.6 Hz, 1H), 6.99-6.79 (m, 3H), 5.17 (s, 1H), 4.18 (s, 2H), 4.13 (s, 2H), 3.64 (d, J=6.8 Hz, 2H), 3.19 (s, 2H), 2.61 (s, 3H), 1.96-1.83 (m, 2H), 1.77-1.56 (m, 2H), 1.48-1.31 (m, 2H), 0.90 (t, J=7.2 Hz, 3H) ppm. MS: M/e 415 (M+1)$^+$.

Compound A105 and Compound A106: (R or S)-3-((4-amino-7-(3-fluoro-4-(2-(methylamino)ethoxy)benzyl)imidazo[2,1-f][1,2,4]triazin-2-yl)oxy)hexan-1-ol, and (S or R)-3-((4-amino-7-(3-fluoro-4-(2-(methylamino)ethoxy)benzyl)imidazo[2,1-f][1,2,4]triazin-2-yl)oxy)hexan-1-ol Compound A91 3-((4-amino-7-(3-fluoro-4-(2-(methylamino)ethoxy)benzyl)imidazo[2,1-f][1,2,4]triazin-2-yl)oxy)hexan-1-ol was separated into two optical isomers Compound A105 and Compound A106 by prep-SFC. The condition of prep-SFC was below.

| | |
|---|---|
| Column | CHIRALPAK AD-H |
| Column size | 5 cm × 25 cm, 5 um |
| Injection | 4.8 mL |
| Mobile phase | CO2:IPA(2 mMNH3—MeOH) = 55:45 |
| Flow rate | 200 mL/min |
| Wave length | UV 220 nm |
| Temperature | 35° C. |
| Sample solution | 36.5 mg/ml in MeOH:DCM = 3:1 |

Compound A105 (R or S optical isomer 1): $^1$HNMR (400 MHz, CD$_3$OD) δ 7.31 (s, 1H), 7.12-6.99 (m, 3H), 5.21-5.10 (m, 1H), 4.18-4.08 (m, 4H), 3.70-3.58 (m, 2H), 3.03-2.92 (m, 2H), 2.47 (s, 3H), 1.96-1.82 (m, 2H), 1.80-1.60 (m, 2H), 1.45-1.30 (m, 2H), 0.90 (t, J=6.8 Hz, 3H) ppm. MS: M/e 433 (M+1)$^+$.

Compound A106 (S or R optical isomer 2): $^1$HNMR (400 MHz, CD$_3$OD) δ 7.31 (s, 1H), 7.12-6.98 (m, 3H), 5.22-5.12 (m, 1H), 4.19-4.11 (m, 4H), 3.70-3.59 (m, 2H), 3.04-2.97 (m, 2H), 2.49 (s, 3H), 1.96-1.81 (m, 2H), 1.79-1.58 (m, 2H), 1.50-1.30 (m, 2H), 0.90 (t, J=7.2 Hz, 3H) ppm. MS: M/e 433 (M+1)$^+$.

Compound A107: (R or S)-3-((4-amino-7-(2-methyl-4-(2-(methylamino)ethoxy)benzyl)imidazo[2,1-f][1,2,4]triazin-2-yl)oxy)hexan-1-ol Step A: tert-butyl (2-(4-formyl-3-methylphenoxy)ethyl)(methyl)carbamate To a solution of 4-hydroxy-2-methylbenzaldehyde (1.36 g, 10 mmol) in THF (20 mL) was added tert-butyl (2-hydroxyethyl)(methyl)carbamate (1.7 g, 10 mmol) and PPh$_3$ (3.4 g, 13 mmol), The mixture was protected by nitrogen and cooled down to 0 degree. A solution of DIAD (2.6 g, 13 mmol) in THE (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1.5 g, 51.2%). MS: m/e: 294 (M+1)$^+$.

Step B: tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-3-methylphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (530 mg, 0.82 mmol) in THF (10 mL) was added a solution of n-BuLi (1.6 M, 1 mL, 1.6 mmol) drop wise maintaining the temperature between −75~−65° C. After 1 h, a suspension of tert-butyl (2-(4-formyl-3-methylphenoxy)ethyl)(methyl)carbamate (400 mg, 1.36 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (400 mg, 52.2%). MS: M/e 935 (M+1)$^+$.

Step C: tert-butyl (R or S)-(2-(4-((4-(bis(2,4-dimethoxybenzyl)amino)-2-((1-hydroxyhexan-3-yl)oxy)imidazo[2,1-f][1,2,4]triazin-7-yl)methyl)-3-methylphenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-3-methylphenoxy)ethyl)(methyl)carbamate (400 mg, 0.42 mmol) in MeOH (20 mL) was added Pd/C (400 mg). The mixture was under hydrogen and stirred at room temperature for overnight. The mixture was filtered and the filtrate was concentrated in vacuo. The crude product was purified by column chromatography to give the title product (200 mg, 57.6%). MS: m/e: 829 (M+1)$^+$.

Step D: (R or S)-3-((4-amino-7-(2-methyl-4-(2-(methylamino)ethoxy)benzyl)imidazo[2,1-f][1,2,4]triazin-2-yl)oxy)hexan-1-ol (Compound A107)

To a mixture of the product of step C (200 mg, 0.24 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (36 mg, 34.9%). 1H NMR (400 MHz, DMSO-d6) δ 8.10 (s, 1H), 7.98 (s, 1H), 7.13 (s, 1H), 7.08 (d, J=8.1 Hz, 1H), 6.77 (s, 1H), 6.68 (d, J=7.9 Hz, 1H), 5.06 (s, 1H), 4.5 (br.s, 1H), 4.02 (s, 2H), 3.96 (s, 2H), 3.48 (s, 2H), 2.83 (d, J=3.3 Hz, 2H), 2.34 (d, J=2.7 Hz, 3H), 2.27 (s, 3H), 1.77 (s, 2H), 1.60 (s, 2H), 1.39-1.26 (m, 2H), 0.86 (t, J=7.1 Hz, 3H) ppm. MS: M/e 429 (M+1)$^+$.

Compound A108: (R or S)-3-((4-amino-7-(2-chloro-4-(2-(methylamino)ethoxy)benzyl)imidazo[2,1-f][1,2,4]triazin-2-yl)oxy)hexan-1-ol Step A: tert-butyl (2-(3-chloro-4-formylphenoxy)ethyl)(methyl)carbamate To a solution of 2-chloro-4-hydroxybenzaldehyde (1.56 g, 10 mmol) in THF (20 mL) was added tert-butyl (2-hydroxyethyl)(methyl)carbamate (1.75 g, 10 mmol) and PPh$_3$ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (0.8 g, 25.6%). MS: m/e: 314 (M+1)$^+$.

Step B: tert-butyl (2-(4-((2-(((R or S)-1-(benzyloxy)hexan-3-yl)oxy)-4-(bis(4-methoxybenzyl)amino)imidazo[2,1-f][1,2,4]triazin-7-yl)(hydroxy)methyl)-3-chlorophenoxy)ethyl)(methyl)carbamate To a solution of (R or S)-2-((1-(benzyloxy)hexan-3-yl)oxy)-N,N-bis(4-methoxybenzyl)imidazo[2,1-f][1,2,4]triazin-4-amine (288 mg, 0.5 mmol) in THF (10 mL) was added a solution of n-BuLi (1.6 M, 1.25 mL, 2 mmol) drop wise maintaining the temperature between −75~−65° C. After 1 h, a suspension of tert-butyl (2-(3-chloro-4-formylphenoxy)ethyl)(methyl)carbamate (313 mg, 1 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (120 mg, 26.8%). MS: M/e 895 (M+1)$^+$.

Step C: (R or S)-3-((4-amino-7-(2-chloro-4-(2-(methylamino)ethoxy)benzyl)imidazo[2,1-f][1,2,4]triazin-2-yl)oxy)hexan-1-ol (Compound A108)

To a mixture of the product of step C (120 mg, 0.134 mmol) in TFA (4 mL) was added Et$_3$SiH (4 mL) and the resulting mixture was stirred at 85° C. for 4 hours. The mixture was cooled to room temperature and concentrated to dryness. To the residue was added TFA (5 mL) and the reaction was heated at 80° C. overnight. The mixture was concentrated in vacuo and the residue was purified by prep-HPLC to give the target compound (15 mg, 25%). 1H NMR (400 MHz, DMSO-d6) δ 8.13 (s, 1H), 8.00 (s, 1H), 7.25 (d, J=8.4 Hz, 1H), 7.21 (s, 1H), 7.05 (s, 1H), 6.86 (d, J=8.6 Hz, 1H), 5.09-5.01 (m, 1H), 4.5 (br.s, 2H), 4.14 (s, 2H), 4.02 (t, J=4.9 Hz, 2H), 3.48 (d, J=5.3 Hz, 2H), 2.85 (d, J=5.1 Hz, 2H), 2.35 (s, 3H), 1.77 (d, J=6.0 Hz, 2H), 1.59 (d, J=4.6 Hz, 2H), 1.31 (dt, J=14.5, 7.0 Hz, 2H), 0.85 (t, J=7.2 Hz, 3H) ppm. MS: M/e 449 (M+1)$^+$.

Compound A109: (3R or S)-3-((4-amino-7-((6-((1-(methylamino)propan-2-yl)oxy)pyridin-3-yl)methyl)imidazo [2,1-f][1,2,4]triazin-2-yl)oxy)hexan-1-ol

Step A: tert-butyl (2-hydroxypropyl)(methyl)carbamate

To a solution of tert-butyl methyl(2-oxoethyl)carbamate (3.9 g, 22.5 mmol) in THF (80 mL) was added CH$_3$BrMg (24.8 mL, 24.8 mmol) under N$_2$ at −0° C. The reaction mixture was stirred for 1 h at 25° C. After completed, the reaction mixture was quenched with aq NH$_4$Cl (50 mL) and extracted with EtOAc (3×50 mL). The combined organic layers was dried over Na$_2$SO$_4$ and concentrated under vacuum to get a residue. The residue was purified by column chromatography on silica gel eluting with ethyl acetate in petroleum ether (50%) to afford the title compound (3.87 g, 91%). $^1$H NMR (400 MHz, DMSO-d$_6$) δ 4.64 (s, 1H), 3.77 (d, J=5.6 Hz, 1H), 3.14 (dd, J=13.6, 5.2 Hz, 1H), 2.97 (dd, J=13.6, 6.8 Hz, 1H), 2.89-2.75 (m, 3H), 1.36 (s, 9H), 1.00 (d, J=5.6 Hz, 3H) ppm.

Step B: tert-butyl (2-(4-formylphenoxy)propyl)(methyl)carbamate

To a solution of 6-chloronicotinaldehyde (500 mg, 3.52 mmol), tert-butyl (2-hydroxypropyl)(methyl)carbamate (800 mg, 4.23 mmol), Pd$_2$(dba)$_3$ (240 mg, 0.262 mmol) and Cs$_2$CO$_3$ (2.3 g, 7.05 mmol) in dioxane (10 mL) were added RuPhos (247 g, 0.528 mmol) under N$_2$. The reaction mixture was stirred for 12 h at 95° C. The mixture was filtered and the filtrate was combined together and concentrated in vacuo. The residue was purified by column chromatography on silica gel eluting with ethyl acetate in petroleum ether (30%) to afford the title compound (600 mg, 58%). $^1$H NMR (400 MHz, DMSO-d$_6$) δ 9.95 (s, 1H), 8.72 (s, 1H), 8.11 (d, J=8.4 Hz, 1H), 6.91 (s, 1H), 5.57 (s, 1H), 3.43 (s, 2H), 2.80 (d, J=9.2 Hz, 3H), 1.35 (s, 9H), 1.27 (d, J=5.6 Hz, 3H) ppm. MS: M/e 295 (M+H)$^+$.

Step C: tert-butyl (2-((5-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)pyridin-2-yl)oxy)propyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (600 mg, 0.934 mmol) in THF (15 mL) was added n-BuLi (0.88 mL, 1.41 mmol) under N$_2$ at −78° C. After stirring for 0.5 h at −78° C., tert-butyl (2-(4-formylphenoxy)propyl)(methyl)carbamate (328 mg, 1.12 mmol) was added. The reaction mixture was stirred for 2.5 h at −78° C. After completed, the reaction mixture was quenched with aq NH$_4$Cl (30 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (510 mg, 58%). MS: M/e 936 (M+H)$^+$.

Step D: tert-butyl (2-((5-((4-(bis(2,4-dimethoxybenzyl)amino)-2-(((R or S)-1-hydroxyhexan-3-yl)oxy)imidazo[2,1-f][1,2,4]triazin-7-yl)methyl)pyridin-2-yl)oxy) propyl)(methyl)carbamate To a solution of tert-butyl (2-((5-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl) pyridin-2-yl)oxy)propyl)(methyl)carbamate (410 mg, 0.438 mmol) in MeOH (30 mL) was added Pd/C (410 mg) and AcOH (0.4 mL). The reaction mixture was stirred for 12 h at 40° C. under H$_2$ (1 atm). The mixture was filtered and the filtrate was combined together and concentrated in vacuo. The residue was purified by column chromatography on silica gel eluting with ethyl acetate in petroleum ether (70%) to afford the title compound (180 mg, 50%). MS: M/e 830 (M+H)$^+$.

Step E: (3R or S)-3-((4-amino-7-((6-((1-(methylamino)propan-2-yl)oxy)pyridin-3-yl)methyl)imidazo [2,1-f][1,2,4]triazin-2-yl)oxy)hexan-1-ol (Compound A109)

tert-butyl (2-((5-((4-(bis(2,4-dimethoxybenzyl)amino)-2-(((R or S)-1-hydroxyhexan-3-yl)oxy)imidazo[2,1-f][1,2,4]triazin-7-yl)methyl)pyridin-2-yl)oxy) propyl)(methyl) carbamate (180 mg, 0.217 mmol) was dissolved in TFA (3 mL) and H$_2$O (0.3 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust pH=1-2. The aqueous phase was washed with DCM (3×20 mL) and based with 2 N NaOH to adjust pH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=15/1) to afford the title compound (50 mg, 53%). $^1$H NMR (400 MHz, CD$_3$OD) δ 8.09 (d, J=13.6 Hz, 1H), 7.66-7.54 (m, 1H), 7.33 (s, 1H), 6.72 (d, J=8.4 Hz, 1H), 5.30-5.13 (m, 2H), 4.14 (s, 2H), 3.65 (s, 2H), 2.94-2.69 (m, 2H), 2.41 (s, 3H), 1.98-1.80 (m, 2H), 1.80-1.55 (m, 2H), 1.53-1.34 (m, 2H), 1.29 (d, J=6.0 Hz, 3H), 0.92 (t, J=7.2 Hz, 3H) ppm. MS: M/e 430 (M+H)$^+$.

Compound A110: (R or S)-3-((4-amino-7-(4-(3-(methylamino)propyl)benzyl)imidazo[2,1-f][1,2,4]triazin-2-yl)oxy)hexan-1-ol Step A: 3-(4-bromophenyl)-N-methylpropanamide To a solution of 3-(4-bromophenyl)propanoic acid (2 g, 8.73 mmol) and CH$_3$NH$_2$ HCl (712 mg, 10.47 mmol) and HATU (3.98 g, 10.47 mmol) in DMF (20 mL) was added DIEA (2.7 g, 20.93 mmol) under N$_2$ at -0° C. The reaction mixture was stirred for 12 h at 25° C. After completed, the reaction mixture was quenched with ice water (50 mL) and extracted with EtOAc (3×80 mL). The combined organic layers was washed with water (50 mL), brine (3×50 mL), dried over Na$_2$SO$_4$ and concentrated under vacuum to get a residue. The residue was purified by column chromatography on silica gel eluting with ethyl acetate in petroleum ether (60%) to afford the title compound (3 g, crude). MS: M/e 242, 244. (M+H)$^+$.

Step B: 3-(4-bromophenyl)-N-methylpropan-1-amine

To a solution of 3-(4-bromophenyl)-N-methylpropanamide (2.6 g, crude) in THF (50 mL) was added BH$_3$ in THF (42 mL, 42.0 mmol) under N$_2$ at 0° C. The reaction mixture was stirred for 0.5 h at 0° C. and another 4 h at 70° C. After completed, the reaction mixture was cooled to 0° C. and MeOH (20 mL) and 6 N HCl (20 mL) were added dropwise. The mixture was reflux for 0.5 h and the solvent was removed by in vacuo. The aqueous phase was based with 50% NaOH and extracted with MTBE (3×80 mL). The combined organic layers was dried over Na$_2$SO$_4$ and concentrated under vacuum to get a crude product (2.5 g). MS: M/e 228, 230. (M+H)$^+$.

Step C: tert-butyl (3-(4-bromophenyl)propyl)(methyl)carbamate

To a solution of 3-(4-bromophenyl)-N-methylpropan-1-amine (2.5 g, crude) in DCM (30 mL) was added Et$_3$N (1.8 g, 17.82 mmol) and (Boc)$_2$O (2.3 g, 10.55 mmol) under N$_2$ at 0° C. The reaction mixture was stirred for 12 h at 25° C. After completed, the reaction mixture was quenched with water (30 mL) and extracted with DCM (3×50 mL). The combined organic layers was dried over Na$_2$SO$_4$ and concentrated under vacuum to get a residue. The residue was purified by column chromatography on silica gel eluting with ethyl acetate in petroleum ether (20%) to afford the title compound (1.8 g, 63% for three steps). $^1$H NMR (400 MHz, DMSO-d$_6$) δ 7.46 (d, J=6.8 Hz, 2H), 7.19 (d, J=6.8 Hz, 2H), 3.15 (s, 2H), 2.76 (s, 3H), 2.52 (s, 2H), 1.73 (s, 2H), 1.35 (s, 9H) ppm. MS: M/e 350, 352 (M+H)$^+$.

Step D: tert-butyl (3-(4-formylphenyl)propyl)(methyl)carbamate

To a solution of tert-butyl (3-(4-bromophenyl)propyl)(methyl)carbamate (1.7 g, 5.18 mmol) in THF (25 mL) was added n-BuLi (4.8 mL, 7.68 mmol) under N$_2$ at -78° C. After stirring for 0.5 h at -78° C., DMF (570 mg, 7.8 mmol) was added dropwise. The reaction mixture was warmed to 25° C. and stirred for 0.5 h. After completed, the reaction mixture was quenched with aq NH$_4$Cl (50 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (40%) to afford the title compound (1.2 g, 84%). $^1$H NMR (400 MHz, DMSO-d$_6$) δ 9.97 (s, 1H), 7.84 (d, J=7.2 Hz, 2H), 7.46 (d, J=7.2 Hz, 2H), 3.18 (s, 2H), 2.77 (s, 3H), 2.64 (s, 2H), 1.80 (s, 2H), 1.36 (s, 9H) ppm. MS: M/e 300 (M+Na)$^+$.

Step E: tert-butyl (3-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)phenyl) propyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (600 mg, 0.934 mmol) in THF (15 mL) was added n-BuLi (0.88 mL, 1.41 mmol) under N$_2$ at -78° C. After stirring for 0.5 h at -78° C., tert-butyl (3-(4-formylphenyl)propyl)(methyl)carbamate (310 mg, 1.12 mmol) was added. The reaction mixture was stirred for 2.5 h at -78° C. After completed, the reaction mixture was quenched with aq NH$_4$Cl (30 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (50%) to afford the title compound (660 mg, 77%). MS: M/e 919 (M+H)$^+$.

Step F: tert-butyl (R or S)-(3-(4-((4-(bis(2,4-dimethoxybenzyl)amino)-2-((1-hydroxyhexan-3-yl)oxy)imidazo[2,1-f][1,2,4]triazin-7-yl)methyl)phenyl)propyl) (methyl)carbamate To a solution of tert-butyl (3-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl) phenyl) propyl)(methyl)carbamate (560 mg, 0.609 mmol) in MeOH (30 mL) was added Pd/C (560 mg) and AcOH (0.5 mL). The reaction mixture was stirred for 12 h at 40° C. under H$_2$ (1 atm). The mixture was filtered and the filtrate was combined together and concentrated in vacuo. The residue was purified by column chromatography on silica gel eluting with ethyl acetate in petroleum ether (60%) to afford the title compound (470 mg, 94%). MS: M/e 813 (M+H)$^+$.

Step G: (R or S)-3-((4-amino-7-(4-(3-(methylamino)propyl)benzyl)imidazo[2,1-f][1,2,4]triazin-2-yl)oxy)hexan-1-ol (Compound A110)

Tert-butyl (R or S)-(3-(4-((4-(bis(2,4-dimethoxybenzyl)amino)-2-((1-hydroxyhexan-3-yl)oxy)imidazo[2,1-f][1,2,4]triazin-7-yl)methyl)phenyl)propyl) (methyl)carbamate (470 mg, 0.578 mmol) was dissolved in TFA (5 mL) and H$_2$O (0.5 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust pH=1~2. The aqueous phase was washed with DCM (3×20 mL) and based with 2 N NaOH to adjust pH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=15/1) to afford the title compound (125 mg, 53%). $^1$H NMR (400 MHz, CD$_3$OD) δ 7.27 (s, 1H), 7.21 (d, J=8.0 Hz, 2H), 7.13 (d, J=7.6 Hz, 2H), 5.18 (s, 1H), 4.16 (s, 2H), 3.65 (s, 2H), 2.63 (dd, J=13.6, 6.8 Hz, 4H), 2.41 (s, 3H), 1.95-1.76 (m, 4H), 1.76-1.58 (m, 2H), 1.41 (s, 2H), 0.91 (t, J=7.2 Hz, 3H) ppm. MS: M/e 413 (M+H)$^+$.

Compound A111: (R or S)-3-((4-amino-7-(2,3-difluoro-4-(2-(methylamino)ethoxy)benzyl)imidazo[2,1-f][1,2,4]triazin-2-yl)oxy)hexan-1-ol Step A: tert-butyl (2-(2,3-difluoro-4-formylphenoxy)ethyl)(methyl)carbamate To a solution of 2,3-difluoro-4-hydroxybenzaldehyde (1.58 g, 10 mmol) in THF (20 mL) was added tert-butyl (2-hydroxyethyl)(methyl)carbamate (1.75 g, 10 mmol) and PPh$_3$ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1.1 g, 34.9%). MS: m/e: 316 (M+1)$^+$.

Step B: tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2,3-difluorophenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (320 mg, 0.5 mmol) in THF (10 mL) was added a solution of n-BuLi (1.6 M, 0.7 mL, 1.1 mmol) drop wise maintaining the temperature between −75~−65° C. After 1 h, a suspension of tert-butyl (2-(2,3-difluoro-4-formylphenoxy)ethyl)(methyl)carbamate (315 mg, 1 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by HPLC to give the target compound (100 mg, 23.3%). MS: M/e 957 (M+1)$^+$.

Step C: tert-butyl (R or S)-(2-(4-((4-(bis(2,4-dimethoxybenzyl)amino)-2-((1-hydroxyhexan-3-yl)oxy)imidazo[2,1-f][1,2,4]triazin-7-yl)methyl)-2,3-difluorophenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2,3-difluorophenoxy)ethyl)(methyl)carbamate (100 mg, 0.104 mmol) in MeOH (20 mL) was added Pd/C (100 mg). The mixture was protected by hydrogen and stirred at room temperature for overnight. The mixture was filtered and the filtrate was concentrated in vacuo. The crude product was purified by column chromatography to give the title product (60 mg, 68.1%). MS: m/e: 851 (M+1)$^+$.

Step D: (R or S)-3-((4-amino-7-(2,3-difluoro-4-(2-(methylamino)ethoxy)benzyl)imidazo[2,1-f][1,2,4]triazin-2-yl)oxy)hexan-1-ol (Compound A111)

To a mixture of the product of step C (60 mg, 0.07 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (4 mg, 12.9%). 1H NMR (400 MHz, CD$_3$OD) δ 7.32 (s, 1H), 6.98 (s, 1H), 6.88 (d, J=8.1 Hz, 1H), 5.17 (s, 1H), 4.20 (s, 4H), 3.63 (s, 2H), 3.14 (s, 2H), 2.57 (s, 3H), 1.89 (s, 2H), 1.68 (d, J=5.7 Hz, 2H), 1.40 (s, 2H), 0.91 (t, J=7.1 Hz, 3H) ppm. MS: M/e 451 (M+1)$^+$.

Compound A112: (R or S)-3-((4-amino-7-(2,5-difluoro-4-(2-(methylamino)ethoxy)benzyl)imidazo[2,1-f][1,2,4]triazin-2-yl)oxy)hexan-1-ol Step A: tert-butyl (2-(2,5-difluoro-4-formylphenoxy)ethyl)(methyl)carbamate To a solution of 2,5-difluoro-4-hydroxybenzaldehyde (316 mg, 2 mmol) in THF (20 mL) was added tert-butyl (2-hydroxyethyl)(methyl)carbamate (350 mg, 2 mmol) and PPh$_3$ (655 mg, 2.5 mmol), The mixture was protected by nitrogen and cooled down to 0 degrees. A solution of DIAD (505 mg, 2.5 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (448 g, 71.1%). MS: m/e: 316 (M+1)$^+$.

Step B: tert-butyl (2-(4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2,5-difluorophenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (448 mg, 0.7 mmol) in THF (10 mL) was added a solution of n-BuLi (1.6 M, 0.9 mL, 1.4 mmol) drop wise maintaining the temperature between −75~−65° C. After 1 h, a suspension of tert-butyl (2-(2,5-difluoro-4-formylphenoxy)ethyl)(methyl)carbamate (310 mg, 1 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by HPLC to give the target compound (280 mg, 41.8%). MS: M/e 957 (M+1)$^+$.

Step C: tert-butyl (R or S)-(2-(4-((4-(bis(2,4-dimethoxybenzyl)amino)-2-((1-hydroxyhexan-3-yl)oxy)imidazo[2,1-f][1,2,4]triazin-7-yl)methyl)-2,5-difluorophenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino)

imidazo[2,1-f][1,2,4]triazin-7-yl)(hydroxy)methyl)-2,5-difluorophenoxy)ethyl)(methyl)carbamate (280 mg, 0.295 mmol) in MeOH (20 mL) was added Pd/C (300 mg). The mixture was protected by hydrogen and stirred at room temperature for overnight. The mixture was filtered and the filtrate was concentrated in vacuo. The crude product was purified by column chromatography to give the title product (110 mg, 44%). MS: m/e: 851 (M+1)$^+$.

Step D: (R or S)-3-((4-amino-7-(2,5-difluoro-4-(2-(methylamino)ethoxy)benzyl)imidazo[2,1-f][1,2,4]triazin-2-yl)oxy)hexan-1-ol (Compound A112)

To a mixture of the product of step C (110 mg, 0.129 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (22 mg, 37.9%). 1H NMR (400 MHz, CD$_3$OD) δ 7.30 (s, 1H), 7.09-7.01 (m, 1H), 7.01-6.88 (m, 1H), 5.25-5.10 (m, 1H), 4.14 (s, 4H), 3.65 (s, 2H), 2.99 (s, 2H), 2.47 (s, 3H), 1.91 (d, J=5.9 Hz, 2H), 1.74-1.63 (m, 2H), 1.40 (s, 2H), 0.90 (d, J=7.2 Hz, 3H) ppm. MS: M/e 451 (M+1)$^+$.

Compound A113: (R or S)-3-((4-amino-7-(2-methoxy-5-(2-(methylamino)ethoxy)benzyl)imidazo[2,1-f][1,2,4]triazin-2-yl)oxy)hexan-1-ol Step A: tert-butyl (2-(3-formyl-4-methoxyphenoxy)ethyl)(methyl)carbamate To a solution of 5-hydroxy-2-methoxybenzaldehyde (1 g, 6.58 mmol), tert-butyl (2-hydroxyethyl)(methyl)carbamate (1.15 g, 6.57 mmol) and PPh$_3$ (2.6 g, 9.92 mmol) in THF (20 mL) was added a solution of DTAD (1.7 g, 7.39 mmol) in THF (20 mL) under N$_2$ at 0° C. The reaction mixture was stirred for 16 h at 25° C. After completed, the reaction mixture was quenched with water (50 mL) and extracted with EtOAc (3×50 mL). The combined organic layers were washed with aq NaHCO$_3$ (3×50 mL), water (30 mL), brine (50 mL), dried over Na$_2$SO$_4$ and concentrated under vacuum to get a residue. The residue was purified by column chromatography on silica gel eluting with ethyl acetate in petroleum ether (20%) to afford the title compound (1.7 g, crude). MS: M/e 332. (M+Na)$^+$.

Step B: tert-butyl (2-(3-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-4-methoxyphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (500 mg, 0.78 mmol) in THF (20 mL) was added n-BuLi (2.4 mL, 3.84 mmol) under N$_2$ at −78° C. After stirring for 0.5 h at −78° C., tert-butyl (2-(3-formyl-4-methoxyphenoxy)ethyl)(methyl)carbamate (720 mg, crude) was added. The reaction mixture was stirred for 2.5 h at −78° C. After completed, the reaction mixture was quenched with aq NH$_4$Cl (50 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (60%) to afford the title compound (370 mg, 50%). MS: M/e 952 (M+1)$^+$.

Step C: tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-4-methoxyphenoxy) ethyl)(methyl)carbamate To a solution of tert-butyl (2-(3-((((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-4-methoxyphenoxy)ethyl)(methyl)carbamate (370 mg, 0.389 mmol) in MeOH (20 mL) was added Pd/C (370 mg) and AcOH (0.3 mL). The reaction mixture was stirred for 12 h at 40° C. under H$_2$ (1 atm). The mixture was filtered and the filtrate was combined together and concentrated in vacuo. The residue was purified by column chromatography on silica gel eluting with ethyl acetate in petroleum ether (80%) to afford the title compound (200 mg, 61%). MS: M/e 845 (M+1)$^+$.

Step D: (R or S)-3-((4-amino-7-(2-methoxy-5-(2-(methylamino)ethoxy)benzyl) imidazo[2,1-f][1,2,4]triazin-2-yl)oxy)hexan-1-ol (Compound A113)

Tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-4-methoxyphenoxy) ethyl)(methyl) carbamate (200 mg, 0.237 mmol) was dissolved in TFA (5 mL) and H$_2$O (0.5 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust pH=1~2. The aqueous phase was washed with DCM (3×20 mL) and based with 2 N NaOH to adjust pH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=15/1) to afford the title compound (60 mg, 57%). $^1$H NMR (400 MHz, CD$_3$OD) δ 7.20 (s, 1H), 6.89 (d, J=8.8 Hz, 1H), 6.84-6.78 (m, 1H), 6.75 (s, 1H), 5.27-5.09 (m, 1H), 4.20-4.04 (m, 2H), 3.99 (t, J=5.2 Hz, 2H), 3.80 (s, 3H), 3.65 (t, J=6.4 Hz, 2H), 2.95 (t, J=5.2 Hz, 2H), 2.45 (s, 3H), 1.90 (d, J=5.2 Hz, 2H), 1.81-1.56 (m, 2H), 1.52-1.30 (m, 2H), 0.91 (t, J=7.2 Hz, 3H) ppm. MS: M/e 445 (M+1)$^+$.

Compound A114: (R or S)-3-((4-amino-7-(3,5-difluoro-4-(2-(methylamino)ethoxy)benzyl)imidazo[2,1-f][1,2,4]triazin-2-yl)oxy)hexan-1-ol Step A: tert-butyl (2-(2,6-difluoro-4-formylphenoxy)ethyl)(methyl)carbamate To a solution of 3,5-difluoro-4-hydroxybenzaldehyde (1.58 g, 10 mmol) in THF (20 mL) was added tert-butyl (2-hydroxyethyl)(methyl)carbamate (1.7 g, 10 mmol) and PPh$_3$ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (1 g, 31.7%). MS: m/e: 316 (M+1)⁺.

Step B: tert-butyl (2-(4-((2-(((R or S)-1-(benzyloxy)hexan-3-yl)oxy)-4-(bis(3,4-dimethoxybenzyl)amino)imidazo[2,1-f][1,2,4]triazin-7-yl)(hydroxy)methyl)-2,6-difluorophenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (300 mg, 0.5 mmol) in THF (10 mL) was added a solution of n-BuLi (1.6 M, 0.9 mL, 1.5 mmol) drop wise maintaining the temperature between −75~−65° C. After 1 h, a suspension of tert-butyl (2-(2,6-difluoro-4-formylphenoxy)ethyl)(methyl)carbamate (315 mg, 1 mmol) in THF (2 mL) was added dropwise. The resulted mixture was stirred at −70° C. for 2 h and then warmed to room temperature overnight. The reaction was quenched with saturated NH₄Cl solution, extracted with EtOAc (20 mL×3), washed with brine, dried over Na₂SO₄, filtered, and concentrated. The residue was purified by prep-TLC to give the target compound (280 mg, 58.5%). MS: M/e 957 (M+1)⁺.

Step C: tert-butyl (R or S)-(2-(4-((4-(bis(3,4-dimethoxybenzyl)amino)-2-((1-hydroxyhexan-3-yl)oxy)imidazo[2,1-f][1,2,4]triazin-7-yl)methyl)-2,6-difluorophenoxy)ethyl)(methyl)carbamate To a solution of tert-butyl (2-(4-((2-(((R or S)-1-(benzyloxy)hexan-3-yl)oxy)-4-(bis(3,4-dimethoxybenzyl)amino)imidazo[2,1-f][1,2,4]triazin-7-yl)(hydroxy)methyl)-2,6-difluorophenoxy)ethyl)(methyl)carbamate (280 mg, 0.292 mmol) in MeOH (20 mL) was added Pd/C (300 mg). The mixture was protected by hydrogen and stirred at room temperature for overnight. The mixture was filtered and the filtrate was concentrated in vacuo. The crude product was purified by column chromatography to give the title product (140 mg, 56.4%). MS: m/e: 851 (M+1)⁺.

Step D: (R or S)-3-((4-amino-7-(3,5-difluoro-4-(2-(methylamino)ethoxy)benzyl)imidazo[2,1-f][1,2,4]triazin-2-yl)oxy)hexan-1-ol (Compound A114)

To a mixture of the product of step C (140 mg, 0.164 mmol) in TFA (9 mL) was added H₂O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na₂SO₄ and concentrated in vacuo. The crude product was purified by prep-HPLC to give the target compound (9 mg, 12.1%). 1H NMR (400 MHz, CD₃OD) δ 7.38 (s, 1H), 6.98 (s, 1H), 6.96 (s, 1H), 5.20-5.15 (m, 1H), 4.19 (d, J=9.4 Hz, 4H), 3.64 (s, 2H), 3.00 (s, 2H), 2.52 (s, 3H), 1.96-1.84 (m, 2H), 1.75-1.59 (m 2H), 1.52-1.39 (m, 2H), 0.91 (t, J=7.4 Hz, 3H) ppm. MS: M/e 451 (M+1)⁺.

Compound A115: (R or S)-3-((4-amino-7-(2-fluoro-4-(2-(methylamino)ethoxy)benzyl)imidazo[2,1-f][1,2,4]triazin-2-yl)oxy)hexan-1-ol Step A: tert-butyl (2-(3-fluoro-4-formylphenoxy)ethyl)(methyl)carbamate To a solution of 2-fluoro-4-hydroxybenzaldehyde (1.4 g, 10 mmol) in THF (20 mL) was added tert-butyl (2-hydroxyethyl)(methyl)carbamate (1.75 g, 10 mmol) and PPh₃ (3.4 g, 13 mmol), The mixture was protected by nitrogen and cooled down to 0 degrees. A solution of DIAD (2.6 g, 13 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (0.9 g, 30.3%). MS: m/e: 298 (M+1)⁺.

Step B: tert-butyl (2-(4-((2-(((R or S)-1-(benzyloxy)hexan-3-yl)oxy)-4-(bis(3,4-dimethoxybenzyl)amino)imidazo[2,1-f][1,2,4]triazin-7-yl)(hydroxy)methyl)-3-fluorophenoxy)ethyl)(methyl)carbamate To a solution of (R or S)-2-((1-(benzyloxy)hexan-3-yl)oxy)-N,N-bis(4-methoxybenzyl)imidazo[2,1-f][1,2,4]triazin-4-amine (641 mg, 1 mmol) in THF (10 mL) was added a solution of n-BuLi (1.6 M, 1.25 mL, 2 mmol) drop wise maintaining the temperature between −75~−65° C. After 1 h, a suspension of tert-butyl (2-(3-fluoro-4-formylphenoxy)ethyl)(methyl)carbamate (450 mg, 1.5 mmol) in THF (2 mL) was added dropwise. The resulted mixture was stirred at −70° C. for 2 h and then warmed to room temperature overnight. The reaction was quenched with saturated NH₄Cl solution, extracted with EtOAc (20 mL×3), washed with brine, dried over Na₂SO₄, filtered, and concentrated. The residue was purified by prep-TLC to give the target compound (700 mg, 74.6%). MS: M/e 939 (M+1)⁺.

Step C: tert-butyl (R or S)-(2-(4-((4-(bis(3,4-dimethoxybenzyl)amino)-2-((1-hydroxyhexan-3-yl)oxy)imidazo[2,1-f][1,2,4]triazin-7-yl)methyl)-3-fluorophenoxy)ethyl)(methyl)carbamate To a solution of tert-butyl (2-(4-((2-(((R or S)-1-(benzyloxy)hexan-3-yl)oxy)-4-(bis(3,4-dimethoxybenzyl)amino)imidazo[2,1-f][1,2,4]triazin-7-yl)(hydroxy)methyl)-3-fluorophenoxy)ethyl)(methyl)carbamate (700 mg, 0.746 mmol) in MeOH (20 mL) was added Pd/C (700 mg). The mixture was protected by hydrogen and stirred at room temperature for overnight. The mixture was filtered and the filtrate was concentrated in vacuo. The crude product was purified by column chromatography to give the title product (350 mg, 56.4%). MS: m/e: 833 (M+1)⁺.

Step D: (R or S)-3-((4-amino-7-(2-fluoro-4-(2-(methylamino)ethoxy)benzyl)imidazo[2,1-f][1,2,4]triazin-2-yl)oxy)hexan-1-ol (Compound A115)

To a mixture of the product of step C (2.2 g, 2.6 mmol) in TFA (18 mL) was added H₂O (2 mL) and the resulting mixture was stirred at 40° C. for overnight. The mixture was cooled to room temperature and concentrated to dryness. To the residue was added 2N NaOH (20 mL) solution and DCM (60 ml) and stirred at rt for 30 mins. The mixture was separated. The organic phase was dried over Na₂SO₄ and concentrated in vacuo. The crude product was purified by prep-HPLC to give the target compound (0.8 g, 70%). 1H NMR (400 MHz, CD₃OD) δ 7.25 (s, 1H), 7.19-7.14 (m, 1H), 6.78-6.64 (m, 2H), 5.25-5.13 (m, 1H), 4.14-4.06 (m, 4H), 3.76-3.59 (m, 2H), 2.94 (d, J=4.3 Hz, 2H), 2.44 (d, J=3.1 Hz, 3H), 1.90 (s, 2H), 1.75-1.56 (m, 2H), 1.48-1.36 (m, 2H), 0.92 (t, J=7.3 Hz, 3H) ppm. MS: M/e 433 (M+1)⁺.

Compound A116: (R or S)-3-((4-amino-7-(3-methoxy-5-(2-(methylamino)ethoxy)benzyl)imidazo[2,1-f][1,2,4]triazin-2-yl)oxy)hexan-1-ol Step A: tert-butyl (2-(3-formyl-5-methoxyphenoxy)ethyl)(methyl)carbamate To a solution of 3-hydroxy-5-methoxybenzaldehyde (1 g, 6.58 mmol), tert-butyl (2-hydroxyethyl)(methyl)carbamate (1.15 g, 6.57 mmol) and PPh$_3$ (2.6 g, 9.92 mmol) in THF (20 mL) was added a solution of DTAD (1.7 g, 7.39 mmol) in THF (20 mL) under N$_2$ at 0° C. The reaction mixture was stirred for 16 h at 25° C. After completed, the reaction mixture was quenched with water (50 mL) and extracted with EtOAc (3×50 mL). The combined organic layers were washed with aq NaHCO$_3$ (3×50 mL), water (50 mL), brine (50 mL), dried over Na$_2$SO$_4$ and concentrated under vacuum to get a residue. The residue was purified by column chromatography on silica gel eluting with ethyl acetate in petroleum ether (33%) to afford the title compound (2 g, crude). MS: M/e 332 (M+Na)$^+$.

Step B: tert-butyl (2-(3-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-5-methoxyphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (500 mg, 0.78 mmol) in THF (20 mL) was added n-BuLi (3.2 mL, 5.12 mmol) under N$_2$ at −78° C. After stirring for 0.5 h at −78° C., tert-butyl (2-(3-formyl-5-methoxyphenoxy)ethyl)(methyl)carbamate (1.1 g, crude) was added. The reaction mixture was stirred for 2.5 h at −78° C. After completed, the reaction mixture was quenched with aq NH$_4$Cl (30 mL) and extracted with DCM (3×50 mL). The combined organic layers were dried over Na$_2$SO$_4$ and concentrated under vacuum to get a residue. The residue was purified by column chromatography on silica gel eluting with ethyl acetate in petroleum ether (60%) to afford the title compound (250 mg, 34%). MS: M/e 951 (M+1)$^+$.

Step C: tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-5-methoxyphenoxy) ethyl)(methyl)carbamate To a solution of tert-butyl (2-(3-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-5-methoxyphenoxy)ethyl)(methyl)carbamate (250 mg, 0.263 mmol) in MeOH (20 mL) was added Pd/C (250 mg) and AcOH (0.26 mL). The reaction mixture was stirred for 12 h at 40° C. under H$_2$ (1 atm). The mixture was filtered and the filtrate was combined together and concentrated in vacuo. The residue was purified by column chromatography on silica gel eluting with ethyl acetate in petroleum ether (80%) to afford the title compound (120 mg, 54%). MS: M/e 845 (M+1)$^+$.

Step D: (R or S)-3-((4-amino-7-(3-methoxy-5-(2-(methylamino)ethoxy)benzyl) imidazo[2,1-f][1,2,4]triazin-2-yl)oxy)hexan-1-ol (Compound A116)

Tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-5-methoxyphenoxy)ethyl)(methyl) carbamate (120 mg, 0.142 mmol) was dissolved in TFA (4 mL) and H$_2$O (0.4 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust PH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/CH$_3$OH (NH$_3$)=15/1) to afford the title compound (45 mg, 71%). $^1$H NMR (400 MHz, CD$_3$OD) δ 7.31 (s, 1H), 6.56 (s, 1H), 6.46 (s, 1H), 6.42 (s, 1H), 5.21-5.13 (m, 1H), 4.15 (s, 4H), 3.75 (s, 3H), 3.64 (t, J=6.0 Hz, 2H), 3.32 (s, 2H), 2.70 (s, 3H), 1.96-1.79 (m, 2H), 1.78-1.56 (m, 2H), 1.49-1.31 (m, 2H), 0.90 (t, J=7.2 Hz, 3H) ppm. MS: M/e 445 (M+1)$^+$.

Compound A117: (R or S)-3-((4-amino-7-(4-methoxy-3-(2-(methylamino)ethoxy)benzyl)imidazo[2,1-f][1,2,4]triazin-2-yl)oxy)hexan-1-ol Step A: tert-butyl (2-(5-formyl-2-methoxyphenoxy)ethyl)(methyl)carbamate To a solution of 3-hydroxy-4-methoxybenzaldehyde (1 g, 6.58 mmol), tert-butyl (2-hydroxyethyl)(methyl)carbamate (1.15 g, 6.57 mmol) and PPh$_3$ (2.6 g, 9.92 mmol) in THF (20 mL) was added a solution of DIAD (1.7 g, 8.42 mmol) in THF (20 mL) under N$_2$ at 0° C. The reaction mixture was stirred for 16 h at 25° C. After completed, the reaction mixture was quenched with water (50 mL) and extracted with EtOAc (3×50 mL). The combined organic layers were washed with aq Na$_2$CO$_3$ (3×50 mL), water (50 mL), brine (50 mL), dried over Na$_2$SO$_4$ and concentrated under vacuum to get a residue. The residue was purified by column chromatography on silica gel eluting with ethyl acetate in petroleum ether (33%) to afford the title compound (2.8 g, crude). MS: M/e 332. (M+Na)$^+$.

Step B: tert-butyl (2-(5-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2-methoxyphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (500 mg, 0.78 mmol) in THF (20 mL) was added n-BuLi (3.2 mL, 5.12 mmol) under N$_2$ at −78° C. After stirring for 0.5 h at −78° C., tert-butyl (2-(5-formyl-2-methoxyphenoxy)ethyl)(methyl)carbamate (830 mg, crude) was added. The reaction mixture was stirred for 2.5 h at −78° C. After completed, the reaction mixture was quenched with aq NH$_4$Cl (30 mL) and extracted with DCM (3×30 mL). The combined organic layers were dried over Na$_2$SO$_4$ and concentrated under vacuum to get a residue. The residue was purified by column chromatography on silica gel eluting with ethyl acetate in petroleum ether (60%) to afford the title compound (240 mg, 32%). MS: M/e 951 (M+1)$^+$.

Step C: tert-butyl (R or S)-(2-(5-((4-(bis(2,4-dimethoxybenzyl)amino)-2-((1-hydroxyhexan-3-yl)oxy)imidazo[2,1-f][1,2,4]triazin-7-yl)methyl)-2-methoxyphenoxy) ethyl)(methyl)carbamate To a solution of tert-butyl (2-(5-((2-(((R or S)-1-(benzyloxy)hexan-3-yl)oxy)-4-(bis(2,4-dimethoxybenzyl)amino)

imidazo[2,1-f][1,2,4]triazin-7-yl)(hydroxy)methyl)-2-methoxyphenoxy)ethyl)(methyl)carbamate (240 mg, 0.252 mmol) in MeOH (20 mL) was added Pd/C (240 mg) and AcOH (0.24 mL). The reaction mixture was stirred for 12 h at 40° C. under $H_2$ (1 atm). The mixture was filtered and the filtrate was combined together and concentrated in vacuo. The residue was purified by column chromatography on silica gel eluting with ethyl acetate in petroleum ether (80%) to afford the title compound (100 mg, 54%). MS: M/e 845 (M+1)$^+$.

Step D: (R or S)-3-((4-amino-7-(4-methoxy-3-(2-(methylamino)ethoxy)benzyl) imidazo[2,1-f][1,2,4]triazin-2-yl)oxy)hexan-1-ol (Compound A117)

tert-butyl (R or S)-(2-(5-((4-(bis(2,4-dimethoxybenzyl)amino)-2-((1-hydroxyhexan-3-yl)oxy)imidazo[2,1-f][1,2,4]triazin-7-yl)methyl)-2-methoxyphenoxy) ethyl)(methyl)carbamate (100 mg, 0.118 mmol) was dissolved in TFA (4 mL) and $H_2O$ (0.4 mL) under $N_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust PH=13~14 and extracted with DCM/i-PrOH (5/1, 3×100 mL). The combined organic layers were dried over $Na_2SO_4$ and concentrated under vacuum to get a residue. The residue was purified by Prep-TLC (DCM/$CH_3OH$ ($NH_3$)=15/1) to afford the title compound (30 mg, 58%). $^1$H NMR (400 MHz, $CD_3OD$) δ 7.27 (s, 1H), 6.99-6.86 (m, 3H), 5.22-5.18 (m, 1H), 4.18-4.04 (m, 4H), 3.83 (s, 3H), 3.70-3.61 (m, 2H), 3.08 (s, 2H), 2.61-2.49 (m, 3H), 1.96-1.79 (m, 2H), 1.78-1.54 (m, 2H), 1.51-1.34 (m, 2H), 0.90 (t, J=7.2 Hz, 3H) ppm. MS: M/e 445 (M+1)$^+$.

Compound A118: (R or S)-3-((4-amino-7-(2-methoxy-3-(2-(methylamino)ethoxy)benzyl)imidazo[2,1-f][1,2,4]triazin-2-yl)oxy)hexan-1-ol Step A: tert-butyl (2-(3-formyl-2-methoxyphenoxy)ethyl)(methyl)carbamate To a solution of 3-hydroxy-2-methoxybenzaldehyde (1 g, 6.58 mmol), tert-butyl (2-hydroxyethyl)(methyl)carbamate (1.15 g, 6.57 mmol) and $PPh_3$ (2.6 g, 9.92 mmol) in THF (20 mL) was added a solution of DTAD (1.7 g, 7.39 mmol) in THF (20 mL) under $N_2$ at 0° C. The reaction mixture was stirred for 16 h at 25° C. After completed, the reaction mixture was quenched with water (50 mL) and extracted with EtOAc (3×50 mL). The combined organic layers were washed with aq $NaHCO_3$ (3×50 mL), water (50 mL), brine (50 mL), dried over $Na_2SO_4$ and concentrated under vacuum to get a residue. The residue was purified by column chromatography on silica gel eluting with ethyl acetate in petroleum ether (20%) to afford the title compound (2.3 g, crude). MS: M/e 332 (M+Na)$^+$.

Step B: tert-butyl (2-(3-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2-methoxyphenoxy)ethyl)(methyl)carbamate To a solution of (R or S)-2-((1-(benzyloxy)hexan-3-yl)oxy)-N,N-bis(2,4-dimethoxybenzyl)imidazo[2,1-f][1,2,4]triazin-4-amine (500 mg, 0.78 mmol) in THF (20 mL) was added n-BuLi (3.2 mL, 5.12 mmol) under $N_2$ at −78° C.

After stirring for 0.5 h at −78° C., tert-butyl (2-(3-formyl-2-methoxyphenoxy)ethyl)(methyl)carbamate (1.1 g, crude) was added. The reaction mixture was stirred for 2.5 h at −78° C. After completed, the reaction mixture was quenched with aq $NH_4Cl$ (30 mL) and extracted with DCM (3×30 mL). The combined organic layers were dried over $Na_2SO_4$ and concentrated under vacuum to get a residue. The residue was purified by column chromatography on silica gel eluting with ethyl acetate in petroleum ether (60%) to afford the title compound (260 mg, 35%). MS: M/e 951 (M+1)$^+$.

Step C: tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-2-methoxyphenoxy) ethyl)(methyl)carbamate To a solution of tert-butyl (2-(3-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)-2-methoxyphenoxy)ethyl)(methyl)carbamate (260 mg, 0.273 mmol) in MeOH (20 mL) was added Pd/C (260 mg) and AcOH (0.26 mL). The reaction mixture was stirred for 12 h at 40° C. under $H_2$ (1 atm). The mixture was filtered and the filtrate was combined together and concentrated in vacuo. The residue was purified by column chromatography on silica gel eluting with ethyl acetate in petroleum ether (80%) to afford the title compound (150 mg, 65%). MS: M/e 845 (M+1)$^+$.

Step D: (R or S)-3-((4-amino-7-(2-methoxy-3-(2-(methylamino)ethoxy)benzyl) imidazo[2,1-f][1,2,4]triazin-2-yl)oxy)hexan-1-ol (Compound A118)

tert-butyl (R or S)-(2-(3-((4-(bis(2,4-dimethoxybenzyl)amino)-2-((1-hydroxyhexan-3-yl)oxy)imidazo[2,1-f][1,2,4]triazin-7-yl)methyl)-2-methoxyphenoxy) ethyl)(methyl)carbamate (150 mg, 0.177 mmol) was dissolved in TFA (5 mL) and $H_2O$ (0.5 mL) under $N_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust PH=13~14 and extracted with DCM/i-PrOH (5/1, 3×100 mL). The combined organic layers were dried over $Na_2SO_4$ and concentrated under vacuum to get a residue. The residue was purified by Prep-TLC (DCM/$CH_3OH$ ($NH_3$)=15/1) to afford the title compound (48 mg, 61%). $^1$H NMR (400 MHz, $CD_3OD$) δ 7.20 (s, 1H), 7.02-6.91 (m, 2H), 6.85 (d, J=6.8 Hz, 1H), 5.25-5.15 (m, 1H), 4.24-4.11 (m, 4H), 3.79 (s, 3H), 3.65 (t, J=6.0 Hz, 2H), 3.10 (t, J=4.8 Hz, 2H), 2.56 (s, 3H), 1.97-1.81 (m, 2H), 1.79-1.57 (m, 2H), 1.50-1.22 (m, 2H), 0.91 (t, J=7.2 Hz, 3H) ppm. MS: M/e 445 (M+1)$^+$.

Compound A119 and Compound A120: (R or S)-3-((4-amino-7-(4-(2-(methylamino)ethyl)benzyl)imidazo[2,1-f][1,2,4]triazin-2-yl)oxy)hexan-1-ol, and (S or R)-3-((4-amino-7-(4-(2-(methylamino)ethyl)benzyl)imidazo[2,1-f][1,2,4]triazin-2-yl)oxy)hexan-1-ol Compound A95 3-((4-amino-7-(4-(2-(methylamino)ethyl)benzyl)imidazo[2,1-f][1,2,4]triazin-2-yl)oxy)hexan-1-ol (45 mg, 0.168 mmol) was purified by Prep-SFC (Chiral PAK AD-H column, 3 cm*25 cm, 5 m, Flow rate 45 mL/min, Phase: hexane (2 mM NH$_3$-MeOH):IPA=80:20, UV: 220 nm, 25° C.) to afford Compound A119 (20 mg) and Compound A120 (23 mg).

Compound A119 (optical isomer 1): $^1$H NMR (400 MHz, CD$_3$OD) δ 7.29 (s, 1H), 7.24 (d, J=7.6 Hz, 2H), 7.16 (d, J=7.6 Hz, 2H), 5.18 (s, 1H), 4.17 (s, 2H), 3.64 (s, 2H), 2.80 (s, 4H), 2.40 (s, 3H), 1.90 (s, 2H), 1.78-1.55 (m, 2H), 1.49-1.34 (m, 2H), 0.91 (t, J=7.2 Hz, 3H) ppm. MS: M/e 399 (M+1)$^+$.

Compound A120 (optical isomer 2): $^1$H NMR (400 MHz, CD$_3$OD) δ 7.31-7.25 (m, 3H), 7.19 (d, J=7.6 Hz, 2H), 5.25-5.10 (m, 1H), 4.18 (s, 2H), 3.62 (s, 2H), 3.04 (t, J=7.6 Hz, 2H), 2.87 (t, J=7.6 Hz, 2H), 2.56 (s, 3H), 1.94-1.81 (m, 2H), 1.79-1.56 (m, 2H), 1.49-1.34 (m, 2H), 0.92 (t, J=7.2 Hz, 3H) ppm. MS: M/e 399 (M+1)$^+$.

Compound A121: (R or S)-3-((4-amino-7-(2-ethoxy-4-(2-(methylamino)ethoxy) benzyl)imidazo [2,1-f][1,2,4]triazin-2-yl)oxy)hexan-1-ol Step A: 4-chloro-2-ethoxybenzaldehyde To a mixture of 4-chloro-2-hydroxybenzaldehyde (1.56 g, 10 mmol) and K$_2$CO$_3$ (3.45 g, 25 mmol) in DMF (10 mL) was added iodoethane (2.34 g, 15 mmol) at rt and the resulted mixture was stirred at rt for 16 hrs. The mixture was diluted with EA (50 mL), filtered. The filtrate was washed with brine (50 mL×3), dried over Na$_2$SO$_4$ and concentrate. The residue was purified by column chromatography to obtain the title product (1.70 g, yield: 92%). MS: M/e 185 (M+1)$^+$.

Step B: tert-butyl (2-(3-ethoxy-4-formylphenoxy) ethyl)(methyl)carbamate

A mixture of 4-chloro-2-ethoxybenzaldehyde (736 mg, 4 mmol), tert-butyl (2-hydroxyethyl)(methyl)carbamate (1.05 g, 6 mmol), Pd$_2$(dba)$_3$ (183 mg, 0.2 mmol), RuPhos (186 mg, 0.4 mmol) and Cs$_2$CO$_3$ (2.6 g, 8 mmol) in Dioxane (10 mL) was stirred at 100° C. under N$_2$ for 16 hrs. The mixture was cooled and diluted with EA (20 mL), filtered and the filtrate was washed with brine (10 mL×3), dried over Na$_2$SO$_4$ and concentrate. The residue was purified by column chromatography to obtain the title product (500 mg, yield: 38%). MS: M/e 324 (M+1)$^+$.

Step C: tert-butyl (2-(4-((2-(((R or S)-1-(benzyloxy) hexan-3-yl)oxy)-4-(bis(2,4-dimethoxybenzyl)amino) imidazo[2,1-f][1,2,4]triazin-7-yl)(hydroxy)methyl)-3-ethoxyphenoxy)ethyl)(methyl)carbamate To a solution of (R or S)-2-((1-(benzyloxy)hexan-3-yl) oxy)-N,N-bis(2,4-dimethoxybenzyl)imidazo[2,1-f][1,2,4] triazin-4-amine (340 mg, 0.53 mmol) in THF (5 mL) was added n-BuLi (1.6 M, 2.0 mL, 3.2 mmol) at −78° C. in N$_2$ atmosphere. The mixture was stirred at −78° C. for 30 min. Then the solution of tert-butyl (2-(3-ethoxy-4-formylphenoxy)ethyl)(methyl)carbamate (340 mg, 1.05 mmol) in THF (3 mL) was added to the system at −78° C. The reaction was stirred for 30 min, and then warmed to room temperature and stirred for 16 hrs. The reaction was quenched with saturated NH$_4$Cl (00 mL) at room temperature and extracted with EA (10 mL×3). The combined organic phase was washed with brine (10 mL×3), dried over Na$_2$SO$_4$ and concentrated under reduced pressure. The residue was purified by column chromatography to obtain the title compound (125 mg, yield: 25%). MS: M/e 965 (M+1)$^+$.

Step D: tert-butyl (R or S)-(2-(4-((4-(bis(2,4-dimethoxybenzyl)amino)-2-((1-hydroxyhexan-3-yl)oxy) imidazo[2,1-f][1,2,4]triazin-7-yl)methyl)-3-ethoxyphenoxy)ethyl)(methyl)carbamate A mixture of tert-butyl (2-(4-((2-(((R or S)-1-(benzyloxy) hexan-3-yl)oxy)-4-(bis(2,4-dimethoxybenzyl)amino)imidazo[2,1-f][1,2,4]triazin-7-yl)(hydroxy)methyl)-3-ethoxyphenoxy)ethyl)(methyl)carbamate (180 mg, 0.187 mmol), Pd/C (wet, 200 mg) and AcOH (5 drops) in MeOH (5 mL) was stirred at 40° C. under H$_2$ at rt for 16 hrs. The mixture was filtered and the filtrate was concentrated under high vacuum to obtain the title product (85 mg, crude). MS: M/e 859 (M+1)$^+$.

Step E: (R or S)-3-((4-amino-7-(2-ethoxy-4-(2-(methylamino)ethoxy)benzyl)imidazo[2,1-f][1,2,4] triazin-2-yl)oxy)hexan-1-ol (Compound A121)

Tert-butyl (R or S)-(2-(4-((4-(bis(2,4-dimethoxybenzyl) amino)-2-((1-hydroxyhexan-3-yl)oxy)imidazo[2,1-f][1,2,4] triazin-7-yl)methyl)-3-ethoxyphenoxy)ethyl)(methyl) carbamate (85 mg, crude) in TFA (3 mL) was stirred at rt for 6 hrs. The reaction mixture was concentrated under reduced pressure. The residue was diluted with MeOH (3 mL), treated with NaOH (1 mL, 4M), stirred at rt for 1 hour and concentrated to remove MeOH. The resulted aqueous solution was extracted with DCM (3 mL×3). The combined organics was washed with brine (5 mL×2), dried over Na$_2$SO$_4$, concentrated and purified by prep-HPLC to obtain the title compound (5.5 mg, yield: 6% for 2 steps). $^1$H NMR (400 MHz, CD$_3$OD) 7.20-7.11 (m, 2H), 6.59 (s, 1H), 6.50 (d, J=8.0 Hz, 1H), 5.29-5.13 (m, 1H), 4.25-4.16 (m, 2H), 4.09 (s, 2H), 4.07-3.97 (m, 2H), 3.70-3.60 (m, 2H), 3.41-3.34 (m, 2H), 2.73 (s, 3H), 1.96-1.85 (m, 2H), 1.78-1.61 (m, 2H), 1.51-1.39 (m, 2H), 1.37 (t, J=6.8 Hz, 3H), 0.93 (t, J=7.2 Hz, 3H) ppm. MS: M/e 459 (M+1)$^+$.

Compound A122: (R or S)-3-((4-amino-7-((6-(2-(methylamino)propoxy)pyridin-3-yl)methyl)imidazo [2,1-f][1,2,4]triazin-2-yl)oxy)hexan-1-ol Step A: tert-butyl (1-hydroxypropan-2-yl)(methyl)carbamate To a solution of N-(tert-butoxycarbonyl)-N-methylalanine (1 g, 4.93 mmol) in THF (20 mL) was added BH$_3$ (7.5 mL, 7.5 mmol) under N$_2$ at −0° C. The reaction mixture was stirred for 2 h at 0° C. Then water (5 mL) was added dropwise at 0° C. After stirring for 10 min, 10% Na$_2$CO$_3$ (10 mL) was added dropwise. The reaction mixture was stirred for 1 h at 25° C. After completed, the reaction mixture was extracted with EtOAc (3×50 mL). The combined organic layers was washed with brine (3×20 mL), dried over Na$_2$SO$_4$ and concentrated under vacuum to get a crude product (900 mg, 96%). $^1$H NMR (400 MHz, DMSO-d$_6$) δ 4.66 (s, 1H), 4.14-3.86 (m, 1H), 3.43-3.26 (m, 2H), 2.64 (s, 3H), 1.39 (s, 9H), 0.97 (s, 3H).

Step B: tert-butyl (1-((5-formylpyridin-2-yl)oxy) propan-2-yl)(methyl)carbamate

To a solution of 6-chloronicotinaldehyde (570 mg, 4.01 mmol), tert-butyl (1-hydroxypropan-2-yl)(methyl)carbamate (900 mg, 4.76 mmol), Pd$_2$(dba)$_3$·CHCl$_3$ (311 mg, 0.3 mmol) and Cs$_2$CO$_3$ (2.6 g, 7.97 mmol) in dioxane (20 mL) were added RuPhos (280 mg, 0.599 mmol) under N$_2$. The reaction mixture was stirred for 12 h at 95° C. The mixture was filtered and the filtrate was combined together and concentrated in vacuo. The residue was purified by column chromatography on silica gel eluting with ethyl acetate in petroleum ether (25%) to afford the title compound (1 g, 85%). $^1$H NMR (400 MHz, DMSO-d$_6$) δ 9.97 (s, 1H), 8.76 (s, 1H), 8.12 (s, 1H), 6.95 (s, 1H), 4.60-4.16 (m, 3H), 2.69 (s, 3H), 1.47-1.06 (m, 12H) ppm. MS: M/e 295. (M+H)$^+$.

Step C: tert-butyl (1-((5-((2-(((R or S)-1-(benzyloxy)hexan-3-yl)oxy)-4-(bis(2,4-dimethoxybenzyl) amino)imidazo[2,1-f][1,2,4]triazin-7-yl)(hydroxy) methyl)pyridin-2-yl)oxy)propan-2-yl)(methyl) carbamate To a solution of (R or S)-2-((1-(benzyloxy)hexan-3-yl) oxy)-N,N-bis(2,4-dimethoxybenzyl)imidazo[2,1-f][1,2,4] triazin-4-amine (600 mg, 0.934 mmol) in THF (10 mL) was added n-BuLi (0.88 mL, 1.41 mmol) under N$_2$ at −78° C. After stirring for 0.5 h at −78° C., tert-butyl (1-((5-formylpyridin-2-yl)oxy)propan-2-yl)(methyl)carbamate (328 mg, 1.12 mmol) was added. The reaction mixture was stirred for 2.5 h at −78° C. After completed, the reaction mixture was quenched with aq NH$_4$Cl (30 mL) and extracted with DCM (3×30 mL). The combined organic layers were dried over Na$_2$SO$_4$ and concentrated under vacuum to get a residue. The residue was purified by column chromatography on silica gel eluting with ethyl acetate in petroleum ether (70%) to afford the title compound (700 mg, 80%). MS: M/e 936 (M+H)$^+$.

Step D: tert-butyl (1-((5-((4-(bis(2,4-dimethoxybenzyl)amino)-2-(((R or S)-1-hydroxyhexan-3-yl)oxy) imidazo[2,1-f][1,2,4]triazin-7-yl)methyl)pyridin-2-yl)oxy)propan-2-yl)(methyl)carbamate To a solution of tert-butyl (1-((5-((2-(((R or S)-1-(benzyloxy)hexan-3-yl)oxy)-4-(bis(2,4-dimethoxybenzyl)amino) imidazo[2,1-f][1,2,4]triazin-7-yl)(hydroxy)methyl) pyridine-2-yl)oxy)propan-2-yl)(methyl)carbamate (700 mg, 0.748 mmol) in MeOH (40 mL) was added Pd/C (700 mg) and AcOH (0.8 mL). The reaction mixture was stirred for 12 h at 40° C. under H$_2$ (1 atm). The mixture was filtered and the filtrate was combined together and concentrated in vacuo. The residue was purified by column chromatography on silica gel eluting with ethyl acetate in petroleum ether (70%) to afford the title compound (200 mg, 32%). MS: M/e 830 (M+H)$^+$.

Step E: (R or S)-3-((4-amino-7-((6-(2-(methylamino)propoxy)pyridin-3-yl)methyl) imidazo[2,1-f][1,2,4]triazin-2-yl)oxy)hexan-1-ol (Compound A122)

Tert-butyl (1-((5-((4-(bis(2,4-dimethoxybenzyl)amino)-2-(((R or S)-1-hydroxyhexan-3-yl)oxy)imidazo[2,1-f][1,2,4]triazin-7-yl)methyl)pyridin-2-yl)oxy)propan-2-yl) (methyl)carbamate (200 mg, 0.241 mmol was dissolved in TFA (4 mL) and H$_2$O (0.4 mL) under N$_2$. The reaction mixture was stirred for 12 h at 40° C. After completed, the solvent was removed by in vacuo. The residue was diluted with water (20 mL) and DCM (20 mL) and the aqueous phase was acid with 1 N HCl to adjust PH=1~2. The aqueous phase was washed with DCM (3×20 mL) and based with 2 N NaOH to adjust PH=13~14 and extracted with DCM/i-PrOH (5/1, 3×100 mL). The combined organic layers were dried over Na$_2$SO$_4$ and concentrated under vacuum to get a residue. The residue was purified by prep-TLC (DCM/ CH$_3$OH (NH$_3$)=15/1) to afford the title compound (60 mg, 58%). $^1$H NMR (400 MHz, CD$_3$OD) δ 8.13 (s, 1H), 7.67 (s, 1H), 7.36 (s, 1H), 6.81 (d, J=4.8 Hz, 1H), 5.20 (s, 1H), 4.32 (s, 1H), 4.18 (s, 3H), 3.67 (s, 2H), 3.16 (s, 1H), 2.51 (s, 3H), 1.91 (s, 2H), 1.80-1.60 (m, 2H), 1.54-1.31 (m, 2H), 1.23 (s, 3H), 0.94 (s, 3H) ppm. MS: M/e 430 (M+H)$^+$.

Compound A123: (R or S)-3-((4-amino-7-(2,6-difluoro-4-(2-(methylamino)ethoxy)benzyl)imidazo[2, 1-f][1,2,4]triazin-2-yl)oxy)hexan-1-ol Step A: tert-butyl (2-(3,5-difluoro-4-formylphenoxy)ethyl)(methyl)carbamate To a solution of 3,5-difluoro-4-hydroxybenzaldehyde (316 mg, 2 mmol) in THF (10 mL) was added tert-butyl (2-hydroxyethyl)(methyl)carbamate (350 mg, 2 mmol) and PPh$_3$ (655 mg, 2.5 mmol), The mixture was protected by nitrogen and cooled down to 0 degrees. A solution of DIAD (505 mg, 2.5 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (180 mg, 28.5%). MS: m/e: 316 (M+1)$^+$.

Step B: tert-butyl (2-(4-((2-(((R or S)-1-(benzyloxy) hexan-3-yl)oxy)-4-(bis(2,4-dimethoxybenzyl)amino) imidazo[2,1-f][1,2,4]triazin-7-yl)(hydroxy)methyl)- 3,5-difluorophenoxy)ethyl)(methyl)carbamate To a solution of (R or S)-2-((1-(benzyloxy)hexan-3-yl) oxy)-N,N-bis(2,4-dimethoxybenzyl)imidazo[2,1-f][1,2,4] triazin-4-amine (300 mg, 0.5 mmol) in THF (10 mL) was added a solution of n-BuLi (1.6 M, 0.9 mL, 1.5 mmol) drop wise maintaining the temperature between −75~−65° C. After 1 h, a suspension of tert-butyl (2-(3,5-difluoro-4-formylphenoxy)ethyl)(methyl)carbamate (180 mg, 0.57 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (120 mg, 25.1%). MS: M/e 957 (M+1)$^+$.

Step C: tert-butyl (R or S)-(2-(4-((4-(bis(2,4-dimethoxybenzyl)amino)-2-((1-hydroxyhexan-3-yl)oxy) imidazo[2,1-f][1,2,4]triazin-7-yl)methyl)-3,5-difluorophenoxy)ethyl)(methyl)carbamate To a solution of tert-butyl (2-(4-((2-(((R or S)-1-(benzyloxy)hexan-3-yl)oxy)-4-(bis(2,4-dimethoxybenzyl)amino) imidazo[2,1-f][1,2,4]triazin-7-yl)(hydroxy)methyl)-3,5-difluorophenoxy)ethyl)(methyl)carbamate (120 mg, 0.125 mmol) in MeOH (20 mL) was added Pd/C (200 mg). The mixture was protected by hydrogen and stirred at room temperature for overnight. The mixture was filtered and the filtrate was concentrated in vacuo. The crude product was purified by column chromatography to give the title product (60 mg, 56.2%). MS: m/e: 851 (M+1)+.

Step D: (R or S)-3-((4-amino-7-(2,6-difluoro-4-(2-(methylamino)ethoxy)benzyl)imidazo[2,1-f][1,2,4]triazin-2-yl)oxy)hexan-1-ol (Compound A123)

To a mixture of the product of step C (60 mg, 0.07 mmol) in TFA (9 mL) was added H$_2$O (1 mL) and the resulting mixture was stirred at 40° C. for overnight. The mixture was cooled to room temperature and concentrated to dryness. To the residue was added 2N NaOH (10 mL) solution and DCM (20 ml) and stirred at rt for 30 mins. The mixture was separated. The organic phase was dried over Na$_2$SO$_4$ and concentrated in vacuo. The crude product was purified by prep-HPLC to give the target compound (8 mg, 25.2%). 1H NMR (400 MHz, CD$_3$OD) δ 7.21 (s, 1H), 6.68 (d, J=9.2 Hz, 2H), 5.26 (s, 1H), 4.15 (dd, J=12.0, 7.3 Hz, 4H), 3.67 (s, 2H), 3.09 (s, 2H), 2.56 (s, 3H), 1.94 (d, J=6.4 Hz, 2H), 1.72 (s, 2H), 1.45 (s, 2H), 0.97 (t, J=7.4 Hz, 3H) ppm. MS: M/e 451 (M+1)+.

Compound A124: (R or S)-3-((4-amino-7-((4-(2-(methylamino)ethoxy)naphthalen-1-yl)methyl)imidazo[2,1-f][1,2,4]triazin-2-yl)oxy)hexan-1-ol Step A: tert-butyl (2-((4-formylnaphthalen-1-yl)oxy)ethyl)(methyl)carbamate To a solution of 4-hydroxy-1-naphthaldehyde (344 mg, 2 mmol) in THF (10 mL) was added tert-butyl (2-hydroxyethyl)(methyl)carbamate (350 mg, 2 mmol) and PPh$_3$ (655 mg, 2.5 mmol), The mixture was protected by nitrogen and cooled down to 0 degrees. A solution of DIAD (505 mg, 2.5 mmol) in THF (5 ml) was added to the mixture. The reaction mixture was stirred at room temperature for overnight. An aqueous ammonium chloride solution was added and the mixture was extracted with ethyl acetate. The combined organic extracts were dried over sodium sulfate, filtered and evaporated. The crude product was purified by column chromatography to give the title product (400 mg, 60.7%). MS: m/e: 330 (M+1)+.

Step B: tert-butyl (2-((4-((2-(((R or S)-1-(benzyloxy)hexan-3-yl)oxy)-4-(bis(2,4-dimethoxybenzyl)amino)imidazo[2,1-f][1,2,4]triazin-7-yl)(hydroxy)methyl)naphthalen-1-yl)oxy)ethyl)(methyl)carbamate To a solution of (R or S)-2-((1-(benzyloxy)hexan-3-yl)oxy)-N,N-bis(4-methoxybenzyl)imidazo[2,1-f][1,2,4]triazin-4-amine (519 mg, 0.8 mmol) in THF (10 mL) was added a solution of n-BuLi (1.6 M, 1.5 mL, 2.4 mmol) drop wise maintaining the temperature between −75~−65° C. After 1 h, a suspension of tert-butyl (2-((4-formylnaphthalen-1-yl)oxy)ethyl)(methyl)carbamate (400 mg, 1.2 mmol) in THF (2 mL) was added dropwise. The resulted mixture was stirred at −70° C. for 2 h and then warmed to room temperature overnight. The reaction was quenched with saturated NH$_4$Cl solution, extracted with EtOAc (20 mL×3), washed with brine, dried over Na$_2$SO$_4$, filtered, and concentrated. The residue was purified by prep-TLC to give the target compound (220 mg, 22.6%). MS: M/e 971 (M+1)+.

Step C: tert-butyl (R or S)-(2-((4-((4-(bis(2,4-dimethoxybenzyl)amino)-2-((1-hydroxyhexan-3-yl)oxy)imidazo[2,1-f][1,2,4]triazin-7-yl)methyl)naphthalen-1-yl)oxy)ethyl)(methyl)carbamate To a solution of tert-butyl (2-((4-((2-(((R or S)-1-(benzyloxy)hexan-3-yl)oxy)-4-(bis(2,4-dimethoxybenzyl)amino) imidazo[2,1-f][1,2,4]triazin-7-yl)(hydroxy)methyl)naphthalen-1-yl)oxy)ethyl)(methyl)carbamate (220 mg, 0.226 mmol) in MeOH (20 mL) was added Pd/C (300 mg). The mixture was protected by hydrogen and stirred at room temperature for overnight. The mixture was filtered and the filtrate was concentrated in vacuo. The crude product was purified by column chromatography to give the title product (60 mg, 30%). MS: m/e: 865 (M+1)+.

Step D: (R or S)-3-((4-amino-7-((4-(2-(methylamino)ethoxy)naphthalen-1-yl)methyl)imidazo[2,1-f][1,2,4]triazin-2-yl)oxy)hexan-1-ol To a mixture of the product of step C (60 g, 0.069 mmol) in TFA (18 mL) was added H$_2$O (2 mL) and the resulting mixture was stirred at 40° C. for overnight. The mixture was cooled to room temperature and concentrated to dryness. To the residue was added 2N NaOH (20 mL) solution and DCM (60 ml) and stirred at rt for 30 mins. The mixture was separated. The organic phase was dried over Na$_2$SO$_4$ and concentrated in vacuo. The crude product was purified by prep-HPLC to give the target compound (10 mg, 31.1%). 1H NMR (400 MHz, CD$_3$OD) δ 8.41 (s, 1H), 8.06 (s, 1H), 7.53 (s, 2H), 7.33 (s, 1H), 7.12 (s, 1H), 6.91 (s, 1H), 5.22 (s, 1H), 4.58 (s, 2H), 4.33 (s, 2H), 3.68 (s, 2H), 3.23 (s, 2H), 2.61 (s, 3H), 1.93 (s, 2H), 1.74 (s, 2H), 1.41 (s, 2H), 0.91 (s, 3H) ppm. MS: M/e 465 (M+1)+.

Compound C1: 2-butoxy-8-(3-(pyrrolidin-1-ylmethyl)benzyl)pyrazolo[1,5-a][1,3,5]triazin-4-amine Step A: tert-butyl (2-butoxypyrazolo[1,5-a][1,3,5]triazin-4-yl)carbamate To a stirred solution of 2-butoxypyrazolo[1,5-a][1,3,5]triazin-4-amine (50 mg, 0.24 mmol) in THF (15 mL), Di-tert-butyl dicarbonate (130 mg, 0.6 mmol) and DMAP (10 mg, 0.08 mmol) was added. The reaction mixture was stirred at rt overnight. The mixture was diluted H$_2$O (20 mL) and extracted with EtOAc (10 ml×3). The combined organic layers were washed with brine, dried over Na$_2$SO$_4$ and concentrated in vacuo. The crude product was purified by column chromatography to give the product (100 mg, 100%) as white solids. MS: M/e 308 (M+1)+.

Step B: tert-butyl (8-bromo-2-butoxypyrazolo[1,5-a][1,3,5]triazin-4-yl)carbamate To a stirred solution of tert-butyl (2-butoxypyrazolo[1,5-a][1,3,5]triazin-4-yl)carbamate (100 mg, 0.3 mmol) in MeCN (10 mL), NBS (115 mg, 0.6 mmol) was added. The reaction mixture was stirred at rt for 2 h. The mixture was concentrated in vacuo. The crude product was purified by column chromatography to give the product (150 mg, 100%) as white solids. MS: M/e 386 (M+1)+.

Step C: tert-butyl (2-butoxy-8-(hydroxy(3-(pyrrolidin-1-ylmethyl)phenyl)methyl)pyrazolo[1,5-a][1,3,5]triazin-4-yl)carbamate To a stirred solution of tert-butyl (8-bromo-2-butoxypyrazolo[1,5-a][1,3,5]triazin-4-yl)carbamate (150 mg, 0.3 mmol) in THF (10 mL), cooled to −78° C. and under a nitrogen atmosphere, n-BuLi (1.6 M in hexane, 0.75 mmol, 0.47 mL) was added dropwise. After stirring for 20 mins, a solution of 3-(pyrrolidin-1-ylmethyl)benzaldehyde (85 mg, 0.45 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over Na₂SO₄, concentrated in vacuo. The crude product was purified by column chromatography to give the title product (100 mg, 67%). MS: M/e 498 (M+1)$^+$.

Step D: 2-butoxy-8-(3-(pyrrolidin-1-ylmethyl)benzyl)pyrazolo[1,5-a][1,3,5]triazin-4-amine A solution of tert-butyl (2-butoxy-8-(hydroxy(3-(pyrrolidin-1-ylmethyl)phenyl)methyl)pyrazolo[1,5-a][1,3,5]triazin-4-yl)carbamate (100 mg, 0.2 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (10 mg, 13.1%). $^1$H NMR (400 MHz, DMSO-d6)) δ 8.45 (s, 1H), 8.16 (s, 1H), 7.80 (s, 1H), 7.35-7.02 (m, 4H), 4.27 (s, 2H), 3.95 (s, 2H), 3.67 (s, 2H), 2.38-2.32 (m, 4H), 1.68-1.62 (m, 4H), 1.40 (s, 2H), 1.19-1.15 (m, 2H), 0.90-0.85 (m, 3H) ppm. MS: M/e 381 (M+1)$^+$.

Compound C2: 2-butoxy-8-(4-(pyrrolidin-1-ylmethyl)benzyl)pyrazolo[1,5-a][1,3,5]triazin-4-amine Step A: tert-butyl (2-butoxy-8-(hydroxy(4-(pyrrolidin-1ylmethyl)phenyl)methyl)pyrazolo[1,5-a][1,3,5]triazin-4-yl)carbamate To a stirred solution of tert-butyl (8-bromo-2-butoxypyrazolo[1,5-a][1,3,5]triazin-4-yl)carbamate (100 mg, 0.26 mmol) in THF (10 mL), cooled to −78° C. and under a nitrogen atmosphere, n-BuLi (1.6 M in hexane, 0.75 mmol, 0.47 mL) was added dropwise. After stirring for 20 mins, a solution of 4-(pyrrolidin-1-ylmethyl)benzaldehyde (100 mg, 0.52 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over Na₂SO₄, concentrated in vacuo to give the crude product (220 mg, 100%) which was used directly in next step. MS: M/e 497 (M+1)$^+$.

Step B: 2-butoxy-8-(4-(pyrrolidin-1-ylmethyl)benzyl)pyrazolo[1,5-a][1,3,5]triazin-4-amine A solution of tert-butyl (2-butoxy-8-(hydroxy(4-(pyrrolidin-1-ylmethyl)phenyl)methyl)pyrazolo[1,5-a][1,3,5]triazin-4-yl)carbamate (220 mg, 0.26 mmol) in TFA (3 mL) and Et₃SiH (3 mL) was stirred at 80° C. for 2 h. The reaction mixture was concentrated in vacuo to remove TFA and Et₃SiH. The residue was added TFA (5 mL) and stirred at 85° C. overnight. The mixture was cooled down to rt and concentrated in vacuo. The crude product was purified by prep-HPLC to give the product (10 mg, 10.1%). $^1$H NMR (400 MHz, DMSO-d6)) δ 8.47 (s, 1H), 8.17 (s, 1H), 7.87 (s, 1H), 7.19 (s, 4H), 4.26 (t, J=6.4 Hz, 2H), 3.82 (s, 2H), 3.50 (s, 2H), 2.39-2.31 (m, 4H), 1.72-1.61 (m, 6H), 1.40 (dq, J=14.3, 7.2 Hz, 2H), 0.98-0.87 (m, 3H) ppm. MS: M/e 381 (M+1)$^+$.

Compound C3: 5-butoxy-3-((5-chloro-6-(piperazin-1-yl)pyridin-3-yl)methyl)pyrazolo[1,5-c]pyrimidin-7-amine Step A: methyl 7-amino-5-hydroxypyrazolo[1,5-c] pyrimidine-3-carboxylate To a solution of dimethyl 3-oxopentanedioate (50 g, 0.29 mol) in ethanol (500 mL), DMF-DMA (34.5 g, 0.29 mol) was added and the mixture was stirred at rt for 2 hrs. Then hydrazinecarboximidamide hydrochloride (35.4 g, 0.32 mol) was added and the solution was heated at 80° C. for 3 hrs. After cooled down to rt, the precipitated solid was filtered and dried to get the product as a yellow solid (24 g, 40%). $^1$H NMR (400 MHz, DMSO-d6) δ 10.99 (br.s, 1H), 8.24 (s, 1H), 7.82 (br.s, 2H), 6.27 (s, 1H), 3.76 (s, 3H) ppm. MS: M/e 209 (M+1)$^+$ Step B: methyl 7-amino-5-butoxypyrazolo[1,5-c] pyrimidine-3-carboxylate 1-iodobutane (6.6 g, 36 mmol) was added to a solution of methyl 7-amino-5-hydroxypyrazolo[1,5-c]pyrimidine-3-carboxylate (5 g, 24 mmol) in DMF (100 mL). The solution was stirred at rt overnight. Water (50 mL) was added and the precipitated solid was filtered and dried to get the desired product as a yellow solid (6.1 g, 96%). $^1$H NMR (400 MHz, DMSO-d6) δ 8.30 (s, 1H), 8.01 (br.s, 1H), 6.35 (s, 1H), 4.20 (t, J=8.0 Hz, 2H), 3.77 (s, 3H), 1.71-1.66 (m, 2H), 1.45-1.38 (m, 2H), 0.89 (t, J=8.0 Hz, 3H) ppm. MS: M/e 265 (M+1)$^+$.

Step C: methyl 7-(bis(tert-butoxycarbonyl)amino)-5-butoxypyrazolo[1,5-c] pyrimidine-3-carboxylate (Boc)₂O (7.7 g, 35.2 mmol) was added dropwise to a solution of methyl 7-amino-5-butoxypyrazolo[1,5-c]pyrimidine-3-carboxylate (3.1 g, 11.7 mmol) and DMAP (714 mg, 5.9 mmol) in THF (250 mL). After additional, the suspension became clear. It was continued to stir at rt for 2 hrs, then concentrated and purified by CombiFlash (PE:EA=25%) to get the product (4.2 g, 78%). $^1$H NMR (400 MHz, DMSO-d6) δ 8.37 (s, 1H), 7.27 (s, 1H), 7.23 (s, 1H), 4.30 (t, J=8.0 Hz, 2H), 3.91 (s, 3H), 1.80-1.76 (m, 2H), 1.54-1.45 (m, 2H), 1.29 (s, 9H), 0.97 (t, J=8.0 Hz, 3H) ppm. MS: M/e 465 (M+1)$^+$.

Step D: tert-butyl (5-butoxy-3-(hydroxymethyl) pyrazolo[1,5-c]pyrimidin-7-yl) carbamate To a solution of Lithium aluminium hydride (782 mg, 20.6 mmol) in THF (60 mL) at 0° C., methyl 7-(bis(tert-butoxycarbonyl)amino)-5-butoxypyrazolo[1,5-c]pyrimidine-3-carboxylate (4.2 g, 10.3 mmol) in THF (20 mL) was added dropwise. The resulting mixture was stirred gradually to rt over 2 hrs. Then it was quenched with 0.8 mL of water, followed with 0.8 mL of NaOH solution (15%) and 2.4 mL of water. The solid was filtered and the cake was slurried with 100 mL of methanol for 1 hour. After filtration, the filtered cake was once again slurried with 100 mL of methanol. After filtration, the combined filtrate was evaporated to get the desired product (1.9 g, 50%). $^1$H NMR (400 MHz, CD₃OD) δ 7.76 (s, 1H), 6.14 (s, 1H), 4.64 (s, 1H), 4.04 (t, J=8.0 Hz, 2H), 1.79-1.75 (m, 2H), 1.54-1.44 (m, 12H), 0.97 (t, J=8.0 Hz, 3H) ppm. MS: M/e 337 (M+1)$^+$.

Step E: tert-butyl (5-butoxy-3-formylpyrazolo[1,5-c]pyrimidin-7-yl)carbamate

To a cooled solution of tert-butyl (5-butoxy-3-(hydroxymethyl)pyrazolo[1,5-c]pyrimidin-7-yl)carbamate (1.2 g, 3.6 mmol) in THF (110 mL) at 0° C., Dess-Martin reagent (3.1 g, 7.2 mmol) was added. It was stirred at 0° C. for 30 mins, and then gradually to rt for 30 mins. The solution was quenched with water at 0° C. to a clear solution and extracted with ethyl acetate (80 mL). The organic layer was concentrated and purified by CombiFlash (PE:EA=25%) to get the product as a colorless oil (270 mg, 23%). $^1$H NMR (400 MHz, DMSO-d6) δ 10.19 (s, 1H), 9.91 (s, 1H), 8.60 (s, 1H), 7.01 (s, 1H), 4.31 (t, J=8.0 Hz, 2H), 1.76-1.70 (m, 2H), 1.52-1.40 (m, 12H), 0.95 (t, J=8.0 Hz, 3H) ppm. MS: M/e 335 (M+1)$^+$.

Step F: tert-butyl 4-(5-((5-butoxy-7-((tert-butoxy-carbonyl)amino)pyrazolo[1,5-c]pyrimidin-3-yl)(hydroxy)methyl)-3-chloropyridin-2-yl)piperazine-1-carboxylate To a cooled solution of tert-butyl 4-(5-bromo-3-chloropyridin-2-yl)piperazine-1-carboxylate (289 mg, 0.8 mmol) in THF (15 mL) at −78° C. (purged with N$^2$), n-BuLi (1.6 M, 1.2 mL) was added dropwise. After was stirred at −78° C. for 30 mins, tert-butyl (5-butoxy-3-formylpyrazolo[1,5-c]pyrimidin-7-yl)carbamate (270 mg, 0.8 mmol) in THF (5 mL) was added. The resulting mixture was stirred at this temperature for 30 mins, and then warmed to rt for 2 hrs. The solution was quenched with NH$_4$Cl solution (10 mL) and extracted with ethyl acetate (10 mL). The organic layer was dried with Na$_2$SO$_4$, filtered and concentrated to get the crude product, which was further purified by CombiFlash (PE:EA=50%) and prep-TLC (PE:EA=1:1) to get the pure product (80 mg, 16%). MS: M/e 632 (M+1)$^+$.

Step G: 5-butoxy-3-((5-chloro-6-(piperazin-1-yl)pyridin-3-yl)methyl)pyrazolo[1,5-c]pyrimidin-7-amine A mixture of tert-butyl 4-(5-((5-butoxy-7-((tert-butoxycarbonyl)amino) pyrazolo[1,5-c]pyrimidin-3-yl)(hydroxy)methyl)-3-chloropyridin-2-yl)piperazine-1-carboxylate (20 mg, 0.03 mmol) in triethylsilane (0.5 mL) and trifluoroacetic acid (0.5 mL) was heated at 30° C. for 2 hrs. Then it was concentrated under oil pump at 60° C. to get the crude product, which was purified by prep-TLC (DCM:MeOH=7:1) to get the product (5 mg, 38%). $^1$H NMR (400 MHz, CD$_3$OD) δ 8.12 (t, J=8.0 Hz, 1H), 7.75 (d, J=4.0 Hz, 1H), 7.64 (s, 1H), 6.97 (d, J=4.0 Hz, 1H), 5.97 (d, J=8.0 Hz, 1H), 4.12-4.09 (m, 3H), 3.51-3.38 (m, 4H), 2.91-2.65 (m, 4H), 1.76-1.72 (m, 2H), 1.49-1.45 (m, 2H), 0.98 (t, J=8.0 Hz, 3H) ppm. MS: M/e 416 (M+1)$^+$.

Compound C4: 6-propoxy-3-(4-(pyrrolidin-1-ylmethyl)benzyl)imidazo[1,2-b]pyridazin-8-amine Step A: 6-chloro-N,N-bis(4-methoxybenzyl)imidazo[1,2-b]pyridazin-8-amine To a stirred solution of 8-bromo-6-chloroimidazo[1,2-b]pyridazine (2 g, 8.7 mmol) in DMF (20 mL), bis(4-methoxybenzyl)amine (2.7 g, 10.44 mmol) and DIEA (2.3 g, 17.4 mmol) were added. The reaction mixture was stirred at 90° C. overnight. The mixture was diluted with H$_2$O (50 mL) and extracted with EtOAc (20 ml×3). The combined organic phase was washed with brine, dried over Na$_2$SO$_4$ and concentrated in vacuo. The crude product was purified by column chromatography to give the product (2.8 mg, 80%) as white solids. MS: M/e 308 (M+1)$^+$.

Step B: N,N-bis(4-methoxybenzyl)-6-propoxyimidazo[1,2-b]pyridazin-8-amine

To a stirred solution of 6-chloro-N,N-bis(4-methoxybenzyl)imidazo[1,2-b]pyridazin-8-amine (2.2 g, 5.4 mmol) in butyl alcohol (10 mL), sodium butanolate (50 ml, 4M in butyl alcohol) was added. The reaction mixture was stirred at 95° C. overnight. The mixture was concentrated in vacuo. The residue was added H$_2$O (50 mL) and extracted with EtOAc (20 ml×3). The combined organic phase was washed with brine, dried over Na$_2$SO$_4$ and concentrated in vacuo. The crude product was purified by column chromatography to give the product (2 g, 85.8%) as white solids. MS: M/e 437 (M+1)$^+$.

Step C: 8-(bis(4-methoxybenzyl)amino)-6-propoxyimidazo[1,2-b]pyridazine-3-carbaldehyde In a 100 ml round bottom flask was added DMF (5 ml), POCl$_3$ (900 mg, 5.88 mmol) was added to DMF at 0° C. The reaction was stirred at 0° C. for 30 mins. To this solution, N,N-bis(4-methoxybenzyl)-6-propoxyimidazo[1,2-b]pyridazin-8-amine (300 mg, 0.69 mmol) was added. The reaction was stirred at rt overnight. The mixture was added H$_2$O (50 mL) and extracted with EtOAc (20 ml×3). The combined organic phase was washed with brine, dried over Na$_2$SO$_4$ and concentrated in vacuo. The crude product was purified by column chromatography to give the product (300 mg, 94%) as yellow solids. MS: M/e 475 (M+1)$^+$.

Step D: (8-(bis(4-methoxybenzyl)amino)-6-propoxyimidazo[1,2-b]pyridazin-3-yl)(4-(pyrrolidin-1-ylmethyl)phenyl)methanol To a stirred solution of 1-(4-bromobenzyl)pyrrolidine (140 mg, 0.55 mmol) in THF (10 mL), cooled to −78° C. and under a nitrogen atmosphere, n-BuLi (1.6 M in hexane, 0.93 mmol, 0.58 mL) was added dropwise. After stirring for 50 mins, a solution of 8-(bis(4-methoxybenzyl)amino)-6-propoxyimidazo[1,2-b]pyridazine-3-carbaldehyde (150 mg, 0.37 mmol) in THF (2 mL) was slowly added. The reaction mixture was slowly warmed up to rt and stirred for 2 h. The reaction mixture was poured to saturated ammonium chloride solution and extracted by EtOAc (15 mL×3). The combined organic phase was washed with brine, dried over Na$_2$SO$_4$, concentrated in vacuo to give the product (60 mg, 25.6%). MS: M/e: 636 (M+1)$^+$.

Step E: 6-butoxy-3-(4-(pyrrolidin-1-ylmethyl)benzyl)imidazo[1,2-b]pyridazin-8-amine A solution of (8-(bis(4-methoxybenzyl)amino)-6-propoxyimidazo[1,2-b]pyridazin-3-yl)(4-(pyrrolidin-1-ylmethyl)phenyl)methanol (60 mg, 0.09 mmol) in TFA (3 mL) and Et$_3$SiH (3 mL) was stirred at 80° C. for 2 h. The reaction mixture was concentrated in vacuo to remove TFA and Et$_3$SiH. The residue was added TFA (5 mL) and stirred at 85° C. overnight. The mixture was cooled down to rt and concentrated in vacuo. The crude product was purified by prep-HPLC to give the product (5 mg, 14.2%). $^1$H NMR (400 MHz, DMSO-d6) δ 9.83 (s, 1H), 8.04 (s, 1H), 7.74 (s, 1H), 7.39 (d, J=7.5 Hz, 2H), 7.30 (d, J=7.7 Hz, 2H), 7.04 (s, 2H), 4.29 (d, J=5.4 Hz, 2H), 4.20 (t, J=6.1 Hz, 2H), 3.95 (s, 2H), 3.30 (s, 2H), 3.06 (s, 2H), 2.01 (s, 2H), 1.91-1.77 (m, 2H), 1.69-1.56 (m, 2H), 1.35-1.19 (m, 2H), 0.85 (t, J=7.3 Hz, 3H) ppm. MS: M/e 380 (M+1)$^+$.

Compound C5: 6-butoxy-3-((5-methyl-6-(piperazin-1-yl)pyridin-3-yl)methyl)imidazo[1,2-b]pyridazin-8-amine Step A: tert-butyl 4-(5-((8-(bis(4-methoxybenzyl)amino)-6-butoxyimidazo[1,2-b]pyridazin-3-yl)(hydroxy)methyl)-3-methylpyridin-2-yl)piperazine-1-carboxylate To a stirred solution of tert-butyl 4-(5-bromo-3-methylpyridin-2-yl)piperazine-1-carboxylate (180 mg, 0.44 mmol) in THF (10 mL), cooled to −78° C. and under a nitrogen atmosphere, n-BuLi (1.6 M in hexane, 0.99 mmol, 0.618 mL) was added dropwise. After stirring for 50 mins, a solution of 8-(bis(4-methoxybenzyl)amino)-6-propoxy-imidazo[1,2-b]pyridazine-3-carbaldehyde (201 mg, 0.66 mmol) in THF (2 mL) was slowly added. The reaction mixture was slowly warmed up to rt and stirred for 2 h. The reaction mixture was poured into saturated ammonium chloride solution and extracted by EtOAc (15 mL×3). The combined organic phase was washed with brine, dried over $Na_2SO_4$, concentrated in vacuo to give the product (120 mg, 24.2%). MS: M/e: 752 (M+1)$^+$.

Step B: 6-butoxy-3-((5-methyl-6-(piperazin-1-yl)pyridin-3-yl)methyl)imidazo[1,2-b]pyridazin-8-amine A solution of tert-butyl 4-(5-((8-(bis(4-methoxybenzyl)amino)-6-butoxyimidazo[1,2-b]pyridazin-3-yl)(hydroxy)methyl)-3-methylpyridin-2-yl)piperazine-1-carboxylate (120 mg, 0.16 mmol) in TFA (3 mL) and $Et_3SiH$ (3 mL) was stirred at 80° C. for 2 h. The reaction mixture was concentrated in vacuo to remove TFA and $Et_3SiH$. The residue was added TFA (5 mL) and stirred at 85° C. overnight. The mixture was cooled down to rt and concentrated in vacuo. The crude product was purified by prep-HPLC to give the product (10 mg, 15.8%). $^1$H NMR (400 MHz, DMSO-d6) δ 8.68 (br.s, 2H), 8.14-8.10 (m, 1H), 8.05 (s, 1H), 7.89-7.83 (m, 1H), 7.39 (s, 1H), 7.16-7.11 (m, 2H), 4.24 (br.s, 2H), 3.84 (s, 2H), 3.26-3.14 (m, 8H), 2.18 (s, 3H), 1.72-1.59 (m, 2H), 1.33-1.27 (m, 2H), 0.86 (t, J=7.6, 3H) ppm. MS: M/e 396 (M+1)$^+$.

Compound C6: 2-butoxy-7-((5-methyl-6-(piperazin-1-yl)pyridin-3-yl)methyl)-5H-pyrrolo[3,2-d]pyrimidin-4-amine Step A: 2,4-dichloro-5-((2-(trimethylsilyl)ethoxy)methyl)-5H-pyrrolo[3,2-d]pyrimidine To a solution of 2,4-dichloro-5H-pyrrolo[3,2-d]pyrimidine (3.76 g, 20 mmol) in DMF (40 mL), DIPEA (4.2 mL, 24 mmol) and (2-(chloromethoxy)ethyl)trimethylsilane (4.3 mL, 24 mmol) were added. Then the mixture was stirred at room temperature overnight. The reaction was concentrated, diluted with water (5 mL), extracted with EtOAc (30 mL×5). The combined organic layers were washed with brine, dried over $Na_2SO_4$, concentrated and the residue was purified by flash chromatography to give target compound (3 g, 47%) as a white solid. MS: M/e 318 (M+1)$^+$.

Step B: 2-chloro-5-((2-(trimethylsilyl)ethoxy)methyl)-5H-pyrrolo[3,2-d]pyrimidin-4-amine Aqueous ammonia (20 mL) was added to a solution of 2,4-dichloro-5-((2-(trimethylsilyl)ethoxy)methyl)-5H-pyrrolo[3,2-d]pyrimidine (5 g, 15.8 mmol) in propan-2-ol (20 mL), the reaction mixture was stirred in autoclave at 95° C. for 7 hours, extracted with EtOAc (25 mL×4). The combined organic layers were washed with brine, dried over $Na_2SO_4$, concentrated and the residue was purified by flash chromatography to give target compound (3.2 g, 68%) as a white solid. MS: M/e 299 (M+1)$^+$.

Step C: 2-butoxy-5-((2-(trimethylsilyl)ethoxy)methyl)-5H-pyrrolo[3,2-d]pyrimidin-4-amine A mixture of 2-chloro-5-((2-(trimethylsilyl)ethoxy)methyl)-5H-pyrrolo[3,2-d]pyrimidin-4-amine (3 g, 10 mmol) and n-BuONa/n-BuOH (20%, 9.6 ml) was stirred at 80° C. for 5 hours. The solution was quenched with $H_2O$ (10 ml). The aqueous solution was extracted with EA (20 ml×4). The collected organic layers were washed with brine, dried over $Na_2SO_4$, filtered and concentrated. The resulting residue was purified by column chromatography to afford product (3.3 g, 95%). MS: M/e 337 (M+1)$^+$.

Step D: 2-butoxy-5H-pyrrolo[3,2-d]pyrimidin-4-amine

A mixture of 2-butoxy-5-((2-(trimethylsilyl)ethoxy)methyl)-5H-pyrrolo[3,2-d]pyrimidin-4-amine (3.3 g, 10 mmol) and $CF_3COOH$ was stirred at room temperature overnight. The reaction was quenched with saturated $NaHCO_3$ solution. The aqueous solution was extracted with EA (20 ml×3). The collected organic layer was washed with brine, dried over $Na_2SO_4$, filtered and concentrated. The resulting residue was purified by column chromatography to afford the product (1.53 g, 74%). MS: M/e 207 (M+1)$^+$.

Step E: tert-butyl 4-(5-((4-amino-2-butoxy-5H-pyrrolo[3,2-d]pyrimidin-7-yl)(hydroxy)methyl)-3-methylpyridin-2-yl)piperazine-1-carboxylate A mixture of 2-butoxy-5H-pyrrolo[3,2-d]pyrimidin-4-amine (206 mg, 1 mmol), tert-butyl 4-(5-formyl-3-methylpyridin-2-yl)piperazine-1-carboxylate (458 mg, 1.5 mmol) and $K_2CO_3$ (166 mg, 1.5 mmol) in $CH_3OH$ (1 mL) and $H_2O$ (1 mL) was stirred at room temperature for two days. The reaction was quenched with saturated $NaHCO_3$ solution. The aqueous solution was extracted with EA (25 ml×4). The collected organic layers were washed with brine, dried over $Na_2SO_4$, filtered and concentrated. The resulting residue was purified by column chromatography to afford the product (203 mg, 40%) MS: M/e 512 (M+1)$^+$.

Step F: 2-butoxy-7-((5-methyl-6-(piperazin-1-yl)pyridin-3-yl)methyl)-5H-pyrrolo[3,2-d]pyrimidin-4-amine To a stirred solution of product step A (206 mg, 0.5 mmol) in DCM (5 mL) at −15° C., $Et_3SiH$ (0.5 mL) and TFA (0.5 mL) were added. The reaction mixture was stirred at 0° C. overnight. The solution was quenched with saturated $NaHCO_3$ solution (5 mL). The aqueous solution was extracted with EA (10 ml×4). The collected organic layers were washed with brine, dried over $Na_2SO_4$, filtered and concentrated. The resulting residue was purified by column chromatography to afford the product (82 mg, 41%). $^1$H NMR (400 MHz, CDCl$_3$) δ 10.45 (s, 1H), 8.04 (d, J=4 Hz, 1H), 7.46 (s, 1H), 7.16 (d, J=4 Hz, 1H), 6.65 (s, 2H), 4.19

(t, J=4 Hz, 2H), 3.77 (s, 2H), 2.91-2.75 (m, 8H), 1.68-1.61 (m, 2H), 1.42-1.35 (m, 2H), 0.93 (t, J=8.0 Hz, 3H) ppm. MS: M/e 396 (M+1)$^+$.

HEK293-Blue hTLR7 Reporter Assay:

HEK-Blue-hTLR7 cell line (Invivogen, Cat. No. hkb-htlr7) was designed so that the expression of the secreted embryonic alkaline phosphatase (SEAP) was induced by activating NF-κ and AP-1 via stimulating human TLR7 with TLR7 agonists.

HEK-Blue-hTLR7 cells were seeded at a density of $4 \times 10^4$ cells/well in a volume of 180 μL in a 96-well plate in DMEM (Cat. No. 11965-092) supplemented with 10% (v/v) heat-inactivated fetal bovine serum (FBS) (Gibco, 10099-1441), 100 U/ml penicillin and 100 μg/ml streptomycin (Gibco, 15140122) containing 50 U/mL penicillin, 50 mg/mL streptomycin and 10% (v/v) heat-inactivated fetal bovine serum. The cells were settled for 5 hrs, then treated with increasing amounts of tested compounds at 37° C. for 24 hrs. Then 20 μL of the supernatant from each well was incubated with 180 uL Quanti-blue substrate solution at 37° C. for 10-30 mins before the activity of the SEAP was determined at 620-655 nm using a spectrophotometer. The EC50 value for each compound was calculated with GraphPad Prism software using the sigmoidal dose-response function.

TLR7 Stimulation Determined Using HEK-Blue Detection

This assay was designed for studying the stimulation of human TLR7 protein in HELK-Blue hTLR7 tool cell line by monitoring the activation of NF-κB. HEK-Blue hTLR7 cells were obtained by co-transfection of the hTLR7 gene and an optimized secreted embryonic alkaline phosphatase (SLAP) reporter gene into HEK293 cells. The SLAP reporter gene was placed under the control of the IFN-β minimal promoter fused to five NF-κB and AP-1-binding sites. Stimulation with a TLR7 ligand activates NF-κB and AP-1 which induce the expression of SLAP. Levels of SLAP can be easily determined with HEK-Blue Detection, a cell culture medium that allows for real-time detection of SLAP. HLK-Blue Detection contains all the nutrients necessary for cell growth and a specific SLAP color substrate. The hydrolysis of the substrate by SLAP produces a purple/blue color that can be measured with a spectrophotometer.

When growing to 50-80%0 confluency, HLK-Blue hTLR7 cells were plated into 96-well plate (costar 3599) at a density of 40000 cells/well. Then compounds were added with serial dilutions over 10 points with a 0.04 nM-10 μM final concentration range in 0.1% DMSO/BLK-Blue Detection. The plates were then incubated for 16 hr at 37° C. in 500 $CO_2$ and vortex for 30s before measurement. The optical density at 620-655 nm was read on BMG PHLRAstar FSX instrument. The EC50 for each compound was determined by calculating the percentages of the maximum activation identified with Resiquimod.

TABLE 1

Compounds A series ("D" refers to EC50 > 10 μmol; A1-A76 was tested by QUANTI-BLUE assay, A77-A124 was tested by HEK-Blue Detection)

| Compound number | EC50 (nmol) | Compound number | EC50 (nmol) |
|---|---|---|---|
| A1 | 900 | A2 | 920 |
| A3 | D | A4 | 1846 |
| A5 | 1271 | A6 | 1507 |
| A7 | D | A8 | 3029 |
| A9 | D | A10 | 1174 |
| A11 | D | A12 | D |
| A13 | D | A14 | D |
| A15 | D | A16 | D |
| A17 | D | A18 | D |
| A19 | D | A20 | 1749 |
| A21 | 2866 | A22 | 5708 |
| A23 | D | A24 | D |
| A25 | D | A26 | D |
| A27 | D | A28 | 1789 |
| A29 | 2601 | A30 | 3519 |
| A31 | D | A32 | 861 |
| A33 | 1059 | A34 | 3369 |
| A35 | 2068 | A36 | 880 |
| A37 | D | A38 | 1858 |
| A39 | 543 | A40 | 602 |
| A41 | 1591 | A42 | 1380 |
| A43 | 822 | A44 | 1012 |
| A45 | 3845 | A46 | D |
| A47 | D | A48 | D |
| A49 | 4319 | A50 | D |
| A51 | D | A52 | D |
| A53 | 1432 | A54 | D |
| A55 | D | A56 | D |
| A57 | 375 | A58 | 246 |
| A59 | D | A60 | 246 |
| A61 | 183 | A62 | D |
| A63 | 996 | A64 | 3998 |
| A65 | D | A66 | 387 |
| A67 | 585 | A68 | D |
| A69 | 1238 | A70 | D |
| A71 | 1174 | A72 | 462 |
| A73 | D | A74 | D |
| A75 | D | A76 | D |
| A77 | 19.2 | A78 | 23 |
| A79 | 10 | A80 | 446 |
| A81 | 310 | A82 | 5 |
| A83 | 42.6 | A84 | 6.9 |
| A85 | 4.5 | A86 | 57.7 |
| A87 | 10.5 | A88 | D |
| A89 | 10 | A90 | 8.9 |
| A91 | 2.1 | A92 | 122 |
| A93 | 1.7 | A94 | 13.8 |
| A95 | 8.0 | A96 | 4.3 |
| A97 | 1.0 | A98 | 11 |
| A99 | 14.4 | A100 | 15 |
| A101 | 0.78 | A102 | 3.7 |
| A103 | 2.4 | A104 | 10 |
| A105 | 61 | A106 | 1.6 |
| A107 | 1.3 | A108 | 0.8 |
| A109 | 3.4 | A110 | 4.0 |
| A111 | 1.9 | A112 | 0.93 |
| A113 | 24 | A114 | 1 |
| A115 | 0.72 | A116 | 37.8 |
| A117 | 13 | A118 | 11 |
| A119 | 146 | A120 | 3.9 |
| A121 | 0.63 | A122 | 6.0 |
| A123 | 0.7 | A124 | 1.2 |

TABLE 2

Compounds C series ("D" refers to EC50 > 10 μmol; C1-C6 was tested by QUANTI-BLUE assay)

| Compound number | EC50 (nmol) | Compound number | EC50 (nmol) |
|---|---|---|---|
| C1 | D | C2 | D |
| C3 | D | C4 | D |
| C5 | D | C6 | 1075 |

TLR8 Stimulation Determined Using HEK-Blue Detection

This assay was designed for studying the stimulation of human TLR 8 protein in HEK-Blue hTLR8 tool cell line by monitoring the activation of NF-1B. HEK-Blue hTLR8 cells were obtained by co-transfection of the hTLR8 gene and an optimized secreted embryonic alkaline phosphatase (SEAP) reporter gene into HEK293 cells. The SEAP reporter gene was placed under the control of the IFN-β minimal promoter fused to five NF-κB and AP-1-binding sites. Stimulation with a TLR 8 ligand activates NF-κB and AP-1 which induce the expression of SEAP. Levels of SEAP can be easily determined with HEK-Blue Detection, a cell culture medium that allows for real-time detection of SEAP. HEK-Blue Detection contains all the nutrients necessary for cell growth and a specific SEAP color substrate. The hydrolysis of the substrate by SEAP produces a purple/blue color that can be measured with a spectrophotometer.

When growing to 50-80% confluency, HEK-Blue hTLR7/8 cells were plated into 96-well plate (costar 3599) at a density of 40000 cells/well. Then compounds were added with serial dilutions over 10 points with a 1 nM-10 uM final concentration range in 0.1% DMSO/HEK-Blue Detection. The plates were then incubated for 16 hr at 37° C. in 5% $CO_2$. The optical density at 620-655 nm was read on BMG PHERAstar FSX instrument. The EC50 for each compound was determined by calculating the percentages of the maximum activation identified with Resiquimod or Motolimod.

TABLE 3

Compounds for HEK-Blue hTLR8 Cells ("D" refers to EC50 > 10 μmol)

| Compound number | EC50 (nmol) | Compound number | EC50 (nmol) |
|---|---|---|---|
| A8 | 187 | A10 | 572 |
| A43 | 255 | A58 | 183 |
| A77 | 293 | A78 | 1135 |
| A79 | 69 | A80 | D |
| A81 | 6246 | A82 | 22 |
| A83 | 458 | A84 | 192 |
| A85 | 41 | A86 | 541 |
| A87 | 434 | A88 | D |
| A89 | 199 | A90 | 112 |
| A91 | 15 | A92 | 872 |
| A93 | 13.5 | A94 | 146 |
| A95 | 19 | A96 | 29 |
| A97 | 10 | A98 | 163 |
| A99 | 129 | A100 | 195 |
| A101 | 8.6 | A102 | 134 |
| A103 | 47 | A104 | 24 |
| A105 | 622 | A106 | 12 |
| A107 | 16 | A108 | 21 |
| A109 | 47 | A110 | 65 |
| A111 | 47 | A112 | 9 |
| A113 | 98 | A114 | 6.8 |
| A115 | 7 | A116 | 51 |
| A117 | 532 | A118 | 21 |
| A119 | 2972 | A120 | 59 |
| A121 | 19 | A122 | 113 |
| A123 | 15 | A124 | 105 |

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

What is claimed is:
1. A compound of Formula (I),

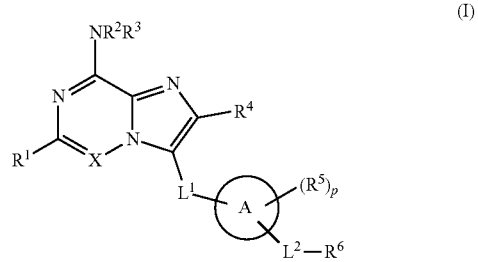

or a pharmaceutically acceptable salt thereof, or a stereoisomer thereof, wherein
X is N;
$L^1$ is —$CH_2$—,
$R^1$ is —$OR^{1a}$, wherein $R^{1a}$ is a branched —$C_{4-8}$ alkyl, wherein the branched —$C_{4-8}$ alkyl is at the alpha position with respect to the oxygen atom;
$R^2$ and $R^3$, at each occurrence, are independently hydrogen;
$R^4$ is hydrogen;
Ring A is phenyl or pyridyl;
$R^5$ is halogen, alkyl, or haloalkyl;
p is a number of 0, 1, 2 or 3;
$L^2$ is —O—;
$R^6$ is alkyl, said alkyl is optionally substituted with one or two or three substituents $R^{6c}$;
$R^{6c}$ is independently hydrogen, halogen, —$OR^{6d}$, —$SR^{6d}$, —$NR^{6d}R^{6e}$, —$COR^{6d}$, —$SO_2R^{6d}$, —C(=O)$NR^{6d}R^{6e}$, or alkyl, said alkyl is optionally substituted with one or two or three substituents $R^{6g}$;
$R^{6d}$ and $R^{6e}$ are independently hydrogen, alkyl, alkenyl, heterocyclyl, or aryl, each of said alkyl, alkenyl, heterocyclyl, or aryl, is optionally substituted with one or two or three substituents $R^{6g}$;
$R^{6g}$, at each occurrence, is independently hydrogen, halogen, —$OR^{6h}$, —$SR^{6h}$, —$NR^{6h}R^{6i}$, —$N(R^{6h})$C(=O)$OR^{6i}$, alkyl, heterocyclyl, aryl, or heteroaryl,
$R^{6h}$ and $R^{6i}$ are independently hydrogen or alkyl.
2. The compound according to claim 1, wherein $R^1$ is —$OR^{1a}$, wherein $R^{1a}$ is butan-2-yl, pentan-2-yl, pentan-3-yl, heptan-2-yl, heptan-3-yl, heptan-4-yl, octan-2-yl, octan-3-yl, octan-4-yl, or octan-5-yl.
3. The compound according to claim 1, wherein $R^5$ is halogen, —$C_{1-8}$alkyl, or -halo$C_{1-8}$alkyl, and p is a number of 0, 1, or 2.
4. The compound according to claim 1, wherein $R^6$ is —$C_{1-8}$alkyl, said —$C_{1-8}$alkyl is optionally substituted with one or two or three substituents $R^{6c}$;
$R^{6c}$ is independently hydrogen, halogen, —$OR^{6d}$, —$SR^{6d}$, —$NR^{6d}R^{6e}$, —$COR^{6d}$, —$SO_2R^{6d}$, —C(=O)$NR^{6d}R^{6e}$, or —$C_{1-8}$alkyl, said —$C_{1-8}$alkyl is independently and optionally substituted with one or two or three substituents $R^{6g}$;
$R^{6d}$ and $R^{6e}$ are independently hydrogen, —$C_{1-8}$alkyl, —$C_{2-8}$alkenyl, heterocyclyl, or aryl, each of said —$C_{1-8}$alkyl, —$C_{2-8}$alkenyl, heterocyclyl, or aryl is optionally substituted with one or two or three substituents $R^{6g}$;
$R^{6g}$, at each occurrence, is independently hydrogen, halogen, —$OR^{6h}$, —$SR^{6h}$, —$NR^{6h}R^{6i}$, —$N(R^{6h})$C(=O)$OR^{6i}$, —$C_{1-8}$alkyl, heterocyclyl, aryl, or heteroaryl, wherein $R^{6h}$ and $R^{6i}$, are independently hydrogen or —$C_{1-8}$alkyl.

5. The compound according to claim 4, wherein $L^2$ is —O—, and $R^6$ is —$C_{1-8}$alkyl, said —$C_{1-8}$alkyl is optionally substituted with one or two $R^{6c}$, wherein $R^{6c}$ is —$C_{1-8}$alkyl, —$NR^{6d}R^{6e}$ or —$COR^{6d}$, wherein $R^{6d}$ and $R^{6e}$ are independently —$C_{1-8}$alkyl optionally substituted with $NH_2$—, alkylamino, or dialkylamino.

6. The compound according to claim 5, wherein $L^2$-$R^6$ is selected from:
3-(methylamino)propoxy, 3-(dimethylamino)propoxy, 3-(diethylamino)propoxy, 2-aminoethoxy, 3-(dimethylamino)-2,2-dimethylpropoxy, methoxy, 2-(methylamino)ethoxy, or 3-aminopropoxy.

7. The compound according to claim 1, wherein ring A is phenyl, and $L^1$ and $L^2$-$R^6$ are in para positions of the phenyl ring, and said phenyl ring is further optionally substituted with one $R^5$.

8. The compound according to claim 1, wherein ring A is pyridyl, and $L^1$ and $L^2$-$R^6$ are in para positions of the pyridyl ring, and said pyridyl ring is further optionally substituted with one $R^5$.

9. A compound, or a pharmaceutically acceptable salt thereof, or a stereoisomer thereof, selected from:
Compound A77: 7-((6-(2-(methylamino)ethoxy)pyridin-3-yl)methyl)-2-(pentan-2-yloxy)imidazo[2,1-f][1,2,4]triazin-4-amine;
Compound A78: 7-((5-methyl-6-(2-(methylamino)ethoxy)pyridin-3-yl)methyl)-2-(pentan-2-yloxy)imidazo[2,1-f][1,2,4]triazin-4-amine;
Compound A83: 7-((6-(2-(methylamino)ethoxy)pyridin-3-yl)methyl)-2-(pentan-3-yloxy)imidazo[2,1-f][1,2,4]triazin-4-amine;
Compound A84: 2-(hexan-3-yloxy)-7-((6-(2-(methylamino)ethoxy)pyridin-3-yl)methyl)imidazo[2,1-f][1,2,4]triazin-4-amine;
Compound A87: 2-(heptan-4-yloxy)-7-((6-(2-(methylamino)ethoxy)pyridin-3-yl)methyl)imidazo[2,1-f][1,2,4]triazin-4-amine;
Compound A89: (S)-2-(sec-butoxy)-7-((6-(2-(methylamino)ethoxy)pyridin-3-yl)methyl)imidazo[2,1-f][1,2,4]triazin-4-amine;
Compound A90: (S)-7-((6-(2-(methylamino)ethoxy)pyridin-3-yl)methyl)-2-(pentan-2-yloxy)imidazo[2,1-f][1,2,4]triazin-4-amine;
Compound A99: (S)-7-(3-fluoro-4-(2-(methylamino)ethoxy)benzyl)-2-(pentan-2-yloxy)imidazo[2,1-f][1,2,4]triazin-4-amine; and
Compound A100: (S)-7-(4-(2-(methylamino)ethoxy)benzyl)-2-(pentan-2-yloxy)imidazo[2,1-f][1,2,4]triazin-4-amine.

* * * * *